United States Patent [19]
Kasibhatla et al.

[11] Patent Number: 6,110,903
[45] Date of Patent: Aug. 29, 2000

[54] BENZIMIDAZOLE INHIBITORS OF FRUCTOSE 1,6-BISPHOSPHATASE

[75] Inventors: Srinivas Rao Kasibhatla; K. Raja Reddy, both of San Diego; Mark D. Erion, Del Mar; Qun Dang, San Diego; Gerard R. Scarlato, La Jolla; M. Rami Reddy, San Diego, all of Calif.

[73] Assignee: Sankyo Company Ltd., Tokyo, Japan

[21] Appl. No.: 09/036,329

[22] Filed: Mar. 6, 1998

Related U.S. Application Data

[60] Provisional application No. 60/040,627, Mar. 7, 1997.

[51] Int. Cl.$^7$ .......................... A61K 31/662; C07F 9/38; C07F 9/06; C07F 9/40
[52] U.S. Cl. .............................................. 514/80; 548/113
[58] Field of Search ................................ 548/113; 514/80

[56] References Cited

U.S. PATENT DOCUMENTS

| | | | |
|---|---|---|---|
| 3,931,206 | 1/1976 | Bowler et al. | 260/295 |
| 4,000,305 | 12/1976 | Bowler et al. | 424/274 |
| 4,278,791 | 7/1981 | Botta et al. | 542/412 |
| 4,939,130 | 7/1990 | Jaeggi et al. | 514/94 |
| 4,968,790 | 11/1990 | DeVries et al. | 536/117 |
| 5,021,443 | 6/1991 | Bru-Magniez et al. | 514/394 |
| 5,124,319 | 6/1992 | Baudy et al. | 514/80 |
| 5,294,608 | 3/1994 | Lang et al. | 514/108 |
| 5,376,665 | 12/1994 | Miyata et al. | 514/301 |
| 5,395,826 | 3/1995 | Naumann et al. | 514/107 |
| 5,414,088 | 5/1995 | Von Der Saal et al. | 546/158 |
| 5,480,874 | 1/1996 | Shoji et al. | 514/80 |
| 5,498,617 | 3/1996 | Naumann et al. | 514/315 |
| 5,519,138 | 5/1996 | Ries et al. | 544/287 |
| 5,658,889 | 8/1997 | Gruber et al. | 514/43 |
| 5,661,174 | 8/1997 | Naumann et al. | 514/416 |
| 5,958,904 | 9/1999 | Cordi et al. | 514/81 |
| 5,985,856 | 11/1999 | Stella et al. | 514/80 |

FOREIGN PATENT DOCUMENTS

| | | |
|---|---|---|
| 1324383 | 11/1993 | Canada. |
| 0 012 909 | 7/1980 | European Pat. Off.. |
| 0 117 429 B1 | 9/1987 | European Pat. Off.. |
| 0 354 322 A2 | 2/1990 | European Pat. Off.. |
| 0 427 799 B1 | 5/1991 | European Pat. Off.. |
| 0604 657 A1 | 7/1994 | European Pat. Off.. |
| 0 620 227 A1 | 10/1994 | European Pat. Off.. |
| 94/07867 | 4/1994 | WIPO. |
| 94/20508 | 9/1994 | WIPO. |

OTHER PUBLICATIONS

Yoshino et al., "Organic phosphorus compounds. 2. Synthesis and coronary vasodilator activity of (Benzothiazolylbenzyl) phosphonate derivatives," *J. Med. Chem.* 32:1528–1532 (1989).

*Primary Examiner*—Johann Richter
*Assistant Examiner*—Sonya N Wright
*Attorney, Agent, or Firm*—Lyon & Lyon LLP

[57] ABSTRACT

Novel benzimidazole compounds of the following structure and their use as fructose-1,6-bisphosphatase inhibitors is described

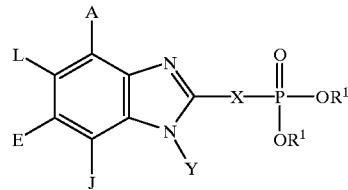

52 Claims, 3 Drawing Sheets

BENZIMIDAZOLE INHIBITORS OF FRUCTOSE 1,6-BISPHOSPHATASE

This application is a provisional of No. 60/040,627 filed Mar. 7, 1997.

FIELD OF THE INVENTION

This invention relates to novel benzimidazole compounds that are inhibitors of Fructose-1,6-bisphosphatase at the AMP site. The invention also relates to the preparation and use of these benzimidazole analogs in the treatment of diabetes, and other diseases where the inhibition of gluconeogenesis, control of blood glucose levels, reduction in glycogen stores, or reduction in insulin levels is beneficial.

BACKGROUND AND INTRODUCTION TO THE INVENTION

Diabetes mellitus (or diabetes) is one of the most prevalent diseases in the world today. Diabetes patients have been divided into two classes, namely type I or insulin-dependent diabetes mellitus and type II or non-insulin dependent diabetes mellitus (NIDDM). Non-insulin-dependent diabetes mellitus (NIDDM) accounts for approximately 90% of all diabetics and is estimated to affect 12–14 million adults in the U. S. alone (6.6% of the population). NIDDM is characterized by both fasting hyperglycemia and exaggerated postprandial increases in plasma glucose levels. NIDDM is associated with a variety of long-term complications, including microvascular diseases such as retinopathy, nephropathy and neuropathy, and macrovascular diseases such as coronary heart disease. Numerous studies in animal models demonstrate a causal relationship between long term complications and hyperglycemia. Recent results from the Diabetes Control and Complications Trial (DCCT) and the Stockholm Prospective Study demonstrate this relationship for the first time in man by showing that insulin-dependent diabetics with tighter glycemic control are at substantially lower risk for development and progression of these complications. Tighter control is also expected to benefit NIDDM patients.

Current therapies used to treat NIDDM patients entail both controlling lifestyle risk factors and pharmaceutical intervention. First-line therapy for NIDDM is typically a tightly-controlled regimen of diet and exercise since an overwhelming number of NIDDM patients are overweight or obese ($\approx$67%) and since weight loss can improve insulin secretion, insulin sensitivity and lead to normoglycemia. Normalization of blood glucose occurs in less than 30% of these patients due to poor compliance and poor response. Patients with hyperglycemia not controlled by diet alone are subsequently treated with oral hypoglycemics or insulin. Until recently, the sulfonylureas were the only class of oral hypoglycemic agents available for NIDDM. Treatment with sulfonylureas leads to effective blood glucose lowering in only 70% of patients and only 40% after 10 years of therapy. Patients that fail to respond to diet and sulfonylureas are subsequently treated with daily insulin injections to gain adequate glycemic control.

Although the sulfonylureas represent a major therapy for NIDDM patients, four factors limit their overall success. First, as mentioned above, a large segment of the NIDDM population do not respond adequately to sulfonylurea therapy (i.e. primary failures) or become resistant (i.e. secondary failures). This is particularly true in NIDDM patients with advanced NIDDM since these patients have severely impaired insulin secretion. Second, sulfonylurea therapy is associated with an increased risk of severe hypoglycemic episodes. Third, chronic hyperinsulinemia has been associated with increased cardiovascular disease although this relationship is considered controversial and unproven. Last, sulfonylureas are associated with weight gain, which leads to worsening of peripheral insulin sensitivity and thereby can accelerate the progression of the disease.

Recent results from the U.K. Diabetes prospective study also showed that patients undergoing maximal therapy of a sulfonylurea, metformin, or a combination of the two, were unable to maintain normal fasting glycemia over the six year period of the study. U.K. Prospective Diabetes Study 16. *Diabetes*, 44:1249–158 (1995). These results further illustrate the great need for alternative therapies. Three therapeutic strategies that could provide additional health benefits to NIDDM patients beyond the currently available therapies, include drugs that would: (i) prevent the onset of NIDDM; (ii) prevent diabetic complications by blocking detrimental events precipitated by chronic hyperglycemia; or (iii) normalize glucose levels or at least decrease glucose levels below the threshold reported for microvascular and macrovascular diseases.

Hyperglycemia in NIDDM is associated with two biochemical abnormalities, namely insulin resistance and impaired insulin secretion. The relative roles of these metabolic abnormalities in the pathogenesis of NIDDM has been the subject of numerous studies over the past several decades. Studies of offspring and siblings of NIDDM patients, mono- and dizygotic twins, and ethnic populations with high incidence of NIDDM (e.g. Pima Indians) strongly support the inheritable nature of the disease.

Despite the presence of insulin resistance and impaired insulin secretion, fasting blood glucose (FBG) levels remain normal in pre-diabetic patients due to a state of compensatory hyperinsulinemia. Eventually, however, insulin secretion is inadequate and fasting hyperglycemia ensues. With time insulin levels decline. Progression of the disease is characterized by increasing FBG levels and declining insulin levels.

Numerous clinical studies have attempted to define the primary defect that accounts for the progressive increase in FBG. Results from these studies indicate that excessive hepatic glucose output (HGO) is the primary reason for the elevation in FBG with a significant correlation found for HGO and FBG once FBG exceeds 140 mg/dL. Kolterman, et al., *J. Clin. Invest.* 68:957, (1981); DeFronzo *Diabetes* 37:667 (1988).

HGO comprises glucose derived from breakdown of hepatic glycogen (glycogenolysis) and glucose synthesized from 3-carbon precursors (gluconeogenesis). A number of radioisotope studies and several studies using $^{13}$C-NMR spectroscopy have shown that gluconeogenesis contributes between 50–100% of the glucose produced by the liver in the postabsorptive state and that gluconeogenesis flux is excessive (2- to 3-fold) in NIDDM patients. Magnusson, et al. *J. Clin. Invest.* 90:1323–1327 (1992); Rothman, et al., *Science* 254: 573–76 (1991); Consoli, et a I. *Diabetes* 38:550–557 (1989).

Gluconeogenesis from pyruvate is a highly regulated biosynthetic pathway requiring eleven enzymes (FIG. 1). Seven enzymes catalyze reversible reactions and are common to both gluconeogenesis and glycolysis. Four enzymes catalyze reactions unique to gluconeogenesis, namely pyruvate carboxylase, phosphoenolpyruvate carboxykinase, fructose-1,6-bisphosphatase and glucose-6-phosphatase. Overall flux through the pathway is controlled by the specific activities of these enzymes, the enzymes that catalyzed the corresponding steps in the glycolytic direction, and by substrate availability. Dietary factors (glucose, fat) and hormones (insulin, glucagon, glucocorticoids, epinephrine) coordinatively regulate enzyme activities in the gluconeogenesis and glycolysis pathways through gene expression and post-translational mechanisms.

Of the four enzymes specific to gluconeogenesis, fructose-1,6-bisphosphatase (hereinafter "FBPase") is the most suitable target for a gluconeogenesis inhibitor based on efficacy and safety considerations. Studies indicate that nature uses the FBPase/PFK cycle as a major control point (metabolic switch) responsible for determining whether metabolic flux proceeds in the direction of glycolysis or gluconeogenesis. Claus, et al., *Mechanisms of Insulin Action*, Belfrage, P. editor, pp.305–321, Elsevier Science 1992; Regen, et al. *J. Theor. Biol.*, 111:635–658 (1984); Pilkis, et al. *Annu. Rev. Biochem*, 57:755–783 (1988). FBPase is inhibited by fructose-2,6-bisphosphate in the cell. Fructose-2,6-bisphosphate binds to the substrate site of the enzyme. AMP binds to an allosteric site on the enzyme.

Synthetic inhibitors of FBPase have also been reported. McNiel reported that fructose-2,6-bisphosphate analogs inhibit FBPase by binding to the substrate site. *J. Med. Chem.*, 106:7851 (1984); U.S. Pat. No. 4,968,790 (1984). These compounds, however, were relatively weak and did not inhibit glucose production in hepatocytes presumably due to poor cell penetration.

Gruber reported that some nucleosides can lower blood glucose in the whole animal through inhibition of FBPase. These compounds exert their activity by first undergoing phosphorylation to the corresponding monophosphate. EP 0 427 799 B1.

Gruber et al. U.S. Pat. No. 5,658,889 described the use of inhibitors of the AMP site of FBPase to treat diabetes.

*J. Med. Chem.* 32:1528–32 (1989) discloses lower alkyl phosphonic esters of benzimidazole compounds where X in formula 1 of the present invention is -pyridyl-$CH_2$—. This publication discusses $Ca^{2+}$ antagonist activity. There is no suggestion that the disclosed compounds were FBPase inhibitors or that they have blood glucose lowering activity. Furthermore, lower alkyl phosphonic esters are not FBPase inhibitors and are not readily hydrolyzed into active compounds within the body.

European patent application EP 0 620 227 A1 discloses certain heterocycles including benzimidazoles having a diphosphonic acid where the X linker in formula 1 of the claims is alkylamino and alkylaminoalkyl. These compounds are said to inhibit bone resorption. There is no suggestion that the disclosed compounds were FBPase inhibitors or that they have blood glucose lowering activity.

German Offenlegungsschrift 2855659 discloses certain free phosphonic acids of benzimidazoles where A is amino and X is alkyl or alkene. These compounds are supposed to be corrosion inhibitors. There is no suggestion that the disclosed compounds were FBPase inhibitors or that they have blood glucose lowering activity.

SUMMARY OF THE INVENTION

Figure 1:
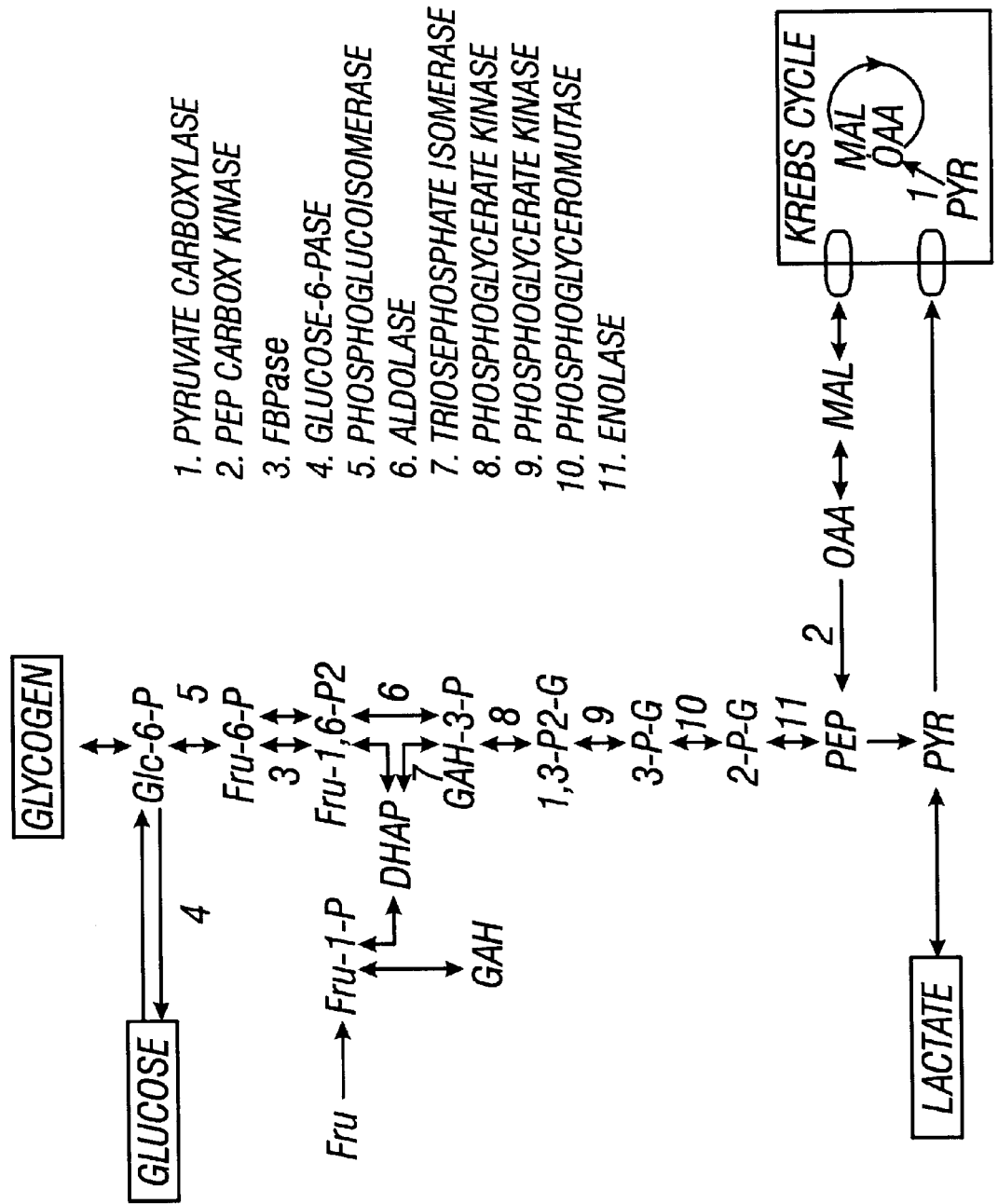
FIG. 1 is a scheme depicting the eleven enzymes of the gluconeogenesis pathway.

The present invention is directed towards novel benzimidazole compounds which bind to the AMP site and are potent FBPase inhibitors. In another aspect, the present invention is directed to the preparation of these novel benzimidazole compounds and to the in vitro and in vivo FBPase inhibitory activity of these compounds. Another aspect of the present invention is directed to the clinical use of the novel FBPase inhibitors as a method of treatment or prevention of diseases responsive to inhibition of gluconeogenesis and in diseases responsive to lowered blood glucose levels.

The compounds are also useful in treating or preventing excess glycogen storage diseases and insulin dependent diseases such as cardiovascular diseases including atherosclerosis.

The invention comprises the novel benzimidazole analogs as specified below in formula 1. Also included in the scope of the present invention are prodrugs of the compounds of formula 1.

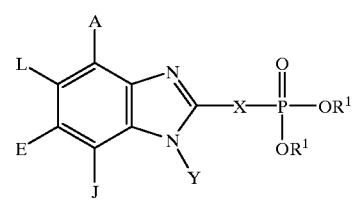

Formula 1

Since these compounds may have asymmetric centers, the present invention is directed not only to racemic mixtures of these compounds, but also to individual stereoisomers. The present invention also includes pharmaceutically acceptable and/or useful salts of the compounds of formula 1, including acid addition salts. The present inventions also encompass prodrugs of compounds of formula 1.

Definitions

In accordance with the present invention and as used herein, the following terms are defined with the following meanings, unless explicitly stated otherwise.

The term "aryl" refers to aromatic groups which have at least one ring having a conjugated pi electron system and includes carbocyclic aryl, heterocyclic aryl and biaryl groups, all of which may be optionally substituted.

Carbocyclic aryl groups are groups wherein the ring atoms on the aromatic ring are carbon atoms. Carbocyclic aryl groups include monocyclic carbocyclic aryl groups and polycyclic or fused compounds such as optionally substituted naphthyl groups.

Heterocyclic aryl groups are groups having from 1 to 4 heteroatoms as ring atoms in the aromatic ring and the remainder of the ring atoms being carbon atoms. Suitable heteroatoms include oxygen, sulfur, and nitrogen. Suitable heteroaryl groups include furanyl, thienyl, pyridyl, pyrrolyl, N-lower alkyl pyrrolyl, pyridyl-N-oxide, pyrimidyl, pyrazinyl, imidazolyl, and the like, all optionally substituted.

The term "biaryl" represents aryl groups containing more than one aromatic ring including both fused ring systems and aryl groups substituted with other aryl groups.

The term "alicyclic" means compounds which combine the properties of aliphatic and cyclic compounds and include but are not limited to aromatic, cycloalkyl and bridged cycloalkyl compounds. The cyclic compound includes heterocycles. Cyclohexenylethyl, cyclohexanylethyl, and norbornyl are suitable alicyclic groups. Such groups may be optionally substituted.

The term "optionally substituted" or "substituted" includes groups substituted by one to four substituents, independently selected from lower alkyl, lower aryl, lower aralkyl, lower alicyclic, hydroxy, lower alkoxy, lower aryloxy, perhaloalkoxy, aralkoxy, heteroaryl, heteroaryloxy, heteroarylalkyl, heteroaralkoxy, azido, amino, guanidino, halogen, lower alkylthio, oxa, ketone, carboxy esters, carboxyl, carboxamido, nitro, acyloxy, alkylamino, aminoalkyl, alkylaminoaryl, alkylaryl, alkylaminoalkyl, alkoxyaryl, arylamino, aralkylamino, phosphonate, sulfonate, carboxamidoalkylaryl, carboxamidoaryl, hydroxyalkyl, haloalkyl, alkylaminoalkylcarboxy, aminocarboxamidoalkyl, cyano, lower alkoxyalkyl, and lower perhaloalkyl.

The term "aralkyl" refers to an alkyl group substituted with an aryl group. Suitable aralkyl groups include benzyl, picolyl, and the like, and may be optionally substituted.

The term "lower" referred to herein in connection with organic radicals or compounds respectively defines such as with up to and including 10, preferably up to and including 6, and advantageously one to four carbon atoms. Such groups may be straight chain, branched, or cyclic.

The terms "arylamino" (a), and "aralkylamino" (b), respectively, refer to the group —NRR' wherein respectively, (a) R is aryl and R' is hydrogen, alkyl, aralkyl or aryl, and (b) R is aralkyl and R' is hydrogen or aralkyl, aryl, alkyl.

The term "acyl" refers to —C(O)R where R is alkyl and aryl.

The term "carboxy esters" refers to —C(O)OR where R is alkyl, aryl, aralkyl, and alicyclic, all optionally substituted.

The term "oxa" refers to =O in an alky

The ter

The term "alkylamino" refers to —NRR' where R and R' are independently selected from hydrogen or alkyl.

The term "carbonylamine" or "carbonylamino" refers to —CONR$_2$ where each R is independently hydrogen or alkyl.

The term "halogen" or "halo" refers to —F, —Cl, —Br and —I.

The term "oxyalkylamino" refers to —O—alk—NR—, where "alk" is an alkylene group and R is H or alkyl.

The term "alkylsulfonate" refers to the group —alk—S(O)$_2$—O— where "alk" is an alkylene group.

The term "alkylaminoalkylcarboxy" refers to the group —alk—NR—alk—C(O)—O— where "alk" is an alkylene group, and R is a H or lower alkyl.

The term "alkylaminocarbonyl" refers to the group —alk—NR—C(O)— where "alk" is an alkylene group, and R is a H or lower alkyl.

The term "oxyalkyl" refers to the group —O—alk— where "alk" is an alkylene group.

The term "alkylcarboxyalkyl" refers to the group —alk—C(O)—O—alkyl where each alk is independently an alkylene group.

The term "alkyl" refers to saturated aliphatic groups including straight-chain, branched chain and cyclic groups. Alkyl groups may be optionally substituted.

The term "bidentate" refers to an alkyl group that is attached by its terminal ends to the same atom to form a cyclic group. For example, propylene imine contains a bidentate propylene group.

The term "cyclic alkyl" refers to alkyl groups that are cyclic.

The term "heterocyclic" and "heterocyclic alkyl" refer to cyclic alkyl groups containing at least one heteroatom. Suitable heteroatoms include oxygen, sulfur, and nitrogen. Heterocyclic groups may be attached through a heteroatom or through a carbon atom in the ring.

The term "alkenyl" refers to unsaturated groups which contain at least one carbon-carbon double bond and includes straight-chain, branched-chain and cyclic groups. Alkene groups may be optionally substituted.

The term "alkynyl" refers to unsaturated groups which contain at least one carbon-carbon triple bond and includes straight-chain, branched-chain and cyclic groups. Alkyne groups may be optionally substituted.

The term "alkylene" refers to a divalent straight chain, branched chain or cyclic saturated aliphatic radical.

The term "acyloxy" refers to the ester group —O—C(O)R, where R is H, alkyl, alkenyl, alkynyl, aryl, aralkyl, or alicyclic.

The term "alkylaryl" refers to the group —alk—aryl— where "alk" is an alkylene group. "Lower alkylaryl" refers to such groups where alkylene is lower alkyl.

The term "alkylamino" refers to the group —alk—NR— wherein "alk" is an alkylene group.

The term "alkyl(carboxyl)" refers to carboxyl substituted off the alkyl chain. Similarly, "alkyl(hydroxy)", "alkyl (phosphonate)", and "alkyl(sulfonate)" refers to substituents off the alkyl chain.

The term "alkylaminoalkyl" refers to the group —alk—NR—alk— wherein each "alk" is an independently selected alkylene, and R is H or lower alkyl. "Lower alkylaminoalkyl" refers to groups where each alkylene group is lower alkyl.

The term "alkylaminoaryl" refers to the group —alk—NR—aryl— wherein "alk" is an alkylene group. In "lower alkylaminoaryl", the alkylene group is lower alkyl.

The term "alkyloxyaryl" refers to an alkylene group substituted with an aryloxy group. In "lower alkyloxyaryl", the alkylene group is lower alkyl.

The term "alkylacylamino" refers to the group —alk—N—(COR)— wherein alk is alkylene and R is lower alkyl. In "lower alkylacylamino", the alkylene group is lower alkyl.

The term "alkoxyalkylaryl" refers to the group —alk—O—alk—aryl— wherein each "alk" is independently an alkylene group. "Lower aloxyalkylaryl" refers to such groups where the alkylene group is lower alkyl.

The term "alkylacylaminoalkyl" refers to the group —alk—N—(COR)—alk— where each alk is an independently selected alkylene group. In "lower alkylacylaminoalkyl" the alkylene groups are lower alkyl.

The term "alkoxy" refers to the group —alk—O— wherein alk is an alkylene group.

The term "alkoxyalkyl" refers to the group —alk—O—alk— wherein each alk is an independently selected alkylene group. In "lower alkoxyalkyl", each alkylene is lower alkyl.

The term "alkylthio" refers to the group —alk—S— wherein alk is alkylene group.

The term "alkylthioalkyl" refers to the group —alk—S—alk— wherein each alk is an independently selected alkylene group. In "lower alkylthioalkyl" each alkylene is lower alkylene.

The term "aralkylamino" refers to an amine substituted with an aralkyl group.

The term "alkylcarboxamido" refers to the group —alk—C(O)N(R)— wherein alk is an alkylene group and R is H or lower alkyl.

The term "alkylcarboxamidoalkyl" refers to the group —alk—C(O)N(R)—alk— wherein each alk is an independently selected alkylene group and R is lower alkyl. In "lower alkylcarboxamidoalkyl" each alkylene is lower alkyl.

The term "alkylcarboxamidoalkylaryl" refers to the group —alk$_1$—C(O)—NH—alk$_2$Ar— wherein alk$_1$ and alk$_2$ are independently selected alkylene groups and alk$_2$ is substituted with an aryl group, Ar. In "lower alkylcarboxamidoalkylaryl", each alkylene is lower alkyl.

The term "heteroalicyclic" refers to an alicyclic group having 1 to 4 heteroatoms selected from nitrogen, sulfur, phosphorus and oxygen.

The term "aminocarboxamidoalkyl" refers to the group —NH—C(O)—N(R)—R wherein each R is an independently selected alkyl group. "Lower aminocaboxamidoalkyl" refers to such groups wherein each R is lower alkyl.

The term "heteroarylalkyl" refers to an alkyl group substituted with a heteroaryl group.

The term "perhalo" refers to groups wherein every C—H bond has been replaced with a C—halo bond on an aliphatic or aryl group. Suitable perhaloalkyl groups include —CF$_3$ and —CFCl$_2$.

The term "guanidine" refers to both —NR—C(NR)—NR$_2$ as well as —N=C(NR$_2$)$_2$ where each R group is independently selected from the group of —H, alkyl, alkenyl, alkynyl, aryl, and alicyclic, all optionally substituted.

The term "amidine" refers to —C(NR)—NR$_2$ where each R group is independently selected from the group of —H, alkyl, alkenyl, alkynyl, aryl, and alicyclic, all optionally substituted.

The term "pharmaceutically acceptable salt" includes salts of compounds of formula 1 and its prodrugs derived from the combination of a compound of this invention and an organic or inorganic acid or base.

The term "prodrug" as used herein refers to any compound that when administered to a biological system generates the "drug" substance either as a result of spontaneous chemical reaction(s) or by enzyme catalyzed or metabolic reaction(s). Reference is made to various prodrugs such as acyl esters, carbonates, and carbamates, included herein. The groups illustrated are exemplary, not exhaustive, and one skilled in the art could prepare other known varieties of prodrugs. Such prodrugs of the compounds of formula 1, fall within the scope of the present invention.

The term "prodrug ester" as employed herein includes, but is not limited to, the following groups and combinations of these groups:

[1] Acyloxyalkyl esters which are well described in the literature (Farquhar et al., *J. Pharm. Sci.* 72, 324–325 (1983)) and are represented by formula A Formula A wherein R, R', and R" are independently H, alkyl, aryl, alkylaryl, and alicyclic; (see WO 90/08155; WO 90/10636).

[2] Other acyloxyalkyl esters are possible in which an alicyclic ring is formed such as shown in formula B. These esters have been shown to generate phosphorus-containing nucleotides inside cells through a postulated sequence of reactions beginning with deesterification and followed by a series of elimination reactions (e.g. Freed et al., *Biochem. Pharm.* 38: 3193–3198 (1989)).

Formula B wherein R is —H, alkyl, aryl, alkylaryl, alkoxy, aryloxy, alkylthio, arylthio, alkylamino, arylamino, cycloalkyl, or alicyclic.

[3] Another class of these double esters known as alkyloxycarbonyloxymethyl esters, as shown in formula A, where R is alkoxy, aryloxy, alkylthio, arylthio, alkylamino, and arylamino; R', and R" are independently H, alkyl, aryl, alkylaryl, and alicyclic, have been studied in the area of β-lactam antibiotics (Tatsuo Nishimura et al. *J. Antibiotics*, 1987, 40(1), 81–90; for a review see Ferres, H., *Drugs of Today*, 1983,19, 499. ). More recently Cathy, M. S., et al. (Abstract from AAPS Western Regional Meeting, April, 1997) showed that these alkyloxycarbonyloxymethyl ester prodrugs on (9-[(R)-2-phosphonomethoxy)propyl]adenine (PMPA) are bioavailable up to 30% in dogs.

[4] Aryl esters have also been used as phosphonate prodrugs (e.g. Erion, DeLambert et al., *J. Med. Chem.* 37:498, 1994; Serafinowska et al., *J. Med. Chem.* 38:1372, 1995). Phenyl as well as mono and poly-substituted phenyl proesters have generated the parent phosphonic acid in studies conducted in animals and in man (Formula C). Another approach has been described where Y is a carboxylic ester ortho to the phosphate. Khamnei and Torrence, *J. Med. Chem.*; 39:4109–4115 (1996).

Formula C wherein Y is H, alkyl, aryl, alkylaryl, alkoxy, acetoxy, halogen, amino, alkoxycarbonyl, hydroxy, cyano, alkylamino, and alicyclic.

[5] Benzyl esters have also been reported to generate the parent phosphonic acid. In some cases, using substituents at the para-position can accelerate the hydrolysis. Benzyl analogs with 4-acyloxy or 4-alkyloxy group [Formula D, X=H, OR or O(CO)R or O(CO)OR] can generate the 4-hydroxy compound more readily through the action of enzymes, e.g. oxidases, esterases, etc. Examples of this class of prodrugs are described in Mitchell et al., *J. Chem. Soc. Perkin Trans.* 1 2345 (1992); Brook, et al. WO 91/19721.

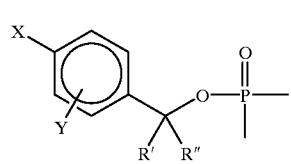

Formula D wherein

X and Y are independently H, alkyl, aryl, alkylaryl, alkoxy, acetoxy, hydroxy, cyano, nitro, perhaloalkyl, halo, or alkyloxycarbonyl; and R' and R" are independently H, alkyl, aryl, alkylaryl, halogen, and alicyclic.

[6] Thio-containing phosphonate proesters have been described that are useful in the delivery of FBPase inhibitors to hepatocytes. These proesters contain a protected thioethyl moiety as shown in formula E. One or more of the oxygens of the phosphonate can be esterified. Since the mechanism that results in de-esterification requires the generation of a free thiolate, a variety of thiol protecting groups are possible. For example, the disulfide is reduced by a reductase-mediated process (Puech et al., *Antiviral Res.,* 22: 155–174 (1993)). Thioesters will also generate free thiolates after esterase-mediated hydrolysis. Benzaria, et al., *J. Med. Chem.,* 39:4958 (1996). Cyclic analogs are also possible and were shown to liberate phosphonate in isolated rat hepatocytes. The cyclic disulfide shown below has not been previously described and is novel.

Formula E

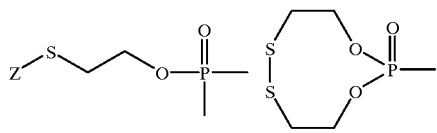

wherein Z is alkylcarbonyl, alkoxycarbonyl, arylcarbonyl, aryloxycarbonyl, or alkylthio.

Other examples of suitable prodrugs include proester classes exemplified by Biller and Magnin (U.S. Pat. No. 5,157,027); Serafinowska et al. (*J. Med. Chem.* 38,1372 (1995)); Starrett et al. (*J. Med. Chem.* 37, 1857 (1994)); Martin et al. *J. Pharm. Sci.* 76, 180 (1987); Alexander et al., *Collect. Czech. Chem. Commun,* 59, 1853 (1994)); and EPO patent application 0 632 048 A1. Some of the structural classes described are optionally substituted, including fused lactones attached at the omega position and optionally substituted 2-oxo-1,3-dioxolenes attached through a methylene to the phosphorus oxygen such as:

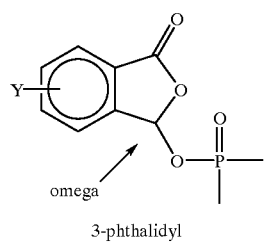

3-phthalidyl

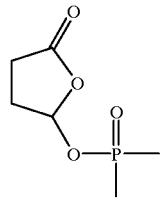

2-oxotetrahydrofuran-5-yl

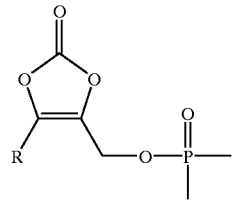

2-oxo-4,5-didehydro-1,3-dioxolanemethyl wherein R is —H, alkyl, cycloalkyl, or alicyclic; and wherein Y is —H, alkyl, aryl, alkylaryl, cyano, alkoxy, acetoxy, halogen, amino, alkylamino, alicyclic, and alkoxycarbonyl.

[7] Propyl phosphonate proesters can also be used to deliver FBPase inhibitors into hepatocytes. These proesters may contain a hydroxyl and hydroxyl group derivatives at the 3-position of the propyl group as shown in formula F. The R and X groups can form a cyclic ring system as shown in formula F. One or more of the oxygens of the phosphonate can be esterified.

Formula F wherein

R is alkyl, aryl, heteroaryl;

X is hydrogen, alkylcarbonyloxy, alkyloxycarbonyloxy; and

Y is alkyl, aryl, heteroaryl, alkoxy, alkylamino, alkylthio, halogen, hydrogen, hydroxy, acetoxy, amino.

[8] The cyclic propyl phosphonate esters as in Formula G are shown to activate to phosphonic acids. The activation of prodrug can be mechanistically explained by in vivo oxidation and elimination steps. These prodrugs inhibit glucose production in isolated rat hepatocytes and are also shown to deliver FBPase inhibitors to the liver following oral administration.

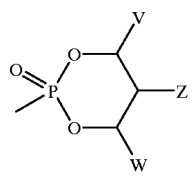

Formula G wherein
- V and W are independently selected from the group consisting of hydrogen, aryl, substituted aryl, heteroaryl, substituted heteroaryl, 1-alkenyl, 1-alkynyl, and -$R^9$; or
- together V and Z are connected to form a cyclic group containing 3–5 atoms, optionally 1 heteroatom, substituted with hydroxy, acyloxy, alkoxycarboxy, or aryloxycarboxy attached to a carbon atom that is three atoms from an oxygen attached to the phosphorus; or
- together V and W are connected to form a cyclic group containing 3 carbon atoms substituted with hydroxy, acyloxy, alkoxycarboxy, alkylthiocarboxy, hydroxymethyl, and aryloxycarboxy attached to a carbon atom that is three atoms from an oxygen attached to the phosphorus;
- Z is selected from the group consisting of —$CH_2OH$, —$CH_2OCOR^3$, —$CH_2OC(O)SR^3$, —$CH_2OCO_2R^3$, —$SR^3$, —$S(O)R^3$, —$CH_2N_3$, —$CH_2NR^2{}_2$, —$CH_2Ar$, —$CH(Ar)OH$, —$CH(CH=CR^2R^2)OH$, —$CH(C\equiv CR^2)OH$, and —$R^2$;
- with the provisos that:
  - a) V, Z, W are not all —H; and
  - b) when Z is —$R^2$, then at least one of V and W is not —H or —$R^9$;
- $R^2$ is selected from the group consisting of $R^3$ and —H;
- $R^3$ is selected from the group consisting of alkyl, aryl, alicyclic, and aralkyl; and
- $R^9$ is selected from the group consisting of alkyl, aralkyl, and alicyclic.

[9] Phosphoramidate derivatives have been explored as potential phosphonate prodrugs (e.g. McGuigan et al., *Antiviral Res.* 1990, 14: 345; 1991, 15: 255. Serafinowska et al., *J. Med. Chem.*, 1995, 38, 1372). Most phosphoramidates are unstable under aqueous acidic conditions and are hydrolyzed to the corresponding phosphonic acids. Cyclic phosphoramidates have also been studied as phosphonate prodrugs because of their potential for greater stability compared to non cyclic phosphoramidates (e.g. Starrett et al., *J. Med. Chem.*, 1994, 37:1857).

Other prodrugs are possible based on literature reports such as substituted ethyls for example, bis(trichloroethyl) esters as disclosed by McGuigan, et al. *Bioorg Med. Chem. Lett.*, 3:1207–1210 (1993), and the phenyl and benzyl combined nucleotide esters reported by Meier, C. et al. *Bioorg. Med. Chem. Lett.*, 7:99–104 (1997).

X group nomenclature as used herein in formula 1 describes the group attached to the phosphonate and ends with the group attached to the 2-position of the benzimidazole ring. For example, when X is alkylamino, the following structure is intended:

(benzimidazole ring)—NR—alk-P(O)(OR$^1$)$_2$

Y group nomenclature likewise ends with the group attached to the ring.

DETAILED DESCRIPTION OF THE INVENTION

Preferred compounds of the present invention are inhibitors of the AMP site of FBPase of the following formula 1:

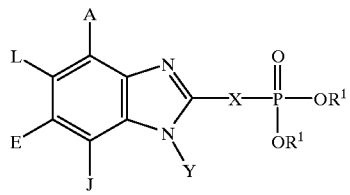

wherein:
- A, E, and L are selected from the group consisting of —$NR^8{}_2$, —$NO_2$, —H, —$OR^7$, —$SR^7$, —$C(O)NR^4{}_2$, halo, —$COR^{11}$, —$SO_2R^3$, guanidine, amidine, —$NHSO_2R^5$, —$SO_2NR^4{}_2$, —CN, sulfoxide, perhaloacyl, perhaloalkyl, perhaloalkoxy, C1–C5 alkyl, C2–C5 alkenyl, C2–C5 alkynyl, and lower alicyclic, or together A and L form a cyclic group, or together L and E form a cyclic group, or together E and J form a cyclic group including aryl, cyclic alkyl, and heterocyclic;
- J is selected from the group consisting of —$NR^8{}_2$, —$NO_2$, —H, $OR^7$, —$SR^7$, —$C(O)NR^4{}_2$, halo, —$C(O)R^{11}$, —CN, sulfonyl, sulfoxide, perhaloalkyl, hydroxyalkyl, perhaloalkoxy, alkyl, haloalkyl, aminoalkyl, alkenyl, alkynyl, alicyclic, aryl, and aralkyl, or together with Y forms a cyclic group including aryl, cyclic alkyl and heterocyclic alkyl;
- X is selected from the group consisting of alkylamino, alkyl(hydroxy), alkyl(carboxyl), alkyl(phosphonate), alkyl, alkenyl, alkynyl, alkyl(sulfonate), aryl, carbonylalkyl, 1,1-dihaloalkyl, aminocarbonylamino, alkylaminoalkyl, alkoxyalkyl, alkylthioalkyl, alkylthio, alkylaminocarbonyl, alkylcarbonylamino, alicyclic, aralkyl, and alkylaryl, all optionally substituted; or together with Y form a cyclic group including aryl, cyclic alkyl, and heterocyclic;
- Y is selected from the group consisting of —H, alkyl, alkenyl, alkynyl, aryl, alicyclic, aralkyl, aryloxyalkyl, alkoxyalkyl, —$C(O)R^3$, —$S(O)_2R^3$, —C(O)—$OR^3$, —$CONHR^3$, —$NR^2{}_2$, and —$OR^3$, all except H are optionally substituted; or together with X form a cyclic group including aryl, cyclic alkyl, and heterocyclic;
- $R^1$ is independently selected from the group consisting of —H, alkyl, aryl, alicyclic where the cyclic moiety contains a carbonate or thiocarbonate, —$C(R^2)_2$—aryl, alkylaryl, —$C(R^2)_2OC(O)NR^2{}_2$, —$NR^2$—$C(O)$—$R^3$, —$C(R^2)_2$—$OC(O)R^3$, $C(R^2)_2$—O—$C(O)OR^3$, —$C(R^2{}_2$ $OC(O)SR^3$, alkyl—S—$C(O)R^3$, alkyl—S—S-alkylhydroxy, and alkyl-S—S—S-alkylhydroxy, or together $R^1$ and $R^1$ are —alkyl—S—S-alkyl to form a cyclic group, or together $R^1$ and $R^1$ are

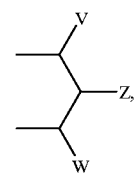

wherein
- V and W are independently selected from the group consisting of hydrogen, aryl, substituted aryl, heteroaryl, substituted heteroaryl, 1-alkenyl, 1-alkynyl, and -$R^9$; or
- together V and Z are connected to form a cyclic group containing 3–5 atoms, optionally 1 heteroatom, substituted with hydroxy, acyloxy, alkoxycarboxy, or aryloxycarboxy attached to a carbon atom that is three atoms from an oxygen attached to the phosphorus; or together V and W are connected to form a cyclic group containing 3 carbon atoms substituted with hydroxy, acyloxy, alkoxycarboxy, alkylthiocarboxy, hydroxymethyl, and aryloxycarboxy attached to a carbon atom that is three atoms from an oxygen attached to the phosphorus;

Z is selected from the group consisting of —CH$_2$OH, —CH$_2$OCOR$^3$, —CH$_2$OC(O)SR$^3$, —CH$_2$OCO$_2$R$^3$, —SR$^3$, —S(O)R$^3$, —CH$_2$N$_3$, —CH$_2$NR$^2_2$, —CH$_2$Ar, —CH(Ar)OH, —CH(CH=CR$^2$R$^2$)OH, —CH(C≡CR$^2$)OH, and —R$^2$;

with the provisos that:
a) V, Z, W are not all —H; and
b) when Z is —R$^2$, then at least one of V and W is not —H or —R$^9$;

R$^2$ is selected from the group consisting of R$^3$ and —H;
R$^3$ is selected from the group consisting of alkyl, aryl, alicyclic, and aralkyl;
R$^4$ is independently selected from the group consisting of —H, lower alkyl, lower alicyclic, lower aralkyl, and lower aryl;
R$^5$ is selected from the group consisting of lower alkyl, lower aryl, lower aralkyl, and lower alicyclic;
R$^6$ is independently selected from the group consisting of —H, and lower alkyl;
R$^7$ is independently selected from the group consisting of —H, lower alkyl, lower alicyclic, lower aralkyl, lower aryl, and —C(O)R$^{10}$;
R$^8$ is independently selected from the group consisting of —H, lower alkyl, lower aralkyl, lower aryl, lower alicyclic, —C(O)R$^{10}$, or together they form a bidendate alkyl;
R$^9$ is selected from the group consisting of alkyl, aralkyl, and alicyclic;
R$^{10}$ is selected from the group consisting of —H, lower alkyl, —NH$_2$, lower aryl, and lower perhaloalkyl;
R$^{11}$ is selected from the group consisting of alkyl, aryl, —OH, —NH$_2$ and —OR$^3$; and
pharmaceutically acceptable prodrugs and salts thereof;
with the provisos that:
a) R$^1$ is not lower alkyl of 1–4 carbon atoms;
b) when X is alkyl or alkene, then A is —N(R$^8_2$);
c) X is not alkylamine and alkylaminoalkyl substituted with phosphonic esters and acids; and
d) A, L, E, J, Y, and X together may only form 0–2 cyclic groups.

Preferred compounds for the method of use claims are inhibitors of the AMP site of FBPase of the following formula 1:

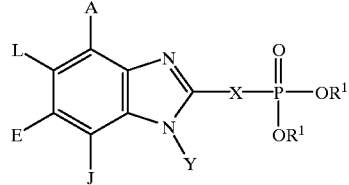

wherein:
A, E, and L are selected from the group consisting of —NR$^8_2$, —NO$_2$, —H, —OR$^7$, —SR$^7$, —C(O)NR$^4_2$, halo, —COR$^{11}$, —SO$_2$R$^3$, guanidine, amidine, —NHSO$_2$R$^5$, —SO$_2$NR$^4_2$, —CN, sulfoxide, perhaloacyl, perhaloalkyl, perhaloalkoxy, C1–C5 alkyl, C2–C5 alkenyl, C2–C5 alkynyl, and lower alicyclic, or together A and L form a cyclic group, or together L and E form a cyclic group, or together E and J form a cyclic group including aryl, cyclic alkyl, and heterocyclic;

J is selected from the group consisting of —NR$^8_2$, —NO$_2$, —H, —OR$^7$, —SR$^7$, —C(O)NR$^4_2$, halo, —C(O)R$^{11}$, —CN, sulfonyl, sulfoxide, perhaloalkyl, hydroxyalkyl, perhaloalkoxy, alkyl, haloalkyl, aminoalkyl, alkenyl, alkynyl, alicyclic, aryl, and aralkyl, or together with Y forms a cyclic group including aryl, cyclic alkyl and heterocyclic alkyl;

X is selected from the group consisting of alkylamino, alkyl(hydroxy), alkyl(carboxyl), alkyl(phosphonate), alkyl, alkenyl, alkynyl, alkyl(sulfonate), aryl, carbonylalkyl, 1,1-dihaloalkyl, aminocarbonylamino, alkylaminoalkyl, alkoxyalkyl, alkylthioalkyl, alkylthio, alkylaminocarbonyl, alkylcarbonylamino, alicyclic, aralkyl, and alkylaryl, all optionally substituted; or together with Y form a cyclic group including aryl, cyclic alkyl, and heterocyclic;

Y is selected from the group consisting of —H, alkyl, alkenyl, alkynyl, aryl, alicyclic, aralkyl, aryloxyalkyl, alkoxyalkyl, —C(O)R$^3$, —S(O)$_2$R$^3$, —C(O)—R$^{11}$, —CONHR$^3$, —NR$^2_2$, and —OR$^3$, all except H are optionally substituted; or together with X form a cyclic group including aryl, cyclic alkyl, and heterocyclic;

R$^1$ is independently selected from the group consisting of —H, alkyl, aryl, alicyclic where the cyclic moiety contains a carbonate or thiocarbonate, —C(R$^2$)$_2$-aryl, alkylaryl, —C(R$^2$)$_2$OC(O)NR$^2_2$, —NR$^2$—C(O)—R$^3$, —C(R$^2$)$_2$—OC(O)R$^3$, C(R$^2$)$_2$—O—C(O)OR$^3$, —C(R$^2_2$OC(O)SR$^3$, alkyl—S—C(O)R$^3$, alkyl—S—S—alkylhydroxy, and alkyl—S—S—S—alkylhydroxy, or together R$^1$ and R$^1$ are —alkyl—S—S—alkyl to form a cyclic group, or together R$^1$ and R$^1$ are

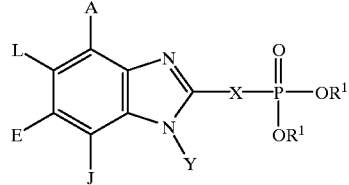

wherein

V and W are independently selected from the group consisting of hydrogen, aryl, substituted aryl, heteroaryl, substituted heteroaryl, 1-alkenyl, 1-alkynyl, and -R$^9$; or together V and Z are connected to form a cyclic group containing 3–5 atoms, optionally 1 heteroatom, substituted with hydroxy, acyloxy, alkoxycarboxy, or aryloxycarboxy attached to a carbon atom that is three atoms from an oxygen attached to the phosphorus; or together V and W are connected to form a cyclic group containing 3 carbon atoms substituted with hydroxy, acyloxy, alkoxycarboxy, alkylthiocarboxy, hydroxymethyl, and aryloxycarboxy attached to a carbon atom that is three atoms from an oxygen attached to the phosphorus;

Z is selected from the group consisting of —CH$_2$OH, —CH$_2$OCOR$^3$, —CH$_2$OC(O)SR$^3$, —CH$_2$OCO$_2$R$^3$, —SR$^3$, —S(O)R$^3$, —CH$_2$N$_3$, —CH$_2$NR$^2_2$, —CH$_2$Ar, —CH(Ar)OH, —CH(CH=CR$^2$R$^2$)OH, —CH(C≡CR$^2$)OH, and —R$^2$;

with the provisos that:
a) V, Z, W are not all —H; and
b) when Z is —R$^2$, then at least one of V and W is not —H or —R$^9$;
R$^2$ is selected from the group consisting of R$^3$ and —H;
R$^3$ is selected from the group consisting of alkyl, aryl, alicyclic, and aralkyl;
R$^4$ is independently selected from the group consisting of —H, lower alkyl, lower alicyclic, lower aralkyl, and lower aryl;
R$^5$ is selected from the group consisting of lower alkyl, lower aryl, lower aralkyl, and lower alicyclic;
R$^6$ is independently selected from the group consisting of —H, and lower alkyl;
R$^7$ is independently selected from the group consisting of —H, lower alkyl, lower alicyclic, lower aralkyl, lower aryl, and —C(O)R$^{10}$;
R$^8$ is independently selected from the group consisting of —H, lower alkyl, lower aralkyl, lower aryl, lower alicyclic, —C(O)R$^{10}$, or together they form a bidentate alkyl;
R$^9$ is selected from the group consisting of alkyl, aralkyl, and alicyclic;
R$^{10}$ is selected from the group consisting of —H, lower alkyl, —NH$_2$, lower aryl, and lower perhaloalkyl;
R$^{11}$ is selected from the group consisting of alkyl, aryl, —OH, —NH$_2$ and —OR$^3$; and
pharmaceutically acceptable prodrugs and salts thereof.

Preferred Compounds of Formula 1

Suitable alkyl groups include groups having from 1 to about 20 carbon atoms. Suitable aryl groups include groups having from 1 to about 20 carbon atoms. Suitable aralkyl groups include groups having from 2 to about 21 carbon atoms. Suitable acyloxy groups include groups having from 1 to about 20 carbon atoms. Suitable alkylene groups include groups having from 1 to about 20 carbon atoms. Suitable alicyclic groups include groups having 3 to about 20 carbon atoms. Suitable heteroaryl groups include groups having from 1 to about 20 carbon atoms and from 1 to 5 heteroatoms, preferably independently selected from nitrogen, oxygen, phosphorous, and sulfur. Suitable heteroalicyclic groups include groups having from 2 to about twenty carbon atoms and from 1 to 5 heteroatoms, preferably independently selected from nitrogen, oxygen, phosphorous, and sulfur.

Preferred A, L, and E groups include —H, —NR$^8$$_2$, —NO$_2$, hydroxy, alkylaminocarbonyl, halogen, —OR$^7$, —SR$^7$, lower perhaloalkyl, and C1–C5 alkyl, or together E and J form a cyclic group. Such a cyclic group may be aromatic, cyclic alkyl, or heterocyclic alkyl, and may be optionally substituted. Suitable aromatic groups include thiazole. Particularly preferred A, L and E groups are —NR$^8$$_2$, —H, hydroxy, halogen, lower alkoxy, lower perhaloalkyl, and lower alkyl.

Preferred A groups include, —NR$^8$$_2$, —H, halogen, lower perhaloalkyl, and lower alkyl.

Preferred L and E groups include —H, lower alkoxy, lower alkyl, and halogen.

Preferred J groups include —H, halogen, lower alkyl, lower hydroxylalkyl, —NR$^8$$_2$, lower R$^8$$_2$N-alkyl, lower haloalkyl, lower perhaloalkyl, lower alkenyl, lower alkynyl, lower aryl, heterocyclic, and alicyclic, or together with Y forms a cyclic group. Such a cyclic group may be aromatic, cyclic alkyl, or heterocyclic, and may be optionally substituted. Particularly preferred J groups include —H, halogen, and lower alkyl, lower hydroxyalkyl, —NR$^8$$_2$, lower R$^8$$_2$N-alkyl, lower haloalkyl, lower alkenyl, alicyclic, and aryl. Especially preferred are alicyclic and lower alkyl.

Preferred X groups include alkyl, alkynyl, aryl, alkoxyalkyl, alkylthio, alkylaminocarbonyl, alkylcarbonylamino, 1,1-dihaloalkyl, carbonylalkyl, alkyl (OH), and alkyl(sulfonate). Particularly preferred is heteroaryl, alkylaminocarbonyl, 1,1-dihaloalkyl, alkyl (sulfonate), and alkoxyalkyl. Also particularly preferred are heteroaryl, alkylaminocarbonyl, and alkoxyalkyl. Especially preferred are methylaminocarbonyl, methoxymethyl, and furanyl.

In one preferred aspect X is not substituted with a phosphonic acid or ester. In another preferred aspect, when X is substituted with a phosphonic acid or ester, then A is —N(R$^8$)$_2$ and Y is not —H. In another preferred aspect, when X is aryl or alkylaryl, these groups are not linked 1,4 through a 6-membered aromatic ring.

Preferred Y groups include —H, alkyl, aralkyl, aryl, and alicyclic, all except —H may be optionally substituted. Particularly preferred are lower alkyl, and alicyclic.

Preferred R$^1$ groups include —H, alkyl, aryl, alicyclic where the cyclic moiety contains a carbonate or thiocarbonate, optionally substituted phenyl, optionally substituted benzyl, optionally substituted alkylaryl, —C(R$^2$)$_2$OC(O)R$^3$, C(R$^2$)$_2$—O—C(O)OR$^3$, —C(R$^2$)$_2$—OC(O)SR$^3$, —alkyl—S—C(O)R$^3$, alkyl—S—S—alkylhydroxyl, and —alkyl—S—S—S—alkylhydroxy, or together R$^1$ and R$^1$ are alkyl—S—S—alkyl to form a cyclic group, or R$^1$ and R$^1$ together are

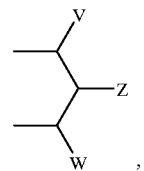

wherein
V and W are independently selected from the group consisting of hydrogen, aryl, substituted aryl, heteroaryl, substituted heteroaryl, 1-alkenyl, 1-alkynyl, and —R$^9$; or
together V and Z are connected to form a cyclic group containing 3–5 atoms, optionally 1 heteroatom, substituted with hydroxy, acyloxy, alkoxycarboxy, or aryloxycarboxy attached to a carbon atom that is three atoms from an oxygen attached to the phosphorus; or
together V and W are connected to form a cyclic group containing 3 carbon atoms substituted with hydroxy, acyloxy, alkoxycarboxy, alkylthiocarboxy, hydroxymethyl, and aryloxycarboxy attached to a carbon atom that is three atoms from an oxygen attached to the phosphorus;
Z is selected from the group consisting of —CH$_2$OH, —CH$_2$OCOR$^3$, —CH$_2$OC(O)SR$^3$, —CH$_2$OCO$_2$R$^3$, —SR$^3$, —S(O)R$^3$, —CH$_2$N$_3$, —CH$_2$NR$^8$$_2$, —CH$_2$Ar, —CH(Ar)OH, —CH(CH=CR$^2$R$^2$)OH, —CH(C≡CR$^2$)OH, and —R$^2$;
with the provisos that:
a) V, Z, W are not all —H; and
b) when Z is —R$^2$, then at least one of V and W is not —H or —R$^9$;
R$^2$ is selected from the group consisting of R$^3$ and —H;
R$^3$ is selected from the group consisting of alkyl, aryl, alicyclic, and aralkyl; and R⁹ is selected from the group consisting of alkyl, aralkyl, and alicyclic.

Preferred such R¹ groups include optionally substituted phenyl, optionally substituted benzyl, —H, and —C(R²)₂OC(O)R³. Also preferred are such groups where at least one R¹ is aryl or —C(R²)₂ aryl. Particularly preferred is H. Also preferred is when at least one R¹ is alkyl, preferably greater than 4 carbon atoms. Another preferred aspect is when at least one R¹ is —C(R²)₂—OC(O)R³, —C(R²)₂—OC(O)OR³, —C(R²)₂—OC(O)SR³. Also particularly preferred is when R¹ and R¹ together are optionally substituted, including fused, lactones attached at the omega position or are optionally substituted 2-oxo-1,3-dioxolenes attached through a methylene to the phosphorus oxygen. Also preferred is when at least one R¹ is —alkyl—S—S—alkylhydroxyl, —alkyl—S—C(O)R³, and —alkyl—S—S—S—alkylhydroxy, or together R¹ and R¹ are —alkyl—S—S—alkyl— to form a cyclic group. Also preferred is where R¹ and R¹ together are

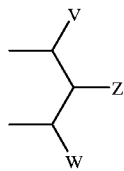

to form a cyclic group,

V and W are independently selected from the group consisting of hydrogen, aryl, substituted aryl, heteroaryl, substituted heteroaryl, 1-alkenyl, 1-alkynyl, and —R⁹; or together V and Z are connected to form a cyclic group containing 3–5 atoms, optionally 1 heteroatom, substituted with hydroxy, acyloxy, alkoxycarboxy, or aryloxycarboxy attached to a carbon atom that is three atoms from an oxygen attached to the phosphorus; or together V and W are connected to form a cyclic group containing 3 carbon atoms substituted with hydroxy, acyloxy, alkoxycarboxy, alkylthiocarboxy, hydroxymethyl, and aryloxycarboxy attached to a carbon atom that is three atoms from an oxygen attached to the phosphorus;

Z is selected from the group consisting of —CH₂OH, —CH₂OCOR³, —CH₂OC(O)SR³, —CH₂OCO₂R³, —SR³, —S(O)R³, —CH₂N₃, -CH₂NR²₂, —CH₂Ar, —CH(Ar)OH, —CH(CH=CR²R²)OH, —CH(C≡CR²)OH, and —R²;

with the provisos that:
a) V, Z, W are not all —H; and
b) when Z is —R², then at least one of V and W is not —H or —R⁹;

R² is selected from the group consisting of R³ and —H;
R³ is selected from the group consisting of alkyl, aryl, alicyclic, and aralkyl; and
R⁹ is selected from the group consisting of alkyl, aralkyl, and alicyclic.

Particularly preferred are such groups wherein V and W both form a 6-membered carbocyclic ring substituted with 0–4 groups, selected from the group consisting of hydroxy, acyloxy, alkoxycarbonyloxy, and alkoxy; and Z is —R². Also particularly preferred are such groups wherein V and W are hydrogen; and Z is selected from the group consisting of hydroxyalkyl, acyloxyalkyl, alkyloxyalkyl, and alkoxycarboxyalkyl. Also particularly preferred are such groups wherein V and W are independently selected from the group consisting of hydrogen, optionally substituted aryl, and optionally substituted heteroaryl, with the proviso that at least one of V and W is optionally substituted aryl or optionally substituted heteroaryl.

Also particularly preferred are such compounds where R¹ is alicyclic where the cyclic moiety contains carbonate or thiocarbonate.

Preferred R⁴ and R⁷ groups include —H, and lower alkyl.

In one preferred aspect A, L, and E are independently —H, lower alkyl, hydroxy, halogen, lower alkoxy, lower perhaloalkyl, and —NR⁸₂; X is aryl, alkoxyalkyl, alkyl, alkylthio, 1,1-dihaloalkyl, carbonylalkyl, alkyl(hydroxy), alkyl(sulfonate), alkylaminocarbonyl, and alkylcarbonylamino; and each R⁴ and R⁷ is independently —H, and lower alkyl. Particularly preferred are such compounds where A, L, and E are independently —H, lower alkyl, halogen, and —NR⁸₂; J is —H, halogen, haloalkyl, hydroxyalkyl, R⁸₂N-alkyl, lower alkyl, lower aryl, heterocyclic, and alicyclic, or together with Y forms a cyclic group; and X is heteroaryl, alkylaminocarbonyl, 1,1-dihaloalkyl, and alkoxyalkyl. Especially preferred are such compounds where A is —H, —NH₂, —F, and —CH₃, L is —H, —F, —OCH₃, —Cl, and —CH₃, E is —H and —Cl, J is —H, halo, C1–C5 hydroxyalkyl, C1–C5 haloalkyl, C1–C5 R⁸₂N-alkyl, C1–C5 alicyclic, and C1–C5 alkyl, X is —CH₂OCH₂—, and 2,5-furanyl, and Y is lower alkyl. Most preferred are the following such compounds and their salts, and prodrug and their salts:

1) A is —NH₂, L is —F, E is —H, J is —H, Y is isobutyl, and X is 2,5-furanyl;
2) A, L, and J are —H, E is —Cl, Y is isobutyl, and X is 2,5-furanyl;
3) A is —NH₂, L is —F, E and J are —H, Y is cyclopropylmethyl, and X is 2,5-furanyl;
4) A is —NH₂, L is —F, E is —H, J is ethyl, Y is isobutyl, and X is 2,5-furanyl;
5) A is —CH₃, L is —Cl, E and J are —H, Y is isobutyl, and X is 2,5-furanyl;
6) A is —NH₂, L is —F, E is —H, J is —Cl, Y is isobutyl, and X is 2,5-furanyl;
7) A is —NH₂, L is —F, E is —H, J is —Br, Y is isobutyl, and X is —CH₂OCH₂; and
8) A, L, E, and J are —CH₃, Y is cyclopropylmethyl, and X is 2,5-furanyl.

Also especially preferred are compounds where A is —NH₂, L is —F, E is —H, J is bromopropyl, bromobutyl, chlorobutyl, cyclopropyl, hydroxypropyl, or N,N-dimethylaminopropyl, and X is 2,5-furanyl. The preferred prodrug is where R¹ is pivaloyloxymethyl or its HCl salt.

In the following examples of preferred compounds, the following prodrugs are preferred:
Acyloxyalkyl esters;
Alkoxycarbonyloxyalkyl esters;
Aryl esters;
Benzyl and substituted benzyl esters;
Disulfide containing esters;
Substituted (1,3-dioxolen-2-one)methyl esters;
Substituted 3-phthalidyl esters;
Cyclic-[2'-hydroxymethyl]-1,3-propanyl diesters and hydroxy protected forms;
Lactone type esters; and all mixed esters resulted from possible combinations of above esters.
Bis-pivaloyloxymethyl esters;
Bis-isobutyryloxymethyl esters;
Cyclic-[2'-hydroxymethyl]-1,3-propanyl diester;

Cyclic-[2'-acetoxymethyl]-1,3-propanyl diester;
Cyclic-[2'-methyloxycarbonyloxymethyl]-1,3-propanyl diester;
Bis-benzoylthiomethyl esters;
Bis-benzoylthioethyl esters;
Bis-benzoyloxymethyl esters;
Bis-p-fluorobenzoyloxymethyl esters;
Bis-6-chloronicotinoyloxymethyl esters;
Bis-5-bromonicotinoyloxymethyl esters;
Bis-thiophenecarbonyloxymethyl esters;
Bis-2-furoyloxymethyl esters;
Bis-3-furoyloxymethyl esters;
Diphenyl esters;
Bis-(4-methoxyphenyl) esters;
Bis-(2-methoxyphenyl) esters;
Bis-(2-ethoxyphenyl) esters;
Mono-(2-ethoxyphenyl) esters;
Bis-(4-acetamidophenyl) esters;
Bis-(4-aceyloxyphenyl) esters;
Bis-(4-hydroxyphenyl) esters;
Bis-(2-acetoxyphenyl) esters;
Bis-(3-acetoxyphenyl) esters;
Bis-(4-morpholinophenyl) esters;
Bis-[4-(1-triazolophenyl) esters;
Bis-(3-N,N-dimethylaminophenyl) esters;
Bis-(2-tetrahydronapthyl) esters;
Bis-(3-chloro-4-methoxy)benzyl esters;
Bis-(3-bromo-4-methoxy)benzyl esters;
Bis-(3-cyano-4-methoxy)benzyl esters;
Bis-(3-chloro-4-acetoxy)benzyl esters;
Bis-(3-bromo-4-acetoxy)benzyl esters;
Bis-(3-cyano-4-acetoxy)benzyl esters;
Bis-(4-chloro)benzyl esters;
Bis-(4-acetoxy)benzyl esters;
Bis-(3,5-dimethoxy-4-acetoxy)benzyl esters;
Bis-(3-methyl-4-acetoxy)benzyl esters;
Bis-(benzyl)esters;
Bis-(3-methoxy-4-acetoxy)benzyl esters;
Bis-(3-chloro-4-acetoxy)benzyl esters;
cyclic-(2,2-dimethylpropyl)phosphonoamidate;
cyclic-(2-hydroxymethylpropyl) ester;
Bis-(6'-hydroxy-3',4'-disulfide)hexyl esters;
Bis-(6'-acetoxy-3',4'-disulfide)hexyl esters;
(3',4'-Dithia)cyclononane esters;
Bis-(5-methyl-1,3-dioxolen-2-one-4-yl)methyl esters;
Bis-(5-ethyl-1,3-dioxolen-2-one-4-yl)methyl esters;
Bis-(5-tert-butyl-1,3-dioxolen-2-one-4-yl)methyl esters;
Bis-3-(5,6,7-trimethoxy)phthalidyl esters;
Bis-(cyclohexyloxycarbonyloxymethyl) esters;
Bis-(isopropyloxycarbonyloxymethyl) esters;
Bis-(ethyloxycarbonyloxymethyl) esters;
Bis-(methyloxycarbonyloxymethyl) esters;
Bis-(isopropylthiocarbonyloxymethyl) esters;
Bis-(phenyloxycarbonyloxymethyl) esters;
Bis-(benzyloxycarbonyloxymethyl) esters;
Bis-(phenylthiocarbonyloxymethyl) esters;
Bis-(p-methoxyphenyloxycarbonyloxymethyl) esters;
Bis-(m-methoxyphenyloxycarbonyloxymethyl) esters;
Bis-(o-methoxyphenyloxycarbonyloxymethyl) esters;
Bis-(o-methylphenyloxycarbonyloxymethyl) esters;
Bis-(p-chlorophenyloxycarbonyloxymethyl) esters;
Bis-(1,4-biphenyloxycarbonyloxymethyl) esters;
Bis-[(2-phthalimidoethyl)oxycarbonyloxymethyl]esters;
Bis-(N-Phenyl, N-methylcarbamoyloxymethyl) esters;
Bis-(2-trichloroethyl) esters;
Bis-(2-bromoethyl) esters;
Bis-(2-iodoethyl) esters;
Bis-(2-azidoethyl) esters;
Bis-(2-acetoxyethyl) esters;
Bis-(2-aminoethyl) esters;
Bis-(2-N,N-diaminoethyl) esters;
Bis-(2-aminoethyl) esters;
Bis-(methoxycarbonylmethyl) esters;
Bis-(2-aminoethyl) esters;
Bis-[N, N-di(2-hydroxyethyl)]amidomethylesters;
Bis-(2-aminoethyl) esters;
Bis-(2-methyl-5-thiozolomethyl) esters;
Bis-(bis-2-hydroxyethylamidomthyl) esters.
Most preferred are the following:
Bis-pivaloyloxymethyl esters;
Bis-isobutyryloxymethyl esters;
cyclic-(2-hydroxymethylpropyl) ester;
cyclic-(2-acetoxymethylpropyl) ester;
cyclic-(2-methyloxycarbonyloxymethylpropyl) ester;
cyclic-(2-cyclohexylcarbonyloxymethylpropyl)ester;
cyclic-(2-aminomethylpropyl)ester;
cyclic-(2-azidomethylpropyl)ester;
Bis-benzoylthiomethyl esters;
Bis-benzoylthioethylesters;
Bis-benzoyloxymethyl esters;
Bis-p-fluorobenzoyloxymethyl esters;
Bis-6-chloronicotinoyloxymethyl esters;
Bis-5-bromonicotinoyloxymethyl esters;
Bis-thiophenecarbonyloxymethyl esters;
Bis-2-furoyloxymethyl esters;
Bis-3-furoyloxymethyl esters;
Diphenyl esters;
Bis-(2-methyl)phenyl esters;
Bis-(2-methoxy)phenyl esters;
Bis-(2-ethoxy)phenyl esters;
Bis-(4-methoxy)phenyl esters;
Bis-(3-bromo-4-methoxy)benzyl esters;
Bis-(4-acetoxy)benzyl esters;
Bis-(3,5-dimethoxy-4-acetoxy)benzyl esters;
Bis-(3-methyl-4-acetoxy)benzyl esters;
Bis-(3-methoxy-4-acetoxy)benzyl esters;
Bis-(3-chloro-4-acetoxy)benzyl esters;
Bis-(cyclohexyloxycarbonyloxymethyl) esters;
Bis-(isopropyloxycarbonyloxymethyl) esters;
Bis-(ethyloxycarbonyloxymethyl) esters;
Bis-(methyloxycarbonyloxymethyl) esters;
Bis-(isopropylthiocarbonyloxymethyl) esters;
Bis-(phenyloxycarbonyloxymethyl) esters;
Bis-(benzyloxycarbonyloxymethyl) esters;
Bis-(phenylthiocarbonyloxymethyl) esters;
Bis-(p-methoxyphenyloxycarbonyloxymethyl) esters;
Bis-(m-methoxyphenyloxycarbonyloxymethyl) esters;
Bis-(o-methoxyphenyloxycarbonyloxymethyl) esters;
Bis-(o-methylphenyloxycarbonyloxymethyl) esters;
Bis-(p-chlorophenyloxycarbonyloxymethyl) esters;
Bis-(1,4-biphenyloxycarbonyloxymethyl) esters;
Bis-[(2-phthalimidoethyl)oxycarbonyloxymethyl]esters;
Bis-(6'-hydroxy-3',4'-disulfide)hexyl esters; and
(3',4'-Disulfide)cyclononane esters.
Bis-(2-bromoethyl) esters;
Bis-(2-aminoethyl) esters;
Bis-(2-N,N-diaminoethyl) esters;
Examples of preferred compounds include, but are not limited to the salts and prodrugs of the compounds of Table 1.

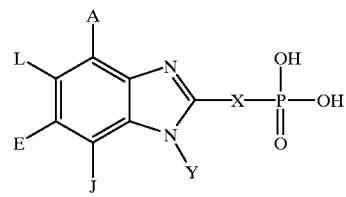

| Table Compound No. | Synthetic Example No. | A | L | E | J1 | Y | X2 |
|---|---|---|---|---|---|---|---|
| 1 | 12.2 | NH2 | H | H | H | cyclohexylethyl | 2,5-furanyl |
| 2 | 12.3 | NH2 | H | H | H | H | 2,5-furanyl |
| 3 | 12.4 | NH2 | H | H | H | methyl | 2,5-furanyl |
| 4 | 12.5 | NH2 | H | H | H | 4-methylbenzyl | 2,5-furanyl |
| 5 | 12.6 | NH2 | H | H | H | 3-CO2Me benzyl | 2,5-furanyl |
| 6 | 12.1 | NH2 | H | H | H | Et | 2,5-furanyl |
| 7 | 12.8 | NH2 | H | H | H | Et | methoxymethyl |
| 8 | 12.9 | NH2 | H | H | H | 3-methylbenzyl | 2,5-furanyl |
| 9 | 12.10 | NH2 | H | H | H | 2-(3-CO2Et-5,6,7,8-tetrahydronapthyl | 2,5-furanyl |
| 10 | 12.11 | NH2 | H | H | H | 2-(3-CO2H-5,6,7,8-tetrahydronapthyl | 2,5-furanyl |
| 11 | 12.12 | NH2 | H | H | H | propyl | 2,5-furanyl |
| 12 | 12.13 | NH2 | H | H | H | norbornylmethyl | 2,5-furanyl |
| 13 | 12.14 | NH2 | H | H | H | 3-CO2H benzyl | 2,5-furanyl |
| 14 | 12.15 | NH2 | H | H | H | cyclopentylmethyl | 2,5-furanyl |
| 15 | 12.16 | NH2 | H | H | H | cyclopropanemethyl | 2,5-furanyl |
| 16 | 12.17 | NH2 | H | H | H | cyclobutylmethyl | 2,5-furanyl |
| 17 | 12.18 | NH2 | H | H | H | 3-methyl-6,6-dimethyl-2-cyclohexenylmethyl | 2,5-furanyl |
| 18 | 12.19 | NH2 | H | H | H | 2-methyl-2-butenyl | 2,5-furanyl |
| 19 | 12.20 | NH2 | H | H | H | 1S,2S,5S-myrtanyl | 2,5-furanyl |
| 20 | 12.21 | NH2 | H | H | H | 4-tBu benzyl | 2,5-furanyl |
| 21 | 12.22 | NH2 | H | H | H | cyclohexylbutyl | 2,5-furanyl |
| 22 | 12.23 | NH2 | H | H | H | cyclohexylpropyl | 2,5-furanyl |
| 23 | 12.24 | NH2 | H | H | H | 3-carboxypropyl | 2,5-furanyl |
| 24 | 12.25 | NH2 | H | H | H | 3-CO2Et propyl | 2,5-furanyl |
| 25 | 12.26 | NH2 | H | H | H | tBu-methylketone | 2,5-furanyl |
| 26 | 12.27 | NH2 | H | H | H | cycloheptylmethyl | 2,5-furanyl |
| 27 | 12.28 | NH2 | H | H | H | cyclohexanylmethyl | 2,5-furanyl |
| 28 | 12.29 | NH2 | H | H | H | benzyl | 2,5-furanyl |
| 29 | 12.30 | NH2 | H | H | H | 3-CF3-benzyl | 2 5 furanyl |
| 30 | 12.31 | NH2 | H | H | H | 3-carbamoylpropyl | 2,5 furanyl |
| 31 | 12.32 | NH2 | H | H | H | 7-hydroxy-3R,7-dimethyloctyl | 2,5-furanyl |
| 32 | 12.33 | NH2 | H | H | H | 4-chlorobutyl | 2,5-furanyl |
| 33 | 12.34 | NH2 | H | H | H | 4-Ph-benzyl | 2,5-furanyl |
| 34 | 12.35 | NH2 | H | H | H | 3-chloropropyl | 2,5-furanyl |
| 35 | 12.36 | NH2 | H | H | H | 4-hydroxybutyl | 2,5-furanyl |
| 36 | 12.37 | NH2 | H | H | H | 3-furanylmethyl | 2,5-furanyl |
| 37 | 12.38 | NH2 | H | H | H | 3-OH-benzyl | 2,5-furanyl |
| 38 | 12.39 | NH2 | H | H | H | 2-OMe-phenethyl | 2,5-furanyl |
| 39 | 12.40 | NH2 | H | H | H | 3-OMe-phenethyl | 2,5-furanyl |
| 40 |  | Me | Cl | H | H | ethyl | 2,5-furanyl |
| 41 | 12.46 | NH2 | H | H | Br | isobutyl | 2,5-furanyl |
| 42 | 12.47 | NH2 | H | H | Br | cyclobutylmethyl | 2,5-furanyl |
| 43 | 12.48 | NH2 | Br | H | H | cyclobutylmethyl | 2,5-furanyl |
| 44 | 12.51 | NH2 | H | H | H | 2-thienylethyl | 2,5-furanyl |
| 45 | 12.52 | NH2 | Et | H | H | isobutyl | 2,5-furanyl |
| 46 | 12.56 | NH2 | H | H | H | 3-NH2-phenethyl | 2,5-furanyl |
| 47 | 12.57 | NH2 | H | H | H | 2-Et-pentyl | methoxymethyl |
| 48 | 12.59 | NH2 | H | H | H | H | 2,5-furanyl |
| 49 | 12.60 | NH2 | Pr | H | H | isobutyl | 2,5-furanyl |
| 50 |  | NH2 | Et | H | H | isobutyl | 2,5-furanyl |
| 51 | 12.62 | NH2 | F | H | Br | isobutyl | 2,5-furanyl |
| 52 | 12.53 | NH2 | F | H | H | isobutyl | 2,5-furanyl |
| 53 | 12.64 | NH2 | F | H | Et | isobutyl | 2,5-furanyl |
| 54 | 12.54 | NH2 | F | H | Cl | isobutyl | 2,5-furanyl |
| 55 |  | NH2 | F | H | Me | isobutyl | 2,5-furanyl |
| 56 |  | NH2 | F | H | Pr | isobutyl | 2,5-furanyl |
| 57 |  | NH2 | F | H | i-Pr | isobutyl | 2,5-furanyl |
| 58 |  | NH2 | F | H | Bu | isobutyl | 2,5-furanyl |
| 59 |  | NH2 | F | H | i-Bu | isobutyl | 2,5-furanyl |
| 60 |  | NH2 | F | H | OMe | isobutyl | 2,5-furanyl |
| 61 |  | NH2 | F | H | OEt | isobutyl | 2,5-furanyl |
| 62 |  | NH2 | F | H | SMe | isobutyl | 2,5-furanyl |

-continued

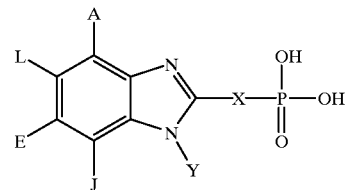

| Table Compound No. | Synthetic Example No. | A | L | E | J¹ | Y | X² |
|---|---|---|---|---|---|---|---|
| 63 | | NH2 | F | H | SEt | isobutyl | 2,5-furanyl |
| 64 | | NH2 | F | H | NEt2 | isobutyl | 2,5-furanyl |
| 65 | | NH2 | F | H | NMe2 | isobutyl | 2,5-furanyl |
| 66 | | NH2 | F | H | I | isobutyl | 2,5-furanyl |
| 67 | | NH2 | F | H | m-OMePhenyl | isobutyl | 2,5-furanyl |
| 66 | | NH2 | F | H | o-OMePhenyl | isobutyl | 2,5-furanyl |
| 69 | | NH2 | F | H | p-F Phenyl | isobutyl | 2,5-furanyl |
| 70 | | NH2 | F | H | o-F Phenyl | isobutyl | 2,5-furanyl |
| 71 | | NH2 | F | H | m-F Phenyl | isobutyl | 2,5-furanyl |
| 72 | | NH2 | F | H | 2-Furanyl | isobutyl | 2,5-furanyl |
| 73 | | NH2 | F | H | 2-thiophenyl | isobutyl | 2,5-furanyl |
| 74 | | NH2 | F | H | 2-Furanylmethyl | isobutyl | 2,5-furanyl |
| 75 | | NH2 | F | H | 2-Thiophenylmethyl | isobutyl | 2,5-furanyl |
| 76 | | NH2 | F | H | CN | isobutyl | 2,5-furanyl |
| 77 | | NH2 | F | H | m-Cl phenyl | isobutyl | 2,5-furanyl |
| 78 | | NH2 | F | H | p-Cl phenyl | isobutyl | 2,5-furanyl |
| 79 | | NH2 | F | H | o-Cl phenyl | isobutyl | 2,5-furanyl |
| 80 | | NH2 | F | H | m-Br Phenyl | isobutyl | 2,5-furanyl |
| 81 | | NH2 | F | H | p-Br Phenyl | isobutyl | 2,5-furanyl |
| 82 | | NH2 | F | H | o-Br Phenyl | isobutyl | 2,5-furanyl |
| 83 | | NH2 | F | H | CF3 | isobutyl | 2,5-furanyl |
| 84 | | NH2 | F | H | cyolopentyl | isobutyl | 2,5-furanyl |
| 85 | | NH2 | F | H | cyclohexyl | isobutyl | 2,5-furanyl |
| 86 | | NH2 | F | H | cyclobutyl | isobutyl | 2,5-furanyl |
| 87 | | NH2 | F | H | cyclopropyl | isobutyl | 2,5-furanyl |
| 88 | | NH2 | F | H | Phenyl | isobutyl | 2,5-furanyl |
| 89 | | NH2 | F | H | cyclopentylmethyl | isobutyl | 2,5-furanyl |
| 90 | | NH2 | F | H | cyclohexylmethyl | isobutyl | 2,5-furanyl |
| 91 | | NH2 | F | H | cyclobutylmethyl | isobutyl | 2,5-furanyl |
| 92 | | NH2 | F | H | cyclopropylmethyl | isobutyl | 2,5-furanyl |
| 93 | | NH2 | F | Cl | F | isobutyl | 2,5-furanyl |
| 94 | | NH2 | F | Cl | Me | isobutyl | 2,5-furanyl |
| 95 | | NH2 | F | Cl | Pr | isobutyl | 2,5-furanyl |
| 96 | | NH2 | F | Cl | i-Pr | isobutyl | 2,5-furanyl |
| 97 | | NH2 | F | Cl | Bu | isobutyl | 2,5-furanyl |
| 98 | | NH2 | F | Cl | i-Bu | isobutyl | 2,5-furanyl |
| 99 | | NH2 | F | Cl | OMe | isobutyl | 2,5-furanyl |
| 100 | | NH2 | F | Cl | OEt | isobutyl | 2,5-furanyl |
| 101 | | NH2 | F | Cl | SMe | isobutyl | 2,5-furanyl |
| 102 | | NH2 | F | Cl | SEt | isobutyl | 2,5-furanyl |
| 103 | | NH2 | F | Cl | NEt2 | isobutyl | 2,5-furanyl |
| 104 | | NH2 | F | Cl | NMe2 | isobutyl | 2,5-furanyl |
| 105 | | NH2 | F | Cl | I | isobutyl | 2,5-furanyl |
| 106 | | NH2 | F | Cl | m-OMePhenyl | isobutyl | 2,5-furanyl |
| 107 | | NH2 | F | Cl | o-OMePhenyl | isobutyl | 2,5-furanyl |
| 108 | | NH2 | F | Cl | p-F Phenyl | isobutyl | 2,5-furanyl |
| 109 | | NH2 | F | Cl | o-F Phenyl | isobutyl | 2,5-furanyl |
| 110 | | NH2 | F | Cl | m-F Phenyl | isobutyl | 2,5-furanyl |
| 111 | | NH2 | F | Cl | 2-Furanyl | isobutyl | 2,5-furanyl |
| 112 | | NH2 | F | Cl | 2-thiophenyl | isobutyl | 2,5-furanyl |
| 113 | | NH2 | F | Cl | 2-Furanylmethyl | isobutyl | 2,5-furanyl |
| 114 | | NH2 | F | Cl | 2-Thiophenylmethyl | isobutyl | 2,5-furanyl |
| 115 | | NH2 | F | Cl | CN | isobutyl | 2,5-furanyl |
| 116 | | NH2 | F | Cl | m-Cl phenyl | isobutyl | 2,5-furanyl |
| 117 | | NH2 | F | Cl | p-Cl phenyl | isobutyl | 2,5-furanyl |
| 118 | | NH2 | F | Cl | o-Cl phenyl | isobutyl | 2,5-furanyl |
| 119 | | NH2 | F | Cl | m-Br Phenyl | isobutyl | 2 5-furanyl |
| 120 | | NH2 | F | Cl | p-Br Phenyl | isobutyl | 2,5-furanyl |
| 121 | | NH2 | F | Cl | o-Br Phenyl | isobutyl | 2,5-furanyl |
| 122 | | NH2 | F | Cl | CF3 | isobutyl | 2,5-furanyl |
| 123 | | NH2 | F | Cl | cyclopentyl | isobutyl | 2,5-furanyl |
| 124 | | NH2 | F | Cl | cyclohexyl | isobutyl | 2,5-furanyl |
| 125 | | NH2 | F | Cl | cyclobutyl | isobutyl | 2,5-furanyl |
| 126 | | NH2 | F | Cl | cyclopropyl | isobutyl | 2,5-furanyl |
| 127 | | NH2 | F | Cl | Phenyl | isobutyl | 2,5-furanyl |
| 128 | | NH2 | F | SMe | Et | isobutyl | 2,5-furanyl |
| 129 | | NH2 | F | SMe | Cl | isobutyl | 2,5-furanyl |

-continued

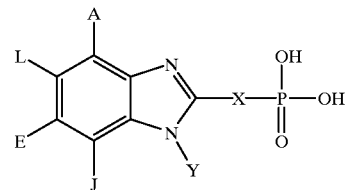

| Table Compound No. | Synthetic Example No. | A | L | E | J¹ | Y | X² |
|---|---|---|---|---|---|---|---|
| 130 | | NH2 | F | SMe | Br | isobutyl | 2,5-furanyl |
| 131 | | NH2 | F | SMe | Me | isobutyl | 2,5-furanyl |
| 132 | | NH2 | F | SMe | Pr | isobutyl | 2,5-furanyl |
| 133 | | NH2 | F | SMe | i-Pr | isobutyl | 2,5-furanyl |
| 134 | | NH2 | F | SMe | Bu | isobutyl | 2,5-furanyl |
| 135 | | NH2 | F | SMe | i-Bu | isobutyl | 2,5-furanyl |
| 136 | | NH2 | F | SMe | OMe | isobutyl | 2,5-furanyl |
| 137 | | NH2 | F | SMe | OEt | isobutyl | 2,5-furanyl |
| 138 | | NH2 | F | SMe | SMe | isobutyl | 2,5-furanyl |
| 139 | | NH2 | F | SMe | SEt | isobutyl | 2,5-furanyl |
| 140 | | NH2 | F | SMe | NEt2 | isobutyl | 2,5-furanyl |
| 141 | | NH2 | F | SMe | NMe2 | isobutyl | 2,5-furanyl |
| 142 | | NH2 | F | SMe | I | isobutyl | 2,5-furanyl |
| 143 | | NH2 | F | SMe | m-OMePhenyl | isobutyl | 2,5-furanyl |
| 144 | | NH2 | F | SMe | o-OMePhenyl | isobutyl | 2,5-furanyl |
| 145 | | NH2 | F | SMe | p-F Phenyl | isobutyl | 2,5-furanyl |
| 146 | | NH2 | F | SMe | o-F Phenyl | isobutyl | 2,5-furanyl |
| 147 | | NH2 | F | SMe | m-F Phenyl | isobutyl | 2,5-furanyl |
| 148 | | NH2 | F | SMe | 2-Furanyl | isobutyl | 2,5-furanyl |
| 149 | | NH2 | F | SMe | 2-thiophenyl | isobutyl | 2,5-furanyl |
| 150 | | NH2 | F | SMe | 2-Furanylmethyl | isobutyl | 2,5-furanyl |
| 151 | | NH2 | F | SMe | 2-Thiophenylmethyl | isobutyl | 2,5-furanyl |
| 152 | | NH2 | F | SMe | CN | isobutyl | 2,5-furanyl |
| 153 | | NH2 | F | SMe | m-Cl phenyl | isobutyl | 2,5-furanyl |
| 154 | | NH2 | F | SMe | p-Cl phenyl | isobutyl | 2,5-furanyl |
| 155 | | NH2 | F | SMe | o-Cl phenyl | isobutyl | 2,5-furanyl |
| 156 | | NH2 | F | SMe | m-Br Phenyl | isobutyl | 2,5-furanyl |
| 157 | | NH2 | F | SMe | p-Br Phenyl | isobutyl | 2,5-furanyl |
| 158 | | NH2 | F | SMe | o-Br Phenyl | isobutyl | 2,5-furanyl |
| 159 | | NH2 | F | SMe | CF3 | isobutyl | 2,5-furanyl |
| 160 | | NH2 | F | SMe | cyclopentyl | isobutyl | 2,5-furanyl |
| 161 | | NH2 | F | SMe | cyclohexyl | isobutyl | 2,5-furanyl |
| 162 | | NH2 | F | SMe | cyclobutyl | isobutyl | 2,5-furanyl |
| 163 | | NH2 | F | SMe | Phenyl | isobutyl | 2,5-furanyl |
| 164 | | NH2 | F | H | F | neopentyl | 2,5-furanyl |
| 165 | | NH2 | F | H | Me | neopentyl | 2,5-furanyl |
| 166 | | NH2 | F | H | Pr | neopentyl | 2,5-furanyl |
| 167 | | NH2 | F | H | i-Pr | neopentyl | 2,5 furanyl |
| 168 | | NH2 | F | H | Bu | neopentyl | 2,5-furanyl |
| 169 | | NH2 | F | H | i-Bu | neopentyl | 2,5-furanyl |
| 170 | | NH2 | F | H | OMe | neopentyl | 2,5-furanyl |
| 171 | | NH2 | F | H | OEt | neopentyl | 2,5-furanyl |
| 172 | | NH2 | F | H | SMe | neopentyl | 2,5-furanyl |
| 173 | | NH2 | F | H | SEt | neopentyl | 2,5-furanyl |
| 174 | | NH2 | F | H | NEt2 | neopentyl | 2,5-furanyl |
| 175 | | NH2 | F | H | NMe2 | neopentyl | 2,5-furanyl |
| 176 | | NH2 | F | H | I | neopentyl | 2,5-furanyl |
| 177 | | NH2 | F | H | m-OMePhenyl | neopentyl | 2,5-furanyl |
| 178 | | NH2 | F | H | o-oMePhenyl | neopentyl | 2,5-furanyl |
| 179 | | NH2 | F | H | p-F Phenyl | neopentyl | 2,5-furanyl |
| 180 | | NH2 | F | H | o-F Phenyl | neopentyl | 2,5-furanyl |
| 181 | | NH2 | F | H | m-F Phenyl | neopentyl | 2,5-furanyl |
| 182 | | NH2 | F | H | 2-Furanyl | neopentyl | 2,5-furanyl |
| 183 | | NH2 | F | H | 2-thiophenyl | neopentyl | 2,5-furanyl |
| 184 | | NH2 | F | H | 2-Furanylmethyl | neopentyl | 2,5-furanyl |
| 185 | | NH2 | F | H | 2-Thiophenylmethyl | neopentyl | 2,5-furanyl |
| 186 | | NH2 | F | H | CN | neopentyl | 2,5-furanyl |
| 187 | | NH2 | F | H | m-Cl phenyl | neopentyl | 2,5-furanyl |
| 188 | | NH2 | F | H | p-Cl phenyl | neopentyl | 2,5-furanyl |
| 189 | | NH2 | F | H | o-Cl phenyl | neopentyl | 2,5-furanyl |
| 190 | | NH2 | F | H | m-Br Phenyl | neopentyl | 2,5-furanyl |
| 191 | | NH2 | F | H | p-Br Phenyl | neopentyl | 2,5-furanyl |
| 192 | | NH2 | F | H | o-Br Phenyl | neopentyl | 2,5-furanyl |
| 193 | | NH2 | F | H | CF3 | necpentyl | 2,5-furanyl |
| 194 | | NH2 | F | H | Phenyl | neopentyl | 2,5-furanyl |
| 195 | | NH2 | F | H | cyclopentyl | neopentyl | 2,5-furanyl |
| 196 | | NH2 | F | H | cyclohexyl | neopentyl | 2,5-furanyl |

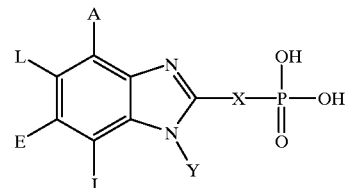

| Table Compound No. | Synthetic Example No. | A | L | E | J¹ | Y | X² |
|---|---|---|---|---|---|---|---|
| 197 | | NH2 | F | H | cyclobutyl | neopentyl | 2,5-furanyl |
| 198 | | NH2 | F | H | cyclopropyl | neopentyl | 2,5-furanyl |
| 199 | 12.61 | NH2 | F | H | H | cyclopropylmethyl | 2,5-furanyl |
| 200 | | NH2 | F | H | F | cyclopropylmethyl | 2,5-furanyl |
| 201 | | NH2 | F | H | Me | cyclopropylmethyl | 2,5-furanyl |
| 202 | | NH2 | F | H | Pr | cyclopropylmethyl | 2,5-furanyl |
| 203 | | NH2 | F | H | i-Pr | cyclopropylmethyl | 2,5-furanyl |
| 204 | | NH2 | F | H | Bu | cyclopropylmethyl | 2,5-furanyl |
| 205 | | NH2 | F | H | i-Bu | cyclopropylmethyl | 2,5-furanyl |
| 206 | | NH2 | F | H | OMe | cyclopropylmethyl | 2,5-furanyl |
| 207 | | NH2 | F | H | OEt | cyclopropylmethyl | 2,5-furanyl |
| 208 | | NH2 | F | H | SMe | cyclopropylmethyl | 2,5-furanyl |
| 209 | | NH2 | F | H | SEt | cyclopropylmethyl | 2,5-furanyl |
| 210 | | NH2 | F | H | NEt2 | cyclopropylmethyl | 2,5-furanyl |
| 211 | | NH2 | F | H | NMe2 | cyclopropylmethyl | 2,5-furanyi |
| 212 | | NH2 | F | H | I | cyclopropylmethyl | 2,5-furanyl |
| 213 | | NH2 | F | H | m-OMePhenyl | cyclopropylmethyl | 2,5-furanyl |
| 214 | | NH2 | F | H | o-OMePhenyl | cyclopropylmethyl | 2,5-furanyl |
| 215 | | NH2 | F | H | p-F Phenyl | cyclopropylmethyl | 2,5-furanyl |
| 216 | | NH2 | F | H | o-F Phenyl | cyclopropylmethyl | 2,5-furanyl |
| 217 | | NH2 | F | H | m-F Phenyl | cyclopropylmethyl | 2,5-furanyl |
| 218 | | NH2 | F | H | 2-Furanyl | cyclopropylmethyl | 2,5-furanyl |
| 219 | | NH2 | F | H | 2-thiophenyl | cyclopropylmethyl | 2,5-furanyl |
| 220 | | NH2 | F | H | 2-Furanylmethyl | cyclopropylmethyl | 2,5-furanyl |
| 221 | | NH2 | F | H | 2-Thiophenylmethyl | cyclopropylmethyl | 2,5-furanyl |
| 222 | | NH2 | F | H | CN | cyclopropylmethyl | 2,5-furanyl |
| 223 | | NH2 | F | H | m-Cl phenyl | cyclopropylmethyl | 2,5-furanyl |
| 224 | | NH2 | F | H | p-Cl phenyl | cyclopropylmethyl | 2,5-furanyl |
| 225 | | NH2 | F | H | o-Cl phenyl | cyclopropylmethyl | 2,5-furanyl |
| 226 | | NH2 | F | H | m-Br Phenyl | cyclopropylmethyl | 2,5-furanyl |
| 227 | | NH2 | F | H | p-Br Phenyl | cyclopropylmethyl | 2,5-furanyl |
| 228 | | NH2 | F | H | o-Br Phenyl | cydopropylmethyl | 2,5-furanyl |
| 229 | | NH2 | F | H | CF3 | cyclopropylmethyl | 2,5-furanyl |
| 230 | | NH2 | F | H | Phenyl | cyclopropylmethyl | 2,5-furanyl |
| 231 | | NH2 | F | H | cyclopentyl | neopentyl | 2,5-furanyl |
| 232 | | NH2 | F | H | cyclohexyl | neopentyl | 2,5-furanyl |
| 233 | | NH2 | F | H | cyclobutyl | neopentyl | 2,5-furanyl |
| 234 | | NH2 | F | H | cyclopropyl | neopentyl | 2,5-furanyl |
| 235 | | NH2 | F | H | cyclopentylmethyl | neopentyl | 2,5-furanyl |
| 236 | | NH2 | F | H | cyclohexylmethyl | neopentyl | 2,5-furanyl |
| 237 | | NH2 | F | H | cyclobutylmethyl | neopentyl | 2,5-furanyl |
| 238 | | NH2 | F | H | cyclopropylmethyl | neopentyl | 2,5-furanyl |
| 239 | | NH2 | F | H | F | cyclobutylmethyl | 2,5-furanyl |
| 240 | | NH2 | F | H | Me | cyclobutylmethyl | 2,5-furanyl |
| 241 | | NH2 | F | H | Pr | cyclobutylmethyl | 2,5-furanyl |
| 242 | | NH2 | F | H | i-Pr | cyclobutylmethyl | 2,5-furanyl |
| 243 | | NH2 | F | H | Bu | cyclobutylmethyl | 2,5-furanyl |
| 244 | | NH2 | F | H | i-Bu | cyclobutylmethyl | 2,5-furanyl |
| 245 | | NH2 | F | H | OMe | cyclobutylmethyl | 2,5-furanyl |
| 246 | | NH2 | F | H | OEt | cyclobutylmethyl | 2,5-furanyl |
| 247 | | NH2 | F | H | SMe | cyclobutylmethyl | 2,5-furanyl |
| 248 | | NH2 | F | H | SEt | cyclobutylmethyl | 2,5-furanyl |
| 249 | | NH2 | F | H | NEt2 | cyctobutylmethyl | 2,5-furanyl |
| 250 | | NH2 | F | H | NMe2 | cyclobutylmethyl | 2,5-furanyl |
| 251 | | NH2 | F | H | I | cyclobutylmethyl | 2,5-furanyl |
| 252 | | NH2 | F | H | m-OMePhenyl | cyclobutylmethyl | 2,5-furanyl |
| 253 | | NH2 | F | H | o-OMePhenyl | cyclobutylmethyl | 2,5-furanyl |
| 254 | | NH2 | F | H | p-F Phenyl | cyclobutylmethyl | 2,5-furanyl |
| 255 | | NH2 | F | H | o-F Phenyl | cyclobutylmethyl | 2,5-furanyl |
| 256 | | NH2 | F | H | m-F Phenyl | cyclobutylmethyl | 2,5-furanyl |
| 257 | | NH2 | F | H | 2-Furanyl | cyclobutylmethyl | 2,5-furanyl |
| 258 | | NH2 | F | H | 2-thiophenyl | cyclobutylmethyl | 2,5-furanyl |
| 259 | | NH2 | F | H | 2-Furanylmethyl | cyclobutylmethyl | 2,5-furanyl |
| 260 | | NH2 | F | H | 2-Thiophenylmethyl | cyclobutylmethyl | 2,5-furanyl |
| 261 | | NH2 | F | H | CN | cyclobutylmethyl | 2,5-furanyl |
| 262 | | NH2 | F | H | m-Cl phenyl | cyclobutylmethyl | 2,5-furanyl |
| 263 | | NH2 | F | H | p-Cl phenyl | cyclobutylmethyl | 2,5-furanyl |

-continued

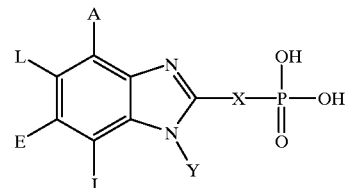

| Table Compound No. | Synthetic Example No. | A | L | E | J¹ | Y | X² |
|---|---|---|---|---|---|---|---|
| 264 | | NH2 | F | H | o-Cl phenyl | cyclobutylmethyl | 2,5-furanyl |
| 265 | | NH2 | F | H | m-Br Phenyl | cyclobutylmethyl | 2,5-furanyl |
| 266 | | NH2 | F | H | p-Br Phenyl | cyclobutylmethyl | 2,5-furanyl |
| 267 | | NH2 | F | H | o-Br Phenyl | cyclobutylmethyl | 2,5-furanyl |
| 268 | | NH2 | F | H | CF3 | cyclobutylmethyl | 2,5-furanyl |
| 269 | | NH2 | F | H | Phenyl | cyclobutylmethyl | 2,5-furanyl |
| 270 | | NH2 | F | F | F | isobutyl | 2,5-furanyl |
| 271 | 12.63 | NH2 | F | Cl | H | isobutyl | 2,5-furanyl |
| 272 | | NH2 | F | F | Et | isobutyl | 2,5-furanyl |
| 273 | | NH2 | F | Cl | Et | isobutyl | 2,5-furanyl |
| 274 | | NH2 | F | H | Et | cyclopropylmethyl | 2,5-furanyl |
| 275 | | NH2 | F | H | Et | cyclobutylmethyl | 2,5-furanyl |
| 276 | | NH2 | F | Me | H | isobutyl | 2,5-furanyl |
| 277 | | NH2 | F | Me | Me | isobutyl | 2,5-furanyl |
| 278 | | NH2 | F | Me | Et | isobutyl | 2,5-furanyl |
| 279 | | NH2 | F | F | Pr | isobutyl | 2,5-furanyl |
| 280 | | NH2 | F | Me | Pr | isobutyl | 2,5-furanyl |
| 281 | | NH2 | F | Cl | Pr | isobutyl | 2,5-furanyl |
| 282 | | NH2 | F | H | H | isobutyl | methoxymethyl |
| 283 | | NH2 | F | H | H | cyclopropylmethyl | methoxymethyl |
| 284 | | NH2 | F | H | Et | isobutyl | methoxymethyl |
| 285 | | NH2 | F | H | Et | cyclopropylmethyl | methoxymethyl |
| 286 | | OH | F | H | F | isobutyl | 2,5-furanyl |
| 287 | | OH | F | H | Me | isobutyl | 2,5-furanyl |
| 288 | | OH | F | H | Pr | isobutyl | 2,5-furanyl |
| 289 | | OH | F | H | i-Pr | isobutyl | 2,5-furanyl |
| 290 | | OH | F | H | Bu | isobutyl | 2,5-furanyl |
| 291 | | OH | F | H | i-Bu | isobutyl | 2,5-furanyl |
| 292 | | OH | F | H | OMe | isobutyl | 2,5-furanyl |
| 293 | | OH | F | H | OEt | isobutyl | 2,5-furanyl |
| 294 | | OH | F | H | SMe | isobutyl | 2,5-furanyl |
| 295 | | OH | F | H | SEt | isobutyl | 2,5-furanyl |
| 296 | | OH | F | H | NEt2 | isobutyl | 2,5-furanyl |
| 297 | | OH | F | H | NMe2 | isobutyl | 2,5-furanyl |
| 298 | | OH | F | H | I | isobutyl | 2,5-furanyl |
| 299 | | OH | F | H | m-OMePhenyl | isobutyl | 2,5-furanyl |
| 300 | | OH | F | H | o-OMePhenyl | isobutyl | 2,5-furanyl |
| 301 | | OH | F | H | p-F Phenyl | isobutyl | 2,5-furanyl |
| 302 | | OH | F | H | o-F Phenyl | isobutyl | 2,5-furanyl |
| 303 | | OH | F | H | m-F Phenyl | isobutyl | 2,5-furanyl |
| 304 | | OH | F | H | 2-Furanyl | isobutyl | 2,5-furanyl |
| 305 | | OH | F | H | 2-thiophenyl | isobutyl | 2,5-furanyl |
| 306 | | OH | F | H | 2-Furanylmethyl | isobutyl | 2,5-furanyl |
| 307 | | OH | F | H | 2-Thiophenylmethyl | isobutyl | 2,5-furanyl |
| 308 | | OH | F | H | CN | isobutyl | 2,5-furanyl |
| 309 | | OH | F | H | m-Cl phenyl | isobutyl | 2,5-furanyl |
| 310 | | OH | F | H | p-Cl phenyl | isobutyl | 2,5-furanyl |
| 311 | | OH | F | H | o-Cl phenyl | isobutyl | 2,5-furanyl |
| 312 | | OH | F | H | m-Br Phenyl | isobutyl | 2,5-furanyl |
| 313 | | OH | F | H | p-Br Phenyl | isobutyl | 2,5-furanyl |
| 314 | | OH | F | H | o-Br Phenyl | isobutyl | 2,5-furanyl |
| 315 | | OH | F | H | CF3 | isobutyl | 2,5-furanyl |
| 316 | | OH | F | H | Phenyl | isobutyl | 2,5-furanyl |
| 317 | | OH | F | H | Cl | isobutyl | 2,5-furanyl |
| 318 | | OH | F | H | Br | isobutyl | 2,5-furanyl |
| 319 | | OH | F | H | Et | isobutyl | 2,5-furanyl |
| 320 | | NH2 | F | F | Cl | isobutyl | 2,5-furanyl |
| 321 | | NH2 | F | F | Br | isobutyl | 2,5-furanyl |
| 322 | 13.51 | NH2 | OH | H | H | isobutyl | 2,5-furanyl |
| 323 | | NH2 | OH | H | F | isobutyl | 2,5-furanyl |
| 324 | | NH2 | OH | H | Me | isobutyl | 2,5-furanyl |
| 325 | | NH2 | OH | H | Pr | isobutyl | 2,5-furanyl |
| 326 | | NH2 | OH | H | i-Pr | isobutyl | 2,5-furanyl |
| 327 | | NH2 | OH | H | Bu | isobutyl | 2,5-furanyl |
| 328 | | NH2 | OH | H | i-Bu | isobutyl | 2,5-furanyl |
| 329 | | NH2 | OH | H | OMe | isobutyl | 2,5-furanyl |
| 330 | | NH2 | OH | H | OEt | isobutyl | 2,5-furanyl |

-continued

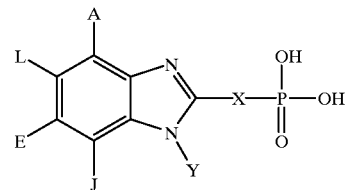

| Table Compound No. | Synthetic Example No. | A | L | E | J¹ | Y | X² |
|---|---|---|---|---|---|---|---|
| 331 |  | NH2 | OH | H | SMe | isobutyl | 2,5-furanyl |
| 332 |  | NH2 | OH | H | SEt | isobutyl | 2,5-furanyl |
| 333 |  | NH2 | OH | H | NEt2 | isobutyl | 2,5-furanyl |
| 334 |  | NH2 | OH | H | NMe2 | isobutyl | 2,5-furanyl |
| 335 |  | NH2 | OH | H | I | isobutyl | 2,5-furanyl |
| 336 |  | NH2 | OH | H | m-OMePhenyl | isobutyl | 2,5-furanyl |
| 337 |  | NH2 | OH | H | o-OMePhenyl | isobutyl | 2,5-furanyl |
| 338 |  | NH2 | OH | H | p-F Phenyl | isobutyl | 2,5-furanyl |
| 339 |  | NH2 | OH | H | o-F Phenyl | isobutyl | 2,5-furanyl |
| 340 |  | NH2 | OH | H | m-F Phenyl | isobutyl | 2,5-furanyl |
| 341 |  | NH2 | OH | H | 2-Furanyl | isobutyl | 2,5-furanyl |
| 342 |  | NH2 | OH | H | 2-thiophenyl | isobutyl | 2,5-furanyl |
| 343 |  | NH2 | OH | H | 2-Furanylmethyl | isobutyl | 2,5-furanyl |
| 344 |  | NH2 | OH | H | 2-Thiophenylmethyl | isobutyl | 2,5-furanyl |
| 345 |  | NH2 | OH | H | CN | isobutyl | 2,5-furanyl |
| 346 |  | NH2 | OH | H | m-Cl phenyl | isobutyl | 2,5-furanyl |
| 347 |  | NH2 | OH | H | p-Cl phenyl | isobutyl | 2,5-furanyl |
| 348 |  | NH2 | OH | H | o-Cl phenyl | isobutyl | 2,5-furanyl |
| 349 |  | NH2 | OH | H | m-Br Phenyl | isobutyl | 2,5-furanyl |
| 350 |  | NH2 | OH | H | p-Br Phenyl | isobutyl | 2,5-furanyl |
| 351 |  | NH2 | OH | H | o-Br Phenyl | isobutyl | 2,5-furanyl |
| 352 |  | NH2 | OH | H | CF3 | isobutyl | 2,5-furanyl |
| 353 |  | NH2 | OH | H | Phenyl | isobutyl | 2,5-furanyl |
| 354 | 12.55 | NH2 | OMe | H | H | isobutyl | 2,5-furanyl |
| 355 |  | NH2 | OMe | H | F | isobutyl | 2,5-furanyl |
| 356 |  | NH2 | OMe | H | Me | isobutyl | 2,5-furanyl |
| 357 |  | NH2 | OMe | H | Pr | isobutyl | 2,5-furanyl |
| 358 |  | NH2 | OMe | H | i-Pr | isobutyl | 2,5-furanyl |
| 359 |  | NH2 | OMe | H | Bu | isobutyl | 2,5-furanyl |
| 360 |  | NH2 | OMe | H | i-Bu | isobutyl | 2,5-furanyl |
| 361 |  | NH2 | OMe | H | OMe | isobutyl | 2,5-furanyl |
| 362 |  | NH2 | OMe | H | OEt | isobutyl | 2,5-furanyl |
| 363 |  | NH2 | OMe | H | SMe | isobutyl | 2,5-furanyl |
| 364 |  | NH2 | OMe | H | SEt | isobutyl | 2,5-furanyl |
| 365 |  | NH2 | OMe | H | NEt2 | isobutyl | 2,5-furanyl |
| 366 |  | NH2 | OMe | H | NMe2 | isobutyl | 2,5-furanyl |
| 367 |  | NH2 | OMe | H | I | isobutyl | 2,5-furanyl |
| 368 |  | NH2 | OMe | H | m-OMePhenyl | isobutyl | 2,5-furanyl |
| 369 |  | NH2 | OMe | H | o-OMePhenyl | isobutyl | 2,5-furanyl |
| 370 |  | NH2 | OMe | H | p-F Phenyl | isobutyl | 2,5-furanyl |
| 371 |  | NH2 | OMe | H | o-F Phenyl | isobutyl | 2,5-furanyl |
| 372 |  | NH2 | OMe | H | m-F Phenyl | isobutyl | 2,5-furanyl |
| 373 |  | NH2 | OMe | H | 2-Furanyl | isobutyl | 2,5-furanyl |
| 374 |  | NH2 | OMe | H | 2-thiophenyl | isobutyl | 2,5-furanyl |
| 375 |  | NH2 | OMe | H | 2-Furanylmethyl | isobutyl | 2,5-furanyl |
| 376 |  | NH2 | OMe | H | 2-Thiophenylmethyl | isobutyl | 2,5-furanyl |
| 377 |  | NH2 | OMe | H | CN | isobutyl | 2,5-furanyl |
| 378 |  | NH2 | OMe | H | m-Cl phenyl | isobutyl | 2,5-furanyl |
| 379 |  | NH2 | OMe | H | p-Cl phenyl | isobutyl | 2,5-furanyl |
| 380 |  | NH2 | OMe | H | o-Cl phenyl | isobutyl | 2,5-furanyl |
| 381 |  | NH2 | OMe | H | m-Br Phenyl | isobutyl | 2,5-furanyl |
| 382 |  | NH2 | OMe | H | p-Br Phenyl | isobutyl | 2,5-furanyl |
| 383 |  | NH2 | OMe | H | o-Br Phenyl | isobutyl | 2,5-furanyl |
| 384 |  | NH2 | OMe | H | CF3 | isobutyl | 2,5-furanyl |
| 385 |  | NH2 | OMe | H | Phenyl | isobutyl | 2,5-furanyl |
| 386 |  | NH2 | Cl | H | F | isobutyl | 2,5-furanyl |
| 387 |  | NH2 | Cl | H | Me | isobutyl | 2,5-furanyl |
| 388 |  | NH2 | Cl | H | Pr | isobutyl | 2,5-furanyl |
| 389 |  | NH2 | Cl | H | i-Pr | isobutyl | 2,5-furanyl |
| 390 |  | NH2 | Cl | H | Bu | isobutyl | 2,5-furanyl |
| 391 |  | NH2 | Cl | H | i-Bu | isobutyl | 2,5-furanyl |
| 392 |  | NH2 | Cl | H | OMe | isobutyl | 2,5-furanyl |
| 393 |  | NH2 | Cl | H | OEt | isobutyl | 2,5-furanyl |
| 394 |  | NH2 | Cl | H | SMe | isobutyl | 2,5-furanyl |
| 395 |  | NH2 | Cl | H | SEt | isobutyl | 2,5-furanyl |
| 396 |  | NH2 | Cl | H | NEt2 | isobutyl | 2,5-furanyl |
| 397 |  | NH2 | Cl | H | NMe2 | isobutyl | 2,5-furanyl |

-continued

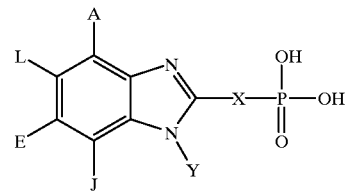

| Table Compound No. | Synthetic Example No. | A | L | E | J¹ | Y | X² |
|---|---|---|---|---|---|---|---|
| 398 | | NH2 | Cl | H | I | isobutyl | 2,5-furanyl |
| 399 | | NH2 | Cl | H | m-OMePhenyl | isobutyl | 2,5-furanyl |
| 400 | | NH2 | Cl | H | o-OMePhenyl | isobutyl | 2,5-furanyl |
| 401 | | NH2 | Cl | H | p-F Phenyl | isobutyl | 2,5-furanyl |
| 402 | | NH2 | Cl | H | o-F Phenyl | isobutyl | 2,5-furanyl |
| 403 | | NH2 | Cl | H | m-F Phenyl | isobutyl | 2,5-furanyl |
| 404 | | NH2 | Cl | H | 2-Furanyl | isobutyl | 2,5-furanyl |
| 405 | | NH2 | Cl | H | 2-thiophenyl | isobutyl | 2,5-furanyl |
| 406 | | NH2 | Cl | H | 2-Furanylmethyl | isobutyl | 2,5-furanyl |
| 407 | | NH2 | Cl | H | 2-Thiophenylmethyl | isobutyl | 2,5-furanyl |
| 408 | | NH2 | Cl | H | CN | isobutyl | 2,5-furanyl |
| 409 | | NH2 | Cl | H | m-Cl phenyl | isobutyl | 2,5-furanyl |
| 410 | | NH2 | Cl | H | p-Cl phenyl | isobutyl | 2,5-furanyl |
| 411 | | NH2 | Cl | H | o-Cl phenyl | isobutyl | 2,5-furanyl |
| 412 | | NH2 | Cl | H | m-Br Phenyl | isobutyl | 2,5-furanyl |
| 413 | | NH2 | Cl | H | p-Br Phenyl | isobutyl | 2,5-furanyl |
| 414 | | NH2 | Cl | H | o-Br Phenyl | isobutyl | 2,5-furanyl |
| 415 | | NH2 | Cl | H | CF3 | isobutyl | 2,5-furanyl |
| 416 | | NH2 | Cl | H | Phenyl | isobutyl | 2,5-furanyl |
| 417 | | NH2 | Cl | H | Et | isobutyl | 2,5-furanyl |
| 418 | | NH2 | Cl | H | Br | isobutyl | 2,5-furanyl |
| 419 | 12.50 | NH2 | Cl | H | Cl | isobutyl | 2,5-furanyl |
| 420 | 12.49 | NH2 | Cl | H | H | isobutyl | 2,5-furanyl |
| 421 | 12.58 | NH2 | Br | Cl | Cl | isobutyl | 2,5-furanyl |
| 422 | | NH2 | Br | H | Cl | isobutyl | 2,5-furanyl |
| 423 | 12.44 | NH2 | Br | H | H | isobutyl | 2,5-furanyl |
| 424 | 12.42 | NH2 | Br | H | Br | isobutyl | 2,5-furanyl |
| 425 | | NH2 | Br | H | F | isobutyl | 2,5-furanyl |
| 426 | | NH2 | Br | H | Me | isobutyl | 2,5-furanyl |
| 427 | | NH2 | Br | H | Pr | isobutyl | 2,5-furanyl |
| 428 | | NH2 | Br | H | i-Pr | isobutyl | 2,5-furanyl |
| 429 | | NH2 | Br | H | Bu | isobutyl | 2,5-furanyl |
| 430 | | NH2 | Br | H | i-Bu | isobutyl | 2,5-furanyl |
| 431 | | NH2 | Br | H | OMe | isobutyl | 2,5-furanyl |
| 432 | | NH2 | Br | H | OEt | isobutyl | 2,5-furanyl |
| 433 | | NH2 | Br | H | SMe | isobutyl | 2,5-furanyl |
| 434 | | NH2 | Br | H | SEt | isobutyl | 2,5-furanyl |
| 435 | | NH2 | Br | H | NEt2 | isobutyl | 2,5-furanyl |
| 436 | | NH2 | Br | H | NMe2 | isobutyl | 2,5-furanyl |
| 437 | | NH2 | Br | H | I | isobutyl | 2,5-furanyl |
| 438 | | NH2 | Br | H | m-OMePhenyl | isobutyl | 2,5-furanyl |
| 439 | | NH2 | Br | H | o-OMePhenyl | isobutyl | 2,5-furanyl |
| 440 | | NH2 | Br | H | p-F Phenyl | isobutyl | 2,5-furanyl |
| 441 | | NH2 | Br | H | o-F Phenyl | isobutyl | 2,5-furanyl |
| 442 | | NH2 | Br | H | m-F Phenyl | isobutyl | 2,5-furanyl |
| 443 | | NH2 | Br | H | 2-Furanyl | isobutyl | 2,5-furanyl |
| 444 | | NH2 | Br | H | 2-thiophenyl | isobutyl | 2,5-furanyl |
| 445 | | NH2 | Br | H | 2-Furanylmethyl | isobutyl | 2,5-furanyl |
| 446 | | NH2 | Br | H | 2-Thiophenylmethyl | isobutyl | 2,5-furanyl |
| 447 | | NH2 | Br | H | CN | isobutyl | 2,5-furanyl |
| 448 | | NH2 | Br | H | m-Cl phenyl | isobutyl | 2,5-furanyl |
| 449 | | NH2 | Br | H | p-Cl phenyl | isobutyl | 2,5-furanyl |
| 450 | | NH2 | Br | H | o-Cl phenyl | isobutyl | 2,5-furanyl |
| 451 | | NH2 | Br | H | m-Br Phenyl | isobutyl | 2,5-furanyl |
| 452 | | NH2 | Br | H | p-Br Phenyl | isobutyl | 2,5-furanyl |
| 453 | | NH2 | Br | H | o-Br Phenyl | isobutyl | 2,5-furanyl |
| 454 | | NH2 | Br | H | CF3 | isobutyl | 2,5-furanyl |
| 455 | | NH2 | Br | H | Phenyl | isobutyl | 2,5-furanyl |
| 456 | | NH2 | Br | H | Cl | tsobutyl | 2,5-furanyl |
| 457 | | NH2 | Br | H | Et | isobutyl | 2,5-furanyl |
| 458 | | NH2 | Br | Cl | Cl | isobutyl | 2,5-furanyl |
| 459 | | NH2 | Br | Cl | F | isobutyl | 2,5-furanyl |
| 460 | | NH2 | Br | F | Cl | isobutyl | 2,5-furanyl |
| 461 | 12.65 | Et | H | F | NH2 | isobutyl | 2,5-furanyl |
| 462 | 13.1 | H | H | H | H | H | 2,5-furanyl |
| 463 | 13.2 | H | H | H | H | isobutyl | 2,5-furanyl |
| 464 | 13.6 | H | CF3 | H | H | H | 2,5-furanyl |

-continued

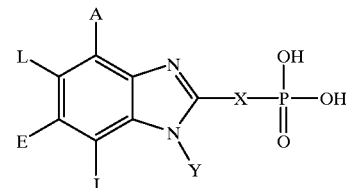

| Table Compound No. | Synthetic Example No. | A | L | E | J¹ | Y | X² |
|---|---|---|---|---|---|---|---|
| 465 | 13.7 | H | F | H | H | H | 2,5-furanyl |
| 466 | 13.8 | H | Cl | Cl | H | H | 2,5-furanyl |
| 467 | 13.9 | H | Cl | H | H | H | 2,5-furanyl |
| 468 | 13.10 | H | Me | H | H | H | 2,5-furanyl |
| 469 | 13.11 | H | t-Bu | H | H | H | 2,5-furanyl |
| 470 | 13.12 | H | H | H | H | Ph | 2,5-furanyl |
| 471 | 13.13 | H | H | H | H | 2-CO2H-Phenyl | 2,5-furanyl |
| 472 | 13.14 | H | NO2 | H | H | H | 2,5-furanyl |
| 473 | 13.15 | Me | Me | H | H | H | 2,5-furanyl |
| 474 | 13.16 | H | Cl | H | H | isobutyl | 2,5-furanyl |
| 475 | 13.17 | H | H | Cl | H | isobutyl | 2,5-furanyl |
| 476 | 13.18 | H | C6H5CO | H | H | H | 2,5-furanyl |
| 477 | 13.19 | amidino-methyl | H | H | H | 2-ethylpentyl | 2,5-furanyl |
| 478 | 13.20 | iso-butyloxy | H | H | H | isobutyl | 2,5-furanyl |
| 479 | 13.21 | OH | H | H | H | isobutyl | 2,5-furanyl |
| 480 | 13.22 | H | F | F | H | H | 2,5-furanyl |
| 481 | 13.23 | H | CO2Me | H | H | H | 2,5-furanyl |
| 482 | 13.24 | H | Me | Me | H | H | 2,5-furanyl |
| 483 | 13.25 | F | H | H | H | neopentyl | 2,5-furanyl |
| 484 | 13.27 | H | H | F | H | isobutyl | 2,5-furanyl |
| 485 | 13.28 | H | F | H | H | isobutyl | 2,5-furanyl |
| 486 |  | pyridyl | H | H | H | H | 2,5-furanyl |
| 487 | 13.32 | Me | H | H | H | H | 2,5-furanyl |
| 488 | 13.33 | H | Cl | H | H | isopropyl | 2,5-furanyl |
| 489 | 13.35 | H | Br | H | H | H | 2,5-furanyl |
| 490 | 13.36 | H | Br | H | H | isobutyl | 2,5-furanyl |
| 491 | 13.37 | H | H | Br | H | isobutyl | 2,5-furanyl |
| 492 | 13.38 | Cl | H | Cl | H | H | 2,5-furanyl |
| 493 | 13.39 | Cl | H | Cl | H | isobutyl | 2,5-furanyl |
| 494 |  | H | H | H | H | Ph | 2,5-furanyl |
| 495 | 13.40 | H | Cl | H | H | Ph | 2,5-furanyl |
| 496 | 13.41 | H | H | Cl | H | Ph | 2,5-furanyl |
| 497 | 13.42 | Br | H | Br | H | H | 2,5-furanyl |
| 498 | 13.43 | Br | H | Br | H | isobutyl | 2,5-furanyl |
| 499 | 13.44 | H | Cl | Cl | H | isobutyl | 2,5-furanyl |
| 500 | 13.45 | H | Cl | Cl | H | cyclopropylmethyl | 2,5-furanyl |
| 501 | 13.46 | H | Cl | F | H | H | 2,5-furanyl |
| 502 | 13.47 | Ph | H | CF3 | H | H | 2,5-furanyl |
| 503 | 13.48 | Br | H | CF3 | H | H | 2,5-furanyl |
| 504 | 13.49 | H | Cl | F | H | cyclopropylmethyl | 2,5-furanyl |
| 505 | 13.50 | H | Cl | F | H | isobutyl | 2,5-furanyl |
| 506 | 13.53 | Me | Me | Br | H | isobutyl | 2,5-furanyl |
| 507 | 13.54 | Me | H | H | H | isobutyl | 2,5-furanyl |
| 508 |  | Me | H | H | H | neopentyl | 2,5-furanyl |
| 509 |  | H | H | Cl | Br | isobutyl | 2,5-furanyl |
| 510 |  | H | H | Cl | Br | isobutyl | 2,5-furanyl |
| 511 |  | H | H | Cl | OH | isobutyl | 2,5-furanyl |
| 512 |  | H | H | Cl | OMe | isobutyl | 2,5-furanyl |
| 513 |  | H | H | Cl | CN | isobutyl | 2,5-furanyl |
| 514 |  | H | H | Cl | CO2H | isobutyl | 2,5-furanyl |
| 515 |  | H | H | Cl | CO2Me | isobutyl | 2,5-furanyl |
| 516 |  | H | H | Cl | CONH2 | isobutyl | 2,5-furanyl |
| 517 |  | H | H | Cl | NHCONH2 | isobutyl | 2,5-furanyl |
| 518 |  | H | H | Cl | Me | isobutyl | 2,5-furanyl |
| 519 |  | H | H | Cl | Et | isobutyl | 2,5-furanyl |
| 520 |  | H | H | Cl | n-Pr | isobutyl | 2,5-furanyl |
| 521 |  | H | H | Cl | i-Pr | isobutyl | 2,5-furanyl |
| 522 |  | H | H | Cl | n-Bu | isobutyl | 2,5-furanyl |
| 523 |  | H | H | Cl | i-butyl | isobutyl | 2,5-furanyl |
| 524 |  | H | H | Cl | n-pentyl | isobutyl | 2,5-furanyl |
| 525 |  | H | H | Cl | i-pentyl | isobutyl | 2,5-furanyl |
| 526 |  | H | H | Cl | neopentyl | isobutyl | 2,5-furanyl |
| 527 |  | H | H | Cl | 2-chloroethyl | isobutyl | 2,5-furanyl |
| 528 |  | H | H | Cl | 2-bromoethyl | isobutyl | 2,5-furanyl |
| 529 |  | H | H | Cl | 2-hydroxyethyl | isobutyl | 2,5-furanyl |

-continued

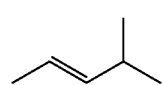

| Table Compound No. | Synthetic Example No. | A | L | E | J¹ | Y | X² |
|---|---|---|---|---|---|---|---|
| 530 | | H | H | Cl | 2-carboxyethyl | isobutyl | 2,5-furanyl |
| 531 | | H | H | Cl | 2-carboxyamidoethyl | isobutyl | 2,5-furanyl |
| 532 | | H | H | Cl | 3-carboxypropyl | isobutyl | 2,5-furanyl |
| 533 | | H | H | Cl | 3-carboxyamidopropyl | isobutyl | 2,5-furanyl |
| 534 | | H | H | Cl | 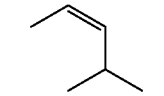 | isobutyl | 2,5-furanyl |
| 535 | | H | H | Cl | | isobutyl | 2,5-furanyl |
| 536 | | H | H | Cl | 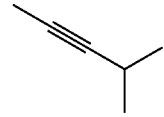 | isobutyl | 2,5-furanyl |
| 537 | | H | H | Cl | Cyclopentyl | isobutyl | 2,5-furanyl |
| 538 | | H | H | Cl | Cyclopentylmethyl | isobutyl | 2,5-furanyl |
| 539 | | H | H | Cl | Cyclopentylethyl | isobutyl | 2,5-furanyl |
| 540 | | H | H | Cl | Phenyl | isobutyl | 2,5-furanyl |
| 541 | | H | H | Cl | benzyl | isobutyl | 2,5-furanyl |
| 542 | | H | H | Cl | phenethyl | isobutyl | 2,5-furanyl |
| 543 | | H | H | Cl | m-chlorophenyl | isobutyl | 2,5-furanyl |
| 544 | | H | H | Cl | p-chlorophenyl | isobutyl | 2,5-furanyl |
| 545 | | H | H | Cl | m-bromophenyl | isobutyl | 2,5-furanyl |
| 546 | | H | H | Cl | p-bromophenyl | isobutyl | 2,5-furanyl |
| 547 | | H | H | Cl | m-hydroxyphenyl | isobutyl | 2,5-furanyl |
| 548 | | H | H | Cl | p-hydroxyphenyl | isobutyl | 2,5-furanyl |
| 549 | | H | H | Cl | m-carboxyphenyl | isobutyl | 2,5-furanyl |
| 550 | | H | H | Cl | p-carboxyphenyl | isobutyl | 2,5-furanyl |
| 551 | | H | H | Cl | m-carboxyamidophenyl | isobutyl | 2,5-furanyl |
| 552 | | H | H | Cl | p-carboxyamidophenyl | isobutyl | 2,5-furanyl |
| 553 | | H | H | Cl | N-pyrrolidinyl | isobutyl | 2,5-furanyl |
| 554 | | H | H | Cl | N-thiomorpholinyl | isobutyl | 2,5-furanyl |
| 555 | | H | H | Cl | N-imidazolyl | isobutyl | 2,5-furanyl |
| 556 | | H | H | Cl | N-piperdinylmethyl | isobutyl | 2,5-furanyl |
| 557 | | H | H | Cl | N-piperazinylmethyl | isobutyl | 2,5-furanyl |
| 558 | | H | H | Cl | N-morpholinylmethyl | isobutyl | 2,5-furanyl |
| 559 | | H | H | Cl | N-pyrrolidinemythyl | isobutyl | 2,5-furanyl |
| 560 | | H | H | Cl | N-piperdinylethyl | isobutyl | 2,5-furanyl |
| 561 | | H | H | Cl | N-piperazinylethyl | isobutyl | 2,5-furanyl |
| 562 | | H | H | Cl | N-morpholinylethyl | isobutyl | 2,5-furanyl |
| 563 | | H | H | Cl | 4-imdazolylethyl | isobutyl | 2,5-furanyl |
| 564 | | H | H | Cl | 4-oxazolylethyl | isobutyl | 2,5-furanyl |
| 565 | | H | H | Cl | 4-thiazolylethyl | isobutyl | 2,5-furanyl |
| 566 | | H | H | Cl | 4-pyrimidylethyl | isobutyl | 2,5-furanyl |
| 567 | | H | H | Cl | 5-pyrimidylethyl | isobutyl | 2,5-furanyl |
| 568 | | F | H | Cl | H | isobutyl | 2,5-furanyl |
| 569 | | Me | H | Cl | H | isobutyl | 2,5-furanyl |
| 570 | | Et | H | Cl | H | isobutyl | 2,5-furanyl |
| 571 | | n-Pr | H | Cl | H | isobutyl | 2,5-furanyl |
| 572 | | i-Pr | H | Cl | H | isobutyl | 2,5-furanyl |
| 573 | | acetyl | H | Cl | H | isobutyl | 2,5-furanyl |
| 574 | | carboxy | H | Cl | H | isobutyl | 2,5-furanyl |
| 575 | | carboxy-amido | H | Cl | H | isobutyl | 2,5-furanyl |
| 576 | | SH | H | Cl | H | isobutyl | 2,5-furanyl |
| 577 | | —NHNH2 | H | Cl | H | isobutyl | 2,5-furanyl |

-continued

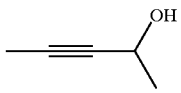

| Table Compound No. | Synthetic Example No. | A | L | E | J¹ | Y | X² |
|---|---|---|---|---|---|---|---|
| 578 | | —NHOH | H | Cl | H | isobutyl | 2,5-furanyl |
| 579 | | H | Et | Cl | H | isobutyl | 2,5-furanyl |
| 580 | | H | CN | Cl | H | isobutyl | 2,5-furanyl |
| 581 | | H | CO2H | Cl | H | isobutyl | 2,5-furanyl |
| 582 | | H | CO2NH2 | Cl | H | isobutyl | 2,5-furanyl |
| 583 | | H | H | Me | H | isobutyl | 2,5-furanyl |
| 584 | | H | H | acetenyl | H | isobutyl | 2,5-furanyl |
| 585 | | H | H | ethynyl | H | isobutyl | 2,5-furanyl |
| 586 | | H | H | ethyl | H | isobutyl | 2,5-furanyl |
| 587 | | H | H | NO2 | H | isobutyl | 2,5-furanyl |
| 588 | | H | H | NH2 | H | isobutyl | 2,5-furanyl |
| 589 | | H | H | CN | H | isobutyl | 2,5-furanyl |
| 590 | | H | H | SMe | H | isobutyl | 2,5-furanyl |
| 591 | | H | H | OMe | H | isobutyl | 2,5-furanyl |
| 592 | | H | H | phenyl | H | isobutyl | 2,5-furanyl |
| 593 | | H | H | Cl | H | m-OHPh | 2,5-furanyl |
| 594 | | H | H | Cl | H | p-OHPh | 2,5-furanyl |
| 595 | | H | H | Cl | H | m-CO2HPh | 2,5-furanyl |
| 596 | | H | H | Cl | H | p-CO2HPh | 2,5-furanyl |
| 597 | | H | H | Cl | H | m-CONH2Ph | 2,5-furanyl |
| 598 | | H | H | Cl | H | p-CO2HPh | 2,5-furanyl |
| 599 | | H | H | Cl | H | m-ClPh | 2,5-furanyl |
| 600 | | H | H | Cl | H | p-ClPh | 2,5-furanyl |
| 601 | | H | H | Cl | H | COCH2CH3 | 2,5-furanyl |
| 602 | | H | H | Cl | H | COPh | 2,5-furanyl |
| 603 | | H | H | Cl | H | SO2CH3 | 2,5-furanyl |
| 604 | | H | H | Cl | H | SO2Ph | 2,5-furanyl |
| 605 | | H | H | Cl | H | isobutyl | 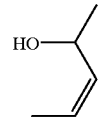 |
| 606 | | H | H | Cl | H | isobutyl | 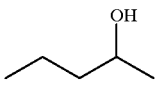 |
| 607 | | H | H | Cl | H | isobutyl | 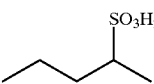 |
| 608 | | H | H | Cl | H | isobutyl | 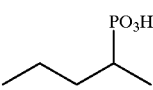 |
| 609 | | H | H | Cl | H | isobutyl | 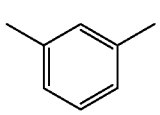 |
| 610 | | H | H | Cl | H | isobutyl | 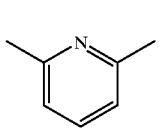 |
| 611 | | H | H | Cl | H | isobutyl |  |

-continued
| Table Compound No. | Synthetic Example No. | A | L | E | J¹ | Y | X² |
|---|---|---|---|---|---|---|---|
| 612 | | H | H | Cl | H | isobutyl | 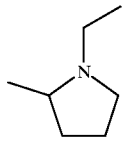 |
| 613 | | H | H | Cl | H | isobutyl | 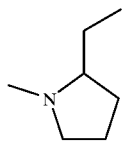 |
| 614 | | H | H | Cl | H | isobutyl | 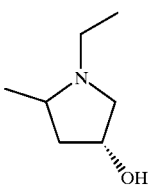 |
| 615 | | H | H | Cl | H | isobutyl | 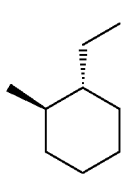 |
| 616 | | H | H | Cl | H | isobutyl | 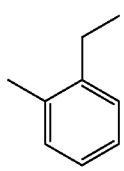 |
| 617 | | H | H | Cl | H | isobutyl | 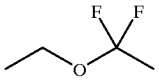 |
| 618 | | H | H | Cl | H | isobutyl | 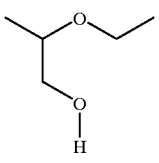 |
| 619 | | H | H | Cl | H | isobutyl | 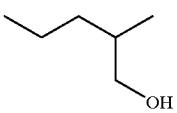 |

-continued

| Table Compound No. | Synthetic Example No. | A | L | E | J¹ | Y | X² |
|---|---|---|---|---|---|---|---|
| 620 | | H | H | Cl | H | isobutyl | 2-aminopentyl (NH₂ on C2 of pentyl chain) |
| 621 | | H | H | Cl | H | isobutyl | 2-hydroxypentyl (OH on C2 of pentyl chain) |
| 622 | | H | H | Cl | H | isobutyl | pent-3-en-2-one |
| 623 | | H | H | Cl | H | isobutyl | N-ethylacetamide |
| 624 | | H | H | Cl | H | isobutyl | N-ethylmethanesulfonamide |
| 625 | | H | H | Cl | H | isobutyl | N-methylpropanamide |
| 626 | | H | H | Cl | H | isobutyl | N-(2-azidoethyl)-N-ethyl acetamide (C2, N3 labels) |
| 627 | | H | H | Cl | H | isobutyl | N-(2-azidoethyl)-N-ethyl-N'-oxide derivative (C2, N3 labels) |
| 628 | | H | H | Cl | H | isobutyl | 3-(ethylamino)-butanol substituent |
| 629 | | H | H | Cl | H | isobutyl | 3-(ethylamino)-butanoic acid substituent |

-continued

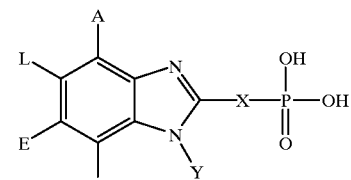

| Table Compound No. | Synthetic Example No. | A | L | E | J¹ | Y | X² |
|---|---|---|---|---|---|---|---|
| 630 | | H | H | Cl | H | isobutyl | OH / OH (diol) |
| 631 | | H | H | Cl | H | isobutyl | CO₂H (branched chain) |
| 632 | 13.63 | H | Cl | Me | Me | isobutyl | 2,5-furanyl |
| 633 | 13.60 | Me | Me | Cl | H | isobutyl | 2,5-furanyl |
| 634 | 13.58 | H | H | Cl | H | cyclopropylmethyl | 2,5-furanyl |
| 635 | | Me | Me | H | H | isobutyl | 2,5-furanyl |
| 636 | 13.56 | H | H | Cl | H | neopentyl | 2,5-furanyl |
| 637 | | Cl | H | Cl | H | neopentyl | 2,5-furanyl |
| 638 | | H | H | F | Et | isobutyl | 2,5-furanyl |
| 639 | | H | H | F | SMe | Et | isobutyl | 2,5-furanyl |
| 640 | | H | F | Cl | Et | isobutyl | 2,5-furanyl |
| 641 | | H | F | Br | Et | isobutyl | 2,5-furanyl |
| 642 | | H | F | Cl | Br | isobutyl | 2,5-furanyl |
| 643 | | H | H | Cl | H | neopentyl | 2,5-furanyl |
| 644 | | H | F | F | H | H | 2,5-furanyl |
| 645 | | NH2 | F | H | 2,6-difluorophenyl | isobutyl | methoxymethyl |
| 646 | | NH2 | F | H | Br | isobutyl | methoxymethyl |
| 647 | | NH2 | F | H | H | isobutyl | methoxymethyl |
| 648 | | NH2 | F | H | Et | isobutyl | methoxymethyl |
| 649 | | NH2 | F | H | Cl | isobutyl | methoxymethyl |
| 660 | | NH2 | F | H | Me | isobutyl | methoxymethyl |
| 651 | | NH2 | F | H | Pr | isobutyl | methoxymethyl |
| 652 | | NH2 | F | H | i-Pr | isobutyl | methoxymethyl |
| 653 | | NH2 | F | H | Bu | isobutyl | methoxymethyl |
| 654 | | NH2 | F | H | i-Bu | isobutyl | methoxymethyl |
| 655 | | NH2 | F | H | OMe | isobutyl | methoxymethyl |
| 656 | | NH2 | F | H | OEt | isobutyl | methoxymethyl |
| 657 | | NH2 | F | H | SMe | isobutyl | methoxymethyl |
| 658 | | NH2 | F | H | SEt | isobutyl | methoxymethyl |
| 659 | | NH2 | F | H | NEt2 | isobutyl | methoxymethyl |
| 660 | | NH2 | F | H | NMe2 | isobutyl | methoxymethyl |
| 661 | | NH2 | F | H | I | isobutyl | methoxymethyl |
| 662 | | NH2 | F | H | m-OMePhenyl | isobutyl | methoxymethyl |
| 663 | | NH2 | F | H | o-OMePhenyl | isobutyl | methoxymethyl |
| 664 | | NH2 | F | H | p-F Phenyl | isobutyl | methoxymethyl |
| 665 | | NH2 | F | H | o-F Phenyl | isobutyl | methoxymethyl |
| 666 | | NH2 | F | H | m-F Phenyl | isobutyl | methoxymethyl |
| 667 | | NH2 | F | H | 2-Furanyl | isobutyl | methoxymethyl |
| 668 | | NH2 | F | H | 2-thiophenyl | isobutyl | methoxymethyl |
| 669 | | NH2 | F | H | 2-Furanylmethyl | isobutyl | methoxymethyl |
| 670 | | NH2 | F | H | 2-Thiophenymethyl | isobutyl | methoxymethyl |
| 671 | | NH2 | F | H | CN | isobutyl | methoxymethyl |
| 672 | | NH2 | F | H | m-Cl phenyl | isobutyl | methoxymethyl |
| 673 | | NH2 | F | H | p-Cl phenyl | isobutyl | methoxymethyl |
| 674 | | NH2 | F | H | o-Cl phenyl | isobutyl | methoxymethyl |
| 675 | | NH2 | F | H | m-Br Phenyl | isobutyl | methoxymethyl |
| 676 | | NH2 | F | H | p-Br Phenyl | isobutyl | methoxymethyl |
| 677 | | NH2 | F | H | o-Br Phenyl | isobutyl | methoxymethyl |
| 678 | | NH2 | F | H | CF3 | isobutyl | methoxymethyl |
| 679 | | NH2 | F | H | cyclopentyl | isobutyl | methoxymethyl |
| 680 | | NH2 | F | H | cyclohexyl | isobutyl | methoxymethyl |
| 681 | | NH2 | F | H | cyclobutyl | isobutyl | methoxymethyl |
| 682 | | NH2 | F | H | cyclopropyl | isobutyl | methoxymethyl |
| 683 | | NH2 | F | H | Phenyl | isobutyl | methoxymethyl |
| 684 | | NH2 | F | H | cyclopentylmethyl | isobutyl | methoxymethyl |
| 685 | | NH2 | F | H | cyclohexylmethyl | isobutyl | methoxymethyl |
| 686 | | NH2 | F | H | cyclobutylmethyl | isobutyl | methoxymethyl |

-continued

*[Structure: benzimidazole with substituents A, L, E, J at positions, N-Y, 2-X-P(=O)(OH)₂]*

| Table Compound No. | Synthetic Example No. | A | L | E | J¹ | Y | X² |
|---|---|---|---|---|---|---|---|
| 687 | | NH2 | F | H | cyclopropylmethyl | isobutyl | methoxymethyl |
| 688 | | NH2 | F | H | Et | neopentyl | 2,5-furanyl |
| 689 | | NH2 | F | H | Et | Ph | 2,5-furanyl |
| 690 | | NH2 | F | H | Et | isobutyl | *pentan-2-ol* |
| 691 | | NH2 | F | H | Et | isobutyl | *2-fluoropentyl* |
| 692 | | NH2 | F | H | Et | isobutyl | *2,2-difluoro-2-methylbutyl* |
| 693 | | NH2 | F | H | Et | isobutyl | *2-aminopentyl* |
| 694 | | NH2 | F | H | Et | isobutyl | CONHCH2 |
| 695 | | NH2 | F | H | Et | isobutyl | NHCOCH2 |
| 696 | | NH2 | F | Cl | Et | isobutyl | *pentan-2-ol* |
| 697 | | NH2 | F | Cl | Et | isobutyl | *2-fluoropentyl* |
| 698 | | NH2 | F | Cl | Et | isobutyl | *2-aminopentyl* |
| 699 | | NH2 | F | Cl | Et | isobutyl | *2,2-difluoro-2-methylbutyl* |
| 700 | | NH2 | F | Cl | Et | isobutyl | CONHCH2 |
| 701 | | NH2 | F | Cl | Et | isobutyl | NHCOCH2 |
| 702 | 13.4 | H | —(CH₂)₃— | | H | isobutyl | 2,5-furanyl |
| 703 | 13.3 | H | —(CH₂)₃— | | H | H | 2,5-furanyl |
| 704 | | H | H | | —(CH₂)₃— | 1,7-cyclohexyl | 2,5-furanyl |
| 705 | | Me | Me | Cl | Et | cyclopropylmethyl | 2,5-furanyl |
| 706 | | Me | Me | Cl | Cl | cyclopropylmethyl | 2,5-furanyl |
| 707 | | Me | Me | Cl | H | cyclopropylmethyl | methoxymethyl |
| 708 | | Me | Me | Cl | H | cyclopropylmethyl | *2,2-difluoro-2-methylbutyl* |
| 709 | | Me | Me | Cl | H | cyclopropylmethyl | *2-aminopentyl* |

-continued

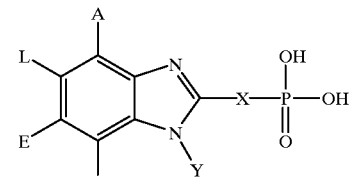

| Table Compound No. | Synthetic Example No. | A | L | E | J¹ | Y | X² |
|---|---|---|---|---|---|---|---|
| 710 | | Me | Me | Cl | H | cyclopropylmethyl | (2-fluoropentyl) |
| 711 | | Me | Me | Cl | H | cyclopropylmethyl | (4-hydroxypentan-2-yl) |
| 712 | | Me | Me | Cl | H | cyclopropylmethyl | NHCOCH2 |
| 713 | | Me | Me | Cl | H | cyclopropylmethyl | CONHCH2 |
| 714 | | Me | Me | Cl | H | Ph | 2,5-furanyl |
| 715 | | Me | Me | Cl | H | cyclobutylmethyl | 2,5-furanyl |
| 716 | | Me | Me | Cl | F | cyclopropylmethyl | 2,5-furanyl |
| 717 | | Me | Me | Cl | Pr | cyclopropylmethyl | 2,5-furanyl |
| 718 | | Me | Me | Cl | Bu | cyclopropylmethyl | 2,5-furanyl |
| 719 | | Me | Me | Cl | OMe | cyclopropylmethyl | 2,5-furanyl |
| 720 | | Me | Me | Cl | OEt | cyclopropylmethyl | 2,5-furanyl |
| 721 | | Me | Me | Cl | i-Pr | cyclopropylmethyl | 2,5-furanyl |
| 722 | | Me | Me | SMe | H | cyclopropylmethyl | 2,5-furanyl |
| 723 | | Me | Me | F | H | cyclopropylmethyl | 2,5-furanyl |
| 724 | | Me | Me | Me | H | cyclopropylmethyl | 2,5-furanyl |
| 725 | | Cl | Cl | Cl | H | cyclopropylmethyl | 2,5-furanyl |
| 726 | | Me | Cl | Cl | H | cyclopropylmethyl | 2,5-furanyl |
| 727 | | Cl | Me | Cl | H | cyclopropylmethyl | 2,5-furanyl |
| 728 | | Cl | Cl | Me | H | cyclopropylmethyl | 2,5-furanyl |
| 729 | 12.7 | NH2 | H | H | H | isobutyl | 2,5-furanyl |
| 730 | 12.41 | NH2 | H | H | H | 3-thienylmethyl | 2,5-furanyl |
| 731 | 12.43 | NH2 | H | H | H | 1-hydroxypropyl-3-yl | 2,5-furanyl |
| 732 | 13.34 | H | F | F | H | isobutyl | 2,5-furanyl |
| 733 | 13.55 | H | H | H | Me | neopentyl | 2,5-furanyl |
| 734 | 13.57 | H | Cl | H | H | cyclopropylmethyl | 2,5-furanyl |
| 735 | 13.61 | Me | Me | Cl | H | cyclopropylmethyl | 2,5-furanyl |
| 736 | 13.62 | H | H | Me | Me | isobutyl | 2,5-furanyl |
| 737 | 13.64 | H | F | H | Br | isobutyl | 2,5-furanyl |
| 738 | 13.65 | H | H | Cl | H | 3-methoxyphenyl | 2,5-furanyl |
| 739 | 13.66 | H | H | H | H | H | —C(O)NHCH2— |
| 740 | | Me | F | H | Br | isobutyl | 2,5-furanyl |
| 741 | | Me | F | H | H | isobutyl | 2,5-furanyl |
| 742 | | Me | F | H | Et | isobutyl | 2,5-furanyl |
| 743 | | Me | F | H | Cl | isobutyl | 2,5-furanyl |
| 744 | | Me | F | H | Me | isobutyl | 2,5-furanyl |
| 745 | | Me | F | H | Pr | isobutyl | 2,5-furanyl |
| 746 | | Me | F | H | i-Pr | isobutyl | 2,5-furanyl |
| 747 | | Me | F | H | Bu | isobutyl | 2,5-furanyl |
| 748 | | Me | F | H | i-Bu | isobutyl | 2,5-furanyl |
| 749 | | Me | F | H | OMe | isobutyl | 2,5-furanyl |
| 750 | | Me | F | H | OEt | isobutyl | 2,5-furanyl |
| 751 | | Me | F | H | SMe | isobutyl | 2,5-furanyl |
| 752 | | Me | F | H | SEt | isobutyl | 2,5-furanyl |
| 753 | | Me | F | H | NEt2 | isobutyl | 2,5-furanyl |
| 754 | | Me | F | H | NMe2 | isobutyl | 2,5-furanyl |
| 755 | | Me | F | H | I | isobutyl | 2,5-furanyl |
| 756 | | Me | F | H | m-OMePhenyl | isobutyl | 2,5-furanyl |
| 757 | | Me | F | H | o-OMephenyl | isobutyl | 2,5-furanyl |
| 758 | | Me | F | H | p-F Phenyl | isobutyl | 2,5-furanyl |
| 759 | | Me | F | H | o-F Phenyl | isobutyl | 2,5-furanyl |
| 760 | | Me | F | H | m-F Phenyl | isobutyl | 2,5-furanyl |
| 761 | | Me | F | H | 2-Furanyl | isobutyl | 2,5-furanyl |
| 762 | | Me | F | H | 2-thiophenyl | isobutyl | 2,5-furanyl |
| 763 | | Me | F | H | 2-Furanylmethyl | isobutyl | 2,5-furanyl |
| 764 | | Me | F | H | 2-Thiophenylmethyl | isobutyl | 2,5-furanyl |
| 765 | | Me | F | H | CN | isobutyl | 2,5-furanyl |
| 766 | | Me | F | H | m-Cl phenyl | isobutyl | 2,5-furanyl |
| 767 | | Me | F | H | p-Cl phenyl | isobutyl | 2,5-furanyl |
| 768 | | Me | F | H | o-Cl phenyl | isobutyl | 2,5-furanyl |

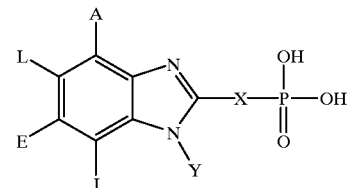

| Table Compound No. | Synthetic Example No. | A | L | E | J¹ | Y | X² |
|---|---|---|---|---|---|---|---|
| 769 | | Me | F | H | m-Br Phenyl | isobutyl | 2,5-furanyl |
| 770 | | Me | F | H | p-Br Phenyl | isobutyl | 2,5-furanyl |
| 771 | | Me | F | H | o-Br Phenyl | isobutyl | 2,5-furanyl |
| 773 | | Me | F | H | CF3 | isobutyl | 2,5-furanyl |
| 774 | | Me | F | H | cyclopentyl | isobutyl | 2,5-furanyl |
| 775 | | Me | F | H | cyclohexyl | isobutyl | 2,5-furanyl |
| 776 | | Me | F | H | cyclobutyl | isobutyl | 2,5-furanyl |
| 777 | | Me | F | H | cyclopropyl | isobutyl | 2,5-furanyl |
| 778 | | Me | F | H | Phenyl | isobutyl | 2,5-furanyl |
| 779 | | Me | F | H | cyclopentylmethyl | isobutyl | 2,5-furanyl |
| 780 | | Me | F | H | cyclohexylmethyl | isobutyl | 2,5-furanyl |
| 781 | | Me | F | H | cyclobutylmethyl | isobutyl | 2,5-furanyl |
| 782 | | Me | F | H | cyclopropylmethyl | isobutyl | 2,5-furanyl |
| 783 | | H | F | H | Br | isobutyl | 2,5-furanyl |
| 784 | | H | F | H | H | isobutyl | 2,5-furanyl |
| 785 | | H | F | H | Et | isobutyl | 2,5-furanyl |
| 786 | | H | F | H | Cl | isobutyl | 2,5-furanyl |
| 787 | | H | F | H | Me | isobutyl | 2,5-furanyl |
| 788 | | H | F | H | Pr | isobutyl | 2,5-furanyl |
| 789 | | H | F | H | i-Pr | isobutyl | 2,5-furanyl |
| 790 | | H | F | H | Bu | isobutyl | 2,5-furanyl |
| 791 | | H | F | H | i-Bu | isobutyl | 2,5-furanyl |
| 792 | | H | F | H | OMe | isobutyl | 2,5-furanyl |
| 793 | | H | F | H | OEt | isobutyl | 2,5-furanyl |
| 794 | | H | F | H | SMe | isobutyl | 2,5-furanyl |
| 795 | | H | F | H | SEt | isobutyl | 2,5-furanyl |
| 796 | | H | F | H | NEt2 | isobutyl | 2,5-furanyl |
| 797 | | H | F | H | NMe2 | isobutyl | 2,5-furanyl |
| 798 | | H | F | H | I | isobutyl | 2,5-furanyl |
| 799 | | H | F | H | m-OMePhenyl | isobutyl | 2,5-furanyl |
| 800 | | H | F | H | o-OMePhenyl | isobutyl | 2,5-furanyl |
| 801 | | H | F | H | p-F Phenyl | isobutyl | 2,5-furanyl |
| 802 | | H | F | H | o-F Phenyl | isobutyl | 2,5-furanyl |
| 803 | | H | F | H | m-F Phenyl | isobutyl | 2,5-furanyl |
| 804 | | H | F | H | 2-Furanyl | isobutyl | 2,5-furanyl |
| 805 | | H | F | H | 2-thiophenyl | isobutyl | 2,5-furanyl |
| 806 | | H | F | H | 2-Furanylmethyl | isobutyl | 2,5-furanyl |
| 807 | | H | F | H | 2-Thiophenylmethyl | isobutyl | 2,5-furanyl |
| 808 | | H | F | H | CN | isobutyl | 2,5-furanyl |
| 809 | | H | F | H | m-Cl phenyl | isobutyl | 2,5-furanyl |
| 810 | | H | F | H | p-Cl phenyl | isobutyl | 2,5-furanyl |
| 811 | | H | F | H | o-Cl phenyl | isobutyl | 2,5-furanyl |
| 812 | | H | F | H | m-Br Phenyl | isobutyl | 2,5-furanyl |
| 813 | | H | F | H | p-Br Phenyl | isobutyl | 2,5-furanyl |
| 814 | | H | F | H | o-Br Phenyl | isobutyl | 2,5-furanyl |
| 815 | | H | F | H | CF3 | isobutyl | 2,5-furanyl |
| 816 | | H | F | H | cyclopentyl | isobutyl | 2,5-furanyl |
| 817 | | H | F | H | cyclohexyl | isobutyl | 2,5-furanyl |
| 818 | | H | F | H | cyclobutyl | isobutyl | 2,5-furanyl |
| 819 | | H | F | H | cyclopropyl | isobutyl | 2,5-furanyl |
| 820 | | H | F | H | Phenyl | isobutyl | 2,5-furanyl |
| 821 | | H | F | H | cyclopentylmethyl | isobutyl | 2,5-furanyl |
| 822 | | H | F | H | cyclohexylmethyl | isobutyl | 2,5-furanyl |
| 823 | | H | F | H | cyclobutylmethyl | isobutyl | 2,5-furanyl |
| 824 | | H | F | H | cyclopropylmethyl | isobutyl | 2,5-furanyl |
| 825 | | Cl | F | H | Br | isobutyl | 2,5-furanyl |
| 826 | | Cl | F | H | H | isobutyl | 2,5-furanyl |
| 827 | | Cl | F | H | Et | isobutyl | 2,5-furanyl |
| 828 | | Cl | F | H | Cl | isobutyl | 2,5-furanyl |
| 829 | | Cl | F | H | Me | isobutyl | 2,5-furanyl |
| 830 | | Cl | F | H | Pr | isobutyl | 2,5-furanyl |
| 831 | | Cl | F | H | i-Pr | isobutyl | 2,5-furanyl |
| 832 | | Cl | F | H | Bu | isobutyl | 2,5-furanyl |
| 833 | | Cl | F | H | i-Bu | isobutyl | 2,5-furanyl |
| 834 | | Cl | F | H | OMe | isobutyl | 2,5-furanyl |
| 835 | | Cl | F | H | OEt | isobutyl | 2,5-furanyl |
| 836 | | Cl | F | H | SMe | isobutyl | 2,5-furanyl |

-continued

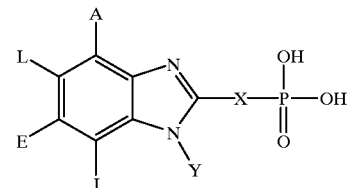

| Table Compound No. | Synthetic Example No. | A | L | E | J¹ | Y | X² |
|---|---|---|---|---|---|---|---|
| 837 | | Cl | F | H | SEt | isobutyl | 2,5-furanyl |
| 838 | | Cl | F | H | NEt2 | isobutyl | 2,5-furanyl |
| 839 | | Cl | F | H | NMe2 | isobutyl | 2,5-furanyl |
| 840 | | Cl | F | H | I | isobutyl | 2,5-furanyl |
| 841 | | Cl | F | H | m-OMePhenyl | isobutyl | 2,5-furanyl |
| 842 | | Cl | F | H | o-OMePhenyl | isobutyl | 2,5-furanyl |
| 843 | | Cl | F | H | p-F Phenyl | isobutyl | 2,5-furanyl |
| 844 | | Cl | F | H | o-F Phenyl | isobutyl | 2,5-furanyl |
| 845 | | Cl | F | H | m-F Phenyl | isobutyl | 2,5-furanyl |
| 846 | | Cl | F | H | 2-Furanyl | isobutyl | 2,5-furanyl |
| 847 | | Cl | F | H | 2-thiophenyl | isobutyl | 2,5-furanyl |
| 848 | | Cl | F | H | 2-Furanylmethyl | isobutyl | 2,5-furanyl |
| 849 | | Cl | F | H | 2-Thiophenylmethyl | isobutyl | 2,5-furanyl |
| 850 | | Cl | F | H | CN | isobutyl | 2,5-furanyl |
| 851 | | Cl | F | H | m-Cl phenyl | isobutyl | 2,5-furanyl |
| 852 | | Cl | F | H | p-Cl phenyl | isobutyl | 2,5-furanyl |
| 853 | | Cl | F | H | o-Cl phenyl | isobutyl | 2 5-furanyl |
| 854 | | Cl | F | H | m-Br Phenyl | isobutyl | 2,5-furanyl |
| 855 | | Cl | F | H | p-Br Phenyl | isobutyl | 2,5-furanyl |
| 856 | | Cl | F | H | o-Br Phenyl | isobutyl | 2,5-furanyl |
| 857 | | Cl | F | H | CF3 | isobutyl | 2,5-furanyl |
| 858 | | Cl | F | H | cyclopentyl | isobutyl | 2,5-furanyl |
| 859 | | Cl | F | H | cyclohexyl | isobutyl | 2,5-furanyl |
| 860 | | Cl | F | H | cyclobutyl | isobutyl | 2,5-furanyl |
| 861 | | Cl | F | H | cyclopropyl | isobutyl | 2,5-furanyl |
| 862 | | Cl | F | H | Phenyl | isobutyl | 2,5-furanyl |
| 883 | | Cl | F | H | cyclopentylmethyl | isobutyl | 2,5-furanyl |
| 864 | | Cl | F | H | cyclohexylmethyl | isobutyl | 2,5-furanyl |
| 885 | | Cl | F | H | cyclobutylmethyl | isobutyl | 2,5-furanyl |
| 866 | | Cl | F | H | cyclopropylmethyl | isobutyl | 2,5-furanyl |
| 867 | | Cl | F | H | Br | isobutyl | methoxymethyl |
| 868 | | Cl | F | H | H | isobutyl | methoxymethyl |
| 869 | | Cl | F | H | Et | isobutyl | methoxymethyl |
| 870 | | Cl | F | H | Cl | isobutyl | methoxymethyl |
| 871 | | Cl | F | H | Me | isobutyl | methoxymethyl |
| 872 | | Cl | F | H | Pr | isobutyl | methoxymethyl |
| 873 | | Cl | F | H | i-Pr | isobutyl | methoxymethyl |
| 874 | | Cl | F | H | Bu | isobutyl | methoxymethyl |
| 875 | | Cl | F | H | i-Bu | isobutyl | methoxymethyl |
| 876 | | Cl | F | H | OMe | isobutyl | methoxymethyl |
| 877 | | Cl | F | H | OEt | isobutyl | methoxymethyl |
| 878 | | Cl | F | H | SMe | isobutyl | methoxymethyl |
| 879 | | Cl | F | H | SEt | isobutyl | methoxymethyl |
| 880 | | Cl | F | H | NEt2 | isobutyl | methoxymethyl |
| 881 | | Cl | F | H | NMe2 | isobutyl | methoxymethyl |
| 882 | | Cl | F | H | I | isobutyl | methoxymethyl |
| 883 | | Cl | F | H | m-OMePhenyl | isobutyl | methoxymethyl |
| 884 | | Cl | F | H | o-OMePhenyl | isobutyl | methoxymethyl |
| 885 | | Cl | F | H | p-F Phenyl | isobutyl | methoxymethyl |
| 886 | | Cl | F | H | o-F Phenyl | isobutyl | methoxymethyl |
| 887 | | Cl | F | H | m-F Phenyl | isobutyl | methoxymethyl |
| 888 | | Cl | F | H | 2-Furanyl | isobutyl | methoxymethyl |
| 889 | | Cl | F | H | 2-thiophenyl | isobutyl | methoxymethyl |
| 890 | | Cl | F | H | 2-Furanylmethyl | isobutyl | methoxymethyl |
| 891 | | Cl | F | H | 2-Thiophenylmethyl | isobutyl | methoxymethyl |
| 892 | | Cl | F | H | CN | isobutyl | methoxymethyl |
| 893 | | Cl | F | H | m-Cl phenyl | isobutyl | methoxymethyl |
| 894 | | Cl | F | H | p-Cl phenyl | isobutyl | methoxymethyl |
| 895 | | Cl | F | H | o-Cl phenyl | isobutyl | methoxymethyl |
| 896 | | Cl | F | H | m-Br Phenyl | isobutyl | methoxymethyl |
| 897 | | Cl | F | H | p-Br Phenyl | isobutyl | methoxymethyl |
| 898 | | Cl | F | H | o-Br Phenyl | isobutyl | methoxymethyl |
| 899 | | Cl | F | H | CF3 | isobutyl | methoxymethyl |
| 900 | | Cl | F | H | cyclopentyl | isobutyl | methoxymethyl |
| 901 | | Cl | F | H | cyclohexyl | isobutyl | methoxymethyl |
| 902 | | Cl | F | H | cyclobutyl | isobutyl | methoxymethyl |
| 903 | | Cl | F | H | cyclopropyl | isobutyl | methoxymethyl |

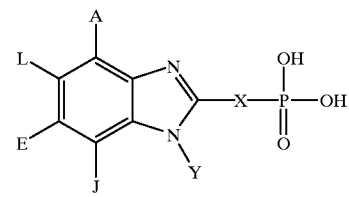

| Table Compound No. | Synthetic Example No. | A | L | E | J¹ | Y | X² |
|---|---|---|---|---|---|---|---|
| 904 | | Cl | F | H | Phenyl | isobutyl | methoxymethyl |
| 905 | | Cl | F | H | cyclopentylmethyl | isobutyl | methoxymethyl |
| 906 | | Cl | F | H | cyclohexylmethyl | isobutyl | methoxymethyl |
| 907 | | Cl | F | H | cyclobutylmethyl | isobutyl | methoxymethyl |
| 908 | | Cl | F | H | cyclopropylmethyl | isobutyl | methoxymethyl |
| 909 | | H | F | H | Br | isobutyl | methoxymethyl |
| 910 | | H | F | H | H | isobutyl | methoxymethyl |
| 911 | | H | F | H | Et | isobutyl | methoxymethyl |
| 912 | | H | F | H | Cl | isobutyl | methoxymethyl |
| 913 | | H | F | H | Me | isobutyl | methoxymethyl |
| 914 | | H | F | H | Pr | isobutyl | methoxymethyl |
| 915 | | H | F | H | i-Pr | isobutyl | methoxymethyl |
| 916 | | H | F | H | Bu | isobutyl | methoxymethyl |
| 917 | | H | F | H | i-Bu | isobutyl | methoxymethyl |
| 918 | | H | F | H | OMe | isobutyl | methoxymethyl |
| 919 | | H | F | H | OEt | isobutyl | methoxymethyl |
| 920 | | H | F | H | SMe | isobutyl | methoxymethyl |
| 921 | | H | F | H | SEt | isobutyl | methoxymethyl |
| 922 | | H | F | H | NEt2 | isobutyl | methoxymethyl |
| 923 | | H | F | H | NMe2 | isobutyl | methoxymethyl |
| 924 | | H | F | H | I | isobutyl | methoxymethyl |
| 925 | | H | F | H | m-OMePhenyl | isobutyl | methoxymethyl |
| 926 | | H | F | H | o-OMePhenyl | isobutyl | methoxymethyl |
| 927 | | H | F | H | p-F Phenyl | isobutyl | methoxymethyl |
| 928 | | H | F | H | o-F Phenyl | isobutyl | methoxymethyl |
| 929 | | H | F | H | m-F Phenyl | isobutyl | methoxymethyl |
| 930 | | H | F | H | 2-Furanyl | isobutyl | methoxymethyl |
| 931 | | H | F | H | 2-thiophenyl | isobutyl | methoxymethyl |
| 932 | | H | F | H | 2-Furanylmethyl | isobutyl | methoxymethyl |
| 933 | | H | F | H | 2-Thiophenylmethyl | isobutyl | methoxymethyl |
| 934 | | H | F | H | CN | isobutyl | methoxymethyl |
| 935 | | H | F | H | m-Cl phenyl | isobutyl | methoxymethyl |
| 936 | | H | F | H | p-Cl phenyl | isobutyl | methoxymethyl |
| 937 | | H | F | H | o-Cl phenyl | isobutyl | methoxymethyl |
| 938 | | H | F | H | m-Br Phenyl | isobutyl | methoxymethyl |
| 939 | | H | F | H | p-Br Phenyl | isobutyl | methoxymethyl |
| 940 | | H | F | H | o-Br Phenyl | isobutyl | methoxymethyl |
| 941 | | H | F | H | CF3 | isobutyl | methoxymethyl |
| 942 | | H | F | H | cyclopentyl | isobutyl | methoxymethyl |
| 943 | | H | F | H | cyclohexyl | isobutyl | methoxymethyl |
| 944 | | H | F | H | cyclobutyl | isobutyl | methoxymethyl |
| 945 | | H | F | H | cyclopropyl | isobutyl | methoxymethyl |
| 946 | | H | F | H | Phenyl | isobutyl | methoxymethyl |
| 947 | | H | F | H | cyclopentylmethyl | isobutyl | methoxymethyl |
| 948 | | H | F | H | cyclohexylmethyl | isobutyl | methoxymethyl |
| 949 | | H | F | H | cyclobutylmethyl | isobutyl | methoxymethyl |
| 950 | | H | F | H | cyclopropylmethyl | isobutyl | methoxymethyl |
| 951 | | Me | F | H | Br | isobuyt | methoxymethyl |
| 952 | | Me | F | H | H | isobutyl | methoxymethyl |
| 953 | | Me | F | H | Et | isobutyl | methoxymethyl |
| 954 | | Me | F | H | Cl | isobutyl | methoxymethyl |
| 955 | | Me | F | H | Me | isobutyl | methoxymethyl |
| 956 | | Me | F | H | Pr | isobutyl | methoxymethyl |
| 957 | | Me | F | H | i-Pr | isobutyl | methoxymethyl |
| 958 | | Me | F | H | Bu | isobutyl | methoxymethyl |
| 959 | | Me | F | H | i-Bu | isobutyl | methoxymethyl |
| 960 | | Me | F | H | OMe | isobutyl | methoxymethyl |
| 961 | | Me | F | H | OEt | isobutyl | methoxymethyl |
| 962 | | Me | F | H | SMe | isobutyl | methoxymethyl |
| 963 | | Me | F | H | SEt | isobutyl | methoxymethyl |
| 964 | | Me | F | H | NEt2 | isobutyl | methoxymethyl |
| 965 | | Me | F | H | NMe2 | isobutyl | methoxymethyl |
| 966 | | Me | F | H | I | isobutyl | methoxymethyl |
| 967 | | Me | F | H | m-OMePhenyl | isobutyl | methoxymethyl |
| 968 | | Me | F | H | o-OMePhenyl | isobutyl | methoxymethyl |
| 969 | | Me | F | H | p-F Phenyl | isobutyl | methoxymethyl |
| 970 | | Me | F | H | o-F Phenyl | isobutyl | methoxymethyl |

-continued

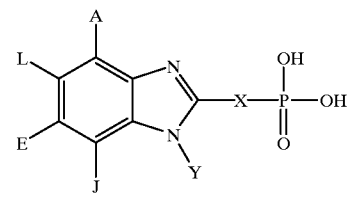

| Table Compound No. | Synthetic Example No. | A | L | E | J¹ | Y | X² |
|---|---|---|---|---|---|---|---|
| 971 | | Me | F | H | m-F Phenyl | isobutyl | methoxymethyl |
| 972 | | Me | F | H | 2-Furanyl | isobutyl | methoxymethyl |
| 973 | | Me | F | H | 2-thiophenyl | isobutyl | methoxymethyl |
| 974 | | Me | F | H | 2-Furanylmethyl | isobutyl | methoxymethyl |
| 975 | | Me | F | H | 2-Thiophenylmethyl | isobutyl | methoxymethyl |
| 976 | | Me | F | H | CN | isobutyl | methoxymethyl |
| 977 | | Me | F | H | m-Cl phenyl | isobutyl | methoxymethyl |
| 978 | | Me | F | H | p-Cl phenyl | isobutyl | methoxymethyl |
| 979 | | Me | F | H | o-Cl phenyl | isobutyl | methoxymethyl |
| 980 | | Me | F | H | m-Br Phenyl | isobutyl | methoxymethyl |
| 981 | | Me | F | H | p-Br Phenyl | isobutyl | methoxymethyl |
| 982 | | Me | F | H | o-Br Phenyl | isobutyl | methoxymethyl |
| 983 | | Me | F | H | CF3 | isobutyl | methoxymethyl |
| 984 | | Me | F | H | cyclopentyl | isobutyl | methoxymethyl |
| 985 | | Me | F | H | cyclohexyl | isobutyl | methoxymethyl |
| 986 | | Me | F | H | cyclobutyl | isobutyl | methoxymethyl |
| 987 | | Me | F | H | cyclopropyl | isobutyl | methoxymethyl |
| 988 | | Me | F | H | Phenyl | isobutyl | methoxymethyl |
| 989 | | Me | F | H | cyclopentylmethyl | isobutyl | methoxymethyl |
| 990 | | Me | F | H | cyclohexylmethyl | isobutyl | methoxymethyl |
| 991 | | Me | F | H | cyclobutylmethyl | isobutyl | methoxymethyl |
| 992 | | Me | F | H | cyclopropylmethyl | isobutyl | methoxymethyl |
| 993 | | Me | F | H | Br | isobutyl | CONHCH2 |
| 994 | | Me | F | H | H | isobutyl | CONHCH2 |
| 995 | | Me | F | H | Et | isobutyl | CONHCH2 |
| 996 | | Me | F | H | Cl | isobutyl | CONHCH2 |
| 997 | | Me | F | H | Me | isobutyl | CONHCH2 |
| 998 | | Me | F | H | Pr | isobutyl | CONHCH2 |
| 999 | | Me | F | H | i-Pr | isobutyl | CONHCH2 |
| 1000 | | Me | F | H | Bu | isobutyl | CONHCH2 |
| 1001 | | Me | F | H | i-Bu | isobutyl | CONHCH2 |
| 1002 | | Me | F | H | OMe | isobutyl | CONHCH2 |
| 1003 | | Me | F | H | OEt | isobutyl | CONHCH2 |
| 1004 | | Me | F | H | SMe | isobutyl | CONHCH2 |
| 1005 | | Me | F | H | SEt | isobutyl | CONHCH2 |
| 1006 | | Me | F | H | NEt2 | isobutyl | CONHCH2 |
| 1007 | | Me | F | H | NMe2 | isobutyl | CONHCH2 |
| 1008 | | Me | F | H | I | isobutyl | CONHCH2 |
| 1009 | | Me | F | H | m-OMePhenyl | isobutyl | CONHCH2 |
| 1010 | | Me | F | H | o-OMePhenyl | isobutyl | CONHCH2 |
| 1011 | | Me | F | H | p-F Phenyl | isobutyl | CONHCH2 |
| 1012 | | Me | F | H | o-F Phenyl | isobutyl | CONHCH2 |
| 1013 | | Me | F | H | m-F Phenyl | isobutyl | CONHCH2 |
| 1014 | | Me | F | H | 2-Furanyl | isobutyl | CONHCH2 |
| 1015 | | Me | F | H | 2-thiophenyl | isobutyl | CONHCH2 |
| 1016 | | Me | F | H | 2-Furanylmethyl | isobutyl | CONHCH2 |
| 1017 | | Me | F | H | 2-Thiophenylmethyl | isobutyl | CONHCH2 |
| 1018 | | Me | F | H | CN | isobutyl | CONHCH2 |
| 1019 | | Me | F | H | m-Cl phenyl | isobutyl | CONHCH2 |
| 1020 | | Me | F | H | p-Cl phenyl | isobutyl | CONHCH2 |
| 1021 | | Me | F | H | o-Cl phenyl | isobutyl | CONHCH2 |
| 1022 | | Me | F | H | m-Br Phenyl | isobutyl | CONHCH2 |
| 1023 | | Me | F | H | p-Br Phenyl | isobutyl | CONHCH2 |
| 1024 | | Me | F | H | o-Br Phenyl | isobutyl | CONHCH2 |
| 1025 | | Me | F | H | CF3 | isobutyl | CONHCH2 |
| 1026 | | Me | F | H | cyclopentyl | isobutyl | CONHCH2 |
| 1027 | | Me | F | H | cyclohexyl | isobutyl | CONHCH2 |
| 1028 | | Me | F | H | cyclobutyl | isobutyl | CONHCH2 |
| 1029 | | Me | F | H | cyclopropyl | isobutyl | CONHCH2 |
| 1030 | | Me | F | H | Phenyl | isobutyl | CONHCH2 |
| 1031 | | Me | F | H | cyclopentylmethyl | isobutyl | CONHCH2 |
| 1032 | | Me | F | H | cyclohexylmethyl | isobutyl | CONHCH2 |
| 1033 | | Me | F | H | cyclobutylmethyl | isobutyl | CONHCH2 |
| 1034 | | Me | F | H | cyclopropylmethyl | isobutyl | CONHCH2 |
| 1035 | | H | F | H | Br | isobutyl | CONHCH2 |
| 1036 | | H | F | H | H | isobutyl | CONHCH2 |
| 1037 | | H | F | H | Et | isobutyl | CONHCH2 |

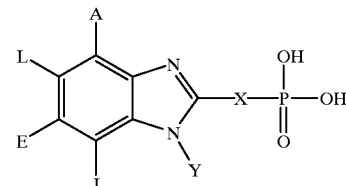

| Table Compound No. | Synthetic Example No. | A | L | E | J$^1$ | Y | X$^2$ |
|---|---|---|---|---|---|---|---|
| 1038 | | H | F | H | Cl | isobutyl | CONHCH2 |
| 1039 | | H | F | H | Me | isobutyl | CONHCH2 |
| 1040 | | H | F | H | Pr | isobutyl | CONHCH2 |
| 1041 | | H | F | H | i-Pr | isobutyl | CONHCH2 |
| 1042 | | H | F | H | Bu | isobutyl | CONHCH2 |
| 1043 | | H | F | H | i-Bu | isobutyl | CONHCH2 |
| 1044 | | H | F | H | OMe | isobutyl | CONHCH2 |
| 1045 | | H | F | H | OEt | isobutyl | CONHCH2 |
| 1046 | | H | F | H | SMe | isobutyl | CONHCH2 |
| 1047 | | H | F | H | SEt | isobutyl | CONHCH2 |
| 1048 | | H | F | H | NEt2 | isobutyl | CONHCH2 |
| 1049 | | H | F | H | NMe2 | isobutyl | CONHCH2 |
| 1050 | | H | F | H | I | isobutyl | CONHCH2 |
| 1051 | | H | F | H | m-OMePhenyl | isobutyl | CONHCH2 |
| 1052 | | H | F | H | o-OMePhenyl | isobutyl | CONHCH2 |
| 1053 | | H | F | H | p-F phenyl | isobutyl | CONHCH2 |
| 1054 | | H | F | H | o-F Phenyl | isobutyl | CONHCH2 |
| 1055 | | H | F | H | m-F Phenyl | isobutyl | CONHCH2 |
| 1056 | | H | F | H | 2-Furanyl | isobutyl | CONHCH2 |
| 1057 | | H | F | H | 2-thiophenyl | isobutyl | CONHCH2 |
| 1058 | | H | F | H | 2-Furanylmethyl | isobutyl | CONHCH2 |
| 1059 | | H | F | H | 2-Thiophenylmethyl | isobutyl | CONHCH2 |
| 1060 | | H | F | H | CN | isobutyl | CONHCH2 |
| 1061 | | H | F | H | m-Cl phenyl | isobutyl | CONHCH2 |
| 1062 | | H | F | H | p-Cl phenyl | isobutyl | CONHCH2 |
| 1063 | | H | F | H | o-Cl phenyl | isobutyl | CONHCH2 |
| 1064 | | H | F | H | m-Br Phenyl | isobutyl | CONHCH2 |
| 1065 | | H | F | H | p-Br Phenyl | isobutyl | CONHCH2 |
| 1066 | | H | F | H | o-Br Phenyl | isobutyl | CONHCH2 |
| 1067 | | H | F | H | CF3 | isobutyl | CONHCH2 |
| 1068 | | H | F | H | cyclopentyl | isobutyl | CONHCH2 |
| 1069 | | H | F | H | cyclohexyl | isobutyl | CONHCH2 |
| 1070 | | H | F | H | cyclobutyl | isobutyl | CONHCH2 |
| 1071 | | H | F | H | cyclopropyl | isobutyl | CONHCH2 |
| 1072 | | H | F | H | Phenyl | isobutyl | CONHCH2 |
| 1073 | | H | F | H | cyclopentylmethyl | isobutyl | CONHCH2 |
| 1074 | | H | F | H | cyclohexylmethyl | isobutyl | CONHCH2 |
| 1075 | | H | F | H | cyclobutylmethyl | isobutyl | CONHCH2 |
| 1076 | | H | F | H | cyclopropylmethyl | isobutyl | CONHCH2 |
| 1077 | | Cl | F | H | Br | isobutyl | CONHCH2 |
| 1078 | | Cl | F | H | H | isobutyl | CONHCH2 |
| 1079 | | Cl | F | H | Et | isobutyl | CONHCH2 |
| 1080 | | Cl | F | H | Cl | isobutyl | CONHCH2 |
| 1081 | | Cl | F | H | Me | isobutyl | CONHCH2 |
| 1082 | | Cl | F | H | Pr | isobutyl | CONHCH2 |
| 1083 | | Cl | F | H | i-Pr | isobutyl | CONHCH2 |
| 1084 | | Cl | F | H | Bu | isobutyl | CONHCH2 |
| 1085 | | Cl | F | H | i-Bu | isobutyl | CONHCH2 |
| 1086 | | Cl | F | H | OMe | isobutyl | CONHCH2 |
| 1087 | | Cl | F | H | OEt | isobutyl | CONHCH2 |
| 1088 | | Cl | F | H | SMe | isobutyl | CONHCH2 |
| 1089 | | Cl | F | H | SEt | isobutyl | CONHCH2 |
| 1090 | | Cl | F | H | NEt2 | isobutyl | CONHCH2 |
| 1091 | | Cl | F | H | NMe2 | isobutyl | CONHCH2 |
| 1092 | | Cl | F | H | I | isobutyl | CONHCH2 |
| 1093 | | Cl | F | H | m-OMePhenyl | isobutyl | CONHCH2 |
| 1094 | | Cl | F | H | o-OMePhenyl | isobutyl | CONHCH2 |
| 1095 | | Cl | F | H | p-F Phenyl | isobutyl | CONHCH2 |
| 1096 | | Cl | F | H | o-F Phenyl | isobutyl | CONHCH2 |
| 1097 | | Cl | F | H | m-F Phenyl | isobutyl | CONHCH2 |
| 1098 | | Cl | F | H | 2-Furanyl | isobutyl | CONHCH2 |
| 1099 | | Cl | F | H | 2-thiophenyl | isobutyl | CONHCH2 |
| 1100 | | Cl | F | H | 2-Furanylmethyl | isobutyl | CONHCH2 |
| 1101 | | Cl | F | H | 2-Thiophenylmethyl | isobutyl | CONHCH2 |
| 1102 | | Cl | F | H | CN | isobutyl | CONHCH2 |
| 1103 | | Cl | F | H | m-Cl phenyl | isobutyl | CONHCH2 |
| 1104 | | Cl | F | H | p-Cl phenyl | isobutyl | CONHCH2 |

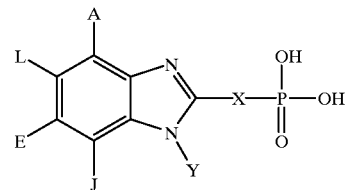

| Table Compound No. | Synthetic Example No. | A | L | E | J¹ | Y | X² |
|---|---|---|---|---|---|---|---|
| 1105 | | Cl | F | H | o-Cl phenyl | isobutyl | CONHCH2 |
| 1106 | | Cl | F | H | m-Br Phenyl | isobutyl | CONHCH2 |
| 1107 | | Cl | F | H | p-Br Phenyl | isobutyl | CONHCH2 |
| 1108 | | Cl | F | H | o-Br Phenyl | isobutyl | CONHCH2 |
| 1109 | | Cl | F | H | CF3 | isobutyl | CONHCH2 |
| 1110 | | Cl | F | H | cyclopentyl | isobutyl | CONHCH2 |
| 1111 | | Cl | F | H | cyclohexyl | isobutyl | CONHCH2 |
| 1112 | | Cl | F | H | cyclobutyl | isobutyl | CONHCH2 |
| 1113 | | Cl | F | H | cyclopropyl | isobutyl | CONHCH2 |
| 1114 | | Cl | F | H | Phenyl | isobutyl | CONHCH2 |
| 1115 | | Cl | F | H | cyclopentylmethyl | isobutyl | CONHCH2 |
| 1116 | | Cl | F | H | cyclohexylmethyl | isobutyl | CONHCH2 |
| 1117 | | Cl | F | H | cyclobutylmethyl | isobutyl | CONHCH2 |
| 1118 | | Cl | F | H | cyclopropylmethyl | isobutyl | CONHCH2 |
| 1119 | | Me | F | H | Br | isobutyl | NHCOCH2 |
| 1120 | | Me | F | H | H | isobutyl | NHCOCH2 |
| 1121 | | Me | F | H | Et | isobutyl | NHCOCH2 |
| 1122 | | Me | F | H | Cl | isobutyl | NHCOCH2 |
| 1123 | | Me | F | H | Me | isobutyl | NHCOCH2 |
| 1124 | | Me | F | H | Pr | isobutyl | NHCOCH2 |
| 1125 | | Me | F | H | i-Pr | isobutyl | NHCOCH2 |
| 1126 | | Me | F | H | Bu | isobutyl | NHCOCH2 |
| 1127 | | Me | F | H | i-Bu | isobutyl | NHCOCH2 |
| 1128 | | Me | F | H | OMe | isobutyl | NHCOCH2 |
| 1129 | | Me | F | H | OEt | isobutyl | NHCOCH2 |
| 1130 | | Me | F | H | SMe | isobutyl | NHCOCH2 |
| 1131 | | Me | F | H | SEt | isobutyl | NHCOCH2 |
| 1132 | | Me | F | H | NEt2 | isobutyl | NHCOCH2 |
| 1133 | | Me | F | H | NMe2 | isobutyl | NHCOCH2 |
| 1134 | | Me | F | H | I | isobutyl | NHCOCH2 |
| 1135 | | Me | F | H | m-OMePhenyl | isobutyl | NHCOCH2 |
| 1136 | | Me | F | H | o-OMePhenyl | isobutyl | NHCOCH2 |
| 1137 | | Me | F | H | p-F Phenyl | isobutyl | NHCOCH2 |
| 1138 | | Me | F | H | o-F Phenyl | isobutyl | NHCOCH2 |
| 1139 | | Me | F | H | m-F Phenyl | isobutyl | NHCOCH2 |
| 1140 | | Me | F | H | 2-Furanyl | isobutyl | NHCOCH2 |
| 1141 | | Me | F | H | 2-thiophenyl | isobutyl | NHCOCH2 |
| 1142 | | Me | F | H | 2-Furanylmethyl | isobutyl | NHCOCH2 |
| 1143 | | Me | F | H | 2-Thiophenylmethyl | isobutyl | NHCOCH2 |
| 1144 | | Me | F | H | CN | isobutyl | NHCOCH2 |
| 1145 | | Me | F | H | m-Cl phenyl | isobutyl | NHCOCH2 |
| 1146 | | Me | F | H | p-Cl phenyl | isobutyl | NHCOCH2 |
| 1147 | | Me | F | H | o-Cl phenyl | isobutyl | NHCOCH2 |
| 1148 | | Me | F | H | m-Br Phenyl | isobutyl | NHCOCH2 |
| 1149 | | Me | F | H | p-Br Phenyl | isobutyl | NHCOCH2 |
| 1150 | | Me | F | H | o-Br Phenyl | isobutyl | NHCOCH2 |
| 1151 | | Me | F | H | CF3 | isobutyl | NHCOCH2 |
| 1152 | | Me | F | H | cyclopentyl | isobutyl | NHCOCH2 |
| 1153 | | Me | F | H | cyclohexyl | isobutyl | NHCOCH2 |
| 1154 | | Me | F | H | cyclobutyl | isobutyl | NHCOCH2 |
| 1155 | | Me | F | H | cyclopropyl | isobutyl | NHCOCH2 |
| 1156 | | Me | F | H | Phenyl | isobutyl | NHCOCH2 |
| 1157 | | Me | F | H | cyclopentylmethyl | isobutyl | NHCOCH2 |
| 1158 | | Me | F | H | cyclohexylmethyl | isobutyl | NHCOCH2 |
| 1159 | | Me | F | H | cyclobutylmethyl | isobutyl | NHCOCH2 |
| 1160 | | Me | F | H | cyclopropylmethyl | isobutyl | NHCOCH2 |
| 1161 | | H | F | H | Br | isobutyl | NHCOCH2 |
| 1162 | | H | F | H | H | isobutyl | NHCOCH2 |
| 1163 | | H | F | H | Et | isobutyl | NHCOCH2 |
| 1164 | | H | F | H | Cl | isobutyl | NHCOCH2 |
| 1165 | | H | F | H | Me | isobutyl | NHCOCH2 |
| 1166 | | H | F | H | Pr | isobutyl | NHCOCH2 |
| 1167 | | H | F | H | i-Pr | isobutyl | NHCOCH2 |
| 1168 | | H | F | H | Bu | isobutyl | NHCOCH2 |
| 1169 | | H | F | H | i-Bu | isobutyl | NHCOCH2 |
| 1170 | | H | F | H | OMe | isobutyl | NHCOCH2 |
| 1171 | | H | F | H | OEt | isobutyl | NHCOCH2 |

-continued

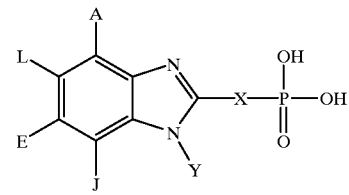

| Table Compound No. | Synthetic Example No. | A | L | E | J¹ | Y | X² |
|---|---|---|---|---|---|---|---|
| 1172 | | H | F | H | SMe | isobutyl | NHCOCH2 |
| 1173 | | H | F | H | SEt | isobutyl | NHCOCH2 |
| 1174 | | H | F | H | NEt2 | isobutyl | NHCOCH2 |
| 1175 | | H | F | H | NMe2 | isobutyl | NHCOCH2 |
| 1176 | | H | F | H | I | isobutyl | NHCOCH2 |
| 1177 | | H | F | H | m-OMePhenyl | isobutyl | NHCOCH2 |
| 1178 | | H | F | H | o-OMePhenyl | isobutyl | NHCOCH2 |
| 1179 | | H | F | H | p-F Phenyl | isobutyl | NHCOCH2 |
| 1180 | | H | F | H | o-F Phenyl | isobutyl | NHCOCH2 |
| 1181 | | H | F | H | m-F Phenyl | isobutyl | NHCOCH2 |
| 1182 | | H | F | H | 2-Furanyl | isobutyl | NHCOCH2 |
| 1183 | | H | F | H | 2-thiophenyl | isobutyl | NHCOCH2 |
| 1184 | | H | F | H | 2-Furanylmethyl | isobutyl | NHCOCH2 |
| 1185 | | H | F | H | 2-Thiophenylmethyl | isobutyl | NHCOCH2 |
| 1186 | | H | F | H | CN | isobutyl | NHCOCH2 |
| 1187 | | H | F | H | m-Cl phenyl | isobutyl | NHCOCH2 |
| 1188 | | H | F | H | p-Cl phenyl | isobutyl | NHCOCH2 |
| 1189 | | H | F | H | o-Cl phenyl | isobutyl | NHCOCH2 |
| 1190 | | H | F | H | m-Br Phenyl | isobutyl | NHCOCH2 |
| 1191 | | H | F | H | p-Br Phenyl | isobutyl | NHCOCH2 |
| 1192 | | H | F | H | o-Br Phenyl | isobutyl | NHCOCH2 |
| 1193 | | H | F | H | CF3 | isobutyl | NHCOCH2 |
| 1194 | | H | F | H | cyclopentyl | isobutyl | NHCOCH2 |
| 1195 | | H | F | H | cyclohexyl | isobutyl | NHCOCH2 |
| 1196 | | H | F | H | cyclobutyl | isobutyl | NHCOCH2 |
| 1197 | | H | F | H | cyclopropyl | isobutyl | NHCOCH2 |
| 1198 | | H | F | H | Phenyl | isobutyl | NHCOCH2 |
| 1199 | | H | F | H | cyclopentylmethyl | isobutyl | NHCOCH2 |
| 1200 | | H | F | H | cyclohexylmethyl | isobutyl | NHCOCH2 |
| 1201 | | H | F | H | cyclobutylmethyl | isobutyl | NHCOCH2 |
| 1202 | | H | F | H | cyclopropylmethyl | isobutyl | NHCOCH2 |
| 1203 | | Cl | F | H | Br | isobutyl | NHCOCH2 |
| 1294 | | Cl | F | H | H | isobutyl | NHCOCH2 |
| 1205 | | Cl | F | H | Et | isobutyl | NHCOCH2 |
| 1206 | | Cl | F | H | Cl | isobutyl | NHCOCH2 |
| 1207 | | Cl | F | H | Me | isobutyl | NHCOCH2 |
| 1208 | | Cl | F | H | Pr | isobutyl | NHCOCH2 |
| 1209 | | Cl | F | H | i-Pr | isobutyl | NHCOCH2 |
| 1210 | | Cl | F | H | Bu | isobutyl | NHCOCH2 |
| 1211 | | Cl | F | H | i-Bu | isobutyl | NHCOCH2 |
| 1212 | | Cl | F | H | OMe | isobutyl | NHCOCH2 |
| 1213 | | Cl | F | H | OEt | isobutyl | NHCOCH2 |
| 1214 | | Cl | F | H | SMe | isobutyl | NHCOCH2 |
| 1215 | | Cl | F | H | SEt | isobutyl | NHCOCH2 |
| 1216 | | Cl | F | H | NEt2 | isobutyl | NHCOCH2 |
| 1217 | | Cl | F | H | NMe2 | isobutyl | NHCOCH2 |
| 1218 | | Cl | F | H | I | isobutyl | NHCOCH2 |
| 1219 | | Cl | F | H | m-OMePhenyl | isobutyl | NHCOCH2 |
| 1220 | | Cl | F | H | o-OMePhenyl | isobutyl | NHCOCH2 |
| 1221 | | Cl | F | H | p-F Phenyl | isobutyl | NHCOCH2 |
| 1222 | | Cl | F | H | o-F Phenyl | isobutyl | NHCOCH2 |
| 1223 | | Cl | F | H | m-F Phenyl | isobutyl | NHCOCH2 |
| 1224 | | Cl | F | H | 2-Furanyl | isobutyl | NHCOCH2 |
| 1225 | | Cl | F | H | 2-thiophenyl | isobutyl | NHCOCH2 |
| 1226 | | Cl | F | H | 2-Furanylmethyl | isobutyl | NHCOCH2 |
| 1227 | | Cl | F | H | 2-Thiophenylmethyl | isobutyl | NHCOCH2 |
| 1228 | | Cl | F | H | CN | isobutyl | NHCOCH2 |
| 1229 | | Cl | F | H | m-Cl phenyl | isobutyl | NHCOCH2 |
| 1230 | | Cl | F | H | p-Cl phenyl | isobutyl | NHCOCH2 |
| 1231 | | Cl | F | H | o-Cl phenyl | isobutyl | NHCOCH2 |
| 1232 | | Cl | F | H | m-Br Phenyl | isobutyl | NHCOCH2 |
| 1233 | | Cl | F | H | p-Br Phenyl | isobutyl | NHCOCH2 |
| 1234 | | Cl | F | H | o-Br Phenyl | isobutyl | NHCOCH2 |
| 1235 | | Cl | F | H | CF3 | isobutyl | NHCOCH2 |
| 1235 | | Cl | F | H | cyclopentyl | isobutyl | NHCOCH2 |
| 1237 | | Cl | F | H | cyclohexyl | isobutyl | NHCOCH2 |
| 1238 | | Cl | F | H | cyclobutyl | isobutyl | NHCOCH2 |

-continued

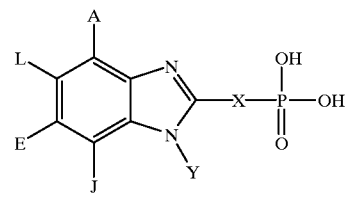

| Table Compound No. | Synthetic Example No. | A | L | E | J¹ | Y | X² |
|---|---|---|---|---|---|---|---|
| 1239 | | Cl | F | H | cyclopropyl | isobutyl | NHCOCH2 |
| 1240 | | Cl | F | H | Phenyl | isobutyl | NHCOCH2 |
| 1241 | | Cl | F | H | cyclopentylmethyl | isobutyl | NHCOCH2 |
| 1242 | | Cl | F | H | cyclohexylmethyl | isobutyl | NHCOCH2 |
| 1243 | | Cl | F | H | cyclobutylmethyl | isobutyl | NHCOCH2 |
| 1244 | | Cl | F | H | cyclopropylmethyl | isobutyl | NHCOCH2 |
| 1245 | | Me | Me | Cl | H | isobutyl | 2,5-furanyl |
| 1246 | 13.62 | H | H | Me | Me | isobutyl | 2,5-furanyl |
| 1247 | 13.63 | H | Cl | Me | Me | isobutyl | 2,5-furanyl |
| 1248 | 13.67 | H | F | H | Br | isobutyl | 2,5-furanyl |
| 1249 | 13.68 | H | F | NO₂ | Br | isobutyl | 2,5-furanyl |
| 1250 | 13.69 | H | F | NH₂ | Br | isobutyl | 2,5-furanyl |
| 1251 | 13.70 | NH₂ | Cl | Me | Me | isobutyl | 2,5-furanyl |
| 1252 | 12.66 | NH₂ | F | H | cyclopropyl | isobutyl | 2,5-furanyl |
| 1253 | 12.67 | NH₂ | F | H | phenyl | isobutyl | 2,5-furanyl |
| 1254 | 12.68 | NH₂ | F | H | p-F-phenyl | isobutyl | 2,5-furanyl |
| 1255 | 12.69 | NH₂ | F | H | p-Cl-Phenyl | isobutyl | 2,5-furanyl |
| 1256 | 12.70 | NH₂ | F | H | vinyl | isobutyl | 2,5-furanyl |
| 1257 | 13.71 | H | F | NMe₂ | F | isobutyl | 2,5-furanyl |
| 1258 | 13.72 | H | H | H | CH₂OH | isobutyl | 2,5-furanyl |
| 1259 | 12.71 | NH₂ | F | H | 4-Me-pentyl | isobutyl | 2,5-furanyl |
| 1260 | 13.73 | H | F | H | Br | H | 2,5-furanyl |
| 1261 | 13.74 | NO₂ | F | H | Br | H | 2,5-furanyl |
| 1262 | 13.75 | H | F | NO₂ | Br | H | 2,5-furanyl |
| 1263 | 12.73 | NH₂ | F | H | H | 2-Et-butyl | 2,5-furanyl |
| 1264 | 12.72 | NH₂ | F | H | 3,3-diMe-butyl | isobutyl | 2,5-furanyl |
| 1265 | 12.74 | NH₂ | F | H | m-OMe-phenyl | isobutyl | 2,5-furanyl |
| 1266 | 13.77 | NHCOMe | F | H | Et | isobutyl | 2,5-furanyl |
| 1267 | 13.76 | H | F | NHCOMe | Br | isobutyl | 2,5-furanyl |
| 1268 | 12.75 | NH₂ | F | H | Et | cyclopropylmethyl | 2,5-furanyl |
| 1269 | 12.76 | NH₂ | F | H | H | 3-pentyl | 2,5-furanyl |
| 1270 | 13.79 | H | F | NMe₂ | Br | isobutyl | 2,5-furanyl |
| 1271 | 13.78 | NMe₂ | F | H | Et | isobutyl | 2,5-furanyl |
| 1272 | 12.77 | H | F | F | F | isobutyl | 2,5-furanyl |
| 1273 | 12.78 | F | F | F | H | isobutyl | 2,5-furanyl |
| 1274 | 13.80 | H | F | Cl | Et | H | 2,5-furanyl |
| 1275 | 13.81 | Et | Cl | F | H | isobutyl | 2,5-furanyl |
| 1276 | 13.83 | Me | Me | Me | Me | isobutyl | 2,5-furanyl |
| 1277 | 13.82 | Me | Me | Me | Me | H | 2,5-furanyl |
| 1278 | 12.79 | NH₂ | F | H | 3-OH-propyl | isobutyl | 2,5-furanyl |
| 1279 | 13.86 | H | H | H | H | H | CONHCHCO₂Me |
| 1280 | 13.84 | Me | H | Me | H | H | 2,5-furanyl |
| 1281 | 13.85 | Me | H | Me | H | isobutyl | 2,5-furanyl |
| 1282 | 13.87 | H | Me | H | Me | isobutyl | 2,5-furanyl |
| 1283 | 12.80 | NH₂ | F | H | 3-Br-propyl | isobutyl | 2,5-furanyl |
| 1284 | 12.81 | NH₂ | F | H | propyl | isobutyl | 2,5-furanyl |
| 1285 | 12.82 | NH₂ | F | H | 4-Br-butyl | isobutyl | 2,5-furanyl |
| 1286 | 12.83 | NH₂ | F | H | 4-Cl-butyl | isobutyl | 2,5-furanyl |
| 1287 | 13.88 | Me | Me | Me | Me | cyclopropylmethyl | 2,5-furanyl |
| 1288 | 13.89 | Me | Me | Cl | H | ethyl | 2,5-furanyl |
| 1289 | 13.90 | Me | Me | Cl | H | 4-Br-butyl | 2,5-furanyl |
| 1290 | 12.85 | Me | Me | Cl | H | cyclopropylmethyl | 2,5-thionyl |
| 1291 | 13.91 | Me | Me | Cl | Br | H | 2,5-furanyl |
| 1292 | 13.92 | Me | Me | Cl | Br | isobutyl | 2,5-furanyl |
| 1293 | 15.1 | NH₂ | F | H | Br | isobutyl | methoxymethyl |
| 1294 | 12.84 | NH₂ | F | H | 3-(N,N-dimethyl)propylamine | isobutyl | 2,5-furanyl |
| 1295 | 13.96 | Br | Cl | Me | Me | isobutyl | 2,5-furanyl |
| 1296 | 13.94 | H | Cl | H | H | n-butylamine | 2,5-furanyl |
| 1297 | 13.95 | H | H | Cl | H | n-butylamine | 2,5-furanyl |
| 1298 | 13.96 | Me | Cl | H | H | isobutyl | 2,5-furanyl |
| 1299 | | H | Me | Cl | H | isobutyl | 2,5-furanyl |
| 1300 | | Cl | Me | Cl | H | isobutyl | 2,5-furanyl |
| 1301 | | NH₂ | F | H | Et | isobutyl | methoxymethyl |

-continued

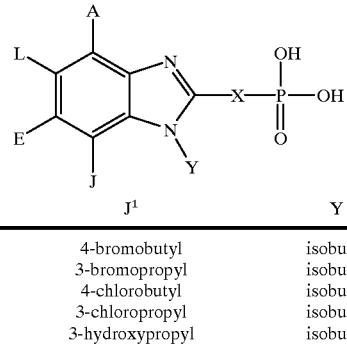

| Table Compound No. | Synthetic Example No. | A | L | E | J[1] | Y | X[2] |
|---|---|---|---|---|---|---|---|
| 1302 | | NH$_2$ | F | H | 4-bromobutyl | isobutyl | methoxymethyl |
| 1303 | | NH$_2$ | F | H | 3-bromopropyl | isobutyl | methoxymethyl |
| 1304 | | NH$_2$ | F | H | 4-chlorobutyl | isobutyl | methoxymethyl |
| 1305 | | NH$_2$ | F | H | 3-chloropropyl | isobutyl | methoxymethyl |
| 1306 | | NH$_2$ | F | H | 3-hydroxypropyl | isobutyl | methoxymethyl |
| 1307 | | NH$_2$ | F | H | 4-hydroxybutyl | isobutyl | methoxymethyl |
| 1308 | | NH$_2$ | F | H | 3-(N,N-dimethyl)propylamine | isobutyl | methoxymethyl |
| 1309 | 17.1 | H | H | H | H | H | —CONHCH$_2$— |
| 1310 | | NH$_2$ | F | H | H | isobutyl | methoxymethyl |
| 1311 | 12.86 | NH$_2$ | F | H | Et | H | 2,5-furanyl |

[1]In the Table for J where structures are depicted, the line on the left side is a direct attachment to the benzimidazole ring.
[2]In the table for X where structures are depicted, the line on the left side is part of the benzimidazole ring, an atom or the left side is attached to the benzimidazole ring, and the line on the right side is attached directly to the P of the phosphonate.

More preferred are the following compounds from Table 1 and salts and prodrugs thereof:
41,42,43,53,55,56,57,58,59,60,62,63,87,88,128,281,282, 322,354, 484,485,490,491,494,504,506,568,638,639,640, 641,642,643,644,645, 646,647,648,649,650,651,654,696, 697,698,699,700,701,705,706,707, 708,709,710,1248, 1249,1251,1252,1253,1254,1255,1256,1259,1263, 1264, 1265,1268,1269,1273,1276,1277,1278,1283,1284,1285, 1286, 1287,1288,1289,1293,1294,1295,1298.

Most preferred are the following compounds from Table 1 and salts and prodrugs thereof:
5-Fluoro-7-bromo-1-isobutyl-2-(2-phosphono-5-furanyl) benzimidazole;
4,5-Dimethyl-6-chloro-1-isopropylmethyl-2-(2-phosphono-5-furanyl) benzimidazole;
6-Chloro-1-phenyl-2-(2-phosphono-5-furanyl) benzimidazole;
5,6-Difluoro-1-isobutyl-2-(2-phosphono-5-furanyl) benzimidazole;
4-Amino-5-chloro-1-isobutyl-2-(2-phosphono-5-furanyl) benzimidazole;
4-Amino-5,7-dichloro-1-isobutyl-2-(2-phosphono-5-furanyl) benzimidazole;
4-Amino-5-fluoro-1-isobutyl-2-(2-phosphono-5-furanyl) benzimidazole;
4-Amino-5-fluoro-7-chloro-1-isobutyl-2-(2-phosphono-5-furanyl)benzimidazole;
4-Amino-5-fluoro-1-cyclopropylmethyl-2-(2-phosphono-5-furanyl) benzimidazole;
4-Amino-5-fluoro-6-chloro-7-ethyl-1-isobutyl-2-(2-phosphono-5-furanyl) benzimidazole;
4-Amino-5-fluoro-6-methylthio-7-ethyl-1-isobutyl-2-(2-phosphono-5-furanyl) benzimidazole;
4-Amino-5-fluoro-7-bromo-1-isobutyl-2-(2-phosphono-5-furanyl)benzimidazole;
4-Amino-5-fluoro-6-chloro-1-isobutyl-2-(2-phosphono-5-furanyl)benzimidazole;
4-Amino-5-fluoro-7-ethyl-1-isobutyl-2-(2-phosphono-5-furanyl)benzimidazole;
1-isobutyl-4-methyl-5-chloro-2(2-phosphono-5-furanyl) benzimidazole;
4-Amino-5-fluoro-7-ethyl-1-isobutylbenzimidazol-2-ylmethyleneoxymethylphosphonic acid;

4-Amino-5,6-difluoro-7-ethyl-1-isobutyl-2-(2-phosphono-5-furanyl) benzimidazole;
4-Amino-5-fluoro-7-ethyl-1-neopentyl-2-(2-phosphono-5-furanyl) benzimidazole;
4-Amino-5-fluoro-7-ethyl-1-cyclopropylmethyl-2-(2-phosphono-5-furanyl) benzimidazole;
4-Amino-5-fluoro-7-ethyl-1-cyclobutylmethyl-2-(2-phosphono-5-furanyl) benzimidazole;
4-Amino-5-fluoro-7-ethyl-1-phenyl-2-(2-phosphono-5-furanyl)benzimidazole;
4-Amino-5-fluoro-7-ethyl-1-isobutyl-2-(1-hydroxy-1-phosphonopropyl) benzimidazole; and
4-Amino-5-fluoro-7-isopropyl-1-isobutyl-2-(2-phosphono-5-furanyl) benzimidazole.
4-Amino-5-fluoro-7-cyclopropyl-1-isobutyl-2-(2-phosphono-5-furanyl) benzimidazole.
4-Amino-5-fluoro-7-phenyl-1-isobutyl-2-(2-phosphono-5-furanyl)benzimidazole.
4-Amino-5-fluoro-7-(4-methylpentyl)-1-isobutyl-2-(2-phosphono-5-furanyl) benzimidazole.
4-Amino-5-fluoro-7-(3-hydroxypropyl)-1-isobutyl-2-(2-phosphono-5-furanyl) benzimidazole.
4-Amino-5-fluoro-7-(3-bromopropyl)-1-isobutyl-2-(2-phosphono-5-furanyl) benzimidazole.
4-Amino-5-fluoro-7-(4-bromobutyl)-1-isobutyl-2-(2-phosphono-5-furanyl) benzimidazole.
4-Amino-5-fluoro-7-(4-chlorobutyl)-1-isobutyl-2-(2-phosphono-5-furanyl) benzimidazole.
4-Amino-5-fluoro-7-(3-N,N-dimethylpropylamine)-1-isobutyl-2-(2-phosphono-5-furanyl) benzimidazole.
4-Amino-5-fluoro-7-bromo-1-isobutyl-2-(1-methoxymethyl-3-phosphono) benzimidazole.
4-Amino-5-fluoro-1-isobutyl-2-(1-methoxymethyl-3-phosphono)benzimidazole.

Synthesis of Compounds of Formula 1

Synthesis of the compounds encompassed by the present invention typically includes some or all of the following general steps: (1) synthesis of the prodrug; (2) phosphonate deprotection; (3) substitution of the heterocycle; (4) substitution or modification of 2-substituent; (5) cyclization to generate benzimidazole ring system; (6) synthesis of the linker-PO$_3$R$_2$; and (7) synthesis of the substituted 1,2- phenylenediamine. A detailed discussion of each step is given below.

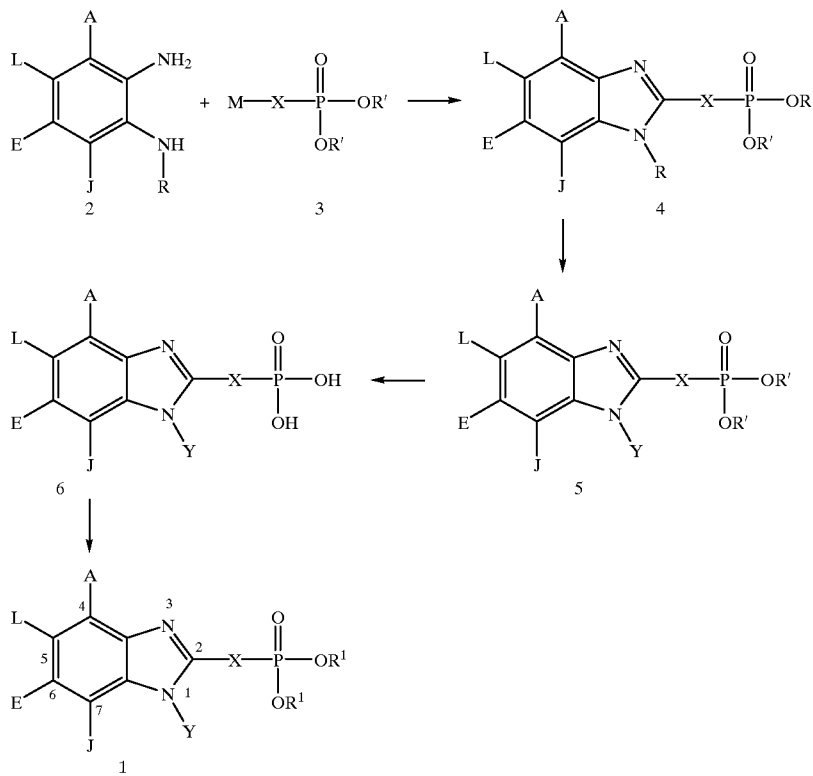

1) Preparation of Phosphonate Prodrugs

Prodrug esters can be introduced at different stages of the synthesis. Most often, these prodrugs are made from the phosphonic acids of formula 6 because of their lability. Advantageously, these prodrug esters can be introduced at an earlier stage, provided they can withstand the reaction conditionms of the subsequent steps.

Compounds of formula 6, can be alkylated with electrophiles (such as alkyl halides, alkyl sulfonates, etc) under nucleophilic substitution reaction conditions to give phosphonate esters. For example, prodrugs of formula 1, where $R^1$ is acyloxymethyl group can be synthesized through direct alkylation of the free phosphonic acid of formula 6 with the desired acyloxymethyl halide (e.g. $Me_3CC(O)OCH_2I$; Elhaddadi, et al *Phosphorus Sulfur,* 1990, 54(1–4): 143; Hoffmann, *Synthesis,* 1988, 62) in presence of base e.g. N. N'-dicyclohexyl-4-morpholinecarboxamidine, Hunigs base, etc. in polar aprotic solvents such as DMF (Starrett, et al, *J. Med. Chem.,* 1994, 1857). These carboxylates include but are not limited to acetate, propionate, isobutyrate, pivalate, benzoate, and other carboxylates. Alternately, these acyloxymethylphosphonate esters can also be synthesized by treatment of the nitrophosphonic acid (A is $NO_2$ in formula 6; Dickson, et al, *J. Med. Chem.,* 1996, 39: 661; Iyer, et al, *Tetrahedron Lett.,* 1989, 30: 7141; Srivastva, et al, *Bioorg. Chem.,* 1984, 12: 118). This methodology can be extended to many other types of prodrugs, such as compounds of formula 1 where R1 is 3-phthalidyl, 2-oxo-4,5-didehydro-1,3-dioxolanemethyl, and 2-oxotetrahydrofuran-5-yl groups, etc. (Biller and Magnin (U.S. Pat. No. 5,157,027); Serafinowska et al. (*J. Med. Chem.* 38: 1372 (1995)); Starrett et al. (*J. Med. Chem.* 37: 1857 (1994)); Martin et al.

*J. Pharm. Sci.* 76:180 (1987); Alexander et al., *Collect. Czech. Chem. Commun,* 59:1853 (1994)); and EPO 0632048A1). N,N-Dimethylformamide dialkyl acetals can also be used to alkylate phosphonic acids (Alexander, P., et al *Collect. Czech. Chem. Commun.,* 1994, 59,1853).

Alternatively, these phosphonate prodrugs or phosphoramidates can also be synthesized, by reaction of the corresponding dichlorophosphonate and an alcohol or an amine (Alexander, et al, *Collect. Czech. Chem. Commun.,* 1994, 59: 1853). For example, the reaction of dichlorophosphonate with phenols and benzyl alcohols in the presence of base (such as pyridine, triethylamine, etc) yields compounds of formula 1 where $R^1$ is aryl (Khamnei, S., et al *J. Med. Chem.,* 1996, 39: 4109; Serafinowska, H. T., et al *J. Med. Chem.,* 1995, 38:1372; De Lombaert, S., et al *J. Med. Chem.,* 1994, 37:498) or benzyl (Mitchell, A. G., et al *J. Chem. Soc. Perkin Trans.* 1, 1992, 38:2345). The disulfide-containing prodrugs, reported by Puech et al., *Antiviral Res.,* 1993, 22: 155, can also be prepared from dichlorophosphonate and 2-hydroxyethyl disulfide under standard conditions.

Such reactive dichlorophosphonate intermediates, can be prepared from the corresponding phosphonic acids and chlorinating agents e.g. thionyl chloride i(Starrett, et al, *J. Med. Chem.,* 1994, 1857), oxalyl chloride (Stowell, et al, *Tetrahedron Lett.,* 1990, 31:3261), and phosphorus pentachloride (Quast, et al, *Synthesis,* 1974, 490). Alternatively, these dichlorophosphonates can also be generated from disilylphosphonate esters (Bhongle, et al, *Synth. Commun.,* 1987, 17: 1071) and dialkylphosphonate esters (Still, et al, *Tetrahedron Lett.,* 1983, 24: 4405; Patois, et al, *Bull. Soc. Chim. Fr.,* 1993, 130: 485).

Furthermore, these prodrugs can be prepared from Mitsunobu reactions (Mitsunobu, *Synthesis,* 1981, 1; Campbell, *J.Org. Chem.,* 1992, 52: 6331), and other acid coupling reagents including, but not limited to, carbodiimides (Alexander, et al, *Collect. Czech. Chem. Commun.,* 1994, 59: 1853; Casara, et al, *Bioorg. Med. Chem. Lett.,* 1992, 2: 145; Ohashi, et al, *Tetrahedron Lett.,* 1988, 29: 1189), and benzotriazolyloxytris-(dimethylamino)phosphonium salts (Campagne, et al, *Tetrahedron Lett.,* 1993, 34: 6743). The prodrugs of formula 1 where $R^1$ is the cyclic carbonate or lactone or phthalidyl can also be synthesized by direct alkylation of free phosphonic acid with the desired halides in the presence of base such as NaH or diisopropylethylamine (Biller and Magnin U.S. Pat. No. 5,157,027; Serafinowska et al. *J. Med. Chem.* 38: 1372 (1995); Starrett et al. *J. Med. Chem.* 37: 1857 (1994); Martin et al. *J. Pharm. Sci.* 76:180 (1987); Alexander et al., *Collect. Czech. Chem. Commun,* 59: 1853 (1994); and EPO 0632048A1).

$R^1$ can also be introduced at an early stage of the synthesis. For example, compounds of formula 1 where $R^1$ is phenyl can be prepared by phosphorylation of 2-furanyl benzimidazole subjected to a strong base (e.g. LDA) and chlorodiphenyl phosphonate. Alternatively, such compounds can be prepared by alkylation of lithiated furfuraldehyde followed by ring closure to the benzimidazole.

The discussion of this step includes various synthetic methods for the preparation of the following types of propane-1,3-diols: i) 1-substituted; ii) 2-substituted; and iii) 1,2- or 1,3-annulated. Different groups on the prodrug part of the molecule ie., on the propane diol moiety can be introduced or modified either during the synthesis of the diols or after the synthesis of the prodrugs.

i) 1-Substituted 1,3-Propane Diols

Propane-1,3-diols can be synthesized by several well known methods in the literature. Aryl Grignard additions to 1-hydroxypropan-3-al gives 1-aryl-substituted propane-1,3-diols (path a). This method will enable conversion of various substituted aryl halides to 1-arylsubstituted-1,3-propane diols (Coppi, et. al., *J. Org. Chem.,* 1988, 53, 911). Aryl halides can also be used to synthesize 1-substituted propanediols by Heck coupling of 1,3-diox-4-ene followed by reduction and hydrolysis (Sakamoto, et. al., *Tetrahedron Lett.,* 1992, 33, 6845). A variety of aromatic aldehydes can be converted to 1-substituted-1,3-propane diols by vinyl Grignard addition followed by hydroboration (path b). Substituted aromatic aldehydes are also useful for lithium-t-butylacetate addition followed by ester reduction (path e)

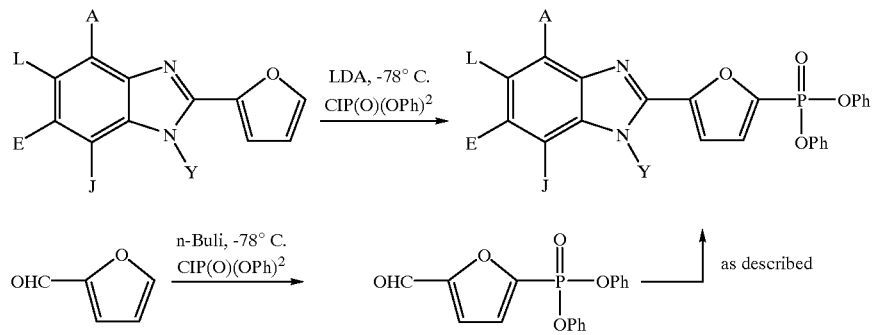

It is envisioned that compounds of formula 1 can be mixed phosphonate esters (e.g. phenyl benzyl phosphonate esters, phenyl acyloxyalkyl phosphonate esters, etc). For example, the chemically combined phenyl-benzyl prodrugs are reported by Meier, et al. *Bioorg. Med. Chem. Lett.,* 1997, 7: 99.

The substituted cyclic propyl phosphonate esters of formula 1, can be synthesized by reaction of the corresponding dichlorophosphonate and the substituted 1,3-propane diol. The following are some methods to prepare the substituted 1,3-propane diols.

Synthesis of the 1,3-Propane Diols Used in the Preparation of Certain Prodrugs (Turner., *J. Org. Chem.,* 1990, 55 4744). In another method, commercially available cinnamyl alcohols can be converted to epoxy alcohols under catalytic asymmetric epoxidation conditions. These epoxy alcohols are reduced by Red-Al to result in enantiomerically pure propane-1,3-diols (path c). Alternatively, enantiomerically pure 1,3-diols can be obtained by chiral borane reduction of hydroxyethyl aryl ketone derivatives (Ramachandran, et. al., *Tetrahedron Left.,* 1997, 38 761). Pyridyl, quinoline, and isoquinoline propan-3-ol derivatives can be oxygenated to 1-substituted propan-1,3-diols by N-oxide formation followed by rearrangement under acetic anhydride conditions (path d) (Yamamoto, et. al., *Tetrahedron,* 1981, 37,1871).

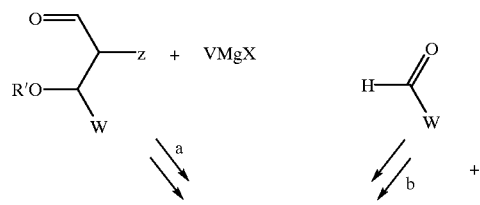

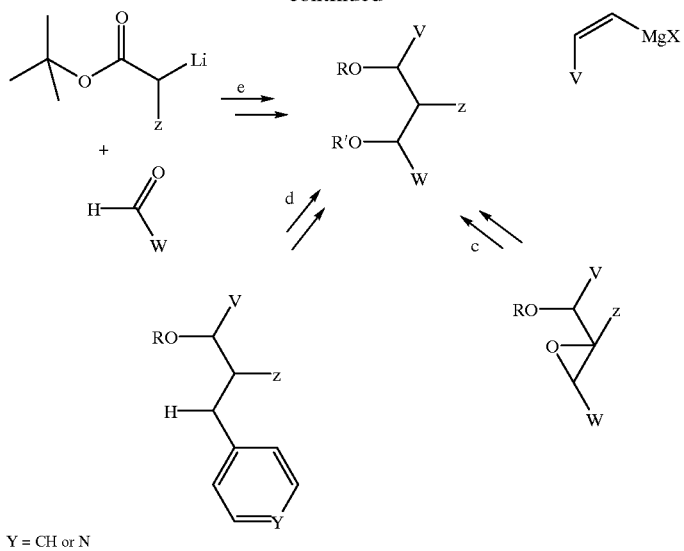

Y = CH or N ii) 2-Substituted 1,3-Propane Diols

Various 2-substituted propane-1,3-diols can be made from commercially available 2-(hydroxymethyl)-1,3-propane diol. Triethyl methanetricarboxylate can be converted to the triol by complete reduction (path a) or diolmonocarboxylic acid derivatives can be obtained by partial hydrolysis and diester reduction (Larock, *Comprehensive Organic Transformations,* VCH, New York, 1989). Nitrotriol is also known to give the triol by reductive elimination (path b) (Latour, et. al., *Synthesis,* 1987, 8, 742). The triol can be derivatized as a mono acetate or carbonate by treatment with alkanoyl chloride, or alkylchloroformate, respectively (path d) (Greene and Wuts, *Protective Groups in Organic Synthesis,* John Wiley, New York, 1990). Aryl substitution effected by oxidation to the aldehyde followed by aryl Grignard additions (path c) and the aldehyde can also be converted to substituted amines by reductive amination reactions (path e).

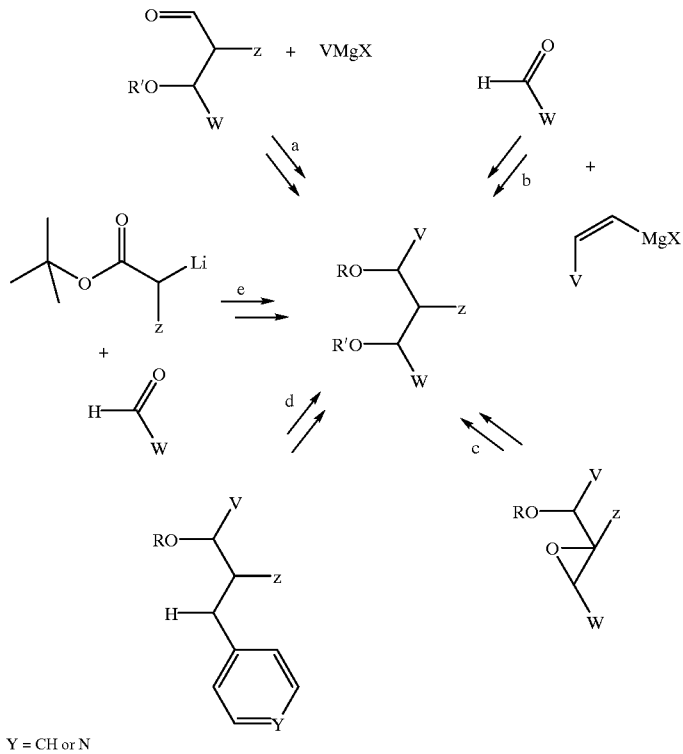

Y = CH or N iii) Annulated 1,3-Propane Diols

Prodrugs of formula 1 where V—Z or V—W are fused by three carbons are made from cyclohexane diol derivatives. Commercially available cis, cis-1,3,5-cyclohexane triol can be used for prodrug formation. This cyclohexanetriol can also be modified as described in the case of 2-substituted propan-1,3-diols to give various analogues. These modifications can either be made before or after formation of prodrugs. Various 1,3-cyclohexane diols can be made by Diels-Alder methodology using pyrone as the diene (Posner, et. al., *Tetrahedron Left.*, 1991, 32, 5295). Cyclohexyl diol derivatives are also made by nitrile oxide olefin-additions (Curran, et. al., *J. Am. Chem. Soc.,* 1985, 107, 6023). Alternatively, cyclohexyl precursors can be made from quinic acid (Rao, et. al., *Tetrahedron Lett.,* 1991, 32, 547.)

2) Phosphonate Deprotection

Compounds of formula 6, may be prepared from phosphonate esters of formula 5, using known phosphate and phosphonate ester cleavage conditions. In general, silyl halides have been used to cleave the various phosphonate esters, followed by mild hydrolysis of the resulting silyl phosphonate esters to give the desired phosphonic acids. Depending on the stability of the products, these reactions are usually accomplished in the presence of acid scavengers such as 1,1,1,3,3,3-hexamethyldisilazane, 2,6-lutidine, etc. Such silyl halides include, chlorotrimethylsilane (Rabinowitz, *J. Org. Chem.,* 1963, 28: 2975), bromotrimethylsilane (McKenna, et al, *Tetrahedron Lett.,* 1977, 155), iodotrimethylsilane (Blackburn, et al, *J. Chem. Soc., Chem. Commun.,* 1978, 870). Alternately, phosphonate esters can be cleaved under strong acid conditions, (e.g HBr, HCl, etc.) in polar solvents, preferably acetic acid (Moffatt, et al, U.S. Pat. No. 3,524,846,1970) or water. These esters can also be cleaved via dichlorophosphonates, prepared by treating the esters with with halogenating agents e.g. phosphorus pentachloride, thionyl chloride, $BBr_3$, etc.(Pelchowicz, et al, *J. Chem. Soc.,* 1961, 238) followed by aqueous hydrolysis to give phosphonic acids. Aryl and benzyl phosphonate esters can be cleaved under hydrogenolysis conditions (Lejczak, et al, *Synthesis,* 1982, 412; Elliott, et al, *J. Med. Chem.,* 1985, 28: 1208; Baddiley, et al, *Nature,* 1953, 171: 76 ) or dissolving metal reduction conditions(Shafer, et al, *J. Am. Chem. Soc.,* 1977, 99: 5118). Electrochemical (Shono, et al, *J. Org. Chem.,* 1979, 44: 4508) and pyrolysis (Gupta, et al, *Synth. Commun.,* 1980, 10: 299) conditions have also been used to cleave various phosphonate esters.

3) Substitution of the Heterocycle

The benzimidazole ring system of formula 4, may require further elaboration to provide desired compounds of formula 5.

i) Substitution of the Phenyl Ring

Electrophilic and nucleophilic substitution reactions enable incorporation of the desired substitutions encompassed by the formula 5. (March, *Advanced Organic Chemistry* by, Wiley-Interscience, 1992, 501–521; 641–654). For example, treatment of the compounds of formula 4, where A is $NH_2$, L and J are hydrogens with NBS, NCS or NIS in halogenated solvents such as carbon tetrachloride or chloroform gives halo-substituted compounds of formula 5 (L and/or J are halogens). Compounds of formula 5, where A is $NO_2$, L and/or J are alkenyl, alkynyl, alkyl, or aryl groups, and Y is H or alkyl, may be prepared from compounds of formula 4, where A is $NO_2$, R is H or alkyl, and L and/or J are halogens, preferably bromide or iodide, through Stille coupling (Stille, *Angew. Chem. Int. Ed. Engl.* 1986, 25: 508–524). Treatment of the compounds of formula 4, where A is $NO_2$, and L and/or J are bromides, with a coupling reagent (e.g. tributyl(vinyl)tin, phenylboronic acid, propargyl alcohol, N,N-propargyl amine etc.) in presence of palladium catalyst [e.g. bis(triphenylphosphine)palladium (II) chloride, tetrakis(triphenylphosphine) palladium(0), etc.] in solvent, such as DMF, toluene, etc. provides the coupling products. The compounds thus obtained can be modified as needed. For example vinyl or propargyl alcohol derivatives can be hydrogenated to give the ethyl or propyl alcohol derivatives respectively. These alcohols can be further modified as required via alkyl halides (ref. Wagner et al. *Tetrahedron Lett.* 1989, 30, 557.) or alkyl sulfonates etc. to a number of substituted alkyls such as amino alkyl compounds by subjecting them to nucleophilic substitution reactions (March, *Advanced Organic Chemistry,* Wiley-Interscience, Fourth Edition, 1992, 293–500). Alternatively, these substitutions can also be done by metal exchange followed by quenching with an appropriate nucleophile (Jerry March, *Advanced Organic Chemistry,* Wiley-Interscience, 1992, 606–609). Nucleophilic addition reactions can also be useful in preparing compounds of formula 5. For example, when A is $NO_2$, L and/or J are halogens, nucleophiles such as alkoxides, thiols, amines, etc. provide the halogen displacement products. (March, *Advanced Organic Chemistry,* Wiley-Interscience, Fourth Edition, 1992, 649–676). Another example is addition reactions, for example cyclopropanation (Vorbruggen et al, *Tetrahedron Lett.* 1975, 629), on the olefins(e g. styryl type) synthesized through Stille coupling.

If required, these substituted compounds can be further modified to the desired products. For example, reduction of the $NO_2$ to $NH_2$ may be done in many different ways, e.g. Pd/C, $H_2$, aq. $Na_2S_2O_4$, etc. (Larock, *Comprehensive Organic Transformations,* VCH, 412–415). These primary aromatic amines can also be modified as needed. For example, N-acetyl derivatives can be prepared by treatment with acetyl chloride or acetic anhydride in the presence of a base such as pyridine. The mono- or di-alkylamines can be synthesized by direct alkylation, using a base such as NaH in polar solvents such as DMF or by reductive alkylation methods (ref. Abdel-Magid et al. *Tetrahedron Lett.* 1990, 31, 5595; also see ref. March, *Advanced Organic Chemistry,* Wiley-Interscience, Fourth Edition, 1992, 898–900 for more methods).

ii) Alkylation of the Imidazole Ring

Alkylation of the heterocycle of formula 4, (where R and J are both H) is obtained through two distinct methods that are amenable to a large number of electrophiles: a) Mitsunobu alkylation, and b) base alkylation.

a) Mitsunobu Alkylation

Alkylation of the benzimidazole ring system of formula 4, is achieved by treatment of an alcohol, triphenylphosphine and dialkylazodicarboxylate with heterocycle and a nonnucleophilic base such as Hunigs base in polar solvents such as $CH_3CN$ (Zwierzak et al, *Liebigs Ann. Chem.* 1986, 402).

b) Base Alkylation

Alternately, the benzimidazole ring system of formula 4 can be deprotonated with a suitable base, preferably cesium carbonate in a polar aprotic solvent such as DMF, and the resulting anion is alkylated with an appropriate electrophilic component Y—L', where L' is a leaving group preferably bromide or iodide.

4) Substitution or Modification of a 2-substituent

Another key intermediate envisioned in the synthesis of compounds of formula 4 are substituted 2-methylbenzimidazoles. These compounds are readily prepared by condensing $Ac_2O$ with the appropriate 1,2-phenylenediamine (Phillips, *J. Chem. Soc.,* 1928, 29: 1305).

These compounds are useful in the synthesis of formula 1, wherein X is $CH_2ZCH_2$ (Z=O,S,NH). For example, compounds where Z=O are readily prepared by treatment of the 2-methylbenzimidazole with a halogenating agent such as NBS followed by reaction with the α-hydroxy phosphonate ester (also see section 6, Synthesis of the Linker-$PO_3R_2$). Alternately, a heterosubstituted methyl phosphonates can also be prepared by displacement reactions on phosphonomethyl halides or sulfonates (Phillion et al, *Tetrahedron Lett.*, 1986, 27: 1477.) with an appropriate nucleophile e.g. 2-hydroxylmethylbenzimidazole compound which can be prepared using a variety of methods, including oxidation of the substituted 2-methylbenzimidazoles.

Similarly, compounds of formula 1, where X is carboxypropyl or sulfonopropyl can be prepared from the reaction of 2-(2-iodoethyl) benzimidazole and corresponding phosphonomethylcarboxylate or phosphonomethylsulfonate (Carretero et al., *Tetrahedron*, 1987, 43, 5125) in the presence of base such as NaH in polar aprotic solvents such as DMF. The substituted 2-(2-iodoethyl) benzimidazole can be prepared from condensation of the corresponding substituted diamine and 3-halopropanaldehyde. Also see ref. Magnin, D. R. et al. *J. Med. Chem.* 1996, 39, 657 for the preparation of α-phosphosulfonic acids.

The componds of formula 4 where X is all carbon e.g. —$(CH_2)_3$— can be prepared by Stille coupling (Stille *Angew. Chem. Int. Ed. Engl.* 1986, 25: 508–524) of the dialkylphosphopropenyl tributylstanne (*J. Org. Chem.* 1993, 58: 6531.) and appropriate 2-bromobenzimidazole (Mistry, et al, *Tetrahedron Lett.*, 1986, 27: 1051).

The componds of formula 4 where X is an amide linker e.g. —$CONHCH_2$— can be synthesized using the following two steps. Treatment of the appropriate 1,2-phenylenediamine with trihalomethylacetamidate preferably trichloromethylacetamidate in polar solvent such as acetic acid followed by hydrolysis of the trihalomethyl group with strong aqueous base (e.g. KOH) gives the benzimidazole-2-carboxylic acid (*Eur. J. Med. Chem.*, 1993, 28: 71). Condensation of the acid with an amino phosphonate e.g. diethyl(aminomethyl)phosphonate in presence of a coupling agent (e.g. pyBOP) in a polar solvent such as methylene chloride provides the amide linked phosphonate.

The componds of formula 4 where X is an amide linker e.g. —$NHCOCH_2$— can be synthesized using the following two steps. Treatment of the appropriate 1,2-phenylenediamine with cyanogenbromide (Johnson, et al, *J. Med. Chem.*, 1993, 36: 3361) in polar solvent such as MeOH gives the 2-amino benzimidazole. Condensation of the 2-aminobenzimidazole with a carboxylic acid e.g. diethyl (carboxymethyl)phosphonate using standard coupling conditions (Klausner, et al, *Synthesis,* 1972, 453) provides the amide linked phosphonate. The 2-aminobenzimidazoles can also be prepared from the 2-bromobenzimidazole via the 2-azidobenzimidazole using known methods (*Chem. Rev.* 1988, 88: 297).

5) Cyclization to Generate Benzimidazole Ring System

The benzimidazole ring systems of formula 4 is preferably assembled by condensation of substituted 1,2-phenylenediamines with an aldehyde (RCHO, where R is e.g. aliphatic, heteroaliphatic, aromatic or heteroaromatic etc.) using known methods; (a) in presence of $Fe^{3+}$ salts, preferably $FeCl_3$, in polar solvents such as DMF, EtOH etc., (b) reflux in non-polar solvents such as toluene followed by oxidation, preferably with iodine (Bistocchi et al, *Collect. Czech. Chem. C,* 1985, 50(9): 1959.)., (c) in cases of protected aldehydes, the first condensation can be achieved in the presence of a dilute inorganic acid, preferably 10% $H_2SO_4$, in polar solvents such as THF, followed by oxidation with $I_2$. Alternatively, this coupling can be achieved with an anhydride (RCOOCOR), a carboxylic acid (RCOOH), with a nitrile (RCN) by methods reported by Hein, et al, *J. Am. Chem. Soc.* 1957, 79, 427.; and Applegate, et al, U.S. Pat. No. 5,310,923; or imidates (R—C(=NH)—OEt) ref. Maryanoff, et al. *J. Med. Chem.* 1995, 38: 16.

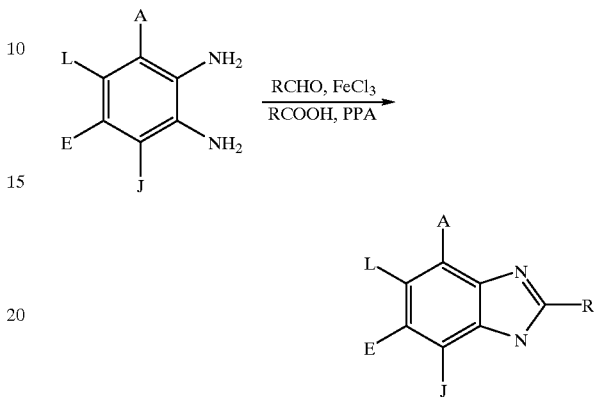

Advantageously, these benzimidazole ring systusingan be constructed using solid phase synthesis (ref: Phillips et al. *Tet. Lett.,* 1996, 37: 4887; Lee et al., *Tet. Lett,* 1998: 35: 201.

6) Synthesis of the Linker-$PO_3R_2$

Coupling of aromatic or aliphatic aldehydes, ketals or acetals of aldehydes, and acid derivatives with attached phophonate esters are particularly well suited for the synthesis of compounds of formula 1.

i) Preparation of Aryl and Heteroaryl Phosphonate Esters

Aryl functionalized phosphonate linkers can be prepared by lithiation of an aromatic ring using methods well described in literature (Gschwend, *Org. React.* 1979, 26, 1; Durst, *Comprehensive Carbanion Chemistry, Vol.* 5, Elsevier, N.Y., 1984) followed by addition of phosphorylating agents (e.g. $ClPO_3R_2$). Phosphonate esters are also introduced by Arbuzov-Michaelis reaction of primary halides (Brill, T. B., *Chem Rev.,* 1984, 84: 577). Aryl halides undergo $Ni^{2+}$ catalysed reaction with trialkylphosphites to give aryl phosphonate containing compounds (Balthazar, et al, *J. Org. Chem.,* 1980, 45: 5425). Aromatic triflates are known to result in phosphonates with $ClPO_3R_2$ in the presence of a palladium catalyst (Petrakis, et al, *J. Am. Chem. Soc.,* 1987, 109: 2831; Lu, et al, *Synthesis,* 1987, 726). In another method, aryl phosphonate esters are prepared from aryl phosphates under anionic rearrangement conditions (Melvin, *Tetrahedron Lett.,* 1981, 22: 3375; Casteel, et al, *Synthesis,* 1991, 691). Using the same method described above, arylphosphate esters, where X is aryloxy, can also be made. N-Alkoxy aryl salts with alkali metal derivatives of dialkyl phosphonate provide general synthesis for heteroaryl-2-phosphonate linkers (Redmore, *J. Org. Chem.,* 1970, 35: 4114).

In the linker phosphonate synthesis, aldehyde, ketone, or carboxylic acid functionalities can also be introduced after the phosphonate ester is formed. A lithiation reaction can be used to incorporate the aldehyde or ketone functionalities, although other methods known to generate aromatic aldehydes or ketones can be envisioned as well (e.g. Vilsmeier-Hack reaction, Reimar-Teimann reaction etc.; Pizey, *Synthetic reagents,* 1974, 1: 1; Wynberg, H., et al, *Org. React.* 1982, 28: 1; palladium catalyzed coupling reaction of acid halides and organotin compounds). For example, for the lithiation reaction, the lithiated aromatic ring can be treated with reagents that directly generate the aldehyde (e.g. DMF, HCOOR, etc.)(Einchorn, J., et al, *Tetrahedron Lett.,* 1986, 27:1791), or the ketone (e.g. Weinreb's amide, RCOOR'). The lithiated aromatic ring can also be treated with reagents that lead to a group that is subsequently transformed into the aldehyde or ketone group using known chemistry (synthesis of aldehyde and ketone from alcohol, ester, cyano, alkene, etc.). It is also envisioned that the sequence of these reactions can be reversed, i.e. the aldehyde and ketone moieties can be incorporated first, followed by the phosphorylation reaction. The order of the reaction will depend on reaction conditions and protecting groups. Prior to the phosphorylation it is also envisioned that it may be advantageous to protect the aldehyde or ketone using well-known methods (acetal, aminal, hydrazone, ketal, etc.), and then the aldehyde or ketone is unmasked after phosphorylation. (*Protective groups in Organic Synthesis,* Greene, T. W., 1991, Wiley, New York).

The above mentioned methods can also be extended to the heteroaryl linkers e.g. pyridine, furan, thiophene etc.

ii) Preparation of Aliphatic and Heteroaliphatic Phosphonate Esters

Compounds of formula 3, where M is $CO_2R$ and X is alkyl can be synthesized using reactions well known in the art. Trialkyl phosphites attack lactones at the β-carbon atom, causing the alkyl-oxygen cleavage of the lactone ring, to yield alkyl(dialkylphosphono)esters. This reaction can be applied to many types of lactones such as β-lactones, γ-lactones etc. as reported by McConnell et al, *J. Am. Chem. Soc.,* 1956, 78, 4453. Alternatively, these type of compounds can be synthesized using the Arbuzov reaction (*Chem. Rev.* 1984, 84: 577). The linkers Ar(Z)alkyl phosphonates (Ar=aryl; Z=O,S etc.) can be prepared from the reaction of substituted aryls e.g. salicylaldehyde with an appropriate phosphonate electrophile [L(CH2)$_n$PO$_3$R$_2$, L is a leaving group, preferably iodine; Walsh et al, *J. Am. Chem. Soc.,* 1956, 78, 4455.] in the presence of a base, preferably $K_2CO_3$ or NaH, in a polar aprotic solvent, such as DMF or DMSO. For the preparation of α-phosphosulfonic acids see ref. Magnin, D. R. et al. *J. Med. Chem.* 1996, 39, 657; and ref. cited therein.

Compounds of formula 3, where M is $CO_2R$ or CHO and X is carbonylalkyl can be synthesized from the acid chlorides (for example H(O)C—CH$_2$C(O)Cl) and P(OEt)$_3$ (*Chem. Rev.* 1984, 84: 577). These α-ketophosphonates can be converted to the α-hydroxyphoshonates and α,α-dihalophosphonates (ref. Smyth, et al. *Tett. Lett.,* 1992, 33, 4137). For another method of synthesizing these α,α-dihalophosphonates see the ref. Martin et al. *Tett. Lett.* 1992, 33, 1839.

Compounds of formula 3, where X is a heteroalkyl linker e.g. —CH$_2$ZCH$_2$— where Z=O,S etc. and M is aldehyde or its protected form such as dialkyl acetal (*Protective groups in Organic Synthesis, Greene, T. W.,* 1991, Wiley, New York) can be prepared by nucleophilic substitution reactions (March, *Advanced Organic Chemistry, Wiley-Interscience, Fourth Edition,* 1992, 293–500) to give unsymmetrical ethers. For example linkers of formula 3, where X is alkyloxymethyl can be synthesized through direct alkylation of the hydroxymethyl phosphonate ester, with the desired alkyl halide [L(CH$_2$)$_n$CH(OMe)$_2$, L is a leaving group, preferably bromine or iodine] in the presence of a base, preferably NaH, in a polar aprotic solvent, such as DMF or DMSO. These methods can be extended to the heteroalkyl linkers e.g. —CH$_2$ZCH$_2$— where Z=S, NH etc.

7) Synthesis of the Substituted 1,2-phenylenediamine 1,2-Phenylenediamines utilized in the preparation of compounds of formula 1, can be synthesized using methods well known in the art.

(a) Compounds of formula 2, where R is H, can be synthesized from simple aromatic: compounds. Most aromatic compounds may be nitrated given the wide variety of nitrating agents available(March, *Advanced Organic Chemistry,* Wiley-Interscience, 1992, 522–525). Primary aromatic amines are often N-acetylated before nitration by treatment with acetyl chloride or acetic anhydride. Nitration of the these acetanilide derivatives using 60% $HNO_3$ and $H_2SO_4$ (Monge et al, *J Med. Chem.,* 1995, 38:1786; Ridd *Chem. Soc. Rev.* 1991, 20: 149–1651, followed by deprotection by strong acid (e.g. $H_2SO_4$, HCl, etc.), and hydrogenation (e.g. $H_2$, Pd/C; $Na_2S_2O_4$; etc.) of the resulting 2-nitroanilines provides the desired substituted 1,2-phenylenediamines. Similarly, substituted arylhalides (F,Cl,Br,I) can also be nitrated to provide α-halonitroaryl compounds followed by nucleophilic addition (e.g. $NH_3$, $NH_2OH$, etc) and reduction to generate the diamines.

(b) Diamines of formula 2, where A is $NO_2$ and R is H, can be produced using the method of Grivas et. al., *Synthesis* 1992, 1283 and Tian et al *J. Chem. Soc. Perkin Trans* 1, 1993, 257 and an appropriate o-nitroaniline. A variety of reactions can be used to substitute the o-nitroaniline. For example halogenation of the nitroaniline (e.g. Br$_2$, Cl$_2$ etc.) gives the corresponding 4,6-disubstituted or mono-substituted nitroaniline which can be further modified at a later stage. The nitro group can be reduced with number of reagents preferably sodium dithionite to provide the corresponding diamine. This diamine is then subjected to nitration conditions by first generating the 2,1,3-benzoselenadiazole with selenium dioxide followed by nitric acid. Substituted nitro-1,2-phenylenediamines are generated by treatment of the nitro-2,1,3-benzoselenadiazole with aqueous hydrogen iodide or $NH_3/H_2S$ (Nyhammar et al, *Acta, Chem. Scand.* 1986, B40: 583). Other methods to simultaneously protect the diamine are also envisioned.

(c) The compounds of formula 2, where R is alkyl or aryl, can be synthesized using the method of Ohmori et al, *J. Med. Chem.* 1996, 39: 3971. Nucleophilic substitution of the o-halonitrobenzenes by treatment with various alkylamines followed by reduction (e.g. $Na_2S_2O_4$) of the nitro group provides the desired compounds. Alternately, the compounds of formula 2, where R is H, can be synthesized from these o-halonitrobenzenes via o-azidonitrobenzenes followed by reduction of the nitro group to provide the desired compound.

(d) Alternately, diamines of formula 2 where R is not H are prepared by reductive alkylation of the o-nitroanilines with various aldehydes(e.g. akyl, aryl etc.) in the presence of a reducing agent preferably NaB(OAc)$_3$ followed by reduction (e.g. $Na_2S_2O_4$; Pd/C, H$_2$ etc.) of the nitro group (Magid et al *Tetrahedron Lett.* 1990, 31: 5595).

Formulations

Compounds of the invention are administered orally in a total daily dose of about 0.1 mg/kg/dose to about 100 mg/kg/dose, preferably from about 0.3 mg/kg/dose to about 30 mg/kg/dose. The most preferred dose range is from 0.5 to 10 mg/kg (approximately 1 to 20 nmoles/kg/dose). The use of time-release preparations to control the rate of release of the active ingredient may be preferred. The dose may be administered in as many divided doses as is convenient. When other methods are used (e.g. intravenous administration), compounds are administered to the affected tissue at a rate from 0.3 to 300 nmol/kg/min, preferably from 3 to 100 nmoles/kg/min. Such rates are easily maintained when these compounds are intravenously administered as discussed below.

For the purposes of this invention, the compounds may be administered by a variety of means including orally, parenterally, by inhalation spray, topically, or rectally in formulations containing pharmaceutically acceptable carriers, adjuvants and vehicles. The term parenteral as used here includes subcutaneous, intravenous, intramuscular, and intraarterial injections with a variety of infusion techniques. Intraarterial and intravenous injection as used herein includes administration through catheters. Oral administration is generally preferred.

Pharmaceutical compositions containing the active ingredient may be in any form suitable for the intended method of administration. When used for oral use for example, tablets, troches, lozenges, aqueous or oil suspensions, dispersible powders or granules, emulsions, hard or soft capsules, syrups or elixirs may be prepared. Compositions intended for oral use may be prepared according to any method known to the art for the manufacture of pharmaceutical compositions and such compositions may contain one or more agents including sweetening agents, flavoring agents, coloring agents and preserving agents, in order to provide a palatable preparation. Tablets containing the active ingredient in admixture with non-toxic pharmaceutically acceptable excipient which are suitable for manufacture of tablets are acceptable. These excipients may be, for example, inert diluents, such as calcium or sodium carbonate, lactose, calcium or sodium phosphate; granulating and disintegrating agents, such as maize starch, or alginic acid; binding agents, such as starch, gelatin or acacia; and lubricating agents, such as magnesium stearate, stearic acid or talc. Tablets may be uncoated or may be coated by known techniques including microencapsulation to delay disintegration and adsorption in the gastrointestinal tract and thereby provide a sustained action over a longer period. For example, a time delay material such as glyceryl monostearate or glyceryl distearate alone or with a wax may be employed.

Formulations for oral use may be also presented as hard gelatin capsules where the active ingredient is mixed with an inert solid diluent, for example calcium phosphate or kaolin, or as soft gelatin capsules wherein the active ingredient is mixed with water or an oil medium, such as peanut oil, liquid paraffin or olive oil.

Aqueous suspensions of the invention contain the active materials in admixture with excipients suitable for the manufacture of aqueous suspensions. Such excipients include a suspending agent, such as sodium carboxymethylcellulose, methylcellulose, hydroxypropyl methylcelluose, sodium alginate, polyvinylpyrrolidone, gum tragacanth and gum acacia, and dispersing or wetting agents such as a naturally occurring phosphatide (e.g., lecithin), a condensation product of an alkylene oxide with a fatty acid (e.g., polyoxyethylene stearate), a condensation product of ethylene oxide with a long chain aliphatic alcohol (e.g., heptadecaethyleneoxycetanol), a condensation product of ethylene oxide with a partial ester derived from a fatty acid and a hexitol anhydride (e.g., polyoxyethylene sorbitan monooleate). The aqueous suspension may also contain one or more preservatives such as ethyl or n-propyl p-hydroxybenzoate, one or more coloring agents, one or more flavoring agents and one or more sweetening agents, such as sucrose or saccharin.

Oil suspensions may be formulated by suspending the active ingredient in a vegetable oil, such as arachis oil, olive oil, sesame oil or coconut oil, or in a mineral oil such as liquid paraffin. The oral suspensions may contain a thickening agent, such as beeswax, hard paraffin or cetyl alcohol. Sweetening agents, such as those set forth above, and flavoring agents may be added to provide a palatable oral preparation. These compositions may be preserved by the addition of an antioxidant such as ascorbic acid.

Dispersible powders and granules of the invention suitable for preparation of an aqueous suspension by the addition of water provide the active ingredient in admixture with a dispersing or wetting agent, a suspending agent, and one or more preservatives. Suitable dispersing or wetting agents and suspending agents are exemplified by those disclosed above. Additional excipients, for example sweetening, flavoring and coloring agents, may also be present.

The pharmaceutical compositions of the invention may also be in the form of oil-in-water emulsions. The oily phase may be a vegetable oil, such as olive oil or arachis oil, a mineral oil, such as liquid paraffin, or a mixture of these. Suitable emulsifying agents include naturally-occurring gums, such as gum acacia and gum tragacanth, naturally occurring phosphatides, such as soybean lecithin, esters or partial esters derived from fatty acids and hexitol anhydrides, such as sorbitan monooleate, and condensation products of these partial esters with ethylene oxide, such as polyoxyethylene sorbitan monooleate. The emulsion may also contain sweetening and flavoring agents.

Syrups and elixirs may be formulated with sweetening agents, such as glycerol, sorbitol or sucrose. Such formulations may also contain a demulcent, a preservative, a flavoring or a coloring agent.

The pharmaceutical compositions of the invention may be in the form of a sterile injectable preparation, such as a sterile injectable aqueous or oleaginous suspension. This suspension may be formulated according to known art using those suitable dispersing or wetting agents and suspending agents which have been mentioned above. The sterile injectable preparation may also be a sterile injectable solution or suspension in a non-toxic parenterally acceptable diluent or solvent, such as a solution in 1,3-butane-diol or prepared as a lyophilized powder. Among the acceptable vehicles and solvents that may be employed are water, Ringer's solution and isotonic sodium chloride solution. In addition, sterile fixed oils may conventionally be employed as a solvent or suspending medium. For this purpose any bland fixed oil may be employed including synthetic mono- or diglycerides. In addition, fatty acids such as oleic acid may likewise be used in the preparation of injectables.

The amount of active ingredient that may be combined with the carrier material to produce a single dosage form will vary depending upon the host treated and the particular mode of administration. For example, a time-release formulation intended for oral administration to humans may contain 20 to 2000 $\mu$mol (approximately 10 to 1000 mg) of active material compounded with an appropriate and convenient amount of carrier material which may vary from about 5 to about 95% of the total compositions. It is preferred that the pharmaceutical composition be prepared which provides easily measurable amounts for administration. For example, an aqueous solution intended for intravenous infusion should contain from about 0.05 to about 50 $\mu$mol (approximately 0.025 to 25 mg) of the active ingredient per milliliter of solution in order that infusion of a suitable volume at a rate of about 30 mL/hr can occur.

As noted above, formulations of the present invention suitable for oral administration may be presented as discrete units such as capsules, cachets or tablets each containing a predetermined amount of the active ingredient; as a powder or granules; as a solution or a suspension in an aqueous or non-aqueous liquid; or as an oil-in-water liquid emulsion or a water-in-oil liquid emulsion. The active ingredient may also be administered as a bolus, electuary or paste.

A tablet may be made by compression or molding, optionally with one or more accessory ingredients. Compressed tablets may be prepared by compressing in a suitable machine the active ingredient in a free flowing form such as a powder or granules, optionally mixed with a binder (e.g., povidone, gelatin, hydroxypropylmethyl cellulose), lubricant, inert diluent, preservative, disintegrant (e.g., sodium starch glycolate, cross-linked povidone, cross-linked sodium carboxymethyl cellulose) surface active or dispersing agent. Molded tablets may be made by molding in a suitable machine a mixture of the powdered compound moistened with an inert liquid diluent. The tablets may optionally be coated or scored and may be formulated so as to provide slow or controlled release of the active ingredient therein using, for example, hydroxypropyl methylcellulose in varying proportions to provide the desired release profile. Tablets may optionally be provided with an enteric coating, to provide release in parts of the gut other than the stomach. This is particularly advantageous with the compounds of formula 1 when such compounds are susceptible to acid hydrolysis.

Formulations suitable for topical administration in the mouth include lozenges comprising the active ingredient in a flavored base, usually sucrose and acacia or tragacanth; pastilles comprising the active ingredient in an inert base such as gelatin and glycerin, or sucrose and acacia; and mouthwashes comprising the active ingredient in a suitable liquid carrier.

Formulations for rectal administration may be presented as a suppository with a suitable base comprising for example cocoa butter or a salicylate.

Formulations suitable for vaginal administration may be presented as pessaries, tampons, creams, gels, pastes, foams or spray formulations containing in addition to the active ingredient such carriers as are known in the art to be appropriate.

Formulations suitable for parenteral administration include aqueous and non-aqueous isotonic sterile injection solutions which may contain antioxidants, buffers, bacteriostats and solutes which render the formulation isotonic with the blood of the intended recipient; and aqueous and non-aqueous sterile suspensions which may include suspending agents and thickening agents. The formulations may be presented in unit-dose or multi-dose sealed containers, for example, ampoules and vials, and may be stored in a freeze-dried (lyophilized) condition requiring only the addition of the sterile liquid carrier, for example water for injections, immediately prior to use. Injection solutions and suspensions may be prepared from sterile powders, granules and tablets of the kind previously described.

Preferred unit dosage formulations are those containing a daily dose or unit, daily sub-dose, or an appropriate fraction thereof, of a fructose 1,6-bisphosphatase inhibitor compound.

It will be understood, however, that the specific dose level for any particular patient will depend on a variety of factors including the activity of the specific compound employed; the age, body weight, general health, sex and diet of the individual being treated; the time and route of administration; the rate of excretion; other drugs which have previously been administered; and the severity of the particular disease undergoing therapy, as is well understood by those skilled in the art.

Utility

FBPase inhibitors at the AMP site may be used to treat diabetes mellitus, lower blood glucose levels, and inhibit gluconeogenesis.

FBPase inhibitors at the AMP site may also be used to treat excess glycogen storage diseases. Excessive hepatic glycogen stores are found in patients with some glycogen storage diseases. Since the indirect pathway contributes significantly to glycogen synthesis (Shulman, G. I. *Phys. Rev.* 72:1019–1035 (1992)), inhibition of the indirect pathway (gluconeogenesis flux) is expected to decrease glycogen overproduction.

FBPase inhibitors at the AMP site may also be used to treat or prevent diseases associated with increased insulin levels. Increased insulin levels are associated with an increased risk of cardiovascular complications and atherosclerosis (Folsom, et al., *Stroke,* 25:66–73 (1994); Howard, G. et al., *Circulation* 93:1809–1817 (1996)). FBPase inhibitors are expected to decrease postprandial glucose levels by enhancing hepatic glucose uptake. This effect is postulated to occur in individuals that are non-diabetic (or pre-diabetic, i.e. without elevated HGO or fasting blood glucose levels). Increased hepatic glucose uptake will decrease insulin secretion and thereby decrease the risk of diseases or complications that arise from elevated insulin levels.

The compounds of this invention and their preparation can be understood further by the examples which illustrate some of the processes by which these compounds are prepared. These examples should not however be construed as specifically limiting the invention and variations of the invention, now known or later developed, are considered to fall within the scope of the present invention as hereinafter claimed.

EXAMPLES

Example 1

Preparation of 2-Furaldehyde-5-diethylphosphonate

Method A

To a solution of 25 mL (147.5 mmol) 2-furaldehyde diethyl acetal in 25 ml of THF at −78° C., was added 96 mL (147.2 mmol) of a 1.6 M BuLi hexane solution. The solution was allowed to stir for 1 h at −78° C. and 24 mL (166.1 mmol) chlorodiethylphosphonate was added and stirred for 0.5 h. The mixture was quenched at −78° C. with a saturated $NH_4Cl$ solution. The precipitates formed were filtered and the filtrate concentrated. The mixture was partitioned between water and $CH_2Cl_2$ and separated. The organic layer was dried with sodium sulfate, filtered and the solvent removed under reduced pressure. The resulting brown oil was treated with 80% acetic acid and heated at 90° C. for 4 h. Chromatography on silica using 75% ethyl acetate/hexanes yielded 9.1 g (39.2 mmol, 26.6%) of a clear oil.

Method B:

To a solution of 2.8 mL (13.75 mmol) TMEDA and 1.0 mL (13.75 mmol) furan in 9 mL of diethyl ether at −78° C., was added 8.6 mL (13.75 mmol) of a 1.6 M BuLi hexane solution. The solution was allowed to stir for 0.5 hour at −78° C. and 2.19 mL (15.25 mmol) chlorodiethylphosphonate was added and stirred for 2 h. The mixture was quenched at −78° C. with a saturated sodium bicarbonate solution, The mixture was partitioned between water and $CH_2Cl_2$ and separated. The organic layer was dried with sodium sulfate, filtered and the solvent removed under reduced pressure. The resulting brown oil was purified through Kugelrohr distillation yielding 1.978 g (9.696 mmol, 70.5%) of a clear oil.

To a solution of 16.01 g (78.41 mmol) 2-diethylphosphonfuran in 400 mL of tetrahydrofuran at −78° C., was added 58.81 mL (117.62 mmol) of a 2M LDA solution. The solution was allowed to stir for 0.3 h at −78°

C. and 9.67 mL (156.82 mmol) methylchloroformate was added and stirred for 0.5 h. The mixture was quenched at −78° C. with a saturated sodium bicarbonate solution. The mixture was partitioned between water and $CH_2Cl_2$ and separated. The organic layer was dried with sodium sulfate, filtered and the solvent removed under reduced pressure. The resulting oil was purified by silica gel chromatography yielding 5.6 g (18.2 mmol, 31%) of a clear yellow oil.

Method C

To a solution of 168 g (1.75 mol) 2-furaldehyde in 500 mL toluene was added 215 mL (1.75 mol) of N,N'-dimethylethylene diamine. The solution was refluxed using a Dean Stark trap to remove $H_2O$. After 2 hours of reflux, the solvent was removed under reduced pressure. The resulting dark mixture was vacuum distilled (3 mm Hg) and the fraction at 59–61° C. was collected yielding 247.8 g (85%) of clear, colorless oil.

A solution of 33.25 g (0.2 mol) furan-2-(N,N'-dimethylimidazolidine) and 30.2 mL (0.2 mol) tetramethylethylenediamine in 125 mL THF was cooled in a dry ice/IPA bath. A solution of 112 mL n-BuLi in hexane(0.28 mol, 2.5M) was added dropwise, maintaining temperature between −50 and −40° C. during addition. The reaction was allowed to warm to 0° C. over 30 minutes and was maintained at 0° C. for 45 minutes. The reaction was then cooled in a dry ice/IPA bath to −55° C. This cooled solution was transferred to a solution of 34.7 mL (0.24 mol) diethylchlorophosphate in 125 mL THF and cooled in a dry ice/IPA bath over 45 minutes maintaining the reaction temperature between −50° C. and −38° C. The reaction was stirred at room temperature overnight. The reaction mixture was evaporated under reduced pressure. Ethyl acetate and $H_2O$ were added to the residue and the layers separated. The $H_2O$ layer was washed with ethyl acetate. The ethyl acetate layers were combined, dried over magnesium sulfate and evaporated under reduced pressure yielding 59.6 g (98%) of a brown oil.

To a solution of 59.6 g 5-diethylphosphonofuran-2-(N,N'-dimethylimidazolidine) in 30 mL $H_2O$ was added 11.5 mL of conc. $H_2SO_4$ dropwise until pH=1 was obtained. The aqueous reaction mixture was extracted with ethyl acetate. The ethyl acetate layer was washed with saturated sodium bicarbonate, dried over magnesium sulfate and evaporated to a brown oil. The brown oil was added to a silica column and was eluted with hexane/ethyl acetate. Product fractions were pooled and evaporated under reduced pressure yielding a dark yellow oil, 28.2 g (62%).

Example 2

Preparation of 5-diethylphosphono-2-thiophenecarboxaldehyde

Step 1

A solution of 1.0 mmol 2-thienyl lithium in THF was treated with 1.0 mmol diethyl chlorophosphate at −78° C. for 1 h. Extraction and chromatography gave diethyl 2-thiophenephosphonate as a clear oil.

Step 2

A solution 1.0 mmol of diethyl 2-thiophenephosphonate in tetrahydrofuran was treated with 1.12 mmol LDA at −78° C. for 20 min. 1.5 mmol methyl formate was added and the reaction was stirred for 1 hr. Extraction and chromotagraphy gave 5-diethylphosphono-2-thiophenecarboxaldehyde as a clear yellow oil.

Example 3

General Methods for the Preparation of Substituted 1.2-Phenylenediamines

Method A

Step 1

Bromination of Nitroanilines.

To a solution of 1.0 mmol of sustituted nitroaniline in 10 mL of $CHCl_3$ or a mixture of $CHCl_3$ and MeOH (7:1) was added a solution containing one equivalent of $Br_2$ in 5 mL of $CHCl_3$ over a period of 30 min. After stirring for 2 days at room temperature, extractive isolation provided the bromination product.

Step 2

Reduction of Nitroanilines

To a solution of 1.0 mmol of substituted nitroaniline in 15 mL of MeOH was added 15 mL of saturated solution of sodium dithionite. Filtration followed by removal of solvent and extraction with EtOAc provided the pure diamine.

Step 3

Preparation of 2.1.3-Benzoselenadiazole

To a solution of 1.0 mmol of substituted diamine in 3 mL of 50% aq. ethanol was added a solution of 1.0 mmol of $SeO_2$ in 1.5 mL of $H_2O$. The mixture quickly thickened to a slurry. The solid separated out, was filtered, washed with water, and dried.

Step 4

Nitration of Benzoselenadiazoles

To a cold (0° C.) suspension of 1.0 mmol of substituted 2,1,3-benzoselenadiazole was added dropwise a solution of 2.0 mmol of $HNO_3$ in 1 mL of $H_2SO_4$. The resultant suspension was stirred for 2 h at 15° C. The dark solution was poured onto ice, filtered, washed with water, and dried.

In the case of 5-fluoro-7-bromo-2,1,3-benzoselenadiazole there were two products in 2:1 ratio, major being the required compound, 4-nitro-5-fluoro-7-bromo-2,1,3-benzoselenadiazole. This was extracted with hot toluene from the byproduct, 4-nitro-5-hydroxy-7-bromo-2,1,3-benzoselenadiazole.

Step 5

Substituted 3-Nitro-1.2-Phenylenediamine Preparation

A mixture of 1.0 mmol of substituted 4-nitro-2,1,3-benzoselenadiazole in 3 mL of 57% Hl was stirred at room temperature for 2 h. Saturated $NaHSO_3$ was added and the mixture was neutralized with concentrated $NH_3$ solution. The product was extracted with $CHCl_3$ (5×10 mL) and the extracts were washed, dried, and evaporated.

Method B

From 2-Nitrohalobenzenes

To a solution of 20 mmol of substituted 2-halonitrobenzene in 70 mL of DMF was added 35 mmol of alkyl or arylamine at 0° C. After 0.5 h TLC (ethyl acetate/hexane 2:1) indicated the completion of reaction. The reaction mixture was evaporated under reacetate and washed withidue was dissolved in ethyl acetate and washed with water. The organic layer was dried, and evaporated to yield the displacement products.

Method C

From 2-Nitroanilines

To a solution of 10 mmol of substituted 2-nitroaniline, 20 mmol of alkyl or arylaldehyde, and 60 mmol of acetic acid in 30 mL of 1,2-dichloroethane was added 30 mmol sodium triacetoxyborohydride at 0° C. The reaction was stirred overnight under nitrogen atmosphere and was quenched with saturated sodium bicarbonate solution. The product was extracted with EtOAc (3×75 mL) and the extract was washed, dried and evaporated. The residue was chromatographed on a silica gel column eluting with hexane-ethyl acetate (3:1) to yield the product.

These nitroanilines can be reduced to 1,2-phenylenediamines by the procedure given in the Example 3, Method A, Step 2.

Example 4

Preparation of 2-Substituted Benzimidazole

Method A

Step 1

A mixture of 1.0 mmol of sustituted 1,2-phenylenediamine and 1.0 mmol of 2-furaldehyde-5- diethylphosphonate in 10 mL of toluene was refluxed (oil bath temp. 140–150° C.) for 1–16 h with a Dean Stark trap to remove water. Solvent was removed under reduced pressure and used the product for the next step without further purification.

Step 2

A solution of 1.0 mmol of this coupled product and 1.0 mmol of $I_2$ in 5 mL of ethanol was stirred at room temperature for 1–16 h. Extraction and chromatography provided the title compound as an orange solid.

Method B

To a solution of 1.0 mmol of substituted 1,2-phenylenediamine and 1.0 mmol of 2-furaldehyde-5-diethylphosphonate in 3 mL of DMF was added 0.2–2.0 mmol of $FeCl_3$ and heated for 1–7 h at 90° C. while bubbling air through the solution. Extraction and chromatography provided the condensation product as an orange solid.

Method C

A solution of 1.0 mmol of substituted 1,2-phenylenediamine and 1.0 mmol ol 2-furaldehyde-5-diethylphosphonate in 2 mL of MeOH and AcOH mixture (3:1) was stirred at room temperature for 16 h. Extraction and chromatography provided the condensation product as a solid.

Method D

A mixture of 1.0 mmol of sustituted 1,2-phenylenediamine and 1.5 mmol of diethylphosphomethyl acetaldehyde dimethyl acetal ether in 4 mL of THF was heated at 75° C. for 40 min. in presence of 0.5 mL of 10% $H_2SO_4$. Solvent was removed under reduced pressure and used for the next step without further purification.

A solution of 1.0 mmol of this coupled product and 1.0 mmol of $I_2$ in 5 mL of ethanol was stirred at room temperature for 16 h. Extraction and chromatography provided the required product.

Example 5

General Procedures for Alkylation

Method A

A suspension of 1.5 mmol cesium carbonate, 1.0 mmol of substituted benzimidazole-2-(5-diethylphosphonate)furan and 1.0 mmol of electrophile in 5 mL of dry DMF was heated at 80° C. for 1–16 h. Extraction and chromatography provided the alkylation product as a yellow solid.

Method B:(Mitsunobu Reaction)

To a suspension of 2.0 mmol of substituted 2-[(5-diethylphosphonate)furanyl]benzimidazole, 6.0 mmol electrophile, 6.0 mmol triphenylphosphine, 5.0 mL diisopropylethylamine and 200 mg 4A molecular sieves in 10 mL of dry $CH_3CN$ was added 12.0 mmol diethyl azodicarboxylate at 0° C. The solution was allowed to warm to room temperature and stirred overnight. Extraction and chromatography provided the alkylation product as a yellow solid.

Example 6

General Procedures for Pd Coupling

Method A

A mixture of 1.0 mmol of bromo substituted 2-[(5-diethylphosphonate)furanyl]benzimidazole compound, 2.0 mmol of vinyltributyltin or allyltributyltin, and 0.1 mmol of $Pd(PPh_3)_2Cl_2$ or $Pd(PPh_3)_4$ in 4 mL of DMF was stirred and heated at 90° C. for 1–16 h. Extraction and chromatography provided the coupled compound.

Method B

A mixture of 1.0 mmol of bromo substituted 2-[(5-diethylphosphonate)furanyl]benzimidazole, 2.0 mmol of propargyl alcohol or any terminal acetylenic compound, 0.1 mmol of $Pd(PPh_3)_2Cl_2$, and 0.1 mmol of CuI in 1 mL of $Et_3N$ and 10 mL of $CH_3CN$ was stirred and heated at 50–80° C. for 1–16 h. Extraction and chromatography provided the coupled compound.

Method C

A mixture of 1.0 mmol of bromo substituted 2-[(5-diethylphosphonate)furanyl]benzimidazole, 5.0 mmol of substituted phenylboronic acid, 0.1 mmol of $Pd(PPh_3)_4$, 5 mL of sat. $Na_2CO_3$ and 2 mL of EtOH in 10 mL of diglyme was stirred and heated at 80–90° C. for 1–16 h. Extraction and chromatography provided the coupled compound.

The compounds thus obtained can be modified as needed. For example vinyl or propargyl alcohol derivatives can be hydrogenated (see Example 9, Method A) to give the ethyl or propyl alcohol derivatives respectively. These alcohol can be further modified as required via alkyl halides (see Example 8) or alkyl sulfonates etc. to number of substituted alkyl compounds by subjecting them to, nucleophilic substitution reactions (March, *Advanced Organic Chemistry*, Wiley-Interscience, Fourth Edition, 1992, 293–500). See Example 7 for the cyclopropanation of the vinyl derivative.

Example 7

Cyclopropynation of the 4-nitro-7-vinyl-5-fluoro-1-isobutyl-2-(2-diethylphosphono-5-furanyl)benzimidazole.

To a suspension of 1.0 mmol of 4-nitro-7-vinyl-5-fluoro-1-isobutyl-2-(2-diethylphosphono-5-furanyl)benzimidazole and 0.1 mmol of $Pd(OAc)_2$ in 8 mL of ether was added an ether solution of diazomethane (generated from 3.0 g of 1-methyl-3-nitro-1-nitrosoguanidine) at 0 ° C. After stirring at room temperature 20 h solvent was removed and the residue chromatographed to give 4-nitro-7-cyclopropyl-5-fluoro-1-isobutyl-2-(2-diethylphosphono-5-furanyl) benzimidazole.

Example 8

Halogenation of the 4-amino-7-(4-hydroxybutyl)-5-fluoro-1-isobutyl-2-(2-diethylphosphono-5-furanyl)benzimidazole.

To a cold (0° C.) solution of 1.0 mmol of 4-amino-7-(4-hydroxybutyl)-5-fluoro-1-isobutyl-2-(2-diethylphosphono-5-furanyl)benzimidazole in 20 mL of $CH_2Cl_2$ was added 3.0 mmol of $PPh_3$ and 3.0 mmol of $CBr_4$. After 40 min. at room temperature solvent was removed and the residue was subjected to chromatography to give 4-amino-7-(4-bromobutyl)-5-fluoro-1-isobutyl-2-(2-diethylphosphono-5-furanyl)benzimidazole. $CCl_4$ gave the corrosponding chloro compound.

Example 9

General Procedures for Reduction

Method A

A mixture of 1.0 mmol of alkylation product and 20 mg of 10% Pd/C in 5 mL of DMF or MeOH was hydrogenated using $H_2$ from a balloon for 0.5–16 h. The reaction mixture was filtered through Celite and chromatographed to provide the reduction product as an oil.

Method B

To a solution of 1.0 mmol of substituted nitroaniline in 15 mL of MeOH was added 15 mL of a saturated solution of sodium dithionite. Filtration followed by removal of solvent and extraction with EtOAc or $CHCl_3$ provided the pure diamine.

These primary aromatic amines can also be modified as needed. For example N-acetyl derivetives can be prepared by treatment with acetyl chloride or acetic anhydride in presence of a base such as pyridine and mono-, or di-alkylamines can be synthesized by direct alkylation (see Example 5 ) or by reductive alkyllation (see Example 3, Method C.).

Example 10

Bromination of 4-amino-i-isobutyl-2-[2-(5-phosphono)furanyl]benzimidazole.

A mixture of 1.0 mmol of 4-amino-i-isobutyl-2-[2-(5-phosphono)furanyl] benzimidazole, and 1.0 mmol of NBS in 5 mL of $CCl_4$ was stirred at room temperature for 4 h. The mixture was processed by filtration and chromatography to provide o-bromo (21%, R.=0.14), p-bromo (25%, R.=0.01) and dibromo (36%, $R_f$=0.23).

When $Br_2$ was used in place of NBS, the dibromo compound was formed exclusively. The same procedures were followed for chlorination.

General procedures for phosphonate hydrolysis

Example 11

$BBr_3$ hydrolysis

To a solution of 1.0 mmol of substituted 2-[(5-diethylphosphonate)furanyl]benzimidazole in 3 mL of anhydrous $CH_2Cl_2$ was added 10 mmol of 1.0 M $BBr_3$ solution in $CH_2Cl_2$ at −78° C. and the mixture was allowed to warm to room temperature. After 16 h, solvent and excess $BBr_3$ were removed under reduced pressure and the residue was taken into 3 mL of water. The precipitate was filtered, washed with water, and MeOH and was dried under vaccum at 50° C.

The following compound was prepared in this manner:

11.1: 4-Amino-5-hydroxy-1-isobutyl-2-(2-phosphono-5-furanyl) benzimidazole. mp=206–209° C.; Anal. Cald. for $C_{15}H_{18}N_3O_5P+2.7H_2O$: C: 45.05; H: 5.90; N: 10.51. Found: C: 44.96; H: 5.78; N: 10.14.

Example 12

TMSBr hydrolysis

To a solution of 1.0 mmol of substituted 2-[(5-diethylphosphonate)furanyl]benzimidazole in 5 mL of anhydrous $CH_2Cl_2$ was added 10.0 mmol TMSBr at 0° C. After 16 h stirring at room temperature the solvent and excess TMSBr were removed under reduced pressure. The residue was taken into 15 mL of a ⅕ mixture of acetone/water and was stirred for 16 h at room temperature. The resulting solid was filtered, washed with water, EtOAc, and MeOH and was dried under vacuum at 50° C.

The following compounds were prepared in this manner:

12.1: 4-Amino-1-ethyl-2-[2-(5-phosphono)furanyl] benzimidazole. mp>250° C.; Anal. Cald. for $C_{13}H_{14}N_3O_4P+1\ H_2O$: C: 48.01; H: 4.96; N: 12.92. 48.46; H: 4.79; N: 12.6.

1.2: 4-Amino-1-cyclohexylethyl-2-[2-(5-phosphono) furanyl] benzimidazole. mp>250° C.; Anal. Cald. for $C_{19}H_{24}N_3O_4P+0.5\ H_2O$: C: 57.28; H: 6.32; N: 10.55. Found: C: 57.04; H: 5.77; N: 10.32.

12.3: 4-Amino-2-[2-(5-phosphono)furanyl]benzimidazole. mp>240° C.; Anal. Cald. for $C_{11}H_{10}N_3O_4P+2H_2O$: C: 41.91; H: 4.48; N: 13.33. Found: C: 41.52; H: 4.34; N: 13.09.

12.4: 4-Amino-1methyl-2-[2-(5-phosphono)furanyl] benzimidazole. mp>230° C.; Anal, Cald. for $C_{12}H_{12}N_3O_4P+1\ H_2$: C: 46.31; H: 4.53; N: 13.50. Found: C: 46.52; H: 4.31; N: 13.37.

12.5: 4-Amino-1-(4-methylbenzyl)-2-[2-(5-phosphono) furanyl] benzimidazole acetic acid salt. mp=222–225° C.; Anal. Cald. for $C_{19}H_{18}N_3O_4P+AcOH\ 0.25H_2O$: C: 56.31; H: 5.06; N: 9.38. Found: C: 56.50; H: 5.23; N: 9.63.

12.6: 4-Amino-1-(3-carbomethoxybenzyl)-2-[2-(5-phosphono)furanyl] benzimidazole. mp=198–202 ° C.; Anal. Cald. for $C_{20}H_{18}N_3O_6P$: C: 55.55; H: 4.39; N: 9.63. Found: C: 55.12; H: 4.29; N: 9.18.

12.7: 4-Amino-1-isobutyl-2-[2-(5-phosphono)furanyl] benzimidazole. mp=195–200° C.; Anal. Cald. for $C_{15}H_{18}N_3O_4P+1.5\ H_2O$: C: 49.73; H: 5.84; N 11.60. Found: C: 50.08; H: 5.51; N: 11.23.

12.8: 4-Amino-1-ethylbenzimidazol-2-yl-methyleneoxymethyl phosphonic acid. mp=208–210° C.; Anal. Cald. for $C_{11}H_{16}N_3O_4P+2.5H_2O$: C: 40.00; H: 6.41; N: 12.72. Found: C: 40.14; H: 5.17; N: 12.37. >88% pure by HPLC.

12.9: 4-Amino-1-(3-methylbenzyl)-2-[2-(5-phosphono) furanyl] benzimidazole. mp>250° C.; Anal. Cald. for $C_{19}H_{18}N_3O_4P+H_2O$: C: 56.86; H: 5.02; N: 10.47. Found: C: 56.66; H: 4.59; N: 10.34.

12.10: 4-Amino-1-[2'-(3"-carboethoxy-5",6",7",8"-tetrahydronaphthyl)ethyl]-2-[2-(5-phosphono)furanyl] benzimidazole. mp 198–202° C.; Anal. Cald. for $C_{26}H_{28}N_3O_6P+H_2O$: C: 59.20; H: 5.73; N: 7.97. Found: C: 59.23; H: 5.54; N: 7.68.

12.11: 4-Amino-1-[2'-(3"-carboxy-5",6",7",8"-tetrahydronaphthyl)ethyl]-2-[8-(5-phosphono)furanyl] benzimidazole. mp=220–224° C.; Anal. Cald. for $C_{24}H_{24}N_3O_6P+2H_2O$: C: 55.71; H: 5.45; N: 8.12. Found: C: 56.18; H: 5.17; N: 7.97.

12.12: 4-Amino-1-propyl-2-[2-(5-phosphono)furanyl] benzimidazole. mp>230° C.; Anal. Cald. for $C_{14}H_{16}N_3O_4P+1.25\ H_2O$: C: 48.91; H: 5.42; N: 12.22. Found: C: 48.88; H: 5.07; N: 12.26.

12.13: 4-Amino-1-norbornylmethyl-2-[2-(5-phosphono) furanyl] benzimidazole. mp>230° C.; Anal. Cald. for $C_{19}H_{22}N_3O_4P+0.75H_2O$: C: 56.93; H: 5.91; N: 10.48. Found: C: 56.97; H: 5.63; N:10.28.

12.14: 4-Amino-1-(3-carboxybenzyl)-2-[2-(5-phosphono) furanyl] benzimidazole. mp>250° C.; Anal. Cald. for $C_{19}H_{16}N_3O_6P+2.5H_2O$: C: 49.79; H; 4.62; N: 9.17. Found: C: 49.30; H: 4.00; N: 8.49. Mass. cald. for $C_{19}H_{16}N_3O_6P$: 413. Found: $MH^+$=414: $MH^-$=412.

12.15: 4-Amino-1-cyclopentanemethyl-2-[2-(5-phosphono) furanyl]-benzimidazole. mp>230° C.; Anal. Cald. for $C_{17}H_{20}N_3O_4P+1.4H_2O$: C: 52.82; H: 5.92; N: 10.87. Found: C: 52.81; H: 5.71; N: 10.51.

12.16: 4-Amino-1-cyclopropanemethyl-2-[2-(5-phosphono) furanyl] benzimidazole. mp>230° C. ; Anal. Cald. for $C_{15}H_{16}N_3O_4P+0.75\ CH_2Cl_2$: C: 47.65; H: 4.44; N: 10.58. Found: C: 47.81; H: 4.57; N: 10.77.

12.17: 4-Amino-1-cyclobutanemethyl-2-[2-(5-phosphono) furanyl] benzimidazole. mp>230° C.; Anal. Cald. for $C_{16}H_{18}N_3O_4P+0.5\ H_2O$: C: 53.93. H: 5.37; N: 11.79. Found: C: 53.89; H: 5.12; N: 11.48.

12.18: 4-Amino-1-(3-methyl-6,6-dimethyl-2-cyclohexenylmethyl)-$^2$-[$^2$-(5-phosphono)furanyl] benzimidazole. mp>220° C. ; Anal. Cald. for $C_{21}H_{24}N_3O_4PNa_2+2\ H_2O$: C: 50.91; H: 5.70; N: 8.48. Found: C: 50.82; H: 5.53; N: 8.26.

12.19: 4-Amino-1-(2-methyl-2-butenyl)-2-[2-(5-phosphono)furanyl] benzimidazole. mp=190–195° C.; Anal. Cald. for $C_{16}H_{18}N_3O_4P+1.5H_2O$: C: 51.34; H: 5.65; N: 11.23. Found: C: 51.68; H: 5.59; N: 11.37.

12.20: 4-Amino-1-[(1S,2S,5S)myrtanyl]-2-[2-(5-phosphono)furanyl] benzimidazole. mp>200° C. ; Anal. Cald. for $C_{21}H_{26}N_3O_4P+1\ H_2O$: C: 58.19; H: 6.51; N: 9.69. Found: C: 58.49; H: 6.12; N: 9.65.

12.21: 4-Amino-1-(4-t-butylbenzyl)-2-[2-(5-phosphono)furanyl] benzimidazole. mp=246–249° C.; Anal. Cald. for $C_{22}H_{21}N_3O_4P+0.66H_2O$: C: 60.40; H: 5.84; N: 9.60. Found: C: 60.37; H: 5.45; N: 8.87. Mass. cald. for $C_{22}H_{21}N_3O_4P$=425. Found: MH$^+$=426; MH$^-$=424.

12.22: 4-Amino-1-(4-cyclohexyl-1-butyl)-2-[2-(5-phosphono) furanyl]benzimidazole. mp>230° C.; Anal. Cald. for $C_{21}H_{28}N_3O_4P+0.6H_2O$: C: 58.90; H: 6.87; N: 9.81. Found: C: 58.67; H: 6.54; N: 9.46.

12.23: 4-Amino-1-(3-cyclohexyl-1-propyl)-2-[2-(5-phosphono) furanyl]benzimidazole. mp>218° C. ; Anal. Cald. for $C_{20}H_{26}N_3O_4P+1.2\ H_2O$: C: 56.52; H: 6.73; N: 9.89. Found: C: 56.71; H: 6.30; N: 9.47.

12.24: 4.-Amino-1-(3-carboxypropyl)-2-[2-(5-phosphono) furanyl] benzimidazole. mp>225° C.; Anal. Cald. for $C_{15}H_{16}N_3O_6P$: C: 49.3; H: 4.42; N: 11.51. Found: C: 49.01; H: 4.22; N: 11.21.

12.25: 4-Amino-1-(3-carboethoxypropyl)-2-[2-(5-phosphono)furanyl] benzimidazole. mp>225° C.; Anal. Cald. for $C_{17}H_{20}N_3O_6P$: C: 51.89; H: 5.13; N: 10.69. Found: C: 51.68; H: 5.08; N: 10.34.

12.26: 4-Amino-1-(t-butylmethylketone)-2-[2-(5-phosphono)furanyl] benzimidazole. mp>225° C. ; Anal. Cald. for $C_{17}H_{20}N_3O_5P+1.3\ H_2O$: C: 50.95; H: 5.68; N: 10.49. Found: C: 50.83; H: 5.21; N: 9.85.

12.27: 4-Amino-1-cycloheptanemethyl-2-[2-(5-phosphono) furanyl] benzimidazole. mp 198° C.; Anal. Cald. for $C_{19}H_{24}N_3O_4P+0.5\ H_2O$: C: 57.27; H: 6.25; N: 10.02. Found: C: 57.46; H: 6.22; N: 9.86.

12.28: 4-Amino-1-cyclohexanemethyl-2-[2-(5-phosphono) furanyl] benzimidazole. mp 210° C.; Anal. Cald. for $C_{18}H_{22}N_3O_4P+0.5$ AcOH: C: 56.29; H: 5.97; N: 10.37. Found: C: 56.00; H: 5.96; N: 10.32.

12.29: 4-Amino-1-benzyl-2-[2-(5-phosphono)furanyl] benzimidazole. mp>250° C.; Anal. Cald. for $C_{18}H_{14}N_3O_4PNa_2+1.6H_2O$: C: 48.78; H: 3.94; N: 9.48. Found: C: 49.10; H: 4.11; N: 8.73. Mass. cald. for $C_{18}H_{16}N_3O_4P$=369. Found: MH$^+$=370; MH$^-$=368.

12.30: 4-Amino-1-(3-trifluoromethylbenzyl)-2-[2-(5-phosphono) furanyl]benzimidazole. mp 235–239° C.; Anal. Cald. for $C_{19}H_{15}N_3O_4PF_3+0.1\ H_2O+1.6CH_3CO_2H$: C: 49.82; H: 4.07; N: 7.85. Found: C: 50.31; H: 4.04; N: 7.38.

12.31: 4-Amino-1-(3-carbamoylpropyl)-2-[2-(5-phosphono) furanyl]benzimidazole. mp>225° C.; Anal. Cald. for $C_{15}H_{17}N_4O_5P$: C: 49.44; H: 4.71; N: 15.38. Found: C: 49.00; H: 5.47; N: 14.06. Mass. cald. for $C_{15}H_{17}N_4O_5P$=364; MH$^+$=365: MH$^-$=363.

12.32: 4-Amino-1-(7-hydroxy-3R,7-dimethyloctyl)-2-[2-(5-phosphono)furanyl]benzimidazole. mp>250° C.; Anal. Cald. for $C_{21}H_{28}N_3O_5PNa_2+1.5\ H_2O$: C: 49.80; H: 6.17; N: 8.30. Found: C: 49.43; H: 6.01; N: 8.10.

12.33: 4-Amino-1-(4-chlorobutyl)-2-[2-(5-phosphono) furanyl] benzimidazole. mp>240° C.; Anal. Cald. for $C_{15}H_{17}N_3O_4ClP+0.5\ H_2O$: C: 47.57; H: 4.79; N: 11.09. Found: C: 47.62; H: 4.57; N: 10.87.

12.34: 4-Amino-1-(4-phenylbenzyl)-2-[2-(5-phosphono) furanyl] benzimidazole. mp>220° C.; Anal. Cald. for $C_{24}H_{20}N_3O_4P+0.66\ H_2O$: C: 63.01; H: 4.70; N: 9.19. Found: (C: 63.09; H: 4.50; N: 8.81.

12.35: 4-Amino-1-(3-chloropropyl)-2-[2-(5-phosphono) furanyl] benzimidazole. mp>>250° C.; Anal. Cald. for $C_{14}H_{15}N_3O_4ClP+0.7\ H_2O$: C: 44.83; H: 4.61; N: 10.37. Found: C:44.50; H:4.29; N:10.96.

12.36: 4-Amino-1-(4-hydroxybutyl)-2-[2-(5-phosphono) furanyl] benzimidazole. mp>>250° C.; Anal. Cald. for $C_{115}H_{16}N_3O_5PNa_2+1.8\ H_2O$: C: 41.68; H:4.71; N: 9.04. Found: C: 41.29; H: 4.60; N: 9.31.

12.37: 4-Amino-1-(3-furanylmethyl)-2-[2-(5-phosphono) furanyl] benzimidazole. mp>>230° C.; Mass. Cald. 358; Obs. 358.

12.38: 4-Amino-1-(3-hydroxybenzyl)-2-[2-(5-phosphono) furanyl] benzimidazole. mp 232–4° C.; Anal. Cald. for $C_{18}H_{16}N_3O_5P+2\ H_2O$: C: 51.31; H: 4.78; N: 9.97. Found: C: 51.01; H: 4.72; N: 10.15.

12.39: 4-Amino-1-[(2-methoxy)phenethyl]-2-[2-(5-phosphono)furanyl] benzimidazole. mp>240° C.; Anal. Cald. for $C_{20}H_{20}N_3O_5P+1\ H_2O$: C: 55.69; H: 5.14; N: 9.64. Found: C: 55.2; H: 4.90; N: 9.35.

12.40: 4-Amino-1-[(3-methoxy)phenethyl]-2-[2-(5-phosphono)furanyl] benzimidazole. mp>240° C.; Anal. Cald. for $C_{20}H_{20}N_3O_5P+1\ H_2O$: C: 55.69; H: 5.14; N: 9.64. Found: C: 55.09; H: 4.71; N: 9.52.

12.41: 4-Amino-1-(3-thienylmethyl)-2-[2-(5-phosphono) furanyl] benzimidazole. mp=200–205° C.; Anal. Cald. for $C_{16}H_{14}N_3O_4PS+1.7\ H_2O$: C: 47.34; H: 4.32; N: 10.35. Found: C: 46.90; H: 3.88; N: 10.05.

12.42: 4-Amino-5,7-dibromo-1-isobutyl-2-[2-(5-phosphono)furanyl] benzimidazole. mp>215° C.; Anal. Cald. for $C_{15}H_{16}Br_2N_3O_4P$: C:36.54; H: 3.27; N: 8.52. Found: C: 36.55; H: 3.22; N: 8.13.

12.43: 4-Amino-1-(1-hydroxyprop-3-yl)-2-[2-(5-phosphono) furanyl]benzimidazole. mp>213° C.;.Mass. Cald. 336; Obs. 336.

12.44: 4-Amino-5-bromo-1-isobutyl-2-[2-(5-phosphono) furanyl] benzimidazole. mp>239° C.; Anal. Cald. for $C_{15}H_{17}N_3O_4BrP+0.5\ H_2O$: C: 42.57; H: 4.29; N: 9.93. Found: C: 42.44; H: 3.99; N: 9.69.

12.45: 4-Amino-1-ethyl-2-[1-(2-phosphonomethyloxy) phenyl] benzimidazole. mp 180–185° C.; Anal. Cald. for $C_{16}H_{18}N_3O_4P+0.8\ H_2O$: C: 53.13; H: 5.46; N: 11.62. Found: C: 52.98; H: 5.20; N: 11.32.

12.46: 4-Amino-7-bromo-1-isobutyl-2-[2-(5-phosphono) furanyl] benzimidazole. mp>230° C.; Anal. Cald. for $C_{15}H_{17}N_3O_4BrP+0.25\ H_2O$: C: 43.03; H: 4.21; N: 10.04. Found: C: 42.69; H:3.87; N: 9.63.

12.47: 4-Amino-7-bromo-1-cyclobutanemethyl-2-[2-(5-phosphono) furanyl]benzimidazole. mp>200° C.; Anal. Cald. for $C_{16}H_{17}BrN_3O_4P+H_2O+0.06$ EtOAc: C: 43.24; H: 4.33; N: 9.38. Found: C: 43.40; H: 3.95; N: 9.11.

12.48: 4-Amino-5-bromo-1-cyclobutanemethyl-2-[2-(5-phosphono) furanyl]benzimidazole. mp>200° C.; >91% pure by HPLC.

12.49: 4-Amino-5-chloro-1-isobutyl-2-[2-(5-phosphono) furanyl] benzimidazole. mp>>240° C.; Anal. Cald. for $C_{15}H_{17}ClN_3O_4P+0.8H_2O$: C: 46.90; H: 4.88; N: 10.94. Found: C: 46.99; H: 4.53; N: 10.76.

12.50: 4-Amino-5,7-dichloro-1-isobutyl-2-(2-phosphono-5-furanyl) benzimidazole. mp=205–207° C.; Anal.Cald. for $C_{15}H_{16}N_3O_4Cl_2P+0.5H_2O$: C: 43.60; H: 4.15; N: 10.17. Found: C: 43.64; H: 4.03; N: 10.02.

12.51: 4-Amino-1-(2-thienylethyl)-2-[2-(5-phosphono) furanyl]benzimidazole. mp=225° C.; Anal. Cald. for $C_{17}H_{16}N_3O_4PS+1.1H_2O$. C: 50.12; H: 4.45 N: 10.31. Found: C,: 49.67; H: 3.96; N: 10.45.

12.52: 4-Amino-5-ethyl-1-isobutyl-2-(2-phosphono-5-furanyl)benzimidazole. mp=220–225° C.; Anal. Cald. for C: 51.34; H: 5.95; N: 10.21.

12.53: 4-Amino-5-fluoro-1-isobutyl-2-(2-phosphono-5-furanyl) benzimidazole. mp=230–235° C.; Anal. Cald. for $C_{15}H_{17}N_3O_4PF+0.8\ H_2O$; C: 49.00; H: 5.10; N: 11.43. Found: C: 49.13; H: 4.81; N: 11.13.

12.54: 4-Amino-5-fluoro-7-chloro-1-isobutyl-2-(2-phosphono-5-furanyl)benzimidazole. mp=220–225° C.; Anal. Cald. for $C_{15}H_{16}N_3O_4FClP+0.9$ HBr; C: 12; H: 3.70; N: 9.12. Found: C: 39.15; H: 3.46; N: 8.77.

12.55: 4-Amino-5-methoxy-1-isobutyl-2-(2-phosphono-5-furanyl)benzimidazole. mp=212–213° C.; Anal. Cald. for $C_{16}H_{20}N_3O_5P+H_2O$: C: 50.13; H: 5.78; N: 10.96. Found: C: 49.93; H: 5.55; N: 10.79.

12.56: 4-Amino-2-[2-(5-phosphono)furanyl]-1-[(3-amino) phenethyl] benzimidazole. mp =297° C.; Anal. Cald. for $C_{19}H_{19}N_4O_4P+0.4$ AcOH $+0.1$ MeCN$+1.5$ $H_2O$: C: 52.97; H: 5.31; N: 12.66. Found: C: 52.83; H: 5.17; N: 11.99. Found: C: 52.65; H: 4.92; N: 12.14.

12.57: 4-Amino-1-[(2-ethyl)pentyl]benzimidazol-2-yl-methylenoxymethyl phosphonic acid. mp=85° C.; Anal. Cald. for $C_{15}H_{24}N_3O_4P+½H_2O+2$ HBr$+⅓$ toluene: C: 38.05; H: 5.49; N: 7.78. Found: C: 38.30; H: 5.45; N: 7.34.

12.58: 4-Amino-5-bromo-6,7-dichloro-2-(2-phosphono-5-furanyl) benzimidazole. mp=224–225° C.; Anal. Cald. for: C: 38.92; H: 3.23; N: 5.92

12.59: 5-Amino-2-(2-Phosphono-5-furanyl)benzimidazole. Anal. Cald. for $C_{11}H_{10}N_3PO_4+CF_3CO_2H+1.5\ H_2O$: C: 37.16; H: 3.36; N: 10.00. Found: C: 37.40; H: 3.31; N: 9.77.

12.60: 4-Amino-5-propyl-1-isobutyl-2-(2-phosphono-5-furanyl) benzimidazole. mp=207–210° C.; Anal. Cald. for $C_{18}H_{24}N_3PO_4+2\ H_2O$: C: 52.30; H: 6.83; N: 10.16. Found: C: 52.05; H: 6.71; N: 9.95.

12.61: 4-Amino-5-fluoro-1-cyclopropylmethyl-2-(2-phosphono-5-furanyl)benzimidazole. mp=258–260° C.; Anal. Cald. for $C_{15}H_{15}N_3O_4P\ F+0.3\ H_2O$: C: 50.51; H: 4.41; N: 11.78. Found: C: 50.21; H: 4.28; N: 11.45.

12.62: 4-Amino-5-fluoro-7-bromo-1-isobutyl-2-(2-phosphono-5-furanyl)benzimidazole. mp=195–200° C.; Anal. Cald. for $C_{15}H_{16}N_3BrFPO_4$: C: 41.69; H: 3.73; N: 9.72. Found: C: 41.59; H: 3.81; N: 9.67.

12.63: 4-Amino-5-fluoro-6-chloro-1-isobutyl-2-(2-phosphono-5-furanyl) benzimidazole. mp=175–180° C.; Anal. Cald. for $C_{15}H_{16}N_3ClFPO_4+2.0\ H_2O$: C: 42.52; H: 4.76; N: 9.92. Found: C: 42.60; H: 4.56; N: 9.81.

12.64: 4-Amino-7-ethyl-5-fluoro-1-isobutyl-2-(2-phosphono-5-furanyl)benzimidazole. mp=245–246° C.; Anal. Cald. for $C_{17}H_{21}N_3O_4FP+0.4\ H_2O$: C: 52.55; H: 5.66; N: 10.81. Found: C: 52.40; H: 5.79; N: 10.47.

12.65: 7-Amino-4-ethyl-6-fluoro-1-isobutyl-2-(2-phosphono-5-furanyl)benzimidazole. mp=249–250° C.; Anal. Cald. for $C_{17}H_{21}N_3O_4FP$: C: 53.54; H: 5.55; N: 11.02. Found: C: 53.20; H: 5.38; N: 10.73.

12.66: 4-Amino-7-cyclopropyl-5-fluoro-1-isobutyl-2-(2-phosphono-5-furanyl)benzimidazole. mp=250–255° C. (dec.); Anal. Cald. for $C_{18}H_{21}N_3O_4FP+0.25\ H_2O$: C: 54.34; H: 5.45; N: 10.56. Found: C: 54.14; H: 5.28; N: 10.31.

12.67: 4-Amino-7-phenyl-5-fluoro-1-isobutyl-2-(2-phosphono-5-furanyl)benzimidazole. mp=240–241° C. (dec.); Anal. Cald. for $C_{21}H_{21}N_3O_4FP+0.05H_2O$: C: 58.62; H: 4.94; N: 9.77. Found: C: 58.27; H: 4.86; N: 9.47.

12.68: 4-Amino-7-p-fluorophenyl-5-fluoro-1-isobutyl-2-(2-phosphono-5-furanyl) benzimidazole. mp=239–240° C. (dec.); Anal. Cald. for $C_{21}H_{20}N_3O_4F_2P$: C: 56.38; H: 4.51; N: 9.39. Found: C: 56.38; H: 4.36; N: 9.14.

12.69: 4-Amino-7-p-chlorophenyl-5-fluoro-1-isobutyl-2-(2-phosphono-5-furanyl)benzimidazole. mp=235–236° C. (dec.); Anal. Cald. for $C_{21}H_{20}N_3O_4FClP$: C: 54.38; H: 4.35; N: 9.06. Found: C: 54.10; H: 4.20; N: 8.73.

12.70: 4-Amino-7-vinyl-5-fluoro-1-isobutyl-2-(2-phosphono-5-furanyl)benzimidazole. mp=238–242° C.; Anal. Cald. for $C_{17}H_{19}N_3O_4FP+1.2\ H_2O$: C: 50.93; H: 5.38; N: 10.48. Found: C: 51.07; H: 5.37; N: 10.12.

12.71: 4-Amino-7-(4-methylpentane)-5-fluoro-1-isobutyl-2-(2-phosphono-5-furanyl)benzimidazole. mp=185–195° C. (dec.); Anal. Cald. for $C_{21}H_{29}N_3O_4FP+0.25\ H_2O$: C: 57.07; H: 6.73; N: 9.51. Found: C: 57.03; H: 6.89; N: 9.24.

12.72: 4-Amino-7-(3,3-dimethylbutane)-5-fluoro-1-isobutyl-2-(2-phosphono-5-furanyl)benzimidazole. mp=200–205° C. (dec.); Anal. Cald. for $C_{21}H_{29}N_3O_4FP+0.75\ H_2O$: C: 55.93; H: 6.82; N: 9.32. Found: C: 55.84; H: 6.62; N: 9.15.

12.73: 4-Amino-5-fluoro-1-(2-ethylbutyl)-2-(2-phosphono-5-furanyl)benzimidazole. mp=178–182° C. (dec.); Anal. Cald. for $C_{17}H_{21}N_3O_4FP+1.0\ H_2O$: C: 51.13; H: 5.80; N: 10.52. Found: C: 51.03; H: 5.58; N: 10.27.

12.74: 4-Amino-7-m-methoxyphenyl-5-fluoro-1-isobutyl-2-(2-phosphono-5-furanyl)benzimidazole. mp=208–212° C. (dec.); Anal. Cald. for $C_{22}H_{23}N_3O_5FP+0.25\ H_2O$: C: 56.96; H: 5.1 1; N: 9.06. Found: C: 57.02; H: 5.14; N: 8.52.

12.75: 4-Amino-7-ethyl-5-fluoro-1-cyclopropylmethyl-2-(2-phosphono-5-furanyl)benzimidazole. mp=178–185° C.; Anal. Cald. for $C_{17}H_{19}N_3O_4FP+1.3\ H_2O$: C: 50.70; H: 5.41; N: 10.43. Found: C: 50.98; H: 5.29; N: 10.05.

12.76: 4-Amino-5-fluoro-1-(3-pentyl)-2-(2-phosphono-5-furanyl)benzimidazole. mp=180–185° C. (dec.); Anal. Cald. for $C_{16}H_{19}N_3O_4FP+1.5\ H_2O$: C: 48.73; H: 5.62; N: 10.66. Found: C: 48.60; H: 5.55; N: 10.49.

12.77: 5,6,7-Trifluoro-1-isobutyl-2-(2-phosphono-5-furanyl) benzimidazole. mp =250–260° C.; Anal. Cald. for $C_{15}H_{14}N_2O_4F_3P$: C: 48.14; H: 3.77; N: 7.49. Found: C: 48.04; H: 3.81; N: 7.43.

12.78: 4,5,6-Trifluoro-1-isobutyl-2-(2-phosphono-5-furanyl) benzimidazole. mp =155–158° C.; Anal. Cald. for $C_{15}H_{14}N_2O_4F_3P$: C: 48.14; H: 3.77; N: 7.49. Found: C: 48.04; H: 3.81; N: 7.43.

12.79: 4-Amino-7-(propane-3-ol)-5-fluoro-1-isobutyl-2-(2-phosphono-5-furanyl)benzimidazole. mp=170–173° C.; Anal. Cald. for $C_{18}H_{23}N_3O_5FP+1.0\ H_2O$: C: 50.35; H: 5.87; N: 9.79. Found: C: 50.31; H: 5.80; N: 9.62.

12.80: 4-Amino-5-fluoro-7-(3-bromopropyl)-1-isobutyl-2-(2-phosphono-5-furanyl)benzimidazole. mp=190–195° C. (dec.); Anal. Cald. for $C_{18}H_{22}N_3O_4FBrP$: C: 45.59; H: 4.68; N: 8.86. Found: C: 45.87; H: 4.87; N: 8.70.

12.81: 4-Amino-5-fluoro-7-n-propyl-1-isobutyl-2-(2-phosphono-5-furanyl)benzimidazole. mp=220–230° C. (dec.); Anal. Cald. for $C_{18}H_{23}N_3O_4FP\ +0.85\ H_2O$: C: 52.64; H: 6.06; N: 10.23. Found: C: 53.00; H: 6.09; N: 9.70.

12.82: 4-Amino-5-fluoro-7-(4-bromobutyl)-1-isobutyl-2-(2-phosphono-5-furanyl)benzimidazole. mp=200–220° C. (dec.); Anal. Cald. for $C_{19}H_{24}N_3O_4FBrP+0.5\ H_2O$: C: 45.89; H: 5.07; N: 8.45. Found: C: 45.61; H: 5.10; N: 8.20.

12.83: 4-Amino-5-fluoro-7-(4-chlorobutyl)-1-isobutyl-2-(2-phosphono-5-furanyl)benzimidazole. mp=210–220° C. (dec.); Anal. Cald. for $C_{19}H_{24}N_3O_4FClP+0.25\ H_2O$: C: 50.90; H: 5.51; N: 9.37. Found: C: 50.96; H: 5.53; N: 9.13.

12.84: 4-Amino-5-fluoro-7-(3-N,N-dimethylpropylamine)-1-isobutyl-2-(2-phosphono-5-furanyl)benzimidazole hydrobromide salt. mp=208–212° C. (dec.); Anal. Cald. for $C_{20}H_{28}N_4O_4FP+1.0Hbr+2.0H_2O$: C: 43.25; H: 5.99; N: 10.09. Found: C: 43.39; H: 5.74; N: 9.90.

12.85: 4,5-Dimethyl-6-chloro-1-cyclopropylmethyl-2-(2-phosphono-5-thionyl)benzimidazole. Anal. Cald. for $C_{17}H_{18}N_2O_3PSCI$: C: 51.45; H: 4.57; N: 7.06; Found: C: 51.28; H: 4.58; N: 6.92.

12.86: 4-Amino-5-fluoro-7-ethyl-1-2(2-phosphono-5-furanyl)benzimidazole. mp=180–1860° C.; Anal. Cald. for $C_{13}H_{13}N_3O_4FP+1.2H_2O$: C: 45.02; H: 4.48, N: 12.11. Found: C: 45.17; H: 4.52; N: 11.81.

Example 13

HBr hydrolysis

A solution of 1.0 mmol of substituted 2-[(5-diethylphosphonate)furanyl]benzimidazole in 10 ml of 30% HBr was heated at 800° C. for 0.5–3 h. The solvent was removed under reduced pressure and the residue was taken into 3 ml of water. The solid precipitated was filtered washed with water and dried under vaccum at 50° C.

The following compounds were prepared in this manner:

13.1: 2-(2-Phosphono-5-furanyl)benzimidazole. mp>250° C.; Anal. Cald. for $C_{11}H_9N_2O_4P+0.55HBr+H_2O$: C: 40.44; H: 3.56; N: 8.57. Found: C: 40.74; H: 3.51; N:,8.53.

13.2: 1-Isobutyl-2-(2-phosphono-5-furanyl)benzimidazole. mp=200–203° C.; Anal. Cald. for $C_{15}H_{17}N_2O_4P+0.75H_2O$: C: 53.97; H: 5.59; N: 8.39. Found: C; 53.70; H: 5.37; N: 8.24.

13.3: 2-[5,6-Indano-1(H)-imidazol-2-yl]furan-5-phosphonic acid. Anal. Cald. for $C_{14}H_{13}N_2PO_4+1.25H_2O$: C: 51.46; H: 4.78; N:.8.57. Found: C: 51.43; H: 4.38; N: 8.44.

13.4: 2-(1-Isobutyl-5,6-indanoimidazol-2-yl)furan-5-phosphonic acid. Anal. Cald. for $C_{18}H_{12}N_2PO_4+0.5H_2O$: C: 58.53; H: 6.00; N: 7.58. Found: C: 58.45; H: 5.62; N:7.44.

13.5: 2-(1,8-Diaza-1,2,3,4-tetrahydroacenaphthen-9-yl)furan-5-phosphonic acid. Anal. Cald. for $C_{14}H_{13}N_2PO_4+0.5HBr+0.5H_2O$: C: 47.54; H: 4.13; N: 7.48. Found: C: 47.33; H: 4.16; N: 7.48.

13.6: 2-(2-Phosphono-5-furanyl)-5-trifluoromethylbenzimidazole. Anal. Cald. for $C_{12}H_8F_3N_2O_4P+1.2H_2$. C:40.74; H: 2.96; N: 7.92; F: 16.11 Found: C: 40.49; H: 2.71; N: 7.89; F: 16.50.

13.7: 2-(2-Phosphono-5-furanyl)-5-fluorobenzimidazole. Anal. Cald. for $C_{11}H_8FN_2O_4P+2/3H_2O$. C: 44.93; H: 3.19; N: 9.53; F: 6.46. Found: C: 44.91 H: 3.05; N: 9.34; F: 6.54.

13.8: 2-(2-Phosphono-5-furanyl)-5,6-dichlorobenzimidazole. Anal. Cald. for $C_{11}H_7C_{12}N_2O_4P+0.25$ AcOH; C: 39.68; H: 2.32; N: 8.05; Cl: 20.37. Found: C: 39.92; H: 2.28; N: 7.87; Cl: 20.10.

13.9: 2-(2-Phosphono-5-furanyl)-5-chlorobenzimidazole. Anal. Cald. for $C_{11}H_8CIN_2O_4P+0.75$ HBr+0.33 $H_2O$; C: 36.17; H: 2.60; N: 7.67; Cl: 9.71. Found: C: 36.53; H: 2.43; N: 7.31; Cl: 9.48.

13.10: 2-(2-Phosphono-5-furanyl)-5-methylbenzimidazole. Anal. Cald. for $C_{12}H_{11}N_2PO_4+H_2O$: C: 48.66; H: 4.42; N: 9.46. Found: C: 48.64; H: 4.20; N: 9.22.

13.11: 2-(2-Phosphono-5-furanyl)-5-(tert-butyl)benzimidazole. Anal. Cald. for $C_{15}H_{17}N_2PO_4+H_2O$: C: 53.26; H: 5.66; N: 8.28. Found: C: 53.04; H: 5.57; N: 7.96.

13.12: 1-Phenyl-2-(2-phosphono-5-furanyl)benzimidazole. mp=196–200° C.; Anal. Cald. for $C_{17}H_{13}N_2PO_4+2H_2O+HBr$: C: 44.66; H: 3.97; N: 6.13. Found: C: 45.06; H: 3.66; N: 6.01.

13.13: 1-(2-Carboxyphenyl)-2-(2-phosphono-5-furanyl)-5-chloro benzimidazole. mp=220–224° C.; Anal. Cald. for $C_{18}H_{12}N_2O_6CIP+H_2O+0.2$ HBr: C: 47.73; H: 3.16; N: 6.18; Cl: 7.83. Found: C: 48.07; H: 2.86 N: 5.98; Cl: 7.78.

13.14: 5-Nitro-2-(2-phosphono-5-furanyl)benzimidazole. Anal. Cald. for $C_{11}H_8N_3PO_6+H_2O$: C: 40.38; H: 3.08; N: 12.84. Found: C: 40.28; H: 2.97; N: 12.47.

13.15: 4,5-Dimethyl-2-(2-phosphono-5-furanyl)benzimidazole. Anal. Cald. for $C_{13}H_{13}N_2PO_4+0.6H_2O$: C: 51.53; H: 4.72; N: 9.24. Found: C: 51.20; H: 4.64; N: 9.13.

13.16: 5-Chloro-1-isobutyl-2-(2-phosphono-5-furanyl)benzimidazole. mp=238° C.; Anal. Cald. for $C_{15}H_{16}CIN_2O_4P+0.33$ HBr; C: 47.23; H: 4.32; N: 7.34; Cl: 9.29. Found: C: 47.37; H: 4.02; N: 6.99; Cl: 9.56.

13.17: 6-Chloro-1-isobutyl-2-(2-phosphono-5-furanyl)benzimidazole. Anal. Cald. for $C_{15}H_{16}CIN_2O_4P+0.5$ HBr: C: 45.59; H: 4.21; N: 7.09; Cl: 8.97. Found: C: 46.02; H: 3.86; N: 7.01; Cl: 8.63.

13.18: 5-Benzophenone-2-(2-phosphono-5-furanyl)benzimidazole. Anal. Cald. for $C_{18}H_{13}N_2O_5P+1.75H_2O+0.25$ HBr: C: 51.47; H: 4.02; N: 6.67; Found: C: 51.63; H: 4.09; N: 6.31.

13.19: 4-Amidinomethyl-2-[2-(5-phosphono)furanyl]-1-[(2-ethyl) pentyl]benzimidazole. mp=225–230° C.; Anal. Cald. for $C_{19}H_{25}N_4O_4P+0.3H_2O$: C: 55.69; H: 6.30; N: 13.67. Found: C: 55.46; H: 5.77; N: 13.16.

13.20: 1-lsobutyl-4-isobutyloxy-2-(2-phosphono-5-furanyl)benzimidazole. mp =350° C.; Anal. Cald. for $C_{19}H_{25}N_2O_5P+1.0H_2O$: C: 55.61; H: 6.63: N: 6.83. Found: C: 55.26; H: 6.41; N: 6.59.

13.21: 4-Hydroxy-1-isobutyl-2-(2-phosphono-5-furanyl)benzimidazole. mp=244–245° C.; Anal. Cald. for $C_{15}H_{17}N_2O_5P+1.1H_2O$: C: 50.59; H: 5.43; N: 7.87. Found: C: 50.33; H: 5.38; N: 7.89.

13.22: 5,6-Difluoro-2-(2-Phosphono-5-furanyl)benzimidazole. Anal. Cald. for $C_{11}H_7N_2PO_4F_2+0.3H_2O$: C: 43.24; H: 2.51; N: 9.17; F: 12.44. Found: C: 43.58; H: 2.63; N: 8.69; F: 12.28.

13.23: 2-(2-Phosphono-5-furanyl)benzimidazole-5-methylcarboxylate. Anal. Cald. for $C_{13}H_{11}N_2O_6P+0.5H_2O+0.25$ HBr: C: 44.43; H: 3.51; N: 7.97; Found: C: 44.41; H: 3.80; N: 8.16.

13.24: 5,6-Dimethyl-2-(2-phosphono-5-furanyl)benzimidazole. Anal. Cald. for $C_{13}H_{13}N_2O_4P+2/3H_2O$: C: 51.34; H: 4.75; N: 9.21. Found: C: 51.48: N: 8.95.

13.25: 4-F-luoro-1-neopentyl-2-(2-phosphonofuranyl)benzimidazole. Anal. Cald. for $C_{16}H_{18}N_2PO_4F+0.1H_2O+0.3$ $CH_3CO_2$: C:53.58; H: 5.25; N: 7.53. Found: C: 53.84; H: 5.12; N: 7.05.

13.26: 2-(2-Phosphonofuranyl)-(4,5-benz)benzimidazole. Anal. Cald. for $C_{15}H_{11}N_2PO_4+1.75H_2O$: C: 52.11; H: 4.23; N: 8.10. Found: C: 52.40; H: 4.34; N: 7.70.

13.27: 6-Fluoro-1-isobutyl-2-(2-phosphono-5-furanyl)benzimidazole. mp=202–205° C.; Anal. Cald. for $C_{15}H_{16}FN_2O_4P+0.25$ HBr+0.5 $H_2O$: C: 49.02; H: 4.73; N: 7.62. Found: C: 48.90; C: 4.89; N: 7.50.

13.28: 5-Fluoro-1-isobutyl-2-(2-phosphono-5-furanyl)benzimidazole. Anal. Cald. for $C_{15}H_{16}FN_2O_4P+0.1$ HBr: C: 52.02; H: 4.69; N: 8.09; F: 5.49. Found: C: 52.07; H: 32; N: 7.88; F: 5.61.

13.29: 2-(2-Phosphonofuranyl)-4,5-(2-methylthiazole)benzimidazole. Anal. Cald. for $C_{13}H_{10}N_3O_4PS+2.25H_2O$: C: 41.55; H: 3.89; N: 11.18; S: 8.53. Found: C: 41.69; H: 3.93; N: 10.99; S: 8.81.

13.30: 1-(4-Pyridyl)-2-(2-phosphono-5-furanyl)benzimidazole. Anal. Cald. for $C_{16}H_{12}N_3PO_4+H_2O+1.25$ 13.31: 2-(2-Phosphonofuranyl)-(4,5-tetramethylene) benzimidazole. Anal. Cald. for $C_{15}H_{15}N_2PO_4+1.5\ H_2O$: C: 52.18; H: 5.25; N: 8.11. Found: C: 52.09; H: 5.01; N: 7.85.

13.32: 4-Methyl-2-(2-phosphonofuranyl)benzimidazole. Anal. Cald. for $C_{12}H_{11}N_2PO_4+H_2O$: C: 48.66; H: 4.42; N: 9.46. Found: C: 48.55; H: 4.51; N: 9.16.

13.33: 5-Chloro-1-isopropyl-2-(2-phosphono-5-furanyl) benzimidazole. mp=192–195° C.; Anal. Cald. for $C_{14}H_{14}N_2O_4PCl+H_2O+0.1\ HBr$: C: 45.84; H: 4.42; N: 7.64; Cl=9.67. Found: C: 45.58; H: 4.30; N: 7.47; Cl=10.63.

13.34: 5,6-Difluoro-1-isobutyl-2-(2-phosphono-5-furanyl) benzimidazole. Anal. Cald. for $Cl_5Hl_5F_2N_2O_4P+0.5\ H_2O$: C: 49.32; H: 4.42; N: 7.67; Found: C: 49.06; H: 4.20; N: 7.60; F: 10.26.

13.35: 5-Bromo-2-(2-phosphono-5-furanyl)benzimidazole. Anal. Cald. for $C_{11}H_8BrN_2O_4P+H_2O+0.05\ HBr$: C: 36.18; H2.77; N: 7.67; Br: 22.98. Found: C: 36.20; H: 2.61; N: 7.45; Br: 22.77.

13.36: 5-Bromo-1-isobutyl-2-(2-phosphono-5-furanyl) benzimidazole. Anal. Cald. for $C_{15}H_{16}BrN_2O_4P+0.75\ H_2O+0.05\ HBr$: C: 43.23; H: 4.24; N: 20.13. Found: C: 43.25; H: 4.18; N: 6.59; Br: 20.30.

13.37: 6-Bromo-1-isobutyl-2-(2-phosphono-5-furanyl) benzimidazole. Anal. Cald. for $C_{15}H_{16}BrN_2O_4P+H_2O+0.05\ HBr$: C: 42.77; H: 4.32; N: 6.65; Br: 19.92. Found: C: 42.49; H: 4.04; N: 6.53; Br: 20.02.

13.38: 4,6-Dichloro-2-(2-phosphono-5-furanyl) benzimidazole. Anal. Cald. for $C_{11}H_7N_2O_4PCl_2+1.5\ H_2O$: C: 36.69; H: 2.80; N: 7.78; Found: C: 36.91; H: 2.64; N: 7.71.

13.39: 4,6-Dichloro-1-isobutyl-2-(2-phosphono-5-furanyl) benzimidazole. mp=155–175° C.; Anal. Cald. for $C_{15}H_{15}N_2O_4\ PCl_2+2/3\ H_2O$: C: 44.90; H: 4.10; N: 6.98. Found: C: 44.96; H: 3.97; N: 6.85.

13.40: 5-Chloro-1-phenyl-2-(2-phosphono-5-furanyl) benzimidazole. Anal. Cald. for $C_{17}H_{12}N_2O_4PCl+1\ H_2O+0.1\ HBr$: C: 50.94; H: 3.55; N: 6,99. Found: C: 51.33; H: 3.63; N: 6.54.

13.41: 6-Chloro-1-phenyl-2-(2-phosphono-5-furanyl) benzimidazole. Anal. Cald. for $C_{17}H_{12}N_2O_4PCl+0.25\ H_2O+0.1HBr$: C: 52.72; H: 3.28; N: 7.23. Found: C: 52.94; H: 2.99; N: 7.03.

13.42: 4,6-Dibromo-2-(2-phosphono-5-furanyl) benzimidazole. Anal. Cald. for $C_{11}H_7Br_2N_2O_4P+1\ H_2O+0.1\ HBr$: C: 29.49; H: 2.05; N: 6.25. Fouonld: C: 29.56; H:2.06; N:6.16.

13.43: 4,6-Dibromo-1-isobutyl-2-(2-phosphono-5-furanyl) benzimidazole. mp=150–210° C.; Anal. Cald. for $C_{15}H_{15}Br_2N_24P+0.25\ H_2O+0.1\ HBr$: C: 36.72; H: 3.20; N: 5.71. Found: C: 36.72; H: 3.24; N: 5.73.

13.44: 5,6-Dichloro-1-isobutyl-2-(2-phosphono-5-furanyl) benzimidazole. mp=225–227° C.; Anal. Cald. for $C_{15}H_{15}C_{12}N_2O_4P+0.25\ H_2O+0.1\ HBr$: C: 44.84; H: 3.91; N: 6.97. Found: C: 44.86; H: 3.85; N: 6.81.

13.45: 5,6-Dichloro-1-cyclopropylmethyl-2-(2-phosphono-5-furanyl) benzimidazole. mp=180–210° C.; Anal. Cald. for $C_{15}H_{13}Cl_2N_2O_4P+0.5\ H_2O+0.1\ HBr$: C: 44.57; H: 3.52; N: 6.93. Found: C: 44.69; H: 3.45; N: 6.66.

13.46: 5-Chloro-6-fluoro-2-(2-phosphono-5-furanyl) benzimidazole. Anal. Cald. for $C_{11}H_7ClFN_2O_4P+0.5\ H_2O$: C: 40.58; H: 2.48; N: 8.60. Found: C: 40.58; H: 2.47; N: 8.29.

13.47: 4-Phenyl-6-trifluoromethyl(2-phosphono-5-furanyl) benzimidazole. $C_{18}H_{12}N_2PO_4F_3+H_2O$: C: 50.72; H: 3.31; N: 6.57. Found: C: 50.58; H: 3.08; N: 6.35.

13.48: 4-Bromo-6-trifluoromethyl(2-phosphono-5-furanyl) benzimidazole. Anal. Cald. for $C_{12}H_7N_2PO_4F_3Br+H_2O$: C: 33.59; H: 2.11; N: 6.53. Found: C: 33.53; H: 1.86; N: 6.43.

13.49: 5-Chloro-6-fluoro-1-methylcyclopropyl-2-(2-phosphono-5-furanyl) benzimidazole. Anal. Cald. for $C_{15}H_{13}N_2PO_4ClF$: C: 48.60; H: 3.53; N: 7.56. Found: C: 48.32; H: 3.55; N: 7.31.

13.50: 5-Chloro-6-fluoro-1-isobutyl-2-(2-phosphono-5-furanyl) benzimidazole. mp=196–199; Anal. Cald. for $C_{15}H_{15}ClFN_2O_4P+1.75\ H_2O$: C: 44.57; H: 4.61; N: 6.93. Found: C: 44.45; H: 4.58; N: 6.87.

13.51: 4-Amino-5-hydroxy-1-isobutyl-2-(2-phosphono-5-furanyl) benzimidazole. mp=206–209° C.; Anal. Cald. for $C_{15}H_{18}N_3O_5P+2.7\ H_2O$: C: 45.05; H: 5.90; N: 10.51. Found: C: 44.96; H: 5.78; N: 10.14.

13.52: 5-Phosphonomethylenoxy-1,2,3,4-tetrahydropyrido[1,2-a] benzimidazole. mp=218–222° C.; Anal. Cald. for $C_{12}H_{15}N_2PO_4+H_2O+0.9\ HBr$: C: 38.63; H: 4.84; N: 7.51. Found: C: 38.96; H: 4.46; N: 7.41.

13.53: 4,5-Dimethyl-6-bromo-1-isobutyl-2-(2-phosphono-5-furanyl) benzimidazole. mp=205–209° C.; Anal. Cald. for $C_{17}H_{20}PN_2O_4Br+0.25\ H_2O$: C: 47.29; H: 4.79; N: 6.49. Found: C: 47.25; H: 4.77; N: 6.06.

13.54: 4-Methyl-1-isobutyl-2-(2-phosphono-5-furanyl) benzimidazole. mp=208–211° C.; Anal. Cald. for $C_{16}H_{19}N_2O_4P+H_2O+0.25\ HBr$: C: 51.58; H: 5.75; N: 7.52. Found: C: 51.49; H: 5.88; N: 7.41.

13.55: 7-Methyl-1-neopentyl-2-(2-phosphono-5-furanyl) benzimidazole. Anal. Cald. for $C_{17}H_{21}N_2O_4P$: C: 58.62; H: 6.08; N: 8.04; Found: C: 58.35; H: 5.97; N: 7.92.

13.56: 6-Chloro-1-neopentyl-2-(2-phosphono-5-furanyl) benzimidazole. Anal. Cald. for $C_{16}H_{18}N_2O_4PCl+0.5\ H_2O$: C: 50.87 H: 5.07 N: 7.42; C: 50.88 H: 4.82 N: 7.29.

13.57: 5-Chloro-1-cyclopropylmethyl-2-(2-phosphono-5-furanyl) benzimidazole. Anal. Cald. for $C_{15}H_{14}N_2O_4PCl+0.75\ H_2O$: C: 49.39; H: 4.24; N: 7.68; Found: C: 49.44; H: 4.01; N:7.52.

13.58: 6-Chloro-1-cyclopropylmethyl-2-(2-phosphono-5-furanyl) benzimidazole. Anal. Cald. for $C_{15}H_{14}N_2O_4PCl+0.5\ H_2O$: C: 49.81; H: 4.18; N: 7.74; Found: C: 49.63; H: 3.93; N: 7.60.

13.59: 5-Phosphonomethylenoxy-1,2,3,4,5,6-hexahydroazapino[1,2-a]benzimnidazole. mp=152–156; Anal. Cald. for $C_{13}H_{17}N_2O_4P+H_2O+0.75\ HBr+0.5\ CH_3CO_2H$: C: 41.52; H: 5.41; N: 6.92; Found: C: 41.34; H: 5.58; N: 6.48.

13.60: 1-lsobutyl-4,5-dimethyl-6-chloro-2-(2-phosphono-5-furanyl) benzimidazole. Anal. Cald. for $C_{17}H_{20}N_2O_4PCI+0.5\ H_2O$ : C: 52.12 H: 5.40 N: 7.15; Found: C: 52.38; H: 5.23; N: 6.54.

13.61: 6-Chloro-4,5-dimethyl-1-cyclopropylmethyl-2-(2-phosphono-5-furanyl)benzimidazole. mp=219–220° C. Anal. Cald. for $C_{17}H_{18}N_2O_4PCl+1.33\ H_2O+0.1\ HBr$: C:49.46; H: 4.99; N:6.79; Found: C:49.74; H:4.94 N:6.49.

13.62: 6,7-Dimethyl-1-isobutyl-2-(2-phosphono-5-furanyl) benzimidazole. Anal. Cald. for $C_{17}H_{21}N_2O_4P$: C: 58.62; H: 6.08; N: 8.04; Found: C: 58.78; H: 5.68; N: 7.79.

13.63: 5-Chloro-6,7-dimethyl-1-isobutyl-2-(2-phosphono-5-furanyl) benzimidazole. Anal. Cald. for $C_{17}H_{20}N_2O_4P+0.25\ H_2O+0.2\ HBr$: C: 50.61; H:5.17; N: 6.94; Found: C: 50.58; H:4.84; N: 6.58.

13.64: 7-Bromo-5-fluoro-1-isobutyl-2-(2-phosphono-5-furanyl) benzimidazole. Anal. Cald. for $C_{15}H_{15}N_2O_4PBrF+0.25\ H_2O$; C: 42.73; H: 3.71; N: 6.64; Br: 18.95; Found: C: 42.86; H: 3.52; N: 6.49; Br: 19.21.

13.65: 6-Chloro-1-(3-methoxyphenyl)-2-(2-phosphono-5-furanyl) benzimidazole. mp=184–1850° C. Anal. Cald.

for $C_{18}H_{14}N_2O_5PCl+1.75\ H_2O$; C: 49.56; H: 4.04; N: 6.42; Found. C: 49.43; H: 3.71; N: 6.28.

13.66: N-(Phosphonomethyl)benzimidazole-2-carboxamide. mp=258–260° C. Anal. Cald. for $CgH_{10}N_3O_4P+0.15\ AcOH$; C: 42.28; H: 4.04; N: 15.91; Found. C: 42.60; H: 4.02; N: 15.70.

13.67: 1-lsobutyl-5-fluoro-7-bromo-2-(2-phosphono-5-furanyl) benzimidazole. mp>250° C. (dec.); Anal. Cald. for $C_{15}H_{15}N_2O_4PBrF+0.25H_2O$: C: 42.73; H: 3.71; N: 6.64. Found: C: 42.86; H: 3.52; N: 6.49.

13.68: 1-Isobutyl-5-fluoro-6-nitro-7-bromo-2-(2-phosphono-5-furanyl) benzimidazole. mp=161–165° C.; Anal. Cald. for $C_{15}H_{14}N_3O_6PBrF+0.25H_2O+1.0CH_3CO_2H$: C: 38.77; H: 3.54; N: 7.98. Found: C: 39.00; H: 3.49; N: 8.22.

13.69: 1-Isobutyl-5-fluoro-6-amino-7-bromo-2-(2-phosphono-5-furanyl) benzimidazole. mp=208–211° C.; Anal. Cald. for $C_{15}H_{16}N_3O_4PBrF+0.5H_2O+0.5CH_3CO_2H$: C: 40.78; H: 4.06; N: 8.92. Found: C: 41.18; H: 4.27; N: 8.59.

13.70: 1-lsobutyl-4-amino-5-chloro-6,7-dimethyl-2-(2-phosphono-5-furanyl) benzirmidazole. Anal. Cald. for $C_{17}H_{21}N_3O_4PCl+0.2\ H_2O$: C: 49.32; H: 5.16; N: 10.15. Found: C: 49.36; H: 4.94; N: 9.81.

13.71: 1-Isobutyl-5,7-difluoro-6-N,N-dimethylamino-2-(2-phosphono-5-furanyl) benzimidazole. mp=176–180° C.; Anal. Cald. for $C_{17}H_{20}N_3O_4PF_2+1.0\ H_2O+1.25\ Hbr+0.25\ C_6H_5CH_3$: C: 41.59; H: 4.70; N: 7.76. Found: C: 41.74; H: 4.65; N: 7.39.

13.72: 1-Isobutyl-7-hydroxymethyl-2-(2-phosphono-5-furanyl) benzimidazole. Anal. Cald. for $C_{16}H_{19}N_2O_5P+0.5H_2O$: C: 53.48; H: 5.61; N: 7.80. Found: C: 53.35; H: 5.34; N: 7.48.

13.73: 5-Fluoro-7-bromo-2-(2-phosphono-5-furanyl) benzimidazole. Anal. Cald. for $C_{11}H_7N_2O_4PBrF+0.1\ H_2O$: C: 36.41; H: 2.00; N: 7.72. Found: C: 36.67; H: 2.28; N: 7.41.

13.74: 4-Nitro-5-fluoro-7-bromo-2-(2-phosphono-5-furanyl) benzimidazole. mp=218–223° C. (dec.); Anal. Cald. for $C_{11}H_6N_3O_6PF+0.75\ H_2O$: C: 31.49; H: 1.80; N: 10.01. Found: C: 31.77; H: 2.19; N: 9.41.

13.75: 5-Fluoro-6-nitro-7-bromo-2-(2-phosphono-5-furanyl) benzimidazole. Anal. Cald. for $C_{11}H_6N_3O_6PBrF+0.25\ H_2O+0.25\ C_3H_6O$: C: 38.77; H: 3.54; N: 7.98. Found: C: 39.00; H: 3.49; N: 8.22.

13.76: 1-Isobutyl-5-fluoro-6-acetamido-7-bromo-2-(2-phosphono-5-furanyl) benzimidazole. mp=217–221° C. (dec.); Anal. Cald. for $C_{17}H_{18}N_3O_5PBrF+1.0\ H_2O$: C: 41.48; H: 4.1; N: 8.54. Found: C: 41.90; H: 4.06; N: 8.08.

13.77: 1-lsobutyl-4-acetamido-5-fluoro-7-ethyl-2-(2-phosphono-5-furanyl) benzimidazole. Anal. Cald. for $C_{19}H_{23}N_3O_5PF+1.0\ H_2O$: C: 51.70; H: 5.71; N: 9.52. Found: C: 52.03; H: 5.56; N: 9.11

13.78: 1-Isobutyl-4-N,N-dimethylamino-5-fluoro-7-ethyl-2-(2-phosphono-5-furanyl) benzimidazole. Anal. Cald. for $C_{19}H_{25}N_3O_4PF+1.25\ H_2O +1.5\ HBr +0.33EtOAc$: C: 41.91; H: 5.48; N: 7.22. Found: C: 42.09; H: 5.41; N: 6.65. 13.79: 1-lsobutyl-5-fluoro-6-N,N-dimethylamino-7-bromo-2-(2-phosphono-5-furanyl) benzimidazole. mp=183–188° C.; Anal. Cald. for $C_{17}H_{20}N_3O_4PBrF+0.33\ H_2O$: C: 43.78; H: 4.47; N: 9.01. Found: C: 43.96; H: 4.60; N: 8.56.

13.80: 5-Fluoro-6-chloro-7-ethyl-2-(2-phosphono-5-furanyl) benzimidazole. mp=165–190° C.; Anal. Cald. for $C_{13}H_{11}N_2O_4PClF+1.33\ H_2O$: C: 42. 3.74; N: 7.60. Found: C: 42.31; H: 3.64; N: 7.43.

13.81: 1-Isobutyl-4-ethyl-5-chloro-6-Fluoro-2-(2-phosphono-5-furanyl) benzimidazole. Anal. Cald. for $C_{17}H_{19}N_2O_4PClF+0.33H_2O+0.25\ HBr$: C: 47.80; H: 4.70; N: 6.56. Found: C: 47.82; H: 4.66; N: 6.25.

13.82: 4,5,6,7-Tetramethyl-2-(2-phosphono-5-furanyl) benzimidazole. mp=202–206° C.; Anal. Cald. for $C_{15}H_{17}N_2O4P+1.6H_2O$: C: 51.42; H: 5.85; N: 8.00. Found: (C: 51.38; H: 5.75; N: 7.75.

13.83: 1-Isobutyl-4,5,6,7-tetramethyl-2-(2-phosphono-5-furanyl) benzimidazole. Anal. Cald. for $C_{19}H_{25}N_2O_4P+0.75H_2O+0.25\ HBr$: C: 55.64; H: 6.57; N: 6.83. Found: C: 55.67; H: 6.49; N: 6.65.

13.84: 4,6-Dimethyl-2-(2-phosphono-5-furanyl) benzimidazole. Anal. Cald. for $C_{13}H_{13}N_2O_4P+1.6H_2O$: C: 48.44; H: 5.1 1; N: 8.69. Found: C: 48.46; H: 5.08; N: 8.62.

13.85: 1-lsobutyl-4,6-dimethyl-2-(2-phosphono-5-furanyl) benzimidazole. Anal. Cald. for $C_{17}H_{21}N_2O_4P+1.0\ H_2O$. mp=209–212° C.; C: 55.73; H: 6.33; 7.65. Found: C: 55.99; H: 6.21; N: 7.57.

13.86: N-(2-Phosphonomethylacetate)benzimidazole-2-carboxamide. Anal. Cald. for $C_{11}H_{12}N_3O_6P+0.5H_2O+0.25\ HBr$. mp=215–218° C.; C: 38.58; H: 3.90; N: 12.27; Found. C: 38.94; H: 4.18; N: 12.43.

13.87: 1-Isobutyl-5,7-dimethyl-2-(2-phosphono-5-furanyl) benzimidazole. Anal. Cald. for $C_{17}H_{21}N_2O_4P+0.75H_2O$. mp=196–200° C.; C: 56.43; H: 6.27; N: 7.74. Found: C: 56.47; H: 6.09; N: 7.59.

13.88:1-Cyclopropylmethyl-4,5,6,7-tetramethyl-2-(2-phosphono-5-furanyl) benzimidazole. Anal. Cald. for $C_{19}H_{23}N_2O_4P+1.25\ H_2O$. mp=207–208 ° C. C: 57.50; H: 6.48; N: 7.06. Found: C: 57.32; H: 6.52; N: 7.06.

13.89: 1-Ethyl-4,5-dimethyl-6-chloro-2-(2-phosphono-5-furanyl) benzimidazole. Anal. Cald. for $C_{15}H_{16}N_2O_4PCl+1.0\ H_2O$. C: 48.33; H: 4.87; N: 7.52. Found: C: 48.04; H: 4.81; N: 7.32.

13.90: 1-(4-Bromobutyl)-4,5-dimethyl-6-chloro-2-(2-phosphono-5-furanyl) benzimidazole. Anal. Cald. for $C_{17}H_{19}N_2O_4PClBr$. mp=212–216° C.; C: 44.23; H: 4.15; N: 6.07. Found: C: 44.07; H: 4.26; N: 5.91.

13.91: 4,5-Dimethyl-6-chloro-7-bromo-2-(2-phosphono-5-furanyl) benzimidazole. Anal. Cald. for $C_{13}H_{11}N_2O_4PBrCl+1.33\ H_2O$. C: 36.35; H:3.21; N: 6.52. Found: C: 36.32; H:3.05; N: 6.41.

13.92: 1-Isobutyl-4,5-dimethyl-6-chloro-7-bromo-2-(2-phosphono-5-furanyl) benzimidazole. Anal. Cald. for $C_{17}H_{19}N_2O_4PBrCl$. C: 44.23; H:4.15; N: 6.07. Found: C: 44.19; H:4.14; N: 5.88

13.93: 1-lsobutyl-6,7-dimethyl-5-chloro-4-bromo-2-(2-phosphono-5-furanyl) benzimidazole. Anal. Cald. for $C_{17}H_{19}N_2O_4PBrCl$. mp=195–201 ° C.; C: 43.38; H:4.28; N: 5.95. Found: C: 43.67; H:4.32; N: 5.54.

13.94: 1-(4-Aminobutyl)-5-chloro-2-(2-phosphono-5-furanyl) benzimidazole hydrochloric acid salt. Anal. Cald. for $C_{15}H_{18}N_3O4PCl_2+1.5H_2O+1.0\ HCl$. mp=236–240° C. (dec.); C: 38.36; H:4.72; N: 8.95. Found: C: 38.13; H:4.64; N: 8.88

13.95: 1-(4-Aminobutyl)-6-chloro-2-(2-phosphono-5-furanyl) benzimidazole. Anal. Calcl. for $C_{15}H_{17}N_3O_4PCl+1.0\ H_2O$. mp=250–252° C. (dec.); C: 46.46; H:4.94; N: 10.84. Found: C: 46.21; H:4.79; N: 10.62

13.96: 1-lsobutyl-4-methyl-5-chloro-2-(2-phosphono-5-furanyl) benzimidazole. Anal. Cald. for $C_{16}H_{18}N_2O_4PCl$. mp=193–196° C.; C: 48.19; H:5.39; N: 7.02. Found: C: 48.24; H:5.19; N: 6.85.

Synthesis Benzimidazoles with ether Linkers

Example 14

Preparation of 2-methyl-4-nitrobenzimidazole

Step 1

To a solution of 7.0 g (45.7 mmol) 3-nitro-1,2-phenylenediamine in 70 mL of dioxane was added 4.34 mL(46.0 mmol) acetic anhydride and the solution was refluxed overnight. The mixture was cooled to room temperature and the solvents were removed under reduced pressure. The resultant syrup was dissolved in 100 mL of dioxane and 100 mL of 2N sodium hydroxide and was heated tci 100° C. for 1 h. The reaction was then cooled, concentrated under reduced pressure, and was partitioned between water and ethyl acetate. The organic phase was evaporated to dryness and the solid was washed with water and was dried at 60° C. overnight to yield 7.1 g (40.1 mmol, 87.6%) of a yellow powder.
Step 2.
Preparation of 1-ethyl-2-methyl-4-nitrobenzimidazole To a solution of 0.47 g (2.65 mmol) 2-methyl-4-nitrobenzimidazole, and 0.12 g (2.92 mmol) of sodium hydride in 10 mL of dry dimethylformamide was added 0.218 mL (2.92 mmol) bromoethane. The mixture was heated overnight at 65° C. The mixture was cooled to room temperature and the solvents were removed under reduced pressure. The resultant syrup was partitioned between water and ethyl acetate. The organic phase was evaporated to dryness and the syrup chromatographed on silica to yield 0.31 g (1.51 mmol, 52%) of a yellow syrup.
Step 3
Preparation of 1-ethyl-2-bromomethyl-4-nitrobenzimidazole To a solution of 0.216 g (1.05 mmol) 1-ethyl-2-methyl-4-nitrobenzimidazole, 50 mL carbon tetrachloride and 0.375 g (2.11 mmol) NBS, was added 50 mg of AIBN. The reaction mixture was heated to 90° C. for five hours and the solution was cooled to room temperature. The solution was concentrated under reduced pressure and the resulting oil was chromatographed on silica to yield 0.16 g (0.57 mmol, 54%) of a light yellow oil.
Step 4
Preparation of 1-ethyl-4-nitro-2-[diethyl(methoxymethyl) phosphonate]benzimidazole To a solution of 0.191 g (1.14 mmol) diethyl (hydroxymethyl)phosphonate, 0.07 g (1.71 mmol) sodium hydride and 10 mL tetrahydrofuran at 0° C. was added a solution of 0.161 g (0.57 mmol) 1-ethyl-2-bromomethyl-4-nitrobenzimidazole in 10 mL of tetrahydrofuran. The reaction was stirred for 10 minutes at 0° C. and quenched with aqueous saturated ammonium chloride. The reaction contents were concentrated and the resultant solution was partitioned between ethyl acetate and $H_2O$. The organic layer was separated and dried over sodium sulfate and the solvent was removed under reduced pressure. The resultant oil was chromatographed on silica with 50% hexane/ethylacetate to yield 0.055 g (0.148 mmol, 26.3 %) of a clear oil.
Step 5.
Preparation of 1-ethyl-4-nitro-2-[3-phospho(methoxymethyl)]benzimidazole Followed the procedure given in the Example 12.
Step 6
Preparation of 1-ethyl-4-amino-2-[3-phospho(methoxymethyl)]benzimidazole Followed the procedure given in the Example 9, Method A.

Example 15

Preparation of 1-isobutyl-4-amino-5-fluoro-7-bromo-2-[3-phospho(methoxymethyl)]benzimidazole
Step 1
Synthesis of diethylphosphomethyl acetaldehyde dimethyl acetal ether To a solution of 1.0 mmol diethyl (hydroxymethyl) phosphonate, 1.5 mmol of sodium hydride in 2 mL DMF at 0° C. was added a solution of 1.2 mmol of bromoacetaldehyde dimethyl acetal. After 3 h. at room temperature the mixture was diluted with 5 mL of water and extracted with ether (4×15 mL). The combined ether layers were concentrated. The residue was chromatographed on a silica gel column eluting with hexane-ethyl acetate (8:1) to yield the product.
Step 2
Preparation of 1-isobutyl-4-nitro-5-fluoro-7-bromo-2-[3-diethylphospho(methoxymethyl)]benzimidazole To a solution of 1.0 mmol of 2-nitro-3-fluoro-5-bromo-6-isobutylamineaniline and 2.0 mmol of diethylphosphomethyl[acetaldehyde dimethyl]acetal ether in 5 mL THF at 0° C. was added 0.5 mL of 10% $H_2SO_4$ and the mixture was heated at 75° C. for 40 min. Solvent was removed under reduced pressure, diluted with water and extracted with EtOAc. The combined EtOAc layers were concentrated. The residue was chromatographed on a silica gel column yield the product.
Step 3

Followed the procedure given in the Example 4, Method A Step 2.
Step 4
Preparation of 1-isobutyl-4-amino-5-fluoro-7-bromo-2-[3-diethylphospho(methoxymethyl)]benzimidazole Followed the procedure given in the Example 9, Method B.
Step 5

Followed the procedure given in the Example 12.
15.1: 4-Amino-5-fluoro-7-bromo-1-isobutyl-2-(1-methoxymethyl-3-phosphono)benzimidazole. mp=200–202° C.(dec.); Anal. Cald. for $C_{13}H_{18}N_3O_4FBrP$: C: 38.07; H: 4.42; N: 10.24. Found: C: 37.87; H: 4.36; N: 10.15.

Example 16

Benzimidazole Phenyl Synthesis
Step 1
Preparation of diethyl-O-formylphenyloxymethylphosphonate To a suspension of 1.0 mmol of salicylaldehyde and 1.5 mmol of $K_2CO_3$ in 3 mL of DMF was added 1.0 mmol of diethyl iodomethylphosphonate and the mixture was heated at 50° C. for 3 days. Extraction and chromatography gave the title compound as an oil.
Step 2
Preparation of diethyl -2-(4-nitrobenzimidazole-2-yl) phenoxymethyl phosphonate A mixture of 1.0 mmol of diethyl-O-formylphenyloxymethyl phosphonate, 1.0 mmol of 3-nitro-1,2-phenylenediamine, and 1.5 mmol of $FeCl_3$ in 5 mL of ethanol was heated at 80° C. for 20 h. Extraction and chromatography gave the title compound. Rf =0.4 in EtOAc.
Step 3
Preparation of diethyl 2-(4-nitro-1-ethyl-benzimidazole-2-yl)phenoxymethylphosphonate.

Followed the procedure given in the Example 5, Method A.
Step 4
Preparation of diethyl 2-(4-amino-1-ethyl-benzimidazole-2-yl)phenoxymethylphosphonate.

Followed the procedure given in the Example 9, Method A.
Step 5
4-Amino-1-ethyl-2-[1-(2-phosphonomethyloxy)phenyl] benzimidazole Followed the procedure given in the Example 12.

Example 17

Preparation of N-(Phosphonomethyl)benzimidazole-2-carboxamide

Step 1

To a solution of 1,2-phenylenediamine (5 g, 46.2 mmol) in 100 mL of acetic acid was added trichloromethylacetamidate (8.97 g, 50.8 mmol).The reaction mixture was stirred for 2 h at room temparature. Precipitated solid was filtered and washed with water and dried. The solid was dissolved in 1N KOH solution and stirred for 1 h. The solution was acidified with 3N hydrochloric acid at 0° C. until pH 4 and the solid formed was filtered and washed with water. The solid 6.7 g (90%) was dried to give a white powder.(*Eur. J. Med. Chem.*, 1993, 28: 71)

Step 2

To a solution of 1.0 g (6.17 mmol) benzimidazole-2-carboxylic acid in 20 mL methylene chloride was added 5 mL diisopropylethylamine and 0.94 g (6.79 mmol,i of diethyl(aminomethyl)phosphonate followed by 4.5 g (9.25 mmol) of PyBOP. The reaction contents were stirred at room temperature for 4h, filtered and eluted through a pad of silica with ethyl acetate. The filtrate was evaporated under reduced pressure and was resuspended in a minimum amount of ethyl acetate. The resulting solid was filtered and dried to give 876 mg of a light yellow powder.

Step 3

Diethylphosphonate hydrolysis was carried out as described in Example 13.

The following compound was prepared in this manner:

17.1: N-(Phosphonomethyl)benzimidazole-2-carboxamide. 250–260° C. (dec.); Anal. cald. for C9H10N3O4P+0.15 AcOH: C: 42.28; H: 4.04; N: 15.91. Found: C: 42.60; H: 4.02; N: 15.70.

Example 18

General Procedure for the Synthesis of Acyloxyalkyl Phosphonate Esters

Method A

To a solution of 1 mmol phosphonic acid in 10 mL of DMF or $CH_3CN$ and 3.0 mmol of Hunigs base or N,N'-dicyclohexyl-4-morpholinecarboxamidine was added 5.0 mmol of the appropriate alkylating agent (For 6-chloronicotinoyloxymethylchloride, 5-bromonicotinoyloxymethylchloride, benzoyloxymethylchloride, p-fluorophenylchloride, 18.9: 4,5-Dimethyl-6-chloro-1-cyclopropylmethyl-2-(5-thionyl-2-bisbenzoylthiomethylphosphonate) benzimidazole. Anal. Cald. for $C_{33}H_{30}N_2O_6PS_2Cl$: C: 58.19; H: 4.44; N: 4.11; Found: C: 58.00; H: 4.50; N: 3.99

18.10: 6-Chloro-1-isobutyl-2-(5-furanyl-2-bisbenzoyloxymethyl phosphonate)benzimidazole. Anal. Cald. for $C_{31}H_{28}N_2O_8PCl+0.3Et\,OAc$: C: 59.55; H: 4.72; N: 4.31; Found: C: 59.95; H: 4.36; N: 3.90

18.11: 6-Chloro-1-isobutyl-2-(5-furanyl-2-bisbenzoylthiomethyl phosphonate)benzimidazole. Anal. Cald. for $C_{31}H_{28}N_2O_6PS_2Cl+1.25\,H_2O$: C: 54.95; H: 4.54; N: 4.13; Found: C: 54.92; H: 4.20; N: 3.93

18.12: 6-Chloro-1-isobutyl-2-(5-furanyl-2-bis-pfluoro-benzoyloxymethyl phosphonate)benzimidazole. Anal. Cald. for $C_{31}H_{26}N_2O_8PS_2ClF_2+0.2\,CH_2Cl_2$: C: 55.44; H: 3.94; N: 4.14; Found: C: 55.43; H: 3.88; N: 3.87

18.13: 6-Chloro-1-isobutyl-2-[5-furanyl-2-bis(6-chloronicotinoyl) oxymethylphosphonate]benzimidazole. Anal. Cald. for $C_{29}H_{24}N_4O_8PCl_3$: C: 50.20; H: 3.49; N: 8.07; Found: C: 50.43; H: 3.32; N: 7.99

18.14: 6-Chloro-1-isobutyl-2-[5-furanyl-2-bis(2-furanoyl) oxymethyl phosphonate]benzimidazole. Anal. Cald. for $C_{27}H_{24}N_2O_{10}PCl$: C: 53.79; H: 4.01; N: 4.65; Found: C: 53.60; H: 4.23; N: 4.68

18.15: 6-Chloro-1-isobutyl-2-[5-furanyl-2-bis(3-furanoyl) oxymethyl phosphonate]benzimidazole. Anal. Cald. for $C_{27}H_{24}N_2O_{10}PCl$: C: 53.79; H: 4.01; N: 4.65; Found: C: 53.82; H: 4.08; N: 4.51

18.16: 6-Chloro-1-isobutyl-2-[5-furanyl-2-bis(2-thiocarbonyl)oxymethyl phosphonate]benzimidazole. Anal. Cald. for $C_{27}H_{24}N_2O_8PS_2Cl+0.75\,H_2O$: C: 50.00; H: 3.96; N: 4.32; Found: C: 49.76; H: 3.94; N: 4.34

18.17: 6-Chloro-1isobutyl-2-[5-furanyl-2-bis(5-bromonicotinoyl) oxymethylphosphonate]benzimidazole. Anal. Cald. for $C_{29}H_{24}N_4O_8PClBr_2+0.1\,EtOAc+1.6\,H_2O$: C: 43.04; H: 3.44; N: 6.83; Found: 43.28; H: 3.36; N: 6.46

Method B

A suspension of 1 mmol of phosphonic acid in 5 mL of thionyl chloride was heated at reflux temperature for 4 h. The reaction mixture was cooled and evaporated to dryness. To the resulting residue was added a solution of 4 mmol of benzoylthioethanol (ref. Lefebvre, l. et al. *J. Med. Chem.* 38, 3941,1995; Benzaria, S. et al. *J. Med. Chem.* 39, 4958,1996) and 2.5 mmol pyridine in 3 mL of methylene chloride. After stirring at 25° C. for 4 h the reaction was subjected to work up and chromatography. thiophenecarbonyloxymethylchloride, 2-furoyloxymethylchloride, 3-furoyloxymethylchloride, benzoyloxymethylchloride see ref. U.S. Pat. No. 5,270,33, Oct., 9, 1991; EP 143 601, Jun. 5, 1985; Chem. Abstr. 104, 5589z, 1986; these chlorides were treated with NaI in $CH_3CN$ to generate the corresponding iodides). The reaction contents were stirred for 2 h and the solvent was removed under reduced pressure. The resultant syrup was chromatographed on silica (ref. EP 0 481 214 Al; J. E. Starrett, et. al. *J. Med. Chem.* 1994 37, 1857).

The following compounds were prepared in this manner:

18.1: 4-Amino-1-isobutyl-2-(5-furanyl-2-bisisobutyryloxymethyl phosphonate)benzimidazole. $MF=C_{23}H_{30}N_3O_8P$; Mass Cald. $MH^+=508$, Obs. $MH^+=508$. $R_f=0.5$ in 1:1 EtOAc:Hexane.

18.2: 4-Amino-5,7-dichloro-1-isobutyl-2-(5-furanyl-2-bispivaloyloxymethyl phosphonate)benzimidazole. Anal. Cald. for $C_{27}H_{36}N_3O_8PCl_2$: C: 51.27; H: 5.74; N: 6.64; Found: C: 51.22; H: 5.50; N: 6.42.

18.3: 6-Chloro-1-isobutyl-2-(2-bis-pivaloyloxymethylphosphono furan-5-yl) benzimidazole. Anal. Cald. for $C_{27}H_{36}N_2O_8PCl$: C:55.62 H:6.22 N:4.80; C:55.93 H:6.23 N:4.66.

18.4: 4-Amino-5-fluoro-7-ethyl-1-isobutyl-2-(5-furanyl-2-bispivaloyloxymethylphosphonate)benzimidazole. Anal. Cald. for $C_{29}H_{41}N_3O_8PF$: C: 57.14; H: 6.78; N: 6.89; Found: C: 57.08; H: 6.77; N: 6.70.

18.5: 4,5-Dimethyl-6-chloro-1-cyclopropylmethyl-2-(5-furanyl-2-bis pivaloyloxymethylphosphonate) benzimidazole. Anal. Cald. for $C_{29}H_{38}N_2O_8PCl$: C: 57.19; H: 6.29; N: 4.60; Found: C: 56.85; H: 6.31; N: 4.53

18.6: 4,5-Dimethyl-6-chloro-1-cyclopropylmethyl-2-(5-thionyl-2-bispivaloyloxymethylphosphonate) benzimidazole. Anal. Cald. for $C_{29}H38N_2O_7PSCl$: C: 55.72; H: 6.13; N: 4.48; Found: C: 56.03; H: 6.01; N: 4.46

18.7: 4-Amino-5-fluoro-7-bromo-1-isobutyl-2-(1-methoxymethyl-3-bispivaloyloxymethylphosphonate) benzimidazole. Anal. Cald. for $C_{27}H_{36}N_3O_8FBrP$: C: 47.03; H: 6.00; N: 6.58. Found: C: 47.15; H: 6.12; N: 6.31

18.8: 6-Chloro-1-isobutyl-2-(5-furanyl-2-bisisobutyryloxymethyl hosphonate)benzimidazole.

Anal. Cald. for $C_{25}H_{32}N_2O_8PCl$: C: 54.11; H: 5.81; N: 5.05; Found: C: 54.05; H: 5.72; N: 4.89

The following compounds were prepared in this manner:

18.18: 6-Chloro-1-isobutyl-2-(5-furanyl-2-bis (benzoylthioethylphosphonate) benzimidazole. Anal. Cald. for $C_{33}H_{32}N_2O_6PS_2Cl$: C: 58.02; H: 4.72; N: 4.10; Found: C: 57.90; H: 4.72; N: 4.04

18.19: 4-Amino-5-fluoro-7-ethyl-1-isobutyl-2-[5-furanyl-2-bis(benzoyloxy-3-butyl)phosphonate]benzimidazole. Anal. Cald. for $C_{39}H_{45}N_3O_8PF+0.5\ H_2O$: C: 63.06; H: 6.24; N: 5.66; Found: C: 62.86; H: 6.13; N: 5.46

18.20: 4,5-Dimethyl-6-chloro-1-cyclopropylmethyl-2-[5-furanyl-2-bis (benzoyloxy-3-butyl)phosphonate] benzimidazole. Anal. Cald. for $C_{39}H_{42}N_2O_8PCl +1.0\ H_2O$: C: 62.36; H: 5.90; N: 3.73; Found: C: 62.32; H: 5.80; N: 3.65

18.21: 6-Chloro-1-isobutyl-2-(5-furanyl-2-bis (acetyloxyethylphosphonate) benzimidazole. Anal. Cald. for $C_{23}H_{28}N_2O_8PCl+0.2\ H_2O$: C: 52.07; H: 5.40; N: 5.28; Found: C: 51.67; H: 5.40; N: 5.07

18.22: 4-Amino-5-fluoro-7-ethyl-1-isobutyl-2-(5-furanyl)-2-bisacetylthioethylphosphonate)benzimidazole. Anal. Cald. for $C_{25}H_{33}N_3O_6PFS_2+0.2\ CH_2Cl_2+0.1\ PhCH_3$; C: 50.84; H: 5.63; N: 6.87 Found: C: 50.74; H: 5.54 N: 6.48.

Example 19

General Procedure for Hydroxyethyldisulfidylethylphosphonate Diester

A suspension of 1 mmol of phosphonic acid in 5 mL of thionyl chloride was heated at reflux temperature for 4 h. The reaction mixture was cooled and evaporated to dryness. To the resulting residue was added a solution of 4 mmol of 2-hydroxyethyl disulfide and 2.5 mmol pyridine in 3 mL of methylene chloride. After stirring at 25° C. for 4 h the reaction was subjected to work up and chromatography.

The following compounds were prepared in this manner:

19.1: 4-Amino-5-fluoro-7-ethyl-1-isobutyl-2-(5-furanyl-2-bis(hydroxyethyidisulfidylethylphosphonate) benzimidazole. Anal. Cald. for $C_{25}H_{37}N_3O_6PFS_4+0.7\ H_2O$; C: 45.06; H: 5.81; N: 6.31; Found: C: 45.24; H: 5.67; N: 5.93.

19.2: 6-Chloro-1-isobutyl-2-(5-furanyl-2-bis (hydroxyethyldisulfidylethylphosphonate)benzimidazole. Anal. Cald. for $C_{23}H_{32}N_2O_6PClS_4+0.5\ H_2O$: C: 43.42; H: 5.23; N: 4.40; Found: C: 43.12; H: 4.94; N: 4.26.

Example 20

General Procedure for Substituted-Benzyl Phosphonate Diesters

Followed the same procedure as in Example 18, Method B.

The following compounds were prepared in this manner:

20.1: 4,5-Dimethyl-6-chloro-1-cyclopropylmethyl-2-(5-furanyl-2-bis-p-chlorobenzylphosphonate) benzimidazole. Anal. Cald. for $C_{31}H_{28}N_2O_4PCL_3+0.25\ H_2O$: C: 58.69; H: 4.53; N: 4.42; Found: C: 58.48; H: 4.62; N: 4.19

20.2: 4,5-Dimethyl-6-chloro-1-cyclopropylmethyl-2-(5-furanyl-2-bis-p-acetoxybenzylphosphonate) benzimidazole. Anal. Cald. for $C_{35}H_{34}N_2O_8PCl$: C: 62.09; H: 5.06; N: 4.14; Found: C: 61.69; H: 4.93; N: 4.10

20.3: 4,5-Dimethyl-6-chloro-1-cyclopropylmethyl-2-(5-furanyl-2-bis-p-acetoxy-m-dimethoxybenzylphosphonate)benzimidazole. Anal. Cald. for $C_{37}H_{40}N_2O_{12}PCl +0.4C_6H_5CH_3$: C: 59.16; H: 5.39; N: 3.47; Found: C: 59.19; H: 5.16; N: 3.34

20.4: 6-,Chloro-1-isobutyl-2-(5-furanyl-2-bis-p-acetoxy-m-methylbenzyl phosphonate)benzimidazole. Anal. Cald. for $C_{35}H_{36}N_2O_8PCl +2.0\ H_2O +0.5C_6H_5CH_3$: C: 60.75; H: 5.83; N: 3.68; Found: C: 60.82; H: 5.55; N: 3.32

20.5: 6-Chloro-1-isobutyl-2-(5-furanyl-2-bis-p-acetoxy-m-methoxybenzyl phosphonate)benzimidazole. Anal. Cald. for $C_{35}H_{36}N_2O_{10}PCl+1.2\ H_2$: C: 57.37; H: 5.28; N: 3.82; Found: C: 57.44; H: 5.16; N: 3.60

20.6: 6-Chloro-1-isobutyl-2-(5-furanyl-2-bis-pacetoxy-m-ch lorobenzyl phosphonate)benzimidazole. Anal. Cald. for $C_{33}H_{30}N_2O_8PCl_3$: C: 55.06; H: 4.20; N: 3.89; Found: C: 54.76; H: 4.33; N: 3.64

20.7: 6-1Chloro-1-isobutyl-2-(5-furanyl-2-bis-benzylphosphonate) benzimidazole. Anal. Cald. for $C_{29}H_{28}N_2O_4PCl$: C: 62.99; H: 5.47; N: 5.07; Found: C: 62.76; H: 5.84; N: 5.20

20.8: 4,5-Dimethyl-6-chloro-1-cyclopropylmethyl-2-(5-furanyl-2-bis-p,m-diacetoxybenzylphosphonate) benzimidazole. Anal. Cald. for $C_{37}H_{36}N_2O_{12}PC'+0.5\ H_2O$: C: 57.26; H: 4.81; N: 3.61; Found: C: 57.02; H: 4.84; N: 3.52.

Example 21

General Procedure for Phenyl Phosphonate Diesters

Followed the same procedure as in Example 18, Method B

The following compounds were prepared in this manner:

21.1: 4,5-Dimethyl-6-chloro-1-cyclopropylmethyl-2-[5-furanyl-2-bis-(5,6,7,8-tertahydro-2-napthyl)phosphonate] benzimidazole. Anal. Cald. for $C_{37}H_{38}N_2O_4PCl$: C: 69.31; H: 5.97; N: 4.37; Found: C: 69.33; H: 6.07; N: 4.14

21.2: 4,5-Dimethyl-6-chloro-1-cyclopropylmethyl-2-(5-furanyl-2-bis-phenyl phosphonate)benzimidazole. Anal. Cald. for $C_{29}H_{26}N_2O_4PCl$: C: 64.63; H: 4.99; N: 5.20; Found: C: 64.58; H: 4.99; N: 5.21

21.3: 4,5-Dimethyl-6-chloro-1-cyclopropylmethyl-2-(5-furanyl-2-bis-o-ethoxyphenylphosphonate) benzimidazole. Anal. Cald. for $C_{33}H_{34}N_2O_6PCl+0.67\ H_2O$: C: 62.60; H: 5.63; N: 4.42; Found: C: 62.57; H: 5.80; N: 4.24

21.4: 4,5-Dimethyl-6-chloro-1-cyclopropylmethyl-2-(5-furanyl-2-mono-o-ethoxyphenylphosphonate) benzimidazole. Anal. Cald. for $C_{25}H_{26}N_2O_5PCl+1.5\ H_2O+0.1HCl$: C: 56.49; H: 5.52; N: 5.27; Found: C: 56.22; H: 5.24; N: 5.01 21.5: 4,5-Dimethyl-6-chloro-1-cyclopropylmethyl-2-(5-furanyl-2-bis-o-methoxyphenylphosphonate)benzimidazole. Anal. Cald. for $C_{31}H_{30}N_2O_6PCl$: C: 62.79; H: 5.10; N: 4.72; Found: C: 62.79; H: 5.30; N: 4.54

21.6: 6.-Chloro-1-isobutyl-2-(5-furanyl-2-bis-phenyl phosphonate) benzimidazole. Anal. Cald. for $C_{27}H_{24}N_2O_4PCl+0.5H_2O$: C: 62.86; H: 4.88; N: 5.43; Found: C: 62.72; H: 4.75; N: 5.54

21.7: 6.Chloro-1-isobutyl-2-(5-furanyl-2-bis-o-acetoxyphenylphosphonate) benzimidazole. Anal. Cald. for $C_{31}H_{28}N_2O_8PCl$: C: 59.77; H: 4.53; N: 4.50; Found: C: 59.33; H: 4.82; N: 4.21

21.8: 6-Chloro-1-isobutyl-2-(5-furanyl-2-bis-p-acetoxyphenylphosphonate) benzimidazole. Anal. Cald. for $C_{31}H_{28}N_2O_8PCl$: C: 59.77; H: 4.53; N: 4.50; Found: C: 59.46; H: 4.67; N: 4.34

21.9: 6-Chloro-1-isobutyl-2-[5-furanyl-2-bis-p-(4-morpholino)phenyl phosphonate]benzimidazole. Anal. Cald. for $C_{35}H_{38}N_4O_6PCl+0.5\ H_2O$: C: 61.27; H: 5.73; N: 8.17; Found: C: 61.62; H: 5.78; N: 7.79

21.10: 6-Chloro-1-isobutyl-2-(5-furanyl-2-bis-p-hydroxyphenylphosphonate) benzimidazole. Anal. Cald. for $C_{27}H_{24}N_2O_6PCl$ +0.75 $H_2O$: C: 58.70; H: 4.65; N: 5.07; Found: C: 58.54; H: 4.43; N: 4.78

21.11: 6-Chloro-1-isobutyl-2-(5-furanyl-2-bis-m-acetoxyphenylphosphonate) benzimidazole. Anal. Cald. for $C_{31}H_{28}N_2O_8PCl$+0.4 $H_2O$: C: 59.08; H: 4.61; N: 4.45; Found: C: 58.82; H: 4.54; N: 4.20

21.12: 6-Chloro-1-isobutyl-2-[5-furanyl-2-bis-(1-triozolo) acetoxyphenyl phosphonate]benzimidazole. Mass. Cald. for $C_{31}H_{26}N_8O_4PCl$: 641(M +H); Found: 641(M+H)

21.13: 6-Chloro-1-isobutyl-2-[5-furanyl-2-bis-m-(N,N-dimethylamino) phenylphosphonate]benzimidazole. Anal. Cald. for $C_{31}H_{34}N_4O_4PCl$+1.5 $H_2O$+0.35 $CH_2Cl_2$: C: 57.95; H: 5.85; N: 8.62; Found: C: 57.94; H: 5.49; N: 8.24

21.14: 6-Chloro-1-isobutyl-2-(5-furanyl-2-bis-pacetamidophenyl phosphonate)benzimidazole. Anal. Cald. for $C_{31}H_{30}N_4O_6PCl$ +0.5 $H_2O$: C: 59.10; H: 4.96; N: 8.89; Found: C: 59.03; H: 5.23; N: 9.68

21.15: 4-Amino-5-fluoro-7-ethyl-1-isobutyl-2-(5-furanyl-2-bis(2-methylphenylphosphonate)benzimidazole. Anal. Cald. for $C_{31}H_{33}N_3O_4PF$+0.7 $H_2O$; C: 64.84; H: 6.04; N: 7.32; Found: C: 64.88; H: 6.12; N: 7.10.

21.16: 4-Amino-5-fluoro-7-ethyl-1-isobutyl-2-(5-furanyl-2-bis(phenylphosphonate)benzimidazole. Anal. Cald. for$C_{29}H_{29}N_3O_4PF$+0.3 $H_2O$; C: 64.63; H: 5.54; N: 7.80; Found: C: 64.61; H: 5.57; N: 7.47.

Example 22

Preparation of (5-Substituted 2-Oxo-1,3-Dioxolen-4-yl)Methyl Phosphonate Prodrugs A solution of 1 mmol phosphonic acid in DMF and 2 mmol of sodium hydride was treated with 4 mmol of 5-substituted-4-bromomethyl-2-oxo-1,3-dioxolene (prepared according to Chem. Pharm. Bull. 1984, 32(6), 2241.) at 25° C. for 24 h. Extraction and chromatography gave the phosphonate prodrug. The following compound was prepared in this manner:

22.1: 4,5-Dimethyl-6-chloro-1-cyclopropylmethyl-2-[5-furanyl-(5-methyl-2-oxo-1,3-dioxolen-4-yl) methylphosphonate]benzimidazole. Anal. Cald. for $C_{27}H_{26}N_2O_{10}PCl$+0.75 $H_2O$: C: 62.79; H: 5.10; N: 4.72; Found: C: 62.79; H: 5.30; N: 4.54

Example 23

General Procedure for the Synthesis of Alkyloxycarbonyloxyalkyl Phosphonate Esters To a solution of 1 mmol phosphonic acid in 5 mL of anhydrous DMF was added 5 mmol of N,N'-dicyclohexyl-4-morpholinecarboxamidine followed by 5 mmol of isopropyloxycarbonyloxymethyliodide (all the alkyl and aryloxy (thio)carbonyloxymethyl iodides were prepared from the commercially available chloromethyl chloroformate according to the reported procedure, Tatsuo Nishimura et al. J. Antibiotics, 1987, 40(1), 81–90). The reaction contents were stirred for 24 h at room temperature and the solvent was removed under reduced pressure. The resultant syrup was chromatographed on silica with 50% EtOAc/Hexanes to yield the required product.

The following compounds were prepared in this manner:

23.1: 4,5-Dimethyl-6-chloro-1-cyclopropylmethyl-2-(5-furanyl-2-biscyclohexyloxycarbonyloxymethylphosphonate) benzimidazole. mp=120–122° C.; Anal. Cald. for $C_{33}H_{42}N_2O_{10}PCl$: C: 57.18; H: 6.1 1; N: 4.04; Found: C: 57.16; H: 6.13; N: 3.99

23.2: 4,5-Dimethyl-6-chloro-1-cyclopropylmethyl-2-(5-furanyl-2-bisethyloxycarbonyloxymethylphosphonate) benzimidazole. Anal. Cald. for $C_{25}H_{32}N_2O_{10}PCl$: C: 51.16; H: 5.50; N: 4.77; Found: C: 51.06; H: 5.30; N: 4.72

23.3: 4,5-Dimethyl-6-chloro-1-cyclopropylmethyl-2-(5-furanyl-2-bisisopropyloxycarbonyloxymethylphosphonate) benzimidazole. Anal. Cald. for $C_{27}H34N_2O_{10}PCl$: C: 52.90; H: 5.59; N: 4.57; Found: C: 52.96; H: 5.56; N: 4.49

23.4: 4,5-Dimethyl-6-chloro-1-cyclopropylmethyl-2-(5-furanyl-2-bisisopropylthiocarbonyloxymethylphosphonate) benzimidazole. Anal. Cald. for $C_{27}H_{34}N_2O_8PClS_2$: C: 50.27; H: 5.31; N: 4.34; Found: C: 49.99; H: 5.35; N: 4.27

23.5: 4,5-Dimethyl-6-chloro-1-cyclopropylmethyl-2-(5-furanyl-2-bisphenylthiocarbonyloxymethylphosphonate) benzimidazole. Anal. Cald. for $C_{33}H_{30}N_2O_8PClS_2$: C: 55.58; H: 4.24; N: 3.93; Found: C: 55.36; H: 4.43; N: 3.77

23.6: 4,5-Dimethyl-6-chloro-1-cyclopropylmethyl-2-(5-furanyl-2-bisphenyloxy carbonyloxymethylphosphonate) benzimidazole. Anal. Cald. for $C_{33}H_{30}N_2O_{10}PCl$+0.5 $H_2O$: C: 55.58; H: 4.24; N: 3.93; Found: C: 55.36; H: 4.43; N: 3.77

23.7: 4,5-Dimethyl-6-chloro-1-cyclopropylmethyl-2-(5-furanyl-2-bismethyloxy carbonyloxymethylphosphonate) benzimidazole. mp=87–85° C.; Anal. Cald. for $C_{33}H_{30}N_2O_8PClS_2$: C: 55.58; H: 4.24; N: 3.93; Found: C: 55.36; H: 4.43; N: 3.77

23.8: 4-Amino-5-fluoro-7-ethyl-1-isobutyl-2-(5-furanyl-2-bisethyloxy carbonyloxymethylphosphonate) benzimidazole. Anal. Cald. for $C_{25}H_{33}N_3O_{10}FP$: C: 51.28; H: 5.68; N: 7.18. Found: 51.51; H: 5.83; N: 7.18

23.9: 6-Chloro-1-isobutyl-2-(5-furanyl-2-bis-p-methoxyphenyloxy carbonyl oxymethylphosphonate) benzimidazole. Anal. Cald. for $C_{33}H_{32}N_2O_{12}PCl$: C: 55.43; H: 4.51; N: 3.92; Found: C: 55.52; H: 4.56; N: 3.47

23.10: 6-Chloro-1-isobutyl-2-(5-furanyl-2-bis-o-methoxyphenyloxycarbonyloxy methylphosphonate) benzimidazole. Anal. Cald. for $C_{33}H_{32}N_2O_{12}PCl$: C: 55.43; H: 4.51; N: 3.92; Found: C: 55.34; H: 4.62; N: 3.66

23.11: 6-Chloro-1-isobutyl-2-(5-furanyl-2-bis-m-methoxyphenyloxycarbonyloxymethylphosphonate) benzimidazole. Anal. Cald. for $C_{33}H_{32}N_2O_{12}PCl$: C: 55.43; H: 4.51; N: 3.92; Found: C: 55.28; H: 4.68; N: 3.83

23.12: 6-Chloro-1-isobutyl-2-(5-furanyl-2-bis-o-methylphenyloxycarbonyl oxymethylphosphonate) benzimidazole. Anal. Cald. for $C_{33}H_{32}N_2O_{10}PCl$: C: 58.03; H: 4.72; N: 4.10; Found: C: 57.78; H: 4.60; N: 3.89

23.13: 6-Chloro-1-isobutyl-2-(5-furanyl-2-bis-p-chlorophenyloxycarbonyl oxymethylphosphonate) benzimidazole. Anal. Cald. for $C_{31}H_{26}N_2O_{10}PCl_3$: C: 51.44; H: 3.62; N: 3.87; Found: C: 51.46; H: 3.86; N: 3.81

23.14: 6-Chloro-1-isobutyl-2-(5-furanyl-2-bis-1,4-biphenyloxycarbonyl oxymethylphosphonate) benzimidazole. mp=112–114° C.; Anal. Cald. for $C_{43}H_{36}N_2O_{10}PCl$: C: 63.98; H: 4.50; N: 3.47; Found: C: 63.90; H: 4.39; N: 3.38

23.15: 6-Chloro-1-isobutyl-2-(5-furanyl-2-bis-phthalylethyloxycarbonyloxy methylphosphonate) benzimidazole. mp=112–114° C.; Anal. Cald. for $C_{43}H_{36}N_2O_{10}PCl$: C: 63.98; H: 4.50; N: 3.47; Found: C: 63.90; H: 4.39; N: 3.38

23.16: 6-Chloro-1-isobutyl-2-[5-furanyl-2-bis-(N-Phenyl, N-methylcarbamoyl) oxymethylphosphonate]

benzimidazole. Anal. Cald. for $C_{33}H_{34}N_4O_8PCl+0.25$ $HI+0.66 H_2O$: C: 54.67; H: 4.95; N: 7.73; Found: 54.71; H: 4.76; N: 7.44

23.17: 6-Chloro-1-isobutyl-2-[5-furanyl-2-mono-(4-morpholinocarbonyloxy methyl)phosphonate] benzimidazole. Anal. Cald. for $C_{21}H_{25}N_3O_7PCl+0.5$ $HI+0.25 H_2O$: C: 44.54; H: 4.63; N: 7.42; Found: 44.59; H: 4.52; N: 7.56

Example 24

General Procedure for the Substituted-Ethyl Phosphonate Diesters.

Followed the same procedure as in Example 18, Method B

The following compounds were prepared in this manner:

24.1: 4,5-Dimethyl-6-chloro-1-cyclopropylmethyl-2-[5-furanyl-2-bis-(2-trichloroethyl)phosphonate] benzimidazole. mp=132–134° C.; Anal. Cald. for $C_{21}H_{20}N_2O_4PCl_7$: C: 39.19; H: 3.13; N: 4.35; Found: C: 39.37; H: 3.28; N: 4,18

24.2: 4,5-Dimethyl-6-chloro-1-cyclopropylmethyl-2-[5-furanyl-2-bis-(2-bromoethyl)phosphonate] benzimidazole. Anal. Cald. for $C_{21}H_{24}N_2O_4PClBr_2$: C: 42.42; H: 4.07; N: 4.71; Found: C: 42.64; H: 4.35; N: 4.65

24.3: 6-Chloro-1-isobutyl-2-[5-fu ranyl-2-bis-(2-azidoethyl) phosphonate] benzimidazole. mp=73–75 ° C.; Anal. Cald. for $C_{19}H_{22}N_8O_4PCl$: C: 46.30; H: 4.50; N: 22.74; Found: C: 46.30; H: 4.39; N: 22.51

The azido compound (24.3) was obtained by reaction of the Compound 6-Chloro-1-isobutyl-2-[5-furanyl-2-bis-(2-iodoethyl)phosphonate]benzimidazole and sodium azide in DMF.

24.4: 6-Chloro-1-isobutyl-2-[5-furanyl-2-bis-(2-aminoethyl)phosphonate] benzimidazole hydrogen chloride salt. mp=160° C.; Anal. Cald. for $C_{19}H_{26}N_4O_4PCl3HCl+1.0 H_2O$: C: 40.16; H: 5.50; N: 9.80; Found: C: 39.88; H: 5.41; N: 9.43

The amino compound (24.4) was obtained by the hydrogenation of the azido compound (24.3) in presence of 10% Pd/C and HCl in EtOAc.

24.5: 4,5-Dimethyl-6-chloro-1-cyclopropylmethyl-2-[5-furanyl-2-bis(2-iodoethyl)phosphonate]benzimidazole. Anal. Cald. for $C_{21}H_{24}N_2O_4PClI_2$: C: 34.44; H: 3.35; N: 4.23; Found: C: 34.69; H: 3.12; N: 4.01.

24.6: 6-Chloro-1-isobutyl-2-[5-furanyl-2-bis(2-N,N-dimethylaminoethyl)phosphonate]benzimidazole hydrogen chloride salt. mp=61–63° C.; Anal. Cald. for $C_{23}H_{34}N_4O_4PCl$: C: 55.59; H: 6.90; N: 11.27; Found: C: 55.34; H: 7.06; N: 11.07.

Example 25

General Procedure for the Synthesis of Phosphonoamidates. (ref. Starret, J. E. et al. *J. Med. Chem.* 37, 1857,1994).

Followed the same procedure as in Example 18, Method B

The following compounds were prepared in this manner:

25.1: 4,5-Dimethyl-6-chloro-1-cyclopropylmethyl-2-[5-furanyl-2-cyclic (2,2-dimethylpropyl)phosphonoamidate] benzimidazole. mp=132–134° C.; Anal. Cald. for $C_{21}H_{20}N_2O_4PCl_7$: C: 39.19; H: 3.13; N: 4.35; Found: C: 39.37; H: 3.28; N: 4.18

Example 26

General General procedure for the synthesis of substituted amidoalkyl esters. (ref. Starret. J. E. et al. *J. Med. Chem.* 37,1857, 1994).

Followed the same procedure as in Example 18, Method B

The following compounds were prepared in this manner:

26.1: 6-Chloro-1-isobutyl-2-[5-furanyl-2-bis-{N,N(2-hydroxyethyl)amido methyl} phosphonate] benzimidazole. Anal. Cald. for $C_{27}H_{38}N_4O_{10}PCl +0.4 CH_2Cl_2+1.0 MeOH$: C: 47.97; H: 6.07; N: 7.88; Found: C: 47.69; H: 5.88; N: 7.53

Example 27

General Procedure for the Synthesis of Alkyloxycarbonylalkyl Esters. (ref. Serafinowska. H. T., et. al. *J. Med. Chem.* 1995 38. 1372).

Followed the same procedure as in Example 18, Method A

The following compounds were prepared in this manner:

27.1: 6-Chloro-1-isobutyl-2-(5-furanyl-2-bismethyloxycarbonylmethyl phosphonate) benzimidazole. Anal. Cald. for $C_{21}H_{24}N_2O_8PCl+1.0 H_2O$: C: 50.56; H: 4.85; N: 5.62; Found: C: 50.53; H: 5.02; N: 5.56

Example 28

General Procedure for the Synthesis of Substituted-Phenylalkyl Esters

Followed the same procedure as in Example 18, Method B

The following compounds were prepared in this manner:

28.1: 4,5-Dimethyl-6-chloro-1-cyclopropylmethyl-2-(5-furanyl-2-bisphenpropylphosphonate)benzimidazole. Anal. Cald. for $C_{35}H_{38}N_2O_4PCl$: C: 68.12; H: 6.21; N: 4.54; Found: C: 67.87; H: 6.32; N: 4.49

28.2: 6-Chloro-1-isobutyl-2-[5-furanyl-2-bis(p-acetoxyphenpropyl) phosphonate]benzimidazole. Anal. Cald. for $C_{37}H_{40}N_2O_8PCl+0.2 H_2O$: C: 62.53; H: 5.73; N: 3.94; Found: C: 62.14; H: 5.67; N: 3.88

28.3: 6-Chloro-1-isobutyl-2-[5-furanyl-2-bis(3-phenyl-3-acetoxypropyl) phosphonate]benzimidazole. Anal. Cald. for $C34H_{40}N_2O_8PCl+1.85 H_2O$: C: 62.02; H: 5.95; N: 3.78; Found: C: 59.63; H: 6.14; N: 3.55

28.4: 6-Chloro-1-isobutyl-2-[5-furanyl-2-bis(p-hydroxyphenpropyl) phosphonate]benzimidazole. Anal. Cald. for $C33H_{36}N_2O_6PCl+0.08 H_2O$: C: 63.48; H: 5.84; N: 4.49; Found: C: 63.05; H: 5.69; N: 4.32

28.5: 6-Chloro-1-isobutyl-2-[5-furanyl-2-bis(p-methoxyphenpropyl) phosphonate]benzimidazole. Anal. Cald. for $C_{35}H_{40}N_2O_6PCl$: C: 64.56; H: 6.19; N: 4.30; Found: C: 64.20; H: 6.13; N: 4.08

28.6: 6-Chloro-1-isobutyl-2-[5-furanyl-2-bis(p,m-dimethoxyphenpropyl) phosphonate]benzimidazole. Anal. Cald. for $C_{37}H_{44}N_2O_9PCl$: C: 62.49; H: 6.24; N: 3.94; Found: C: 62.06; H: 6.02; N: 3.62

Example 29

General Procedure for the Synthesis of Substituted Phthalimide Esters.

To a solution of 1 mmol phosphonic acid in 10 mL of DMF or $CH_3CN$ and 3.0 mmol of Hunigs base or N,N'-dicyclohexyl-4-morpholine carboxamidine is added 5.0 mmol of the substituted 3-bromophthalide. The reaction contents are stirred for 2 h and the solvent is removed under reduced pressure. The resultant syrup is chromatographed on silica(Clayton, J. P. et al. *J. Med. Chem.* 1976 19, 1385.).

Example 30

General Procedure for Cyclic 1.3-Cyclohexyl Phosphonate Diesters

Followed the same procedure as in Example 18, Method B

The following compounds were prepared in this manner:

30.1: 6-Chloro-4,5-dimethyl-1-cyclopropylmethyl-2-[1- hydroxy-3,5-cyclohexylphosphono-5-furanyl]
benzimidazole. mp=211–215° C.; Anal. Cald. for $C_{23}H_{26}$ Cl $N_2O_5P$+2/3 $H_2O$: C: 56.50; H: 5.64; N: 5.73. Found: C: 56.65; H: 5.54 ; N: 5.64.

30.2: 6-Chloro-4,5-dimethyl-1-cyclopropylmethyl-2-[1-acetylhydroxy-3,5-cyclohexylphosphono-5-furanyl] benzimidazole, minor isomer; Anal. Cald. for $C_{25}H_{28}ClN_2O_6P$+1.5 $H_2O$: C: 55.00 ; H: 5.72; N: 5.13. Found: C: 55.19; H: 5.31; N: 4.65.

30.3: 6-Chloro-4,5-dimethyl-1-cyclopropylmethyl-2-[1-acetylhydroxy-3,5-cyclohexylphosphono-5-furanyl] benzimidazole, major isomer; Anal. Cald. for $C_{25}H_{28}ClN_2O_6P$+0.75 $H_2O$ +0.1 EtOAc: C: 56.37; H: 5.64; N: 5.18. Found: C: 56.68; H: 5.69; N: 4.80.

30.4: 6-Chloro-1-isobutyl-2-{2-[5-(1-hydroxy-3,5-cyclohexyl)phosphono] furanyl}benzimidazole, minor isomer. mp>220° C.; Anal. Cald. for $C_{21}H_{24}$ Cl $N_2O_5$ P+1/3 $H_2O$: C: 55.21; H: 5.44; N: 6.13. Found: C: 55.04; H: 5.50; N: 6.00.

30.5: 6-Chloro-1-isobutyl-2-{2-[5-(1-hydroxy-3,5-cyclohexyl)phosphono]furanyl}benzimidazole, major isomer. mp>220° C.; Anal. Cald. for $C_{21}H_{24}$ Cl $N_2O_5$ P: C: 55.94; H: 5.37; N: 6.21. Found: C: 55.73; H: 5.34; N: 6.13.

Example 31

General Procedure for the Cclic Substituted 1.3-propyl Phosphonate Diesters

Followed the same procedure as in Example 18, Method B

The following compounds were prepared in this manner:

31.1: 6-Chloro-1-isobutyl-2-(2-(5-(1-R-phenyl-1,3-propyl) phosphono)furanyl) benzimidazole, major isomer. mp=204–206° C.; Anal. Cald. for $C_{24}H_{24}ClN_2$ O4 P: C: 61.22; H: 5.14; N: 5.95. Found: C: 60.95; H: 5.01; N: 5.88.

31.2: 6-Chloro-1-isobutyl-2-(2-(5-(1-R-phenyl-1,3-propyl) phosphono) furanyl)benzimidazole, minor isomer; Anal. Cald. for $C_{24}H_{24}ClN_2O_4P+H_2O$: C: 58.96; H: 5.36; N: 5.73. Found: C: 58.85; H: 5.48; N: 5.55.

The two diastereomers were separated by column chromatography by eluting with methanol-methylene chloride (5:95).

31.3: 6-Chloro-1-isobutyl-2-{5-[1S-(4-nitrophenyl)-2R-acetylamino-propan-1,3-yl]phosphono-2-furanyl}benzimidazole, major isomer; MH+ Cald. for $C_{26}H_{26}ClN_4O_7P$ : 573.Found: 573.

31.4: 6-Chloro-1-isobutyl-2-{5-[1S-(4-nitrophenyl)-2R-acetylamino-propan-1,3-yl]phosphono-2-furanyl}benzimidazole, minor isomer; Anal. Cald. for $C_{26}H_{26}ClN_4O_7P$+1.6 $H_2O$+0.25 $CH_2Cl_2$: C:50.61; H: 4.81; N: 8.99. Found: C: 50.25; H: 4.37; N: 9.01.

31.5: 6-Chloro-1-isobutyl-2-{5-[1 S-(4-methylthiophenyl)-2S-acetylamino-propan-1,3-yl]phosphono-2-furanyl}benzimidazole; Anal. Cald. for $C_{27}H_{29}ClN_3O_5PS$+1 $H_2O$+0.35 $CH_2Cl_2$: C: 52.83; H: 5.14; 52.44; H: 4.76; N: 6.59.

All three diastereomers were separated by column chromatography by eluting with methanol-methylene chloride (5:95). The substituted 1,3-diol to prepare 31.3, 31.4, 315 was made by the following method.

To a solution of D-threo-2-amino-1-(4-nitrophenyl)-1,3-propane diol (2.0 g, 9.4 mmol) in pyridine (20 mL) was added acetic anhydride (0.9 mL, 9.4 mmol) slowly at 0° C. The reaction was warmed to room temperature and allowed to stir for 1h. Reaction mixture was concentrated under reduced pressure and azeotroped. Column chromatography by elution with ethyl acetate-methylene chloride (4:1) resulted in 1.7 g of pure acetylated product.

31.6: 6-Chloro-1-isobutyl-2-{5-[1-(2-pyridyl)-propan-1,3-yl] phosphono-2-furanyl}benzimidazole. Anal. Cald. for $C_{23}H_{23}ClN_3O_4P$+1.5 $H_2O$+0.3 $CH_2Cl_2$: C: 53.37; H: 5.11; N: 8.01. Found: C: 53.23; H: 4.73; N: 7.69.

31.7: 6-Chloro-1-isobutyl-2-{5-[1-(N-oxo-2-pyridyl)-propan-1,3-yl]phosphono-2-furanyl}benzimidazole. mp=195° C. (dec.); Anal. Cald. for $C_{23}H_{23}ClN_3O_5P$+0.25 $H_2O$+0.25 $CH_2Cl_2$: C: 54.37; H: 4.71; N Found: C: 54.77; H: 4.86; N: 7.76.

31.8: 6-Chloro-1-isobutyl-2-{5-[1-(4-pyridyl)-propan-1,3-yl]phosphono-2-furanyl}benzimidazole. mp=165° C. (dec.); Mass Cald. for $C_{23}H_{23}ClN_3O_4P$: MH+454: Found: MH+454

The substituted 1,3-diol used to prepare 31.6, 31.8 were made by the following 2 step method.

Step A: (J. Org. Chem., 1957, 22, 589)

To a solution of 2-pyridinepropanol (10 g, 72.9 mmol) in acetic acid (75 mL) was added 30% hydrogen peroxide slowly. The reaction mixture was heated to 80° C. for 16 h. The reaction was concentrated under vacuum and the residue was dissolved in acetic anhydride (100 mL) and heated at 110° C. overnight. Acetic anhydride was evaporated upon completion of reaction. Chromatography of the mixture by eluting with methanol-methylene chloride (1:9) resulted in 10.5 g of pure diacetate.

Step B

To a solution of diacetate (5 g, 21.1 mmol) in methanol-water (3:1, 40 mL) was added potassium carbonate (14.6 g, 105.5 mmol). After stirring for 3 h at room temperature, the reaction mixture was concentrated. The residue was chromatographed by eluting with methanol-methylene chloride (1:9) to give crystalline diol.

The compound 31.7 was prepared by the oxidation of the compound 31.6 by the following method.

To a solution of 6-chloro-1-isobutyl-2-{5-[1-(2-pyridyl)-propan-1,3-yl]phosphono-2-furanyl}benzimidazole (172 mg, 0.36 mmol) in methylene chloride was added 3-chloroperoxybenzoic acid (252 mg, 0.72 mmol) at 0° C. The reaction was warmed to room temperature and allowed stir for 3 h. The solvent was evaporated under reduced pressure. Chromatography by elution with methanol-methylenecchloride (5:95) resulted in 100 mg of pure N-oxide.

31.9: 6-Chloro-1-isobutyl-2-{5-[1-(4-fluorophenyl)-propan-1,3-yl]phosphono-2-furanyl}benzimidazole. mp=207–208° C.; Anal. Cald. for $C_{24}H_{23}ClFN_2O_4P$: C: 58.96; H: 4.74; N: 5.73. Found: C: 59.20; H: 4.64; N: 5.59.

31.10: 6-Chloro-1-isobutyl-2-{5-[1-(4-fluorophenyl)-propan-1,3-yl]phosphono-2-furanyl}benzimidazole. mp=176–179° C.; Anal. Cald. for $C_{24}H_{23}ClFN_2O_4P$+ $0.5H_2O$: C: 57.90; H: 4.86; N: 5.63. Found: C: 57.60; H: 4.68; N: 5.54.

The substituted 1,3-diol used to prepare 31.9, 31.10 was made by the following 3 step method.

Step A: (J. Org. Chem., 1988, 53, 911)

To a solution of oxalyl chloride (5.7 mL, 97 mmol) in dichloromethane (200 mL) at −78° C. was added dimethyl sulfoxide (9.2 mL, 130 mmol). The reaction mixture was stirred at −78° C. for 20 min. before addition of 3-(benzyloxy)propan-1-ol (11 g, 65 mmol) in dichloromethane (25 mL). After an hour at −78° C., reaction was quenched with triethylamine (19 mL, 260 mmol) and warmed to room temperature. Work-up and column chromatography by elution with dichloromethane resulted in 8 g of 3-(benzyloxy)propan-1-al.

Step B

To a solution of 3-(benzyloxy)propan-1-al (1 g, 6.1 mmol) in THF at 0° C. was added a 1 M solution of 4-fluorophenylmagnesium bromide in THF (6.7 mL, 6.7 mmol). The reaction was warmed to room temperature and stirred for 1 h. Work-up and column chromatography by elution with dichloromethane resulted in 0.7 g of alcohol.

Step C

To a solution of benzyl ether (500 mg) in ethyl acetate (10 mL) was added 10% $Pd(OH)_2$-C (100 mg). The reaction was stirred under a hydrogen atmosphere for 16 h. The reaction mixture was filtered through Celite and concentrated. Chromatography of the residue by elution with ethyl acetate-dichloromethane (1:1) resulted in 340 mg of product.

31.11: 6-Chloro-1-isobutyl-2-{5-[1-(3-bromo-4-methoxyphenyl)-propan-1,3-yl]phosphono-2-furanyl}benzimidazole, major isomer. mp=167–169° C.; Anal. Cald. for $C_{25}H_{25}BrClN_2O_5P$: C: 51.79; H: 4.35; N: 4.83. Found: C: 51.77; H: 4.25; N: 4.73.

31.12: 6-Chloro-1-isobutyl-2-{5-[1-(3-Bromo-4-methoxyphenyl)-propan-1,3-yl]phosphono-2-furanyl}benzimidazole, minor isomer. Anal. Cald. for $C_{25}H_{25}BrClN_2O_5P+0.55CHCl_3$: C: 47.54; H: 3.99; N: 4.34. Found: C: 47.50; H: 3.89; N: 3.99.

The substituted 1,3-diol to prepare 31.11, 31.12 was made by the following 2 step method.

Step A: (*J. Org. Chem.*, 1990, 55, 4744)

To a solution of diisopropylamine (4.1 mL, 29.4 mmol) in ether (40 mL) at –78° C. was added 2.5M n-butyl lithium (11.8 mL, 29.4 mmol). The reaction was stirred for 15 min before adding t-butyl acetate (4 mL, 29.4 mmol) in ether (10 mL). After 20 min, aldehyde (3 g, 14 mmol) in ether (10 mL) was added and warmed to room temperature where it was stirred for 16 h. Work-up and column chromatography by elution with ethyl acetate-dichloromethane (1:9) resulted in 3.3 g of addition product.

Step B

To a solution of t-butyl ester (1.5 g, 4.5 mmol) in THF (20 mL) was added 1M lithium aluminum hydride at 0° C. The reaction mixture was warmed to room temperature and stirred for 2 h. The reaction was quenched with ethyl acetate and saturated aq. sodium sulfate was added to precipitate the salts. Filtration and concentration of solvent resulted in crude diol. Column chromatography by elution with ethyl acetate-dichloromethane (1:1) gave 970 mg of pure diol.

31.13: 6-Chloro-1-isobutyl-2-{5-[2-(hydroxymethyl)-propan-1,3-yl]phosphono-2-furanyl}benzimidazole. mp=164–165° C.; Anal. Cald. for $C_{19}H_{22}ClN_2O_5P$: C: 53.72; H: 5.22; N: 6.59. Found: C: 53.62; H: 5.18; N: 642.

31.14: 6-Chloro-1-isobutyl-2-{5-[2-(acetoxymethyl)-propan-1,3yl]phosphono-2-furanyl}benzimidazole. mp=132–134° C.; Anal. Cald. for $C_{21}H_{24}ClN_2O_6P$: C: 54.03; H: 5.18; N: 6.00. Found: C: 54.17; H: 4.99; N: 5.81.

31.15: 6-Chloro-1-isobutyl-2-{5-[2-(methoxycarbonyloxymethyl)-propan-1,3-yl ]phosphono-2-furanyl}benzimidazole. mp=138–140° C.; Anal. Cald. for $C_{21}H_{24}ClN_2O_7P$: C: 52.24; H: 5.01; N: 5.80. Found: C: 52.13; H: 5.07; N: 5.51.

31.16: 4-Amino-5-fluoro-7-ethyl-1-isobutyl-2-{5-[2-(acetoxymethyl)-propan-1,3-yl ]phosphono-2-furanyl}benzimidazole; Anal. Cald. for $C_{23}H_{29}FN_3O_6P+$ 0.3 $H_2O$: C: 55.38; H: 5.98; N: 8.42. Found: C: 55.60; H: 6.31; N: 8.02.

31.17: 6-Amino-9-neopentyl-8-{5-[2-(acetoxymethyl)-propan-1,3-yl ]phosphono-2-furanyl}purine. mp=164–165° C.; Anal. Cald. for $C_{20}H_{26}N_5O_6P$: C: 51.84; H: 5.65; N: 15.11. Found: C: 52.12; H: 5.77; N: 14.59.

31.18: 4-Amino-5-fluoro-7-ethyl-1-isobutyl-2-{5-[2-(cyclohexylcarbonyloxymethyl)-propan-1,3-yl] phosphono-2-furanyl}benzimidazole. mp=60–630 C; Anal. Cald. for $C_{28}H_{37}FN_3O_6P$: C: 59.89; H: 6.64; N: 7.48. Found: C: 59.97; H: 6.60; N: 7.33. 31.19: 6-Chloro-1-isobutyl-2-{5-[2-(aminomethyl)-propan-1,3-yl] phosphono-2-furanyl}benzimidazole. mp=158–160° C.; Anal. Cald. for $C_{19}H_{23}ClN_3O_4P$: C: 51.13; H: 5.76; N: 9.41. Found: C: 51.35; H: 5.48; N: 9.05.

The Substituted 1,3-diol to Prepare 31.16 Was Made by the Following Method

Monoacetylation of 2-(hydroxymethyl)-1,3-propanediol: To a solution of 2-(hydroxymethyl)-1,3-propanediol (1 g, 9.4 mmol) in pyridine (7.5 mL) at 0° C. was added acetic anhydride (0.89 mL, 9.4 mmol) slowly. The resulting solution was warmed to room temperature and stirred for 16 h. The reaction was concentrated under reduced pressure and chromatographed by eluting with methanol-dichloromethane (1:9) to give 510 mg of pure acetate.

The substituted 1,3-diol to prepare 31.17 was made by the following method.

Methyl carbonate formation of 2-(hydroxymethyl)-1,3-propanediol: To a solution of 2-(hydroxymethyl)-1,3-propanediol (1 g, 9.4 mmol) in dichloromethane (20 mL) and pyridine (7.5 mL) at 0° C. was added methyl chloroformate (0.79 mL, 9.4 mmol) slowly. The resulting solution was warmed to room temperature and stirred for 16 h. The reaction was concentrated under reduced pressure and chromatographed by eluting with methanoldichloromethane (1:4) to give 650 mg of pure carbonate.

Example 32

General Procedure For 2-(3-phthalidyl)Ethyl Phosphonate Diesters

Followed the same procedure as in Example 18, Method B

The following compounds were prepared in this manner:

32.1: 4,5-Dimethyl-6-chloro-1-cyclopropylmethyl-2-[5-furanyl-2-bis-2-(3-phthalidylethyl)phosphonate] benzimidazole. Anal. Cald. for $C_{37}H_{34}N_2O_8PCl+1.2$ $H_2O$: C: 61.49; H: 5.08; N: 3.88; Found: C: 61.29; H: 4.89; N: 3.72 2-(3-phthalidyl)ethanol was prepared by the following method.

A solution of phthalide-3-acetic acid (1 mmol) in THF was treated with borane dimethylsulfide (1.5 mmol) at 0° C. for 1 h, and 25° C. for 24 h. Extraction and chromatography gave 2-(3-phthalidyl)ethanol as a light yellow oil. TLC: $R_f$=0.25, 50% EtOAc-hexane.

Example 33

Preparation of Benzimidazole Phosphonate Amine Salts

A mixture of 1-cyclopropanemethyl-6-chloro-4,5-dimethyl-2-(2-(5-phosphono)furanyl)benzimidazole (1 mmol) and tris(hydroxymethyl)aminomethane (1.05 mmol) in methanol was stirred at 25°0 C. for 24 h. Evaporation of the solvent gave the salt as an yellow solid.

33.1: 1-cyclopropanemethyl-6-chloro-4,5-dimethyl-2-(2-(5-phosphono)furanyl)benzimidazole tris(hydroxymethyl)

aminomethane. mp 175–178° C.; Anal. calcd. for $C_{21}H_{29}N_3O_7PCl+2.3\ H_2O$: C: 46.42; H: 6.23; N: 7.73. Found: C: 46.16; H: 6.22; N: 7.98.

Examples of use of the method of the invention includes the following. It will be understood that these examples are exemplary and that the method of the invention is not limited solely to these examples.

For the purposes of clarity and brevity, chemical compounds are referred to by synthetic Example number in the biological examples below.

Besides the following Examples, assays that may be useful for identifying compounds which inhibit gluconeogenesis include the following animal models of diabetes:

i. Animals with pancreatic b-cells destroyed by specific chemical cytotoxins such as Alloxan or Streptozotocin (e.g. the Streptozotocin-treated mouse, -rat, dog, and -monkey). Kodama, H., Fujita, M., Yamaguchi, I., *Japanese Journal of Pharmacology* 66, 331–336 (1994) (mouse); Youn, J. H., Kim, J. K., Buchanan, T. A., *Diabetes* 43, 564–571 (1994) (rat); Le Marchand, Y., Loten, E. G., Assimacopoulos-Jannet, F., et al., *Diabetes* 27, 1182–88 (1978) (dog); and Pitkin, R. M., Reynolds, W. A., *Diabetes* 19, 70–85 (1970) (monkey).

ii. Mutant mice such as the C57BL/Ks db/db, C57BL/Ks ob/ob, and C57BL/6J ob/ob strains from Jackson Laboratory, Bar Harbor, and others such as Yellow Obese, T-KK, and New Zealand Obese. Coleman, D. L., Hummel, K. P., *Diabetologia* 3, 238–248 (1967) (C57BL/Ks db/db); Coleman, D. L., *Diabetologia* 14, 141–148 (1978) (C57BL/6J ob/ob); Wolff, G. L., Pitot, H. C., *Genetics* 73, 109–123 (1973) (Yellow Obese); Dulin, W. E., Wyse, B. M., *Diabetologia* 6, 317–323 (1970) (T-KK); and Bielschowsky, M., Bielschowsky, F. Proceedings of the University of Otago Medical School 31, 29–31 (1953) (New Zealand Obese).

iii. Mutant rats such as the Zucker fa/fa Rat rendered diabetic with Streptozotocin or Dexamethasone, the Zucker Diabetic Fatty Rat, and the Wistar Kyoto Fatty Rat. Stolz, K. J., Martin, R. J. *Journal of Nutrition* 112, 997–1002 (1982) (Streptozotocin); Ogawa, A., Johnson, J. H., Ohnbeda, M., McAllister, C. T., Inman, L., Alam, T., Unger, R. H., *The Journal of Clinical Investigation* 90, 497–504 (1992) (Dexamethasone); Clark, J. B., Palmer, C. J., Shaw, W. N., *Proceedings of the Society for Experimental Biology and Medicine* 173, 68–75 (1983) (Zucker Diabetic Fatty Rat); and Idida, H., Shino, A., Matsuo, T., et al., *Diabetes* 30, 1045–1050 (1981) (Wistar Kyoto Fatty Rat).

iv. Animals with spontaneous diabetes such as the Chinese Hamster, the Guinea Pig, the New Zealand White Rabbit, and non-human primates such as the Rhesus monkey and Squirrel monkey. Gerritsen, G. C., Connel, M. A., Blanks, M. C., *Proceedings of the Nutrition Society* 40, 237 245 (1981) (Chinese Hamster); Lang, C. M., Munger, B. L., *Diabetes* 25, 434–443 (1976) (Guinea Pig); Conaway, H. H., Brown, C. J., Sanders, L. L. eta I., *Journal of Heredity* 71, 179–186 (1980) (New Zealand White Rabbit); Hansen, B. C., Bodkin, M. L., *Diabetologia* 29, 713–719 (1986) (Rhesus monkey); and Davidson, I. W., Lang, C. M., Blackwell, W. L., *Diabetes* 16, 395–401 (1967) (Squirrel monkey).

v. Animals with nutritionally induced diabetes such as the Sand Rat, the Spiny Mouse, the Mongolian Gerbil, and the Cohen Sucrose-Induced Diabetic Rat. Schmidt-Nielsen, K., Hainess, H. B., Hackel, D. B., *Science* 143, 689–690 (1964) (Sand Rat); Gonet, A. E., Stauffacher, W., Pictet, R., et al., *Diabetologia* 1, 162–171 (1965) (Spiny Mouse); Boquist, L., *Diabetologia* 8, 274–282 (1972) (Mongolian Gerbil); and Cohen, A. M., Teitebaum, A., Saliternik, R., *Metabolism* 21, 235–240 (1972) (Cohen Sucrose-induced Diabetic Rat).

vi. Any other animal with one of the following or a combination of the following characteristics resulting from a genetic predisposition, genetic engineering, selective breeding, or chemical or nutritional induction: impaired glucose tolerance, insulin resistance, hyperglycemia, obesity, accelerated gluconeogenesis, increased hepatic glucose output.

Biological Examples

Example A

Inhibition of Human Liver FBPase

*E. coli* strain BL21 transformed with a human liver FBPase-encoding plasmid was obtained from Dr. M. R. El-Maghrabi at the State University of New York at Stony Brook. hlFBPase was typically purified from 10 liters of *E. coli* culture as described (M. Gidh-Jain et al. ,1994, *The Journal of Biological Chemistry* 269, pp 27732–27738). Enzymatic activity was measured spectrophotometrically in reactions that coupled the formation of product (fructose 6-phosphate) to the reduction of dimethylthiazoldiphenyltetrazolium bromide (MTT) via NADP and phenazine methosulfate (PMS), using phosphoglucose isomerase and glucose 6-phosphate dehydrogenase as the coupling enzymes. Reaction mixtures (200 $\mu$l) were made up in 96-well microtitre plates, and consisted of 50 mM Tris-HCl, pH 7.4, 100 mM KCl, 5 mM EGTA, 2 mM MgCl2, 0.2 mM NADP, 1 mg/ml BSA, 1 mM MTT, 0.6 mM PMS, 1 unit/mL phosphoglucose isomerase, 2 units/mL glucose 6-phosphate dehydrogenase, and 0.150 mM substrate (fructose 1,6-bisphosphate). Inhibitor concentrations were varied from 0.01 $\mu$M to 10 $\mu$M. Reactions were started by the addition of 0.002 units of pure hlFBPase and were monitored for 7 minutes at 590 nm in a Molecular Devices Plate Reader (37° C.).

Figure 2:
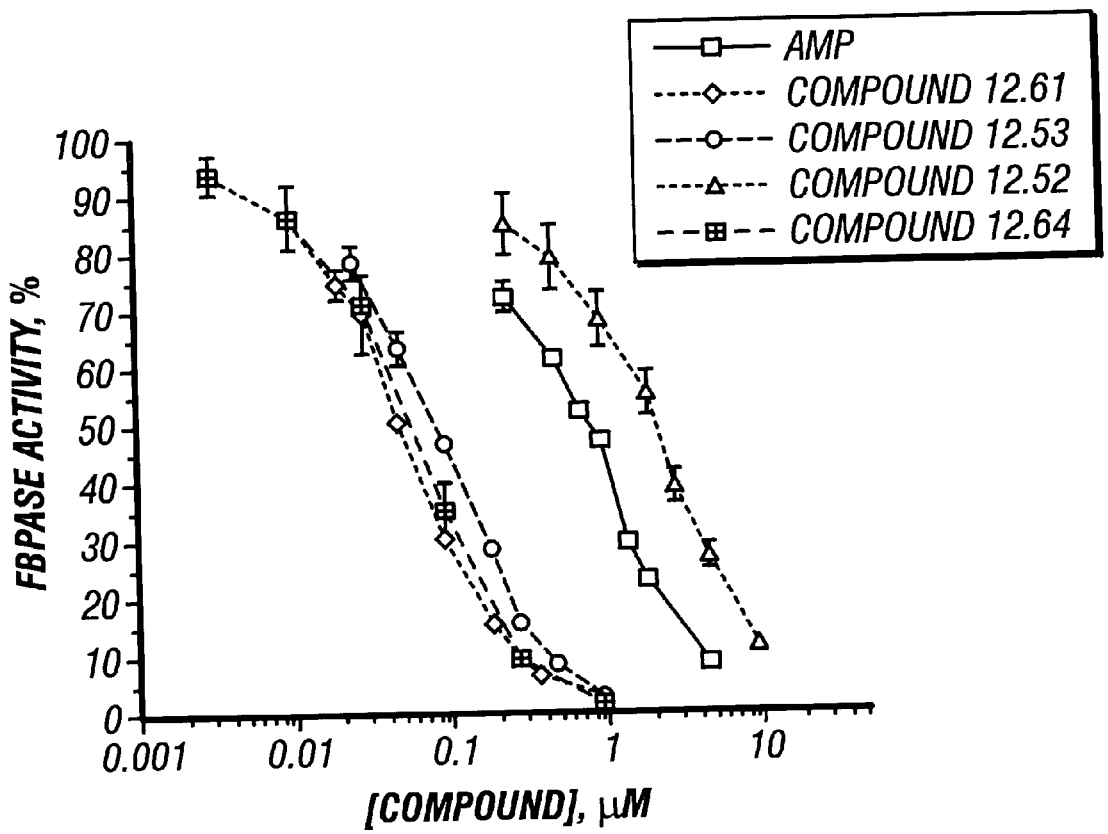
FIG. 2 shows that compounds 12.61, 12.53,12.52, and 12.64 inhibit human liver FBPase activity in vitro in a dose dependent manner.

FIG. 2 shows the concentration-dependent inhibitory activity of compounds 12.61, 12.53, 12.52, and 12.64.

Table 2 below provides the $IC_{50}$ values for several compounds prepared in Examples 12 and 13. The $IC_{50}$ for AMP is 1.0 $\mu$M.

TABLE 2

| Example Compound Number | $IC_{50}$ (human liver FBPase($\mu$M)) |
|---|---|
| 12.6 | 6.5 |
| 12.37 | 4.2 |
| 12.35 | 1.2 |
| 13.5 | 4.7 |
| 12.52 | 2.5 |
| 12.54 | 0.1 |
| 12.57 | 3.8 |
| 13.21 | 2.5 |
| 12.61 | 0.06 |
| 13.25 | 1.8 |
| 12.64 | 0.06 |
| 13.52 | 10.5 |
| 13.56 | 0.78 |
| 13.61 | 0.1 |
| 13.66 | 4.0 |
| 12.80 | 0.035 |
| 12.82 | 0.04 |
| 12.79 | 0.08 |
| 15.1 | 0.18 |
| 12.84 | 0.055 |
| 13.96 | 0.16 |

Inhibitors of FBPase May Also be Identified by Assaying Rat and Mouse Liver FBPase.

Inhibition of Rat Liver and Mouse Liver FBPase

*E. coli* strain BL21 transformed with a rat liver FBPase-encoding plasmid was obtained from Dr. M. R. El-Maghrabi at the State University of New York at Stony Brook, and purified as described (El-Maghrabi, M. R., and Pilkis, S. J. (1991) Biochem. Biophys. Res. Commun. 176: 137–144). Mouse liver FBPase was obtained by homogenizing freshly isolated mouse liver in 100 mM Tris-HCI buffer, pH 7.4, containing 1 mM EGTA, and 10% glycerol. The homogenate was clarified by centrifugation, and the 45–75% ammonium sulfate fraction prepared. This fraction was redissolved in the homogenization buffer and desalted on a PD-10 gel filtration column (Biorad) eluted with same. This partially purified fraction was used for enzyme assays. Both rat liver and mouse liver FBPase were assayed as described for human liver FBPase. Generally, as reflected by higher $IC_{50}$ values, the rat and mouse liver enzymes are less sensitive to inhibition by the compounds tested than the human liver enzyme.

The following Table depicts the IC50 values for several compounds prepared in the Examples:

| Compound | IC50 Rat Liver ($\mu$M) | IC50 Mouse Liver ($\mu$M) |
|---|---|---|
| 12.6 | >20 | >20 |
| 12.37 | >20 | 1.27 |
| 12.35 | >20 | >20 |
| 12.52 | >20 | 0.78 |
| 12.54 | >2 | 1.07 |
| 12.57 | >20 | >20 |
| 12.61 | 2.18 | >20 |
| 12.64 | 0.55 | 1.07 |
| 13.21 | >20 | >20 |
| 13.25 | >2 | >20 |
| 13.56 | >2 | >20 |
| 13.61 | >20 | >20 |
| 13.66 | >20 | >20 |
| 12.80 | 0.15 | 0.3 |
| 12.82 | 0.2 | 0.3 |
| 12.79 | 0.45 | 0.72 |
| 15.1 | 1.0 | 1.5 |
| 12.84 | 0.4 | 0.5 |
| 13.96 | 1.95 | 0.7 |

Example B

AMP Site Binding

To determine whether compounds bind to the allosteric AMP binding site of hlFBPase, the enzyme was incubated with radiolabeled AMP in the presence of a range of test compound concentrations. The reaction mixtures consisted of 25 mM $^3$H-AMP (54 mCi/mmol) and 0–1000 mM test compound in 25 mM Tris-HCl, pH 7.4, 100 mM KCl and 1 mM MgCl$_2$. 1.45 mg of homogeneous FBPase (±1 nmole) was added last. After a 1 minute incubation, AMP bound to FBPase was separated from unbound AMP by means of a centrifugal ultrafiltration unit ("Ultrafree-MC", Millipore) used according to the instructions of the manufacturer. The radioactivity in aliquots (100 $\mu$L) of the upper compartment of the unit (the retentate, which contains enzyme and label) and the lower compartment (the filtrate, which contains unbound label) were quantified using a Beckman liquid scintillation counter. The amount of AMP bound to the enzyme was estimated by comparing the counts in the filtrate (the unbound label) to the total counts in the retentate.

Figure 3:
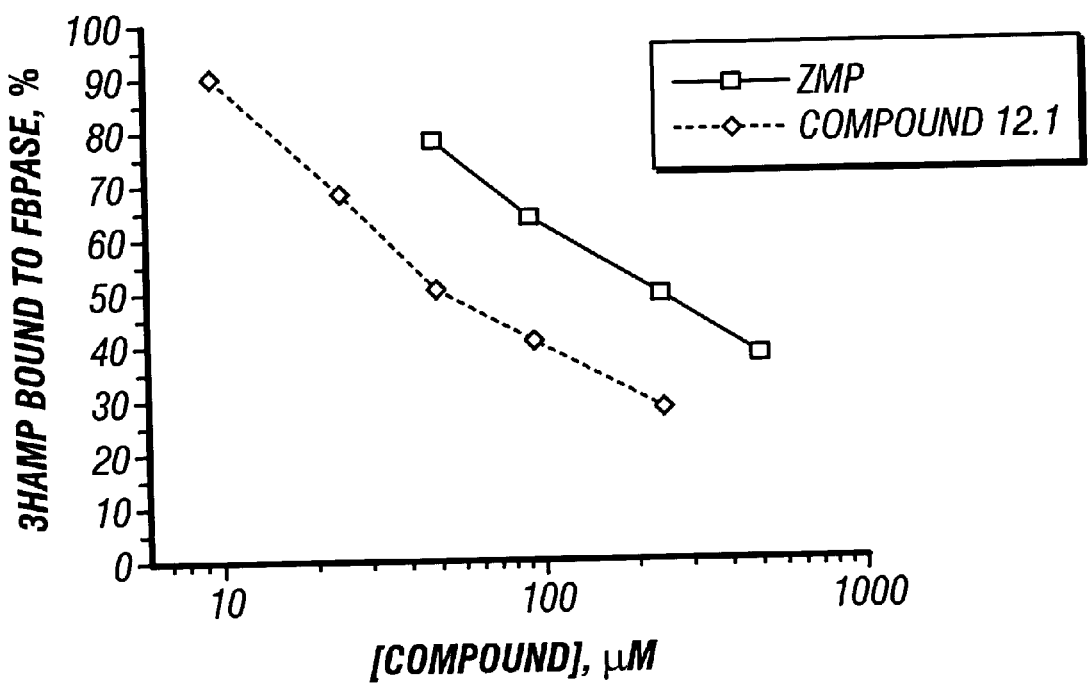
FIG. 3 shows that compound 12.1 and ZMP displaced AMP from human liver FBPase in a dose dependent manner.

As evident from FIG. 3, both 5-aminoimidazole-4-carboxamide riboside monophosphate (ZMP) and compound 12.1 displaced AMP from hlFBPase in a dose-dependent manner, indicating that they bind to the same site on the enzyme as AMP. As expected, compound 12.1 —a more potent hlFBPase inhibitor than ZMP ($IC_{50}$'s=2 and 12 $\mu$M, respectively)- had a lower $ED_{50}$ for AMP displacement than ZMP (50 vs 250 $\mu$M).

Example C

AMP Site/Enzyme Selectivity

To determine the selectivity of compounds towards FBPase, effects of FBPase inhibitors on 5 key AMP binding enzymes were measured using the assays described below:

Adenosine Kinase: Human adenosine kinase was purified from an E. coli expression system as described by Spychala et al. (Spychala, J., Datta, N. S., Takabayashi, K., Datta, M., Fox, I. H., Gribbin, T., and Mitchell, B. S. (1996) Proc. Natl. Acad. Sci. USA 93, 1232–1237). Activity was measured essentially as described by Yamada et al. (Yamada, Y., Goto, H., Ogasawara, N. (1988) Biochim. Biophys. Acta 660, 36–43.) with a few minor modifications. Assay mixtures contained 50 mM TRIS-maleate buffer, pH 7.0, 0.1% BSA, 1 mM ATP 1 mM MgCl$_2$, 1.0 $\mu$M [U-$^{14}$C] adenosine (400–600 mCi/mmol) and varying duplicate concentrations of inhibitor. $^{14}$C-AMP was separated from unreacted $^{14}$C-adenosine by absorption to anion exchange paper (Whatman) and quantified by scintillation counting.

Adenosine Monophosphate Deaminase: Porcine heart AMPDA was purified essentially as described by Smiley et al. (Smiley, K. L., Jr, Berry, A. J., and Suelter, C. H. (1967) J. Biol. Chem. 242, 2502–2506) through the phosphocellulose step. Inhibition of AMPDA activity was determined at 37° C. in a 0.1 mL assay mixture containing inhibitor, ~0.005 U AMPDA, 0.1% bovine serum albumin, 10 mM ATP, 250 mM KCl, and 50 mM MOPS at pH 6.5. The concentration of the substrate AMP was varied from 0.125–10.0 mM. Catalysis was initiated by the addition of enzyme to the otherwise complete reaction mixture, and terminated after 5 minutes by injection into an HPLC system. Activities were determined from the amount of IMP formed during 5 minutes. IMP was separated from AMP by HPLC using a Beckman Ultrasil-SAX anion exchange column (4.6 mm×25 cm) with an isocratic buffer system (12.5 mM potassium phosphate, 30 mM KCl, pH 3.5) and detected spectrophotometrically by absorbance at 254 nm.

Phosphofructokinase: Enzyme (rabbit liver) was purchased from Sigma. Activity was measured at 30° C. in reactions in which the formation of fructose 1,6-bisphosphate was coupled to the oxidation of NADH via the action of aldolase, triosephosphate isomerase, and α-glycerophosphate dehydrogenase. Reaction mixtures (200 $\mu$L) were made up in 96-well microtitre plates and were read at 340 nm in a Molecular Devices Microplate Reader. The mixtures consisted of 200 mM Tris-HCl pH 7.0, 2 mM DTT, 2 mM MgCl$_2$, 0.2 mM NADH, 0.2 mM ATP, 0.5 mM Fructose 6-phosphate, 1 unit aldolase/ml, 3 units/ml triosephosphate isomerase, and 4 units/mL α-glycerophosphate dehydrogenase. Test compound concentrations ranged from 1 to 500 $\mu$M. Reactions were started by the addition of 0.0025 units of phosphofructokinase and were monitored for 15 minutes.

Glycogen Phosphofylase: Enzyme (rabbit muscle) was purchased from Sigma. Activity was measured at 37° C. in reactions in which the formation of glucose 1-phosphate was coupled to the reduction of NADP via phosphoglucomutase and glucose 6-phosphate dehydrogenase. Assays were performed on 96-well microtitre plates and were read at 340 nm on a Molecular Devices Microplate Reader. Reaction mixtures consisted of 20 mM imidazole, pH 7.4, 20 mM MgCl$_2$, 150 mM potassium acetate, 5 mM potassium phosphate, 1 mM DTT, 1 mg/ml BSA, 0.1 mM NADP, 1 unit/mL phosphoglucomutase, 1 unit/mL glucose 6-phosphate dehydrogenase, 0.5% glycogen. Test compound concentrations ranged from 1 to 500 μM. Reactions were started by the addition of 17 μg enzyme and were monitored for 20 minutes.

Adenylate Kinase: Enzyme (rabbit muscle) was purchase from Sigma. Activity was measured at 37° C. in reaction mixtures (100 μL) containing 100 mM Hepes, pH 7.4, 45 mM MgCl$_2$ 1 mM EGTA, 100 mM KCl 2 mg/ml BSA, 1 mM AMP and 2 mM ATP. Reactions were started by addition of 4.4 ng enzyme and terminated after 5 minutes by addition of 17 μL perchloric acid. Precipitated protein was removed by centrifugation and the supernatant neutralized by addition of 33 μL 3 M KOH/3 M KH$_2$CO3. The neutralized solution was clarified by centrifugation and filtration and analyzed for ADP content (enzyme activity) by HPLC using a YMC ODS AQ column (25×4.6 cm). A gradient was run from 0.1 M KH2PO4, pH 6, 8 mM tetrabutyl ammonium hydrogen sulfate to 75% acetonitrile. Absorbance was monitored at 254 nm.

Compound 12.1, a 2 μM hlFBPase inhibitor, was essentially inactive in all of the above described assays except for the AMP deaminase screen: half-maximal inhibition of AMP deaminase was observed at a 42-fold higher concentration than the IC$_{50}$ for FBPase. Compound 12.61 (hlFBPase IC$_{50}$=0.055 μM), in addition to being essentially without effect on adenosine kinase, adenylate kinase, glycogen phosphorylase, and phosphofructokinase, was almost 600-fold less potent on AMP deaminase. Compound 12.64 was tested in the glycogen phosphorylase assay only; no activation of the enzyme was observed at concentrations of drug ranging from 5 to 500 μM. The data suggest that compound 12.61 binds to hlFBPase in a highly selective manner. Table 3 below gives the selectivity data for compounds 12.61 and 12.64.

TABLE 3

| | Selectivity | | |
|---|---|---|---|
| | Compound 12.1 (μM) | Compound 12.61 | Compound 12.64 |
| FBPase (inh.) | 2.0 | 0.055 | 0.055 |
| Adenosine Kinase (inh.) | >>10 | >>100 | |
| Adenylate Kinase (inh.) | >>500 | >>500 | |
| AMP Deaminase (inh.) | 85 | 32 | |
| Glycogen Phosphorylase (act.) | >>200 | >>100 | >>500 |
| Phosphofructokinase (act.) | >>200 | >>100 | |

Example D
Inhibition of Gluconeogenesis in Rat Hepatocytes

Hepatocytes were prepared from overnight fasted Sprague-Dawley rats (250–300 g) according to the procedure of Berry and Friend (Berry, M. N., Friend, D. S., 1969, J. Cell. Biol. 43, 506–520) as modified by Groen (Groen, A. K., Sips, H. J., Vervoorn, R. C., Tager, J. M., 1982, Eur. J. Biochem. 122, 87–93). Hepatocytes (75 mg wet weight/mL) were incubated in 1 ml Krebs-bicarbonate buffer containing 10 mM Lactate, 1 mM pyruvate, 1 mg/mL BSA, and test compound concentrations from 1 to 500 μM. Incubations were carried out in a 95% oxygen, 5% carbon dioxide atmosphere in closed, 50-mL Falcon tubes submerged in a rapidly shaking water bath (37° C.). After 1 hour, an aliquot (0.25 mL) was removed, transferred to an Eppendorf tube and centrifuged. 50 μL of supernatant was then assayed for glucose content using a Sigma Glucose Oxidase kit as per the manufacturer's instructions.

Figure 4:
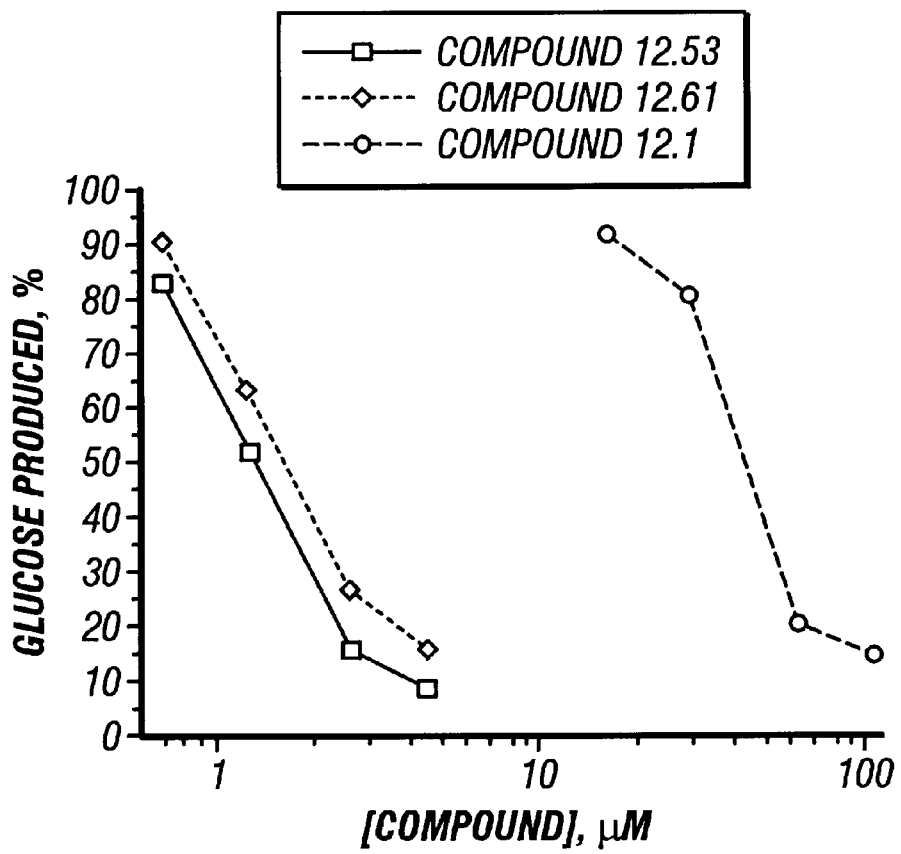
FIG. 4 shows that compounds 12.1, 12.53, and 12.61 inhibit glucose production in vitro in rat hepatocytes.

Compounds 12.1, 12.53, and 12.61 inhibited glucose production from lactate/pyruvate in isolated rat hepatocytes in a dose-dependent manner, with IC$_{50}$'s of 110, 2.4 and 3.3 μM, respectively, as shown in FIG. 4. IC$_{50}$'s for other select compounds in this assay are shown in the Table below. Compound 30.2 is a prodrug of compound 12.50.

| Compound | IC50 Glucose Production, μM |
|---|---|
| 12.42 | 14 |
| 12.44 | 14 |
| 12.50 | 17 |
| 12.54 | 3.6 |
| 12.62 | 5 |
| 12.63 | 16 |
| 12.64 | 2.5 |
| 18.2 | 17 |
| 12.80 | 1.6 |
| 12.82 | 2.2 |
| 12.79 | 1.0 |
| 12.84 | 9 |
| 15.1 | 16 |

FBPase from rat liver is less sensitive to AMP than that from human liver. IC$_{50}$ values are consequently higher in rat hepatocytes than would be expected in human hepatocytes.

Example E
Blood Glucose Lowering in Fasted Rats

Sprague Dawley rats (250–300 g) were fasted for 18 hours and then dosed intraperitoneally with 20 mg/kg of compounds 12.53, 12.61, or 12.64. The vehicle used for drug administration was 50 mM sodium bicarbonate. Blood samples were obtained from the tail vein of conscious animals just prior to injection and one hour post injection. Blood glucose was measured using a HemoCue Inc. glucose analyzer according to the instructions of the manufacturer.

Compound 12.53 lowered blood glucose by 55±14%, compound 12.61 by 48±15%, and compound 12.64 by 64.6±24%.

Example F
Effect of Compound 12.64 on Gluconeogenesis From Lactate/pyruvate in Rat Hepatocytes: Glucose Production Inhibition and Fructose 1,6-bisphosphate Accumulation Isolated rat hepatocytes were prepared as described in Example D and incubated under the identical conditions described. Reactions were terminated by removing an aliquot (250 μL) of cell suspension and spinning it through a layer of oil (0.8 mL silicone/mineral oil, 4/1) into a 10% perchloric acid layer (100 μL). After removal of the oil layer, the acidic cell extract layer was neutralized by addition of ⅓rd volume of 3 M KOH/3 M KH2CO3. After thorough mixing and centrifugation, the supernatant was analyzed for glucose content as described in Example D, and also for fructose 1,6-bisphosphate. Fructose 1,6-bisphosphate was assayed spectrophotometrically by coupling its enzymatic conversion to glycerol 3-phosphate to the oxidation of NADH, which was monitored at 340 nm. Reaction mixtures (1 mL consisted of 200 mM Tris-HCl, pH 7.4, 0.3 mM NADH, 2 units/mL glycerol 3-phsophate dehydrogenase, 2 units/ml triosephosphate isomerase, and 50–100 μL cell extract. After a 30 minute preincubation at 37° C., 1 unit/mL of aldolase was added and the change in absorbance measured until a stable value was obtained. 2 moles of NADH are oxidized in this reaction per mole of fructose 1,6-bisphosphate present in the cell extract.

Figure 5:
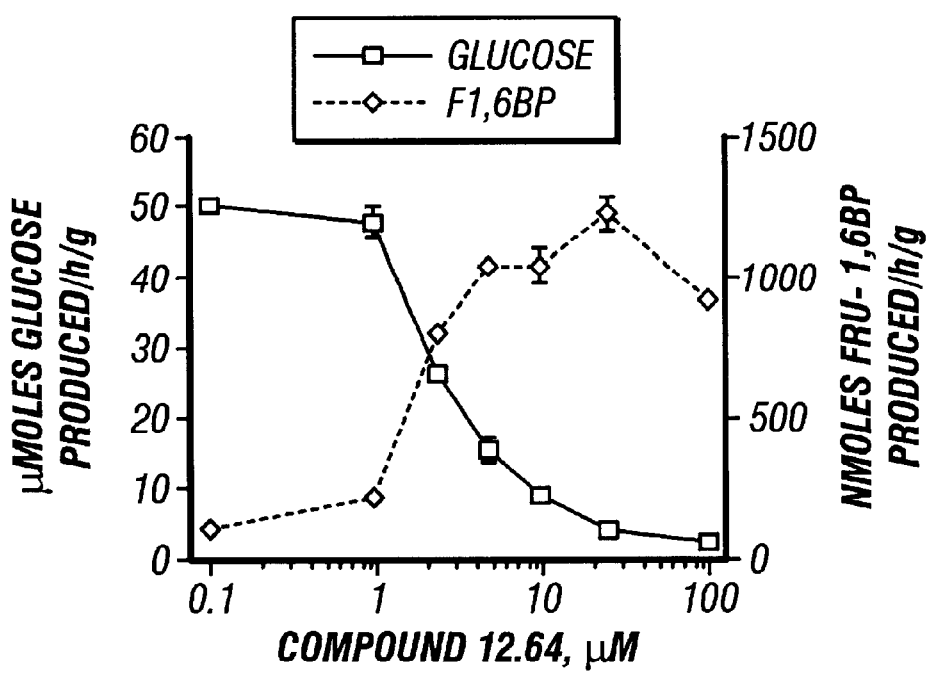
FIG. 5 shows the inhibition of glucose production and the accumulation of fructose-1,6-bisphosphate is dependent on the dose of compound 12.64.

As shown in FIG. 5, compound 12.64 inhibited glucose production from lactate/pyruvate in rat hepatocytes (IC50 approx. 3 μM) The dose-dependent accumulation of fructose 1,6 bisphosphate (the substrate of FBPase) that occurred upon cell exposure to compound 12.64 is consistent with the inhibition of FBPase.

Example G
Analysis of Drug Levels And Liver Accumulation in Rats

Sprague-Dawley rats (250–300 g) were fasted for 18 hours and then dosed intraperitoneally either with saline (n=3) or 20 mgs/kg of FBPase inhibitor (n=4). The vehicle used for drug administration was 10 mM bicarbonate. One hour post injection rats were anesthetized with halothane and a liver biopsy (approx. 1 g) was taken as well as a blood sample (2 ml) from the posterior vena cava. A heparin flushed syringe and needle was used for blood collection. The liver sample was immediately homogenized in ice-cold 10% perchloric acid (3 mL), centrifuged, and the supernatant neutralized with ⅓rd volume of 3 M KOH/3 M $KH_2CO3$. Following centrifugation and filtration, 50 μl of the neutralized extract was analyzed for FBPase inhibitor content by HPLC. A reverse phase YMC ODS AQ column (250×4.6 cm) was used and eluted with a gradient from 10 mM sodium phosphate pH 5.5 to 75% acetonitrile. Absorbance was monitored at 310 nm. (The concentration of fructose-1,6-bisphosphate in liver is also quantified using the method described in Example F. An elevation of fructose-1,6-bisphosphate levels in the livers from the drug-treated group is consistent with the inhibition of glucose production at the level of FBPase in the gluconeogenic pathway.) Blood glucose was measured in the blood sample as described in Example D. Plasma was then quickly prepared by centrifugation and extracted by addition of methanol to 60% (v/v). The methanolic extract was clarified by centrifugation and filtration and then analyzed by HPLC as described above.

Compound 12.64 achieved plasma acid liver levels of 85 μM and 90 nmoles/gram, respectively, one hour post injection of a 20 mg/kg dose.

Example H
Blood Glucose Lowering in Zucker Diabetic Fatty Rats

Zucker Diabetic Fatty rats purchased at 7 weeks of age are used at age 16 weeks in the 24-hour fasted state. The rats are purchased from Genetics Models Inc. and fed the recommended Purina 5008 diet (6.5% fat). Their fasting hyperglycemia at 24 hours generally ranges from 150 mg/dL to 310 mg/dL blood glucose.

FBPase inhibitor is administered at a dose of 50 mg/kg by intraperitoneal injection (n=6). The stock solution is made up at 25 mg/mL in deionized water and adjusted to neutratility by dropwise addition of 5 N NaOH. 5 control animals are dosed with saline. Blood glucose is measured at the time of dosing and 2 hours post dose as described in Example D.

Example I
Inhibition of Gluconeogenesis by FBPase Inhibitor in Zucker Diabetic Fatty Rats Nine Zucker Diabetic Fatty rats (16-weeks old, Genetics Models Inc., Indianapolis, Ind.) were fasted at midnight and instrumented with jugular catheters the following morning. At noon, a dose of 50 mg/kg compound 12.64 (n=3) or saline (n=3) was administered as a bolus via the jugular catheter. After 50 minutes a bolus of $^{14}$C-sodium bicarbonate (40 μCi/100 g body weight) was administered via the same route. 20 minutes later, the animals were quickly anesthetized with intravenous pentobarbitol and a blood sample (1.5 mL) was taken by cardiac puncture. Blood (0.5 mL) was diluted into 6 mL deionized water and protein precipitated by addition of 1 mL zinc sulfate (0.3 N) and 1 mL barium hydroxide (0.3 N). The mixture was centrifuged (20 minutes, 1000×g) and 5 mL of the resulting supernatant was then combined with 1 g of a mixed bed ion exchange resin (1 part AG 50W-X8, 100–200 mesh, hydrogen form and 2 parts of AG 1-X8, 100–200 mesh, acetate form) to separate $^{14}$C-bicarbonate from $^{14}$C-glucose. The slurry was shaken at room temperature for four hours and then allowed to settle. An aliquot of the supernatant (0.5 mL) was then counted in 5 mL scintillation cocktail.

As indicated in the table below, compound 12.64 reduced the incorporation of $^{14}$C-bicarbonate into $^{14}$-C-glucose by approximately 50%.

| Treatment | $^{14}$C-Glucose Produced (cpm/mL blood) | % Glucose Produced |
| --- | --- | --- |
| Saline (n = 3) | 66,651 ± 2365 | 100 |
| 12.64 (n = 3) | 32,827 ± 6130 | 49.2 |

Example J
Blood Glucose Lowering in the Streptozotocin-treated Rat

Diabetes was induced in male Sprague-Dawley rats (250–300 g) by intraperitoneal injection of 55 mg/kg streptozotocin (Sigma Chemical Co.). Six days later, 24 animals were selected with fed blood glucose values (8 am) between 350 and 600 mg/dL and divided into two statistically equivalent groups. Blood glucose was measured in blood obtained from a tall vein nick by means of a HemoCue Inc. (Mission Viejo, Calif.) glucose analyzer. One group of 12 subsequently received compound 12.64 (100 mg/kg intraperitoneally) and the other 12 ("controls") an equivalent volume of saline. Food was removed from the animals. Blood glucose was measured in each animal four hours after dosing, and a second dose of drug or saline was then administered. Four hours later, a final blood glucose measurement was made. As shown in the table below, compound 12.64 significantly reduced fasting blood glucose levels in the treated animal group, 8 hours after the initial dose:

| | Blood glucose, mg/dl | | p value |
| --- | --- | --- | --- |
| Treatment | T = 0h | T = 8h | (relative to controls) |
| Saline (n = 12) | 489 ± 20 | 404 ± 19 | |
| 12.64 (n = 12) | 488 ± 16 | 271 ± 29 | 0.001 |

Example K
Glucose Lowering Following Oral Administration of the Compound of Example 12.64

Compound 12.64 was administered by oral gavage at doses of 30, 100 and 250 mg/kg to 18-hour fasted, Sprague Dawley rats (250–300 g; n=4-5/group). The compound was prepared in deionized water, adjusted to neutrality with sodium hydroxide, and brought into solution by sonication prior administration. Blood glucose was measured immediately prior to dosing, and at 1 hour intervals thereafter. Blood samples were obtained from the tail vein, and measurments made by means of a Hemocue glucose analyzer (Hemocue Inc, Mission Viejo, Calif.) used according to the manufacturer's instructions. The 30 and 100 mg/kg doses were without effect, but profound hypoglycemia was elicited by the 250 mg/kg dose in 4 out of 5 animals dosed, within 1 hour of administration. The average glucose lowering in the four responding animals was 62±8.6% relative to saline-treated controls at the 1 hour time point.

Example L

Estimation of the Oral Bioavailability of Prodrugs of Phosphonic Acids:

Prodrugs were dissolved in 10% ethanol/90% polyethylene glycol (mw 400) and administered by oral gavage at doses of approximately 20 or 40 mg/kg parent compound equivalents to 6-hour fasted, Sprague Dawley rats (220–240 g). The rats were subsequently placed in metabolic cages and urine was collected for 24 hours. The quantity of parent compound excreted into urine was determined by HPLC analysis. An ODS column eluted with a gradient from potassium phosphate buffer, pH 5.5 to acetonitrile was employed for these measurements. Detection was at 310–325 nm. The percentage oral bioavailability was estimated by comparison of the recovery in urine of the parent compound generated from the prodrug, to that recovered in urine 24 hours after intravenous administration of unsubstituted parent compound at 5 approximately 10 mg/kg. Parent compounds were typically dissolved in dimethyl sulfoxide, and administered via the tail vein in animals that were briefly anesthetized with halothane.

For Compound A, 6-amino-9-neopentyl, B-(2-(5-diisobutyryloxymethylphosphono)furanyl purine, a prodrug of parent Compound B, 6-amino-9-neopentyl-8-(2-(5-phosphono)furanyl purine, 6.2% of an oral dose of approximately 20 mg/kg was recovered in urine. For the parent compound, 76.8% of an intravenous dose of approximately 10 mg/kg was recovered. The oral bioavailability of this prodrug was therefore calculated to be 6.2/76.8, or approximately 8%. The oral bioavailability of select other prodrugs are shown in the table below:

| Prodrug (Example No.) | Parent compound (Example No.) | % Oral bioavailability |
| --- | --- | --- |
| 31.14 | 13.17 | 12.5 |
| 18.7 | 15.1 | 6.9 |
| Compound C* | Compound B** | 5.3 |
| 31.13 | 13.17 | 10.9 |
| 31.15 | 13.17 | 14.1 |

*Compound C is 6-amino-0-neopentyl-8-(2-(5-dipivaloyloxymethyl-phosphone)furanyl purine.
**Compound B is 6-amino-9-neopentyl-8-[2-(5-phosphono)]furanyl purine.

We claim:
1. The compounds of formula (1):

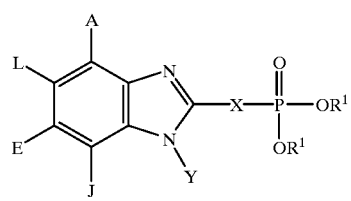

I wherein:
A, E, and L are selected from the group consisting of —$NR^8_2$, —$NO_2$, H, —$OR^7$, —$SR^7$, —$C(O)NR^4_2$, halo, —$COR^{11}$, —$SO_2R^3$, guanidine, amidine, —$NHSO_2R^5$, —$SO_2NR^4_2$, —CN, sulfoxide, perhaloacyl, perhaloalkyl, perhaloalkoxy, C1–C5 alkyl, C2–C5 alkenyl, C2–C5 alkynyl, and lower alicyclic, or together A and L form a cyclic group, or together L and E form a cyclic group, or together E and J form a cyclic group including aryl, cyclic alkyl, and heterocyclic;

J is selected from the group consisting of —$NR^8_2$, —$NO_2$, —H, —$OR^7$, —$SR^7$, —$C(O)NR^4_2$, halo, —$C(O)R^{11}$, —CN, sulfonyl, sulfoxide, perhaloalkyl, hydroxyalkyl, perhaloalkoxy, alkyl, haloalkyl, aminoalkyl, alkenyl, alkynyl, alicyclic, aryl, and aralkyl, or together with Y forms a cyclic group including aryl, cyclic alkyl and heterocyclic alkyl;

X is selected from the group consisting of alkylamino, alkyl(hydroxy), alkyl(carboxyl), alkyl(phosphonate), alkyl, alkenyl, alkynyl, alkyl(sulfonate), aryl, carbonylalkyl, 1,1-dihaloalkyl, aminocarbonylamino, alkylaminoalkyl, alkoxyalkyl, alkylthioalkyl, alkylthio, alkylaminocarbonyl, alkylcarbonylamino, alicyclic, aralkyl, and alkylaryl, all optionally substituted; or together with Y form a cyclic group including aryl, cyclic alkyl, and heterocyclic;

Y is selected from the group consisting of —H, alkyl, alkenyl, alkynyl, aryl, alicyclic, aralkyl, aryloxyalkyl, alkoxyalkyl, —$C(O)R^3$, —$S(O)_2R^3$, —$C(O)$—$R^{11}$, —$CONHR^3$, —$NR^2_2$, and —$OR^3$, all except H are optionally substituted; or together with X form a cyclic group including aryl, cyclic alkyl, and heterocyclic;

$R^1$ is independently selected from the group consisting of —H, alkyl, aryl, alicyclic where the cyclic moiety contains a carbonate or thiocarbonate, —$C(R^2)_2$—aryl, alkylaryl, —$C(R^2)_2OC(O)NR^2_2$, —$NR^2$—$C(O)$—$R^3$, —$C(R^2)_2$—$OC(O)R^3$, $C(R^2)_2$—O—$C(O)OR^3$, —$C(R^2)_2OC(O)SR^3$, alkyl—S—$C(O)R^3$, alkyl—S—S—alkylhydroxy, and alkyl—S—S—alkylhydroxy, or together $R^1$ and $R^1$ are —alkyl—S—S—alkyl to form a cyclic group, or together $R^1$ and $R^1$ are

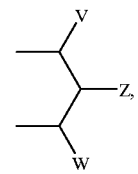

wherein
V and W are independently selected from the group consisting of hydrogen, aryl, substituted aryl, heteroaryl, substituted heteroaryl, 1-alkenyl, 1-alkynyl, and —$R^9$; or together V and Z are connected to form a cyclic group containing 3–5 atoms, optionally 1 heteroatom, substituted with hydroxy, acyloxy, alkoxycarboxy, or aryloxycarboxy attached to a carbon atom that is three atoms from an oxygen attached to the phosphorus; or together V and W are connected to form a cyclic group containing 3 carbon atoms substituted with hydroxy, acyloxy, alkoxycarboxy, alkylthiocarboxy, hydroxymethyl, and aryloxycarboxy attached to a carbon atom that is three atoms from an oxygen attached to the phosphorus;

Z is selected from the group consisting of —$CH_2OH$, —$CH_2OCOR^3$, —$CH_2OC(O)SR^3$, —$CH_2OCO_2R^3$, —$SR^3$, —$S(O)R^3$, —$CH_2N_3$, —$CH_2NR^2_2$, —$CH_2AR$, —$CH(Ar)OH$, —$CH(CH=CR^2R^2)OH$, —$CH(C≡CR^2)OH$, and —$R^2$;

with the provisos that:

a) V, Z, W are not all —H; and
b) when Z is —R², then at least one of V and W is not —H or —R⁹;

R² is selected from the group consisting of R³ and —H;
R³ is selected from the group consisting of alkyl, aryl, alicyclic, and aralkyl;
R⁴ is independently selected from the group consisting of —H, lower alkyl, lower alicyclic, lower aralkyl, and lower aryl;
R⁵ is selected from the group consisting of lower alkyl, lower aryl, lower aralkyl, and lower alicyclic;
R⁶ is independently selected from the group consisting of —H, and lower alkyl;
R⁷ is independently selected from the group consisting of —H, lower alkyl, lower alicyclic, lower aralkyl, lower aryl, and —C(O)R¹⁰;
R⁸ is independently selected from the group consisting of —H, lower alkyl, lower aralkyl, lower aryl, lower alicyclic, —C(O)R¹⁰, or together they form a bidendate alkyl;
R⁹ is selected from the group consisting of alkyl, aralkyl, and alicyclic;
R¹⁰ is selected from the group consisting of —H, lower alkyl, —NH₂, lower aryl, and lower perhaloalkyl;
R¹¹ is selected from the group consisting of alkyl, aryl, —OH, —NH₂ and —OR³; and
pharmaceutically acceptable prodrugs and salts thereof; with the provisos that:
  a) R¹ is not lower alkyl of 1–4 carbon atoms;
  b) when X is alkyl or alkene, then A is —N(R⁸₂);
  c) X is not alkylamine and alkylaminoalkyl substituted with phophosphonic esters and acids; and
  d) A, L, E, J, Y, and X together may only form 0–2 cyclic groups.

2. The compounds of claim 1 wherein when X is substituted with a phosphonic acid or ester, then A is —N(R⁸₂) and Y is not —H.

3. The compounds of claim 1 wherein X is not substituted with a phosphonic acid or ester.

4. The compounds of claim 1, with the additional proviso that when X is aryl or alkylaryl, said aryl or alkylaryl group is not linked 1,4 through a six-membered aromatic ring.

5. The compounds of claim 1 wherein A, L, and E are independently selected from the group consisting of —H, —NR⁸₂, —NO₂, hydroxy, halogen, —OR⁷, alkylaminocarbonyl, —SR⁷, lower perhaloalkyl, and C1–C5 alkyl, or together E and J together form a cyclic group.

6. The compound of claim 5 wherein A, L and E are independently selected from the group consisting of —NR⁸₂, —H, hydroxy, halogen, lower alkoxy, lower perhaloalkyl, and lower alkyl.

7. The compounds of claim 1 wherein A is selected from the group consisting of —NR⁸₂, —H, halogen, lower perhaloalkyl, and lower alkyl.

8. The compounds of claim 1 wherein L and E are independently selected from the group consisting of —H, lower alkoxy, lower alkyl, and halogen.

9. The compounds of claim 1 wherein J is selected from the group consisting of —H, halogen, lower alkyl, lower hydroxyalkyl, —NR⁸₂, lower R⁸₂N-alkyl, lower haloalkyl, lower perhaloalkyl, lower alkenyl, lower alkynyl, lower aryl, heterocyclic, and alicyclic, or together with Y forms a cyclic group.

10. The compounds of claim 9 wherein J is selected from the group consisting of —H, halogen, lower alkyl, lower hydroxyalkyl, —NR⁸₂, lower R⁸₂N-alkyl, lower haloalkyl, lower alkenyl, alicyclic, and aryl.

11. The compounds of claim 1 wherein Y is selected from the group consisting of —H, aralkyl, aryl, alicyclic, and alkyl, all except —H may be optionally substituted.

12. The compounds of claim 11 wherein Y is selected from the group consisting of alicyclic and lower alkyl.

13. The compounds of claim 1 wherein X is selected from the group consisting of alkyl, alkynyl, alkoxyalkyl, alkylthio, aryl, alkylaminocarbonyl, alkylcarbonylamino, 1,1-dihaloalkyl, carbonylalkyl, alkyl(OH), and alkyl (sulfonate).

14. The compounds of claim 13 wherein X is selected from the group consisting of heteroaryl, alkylaminocarbonyl, 1,1-dihaloalkyl, alkyl(sulfonate), and alkoxyalkyl.

15. The compounds of claim 14 wherein X is selected from the group consisting of heteroaryl, alkylaminocarbonyl, and alkoxyalkyl.

16. The compounds of claim 15 wherein X is selected from the group consisting of methylaminocarbonyl, methoxymethyl and furanyl.

17. The compounds of claim 1 wherein each R¹ is independently selected from the group consisting of —H, alkyl, aryl, alicyclic where the cyclic moiety contains a carbonate or thiocarbonate, optionally substituted phenyl, optionally substituted benzyl, optionally substituted alkylaryl, —C(R²)₂OC(O)R³, C(R²)₂—O—C(O)OR³, —C(R²)₂—OC(O)SR³, —alkyl—S—C(O) R³, alkyl—S—S—alkylhydroxy and —alkyl—S—S—S—alkylhydroxy, or together R¹ and R¹ are alkyl—S—S—alkyl to form a cyclic group, or R¹ and R¹ together are

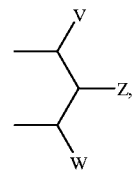

wherein
V and W are independently selected from the group consisting of hydrogen, aryl, substituted aryl, heteroaryl, substituted heteroaryl, 1-alkenyl, 1-alkynyl, and —R⁹; or
together V and Z are connected to form a cyclic group containing 3–5 atoms, optionally 1 heteroatom, substituted with hydroxy, acyloxy, alkoxycarboxy, or aryloxycarboxy attached to a carbon atom that is three atoms from an oxygen attached to the phosphorus; or
together V and W are connected to form a cyclic group containing 3 carbon atoms substituted with hydroxy, acyloxy, alkoxycarboxy, alkylthiocarboxy, hydroxymethyl, and aryloxycarboxy attached to a carbon atom that is three atoms from an oxygen attached to the phosphorus;
Z is selected from the group consisting of —CH₂OH, —CH₂OCOR³, —CH₂OC(O)SR³, —CH₂OCO₂R³, —SR³, —S(O)R³, —CH₂N₃, —CH₂NR²₂, —CH₂Ar, —CH(Ar)OH, —CH(CH=CR²R²)OH, —CH(C≡CR²)OH, and —R²;
with the provisos that:
a) V, Z, W are not all —H; and
b) when Z is —R², then at least one of V and W is not —H or —R⁹;
R² is selected from the group consisting of R³ and —H;
R³ is selected from the group consisting of alkyl, aryl, alicyclic, and aralkyl; and R⁹ is selected from the group consisting of alkyl, aralkyl, and alicyclic.

18. The compounds of claim 17 wherein each R¹ is independently selected from the group consisting of optionally substituted phenyl, optionally substituted benzyl, —C(R²)₂OC(O)R³, and —H.

19. The compounds of claim 18 wherein R¹ is H.

20. The compounds of claim 17 wherein at least one R¹ is aryl, or —C(R²)₂—aryl.

21. The compounds of claim 17 wherein at least one R¹ is —C(R²)₂—OC(O)R³, —C(R²)₂—OC(O)OR³, —C(R²)₂—OC(O)SR³.

22. The compounds of claim 17 wherein at least one R¹ is alkyl—S—S—alkylhydroxyl, —alkyl—S—C(O)R³, and —alkyl—S—S—S—alkylhydroxy, or together R¹ and R¹ are alkyl—S—S—alkyl to form a cyclic group.

23. The compounds of claim 1 wherein together R¹ and R¹ are

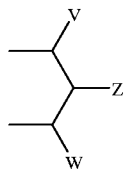

wherein:

V and W are independently selected from the group consisting of hydrogen, aryl, substituted aryl, heteroaryl, substituted heteroaryl, 1-alkenyl, 1-alkynyl, and —R⁹; or together V and Z are connected to form a cyclic group containing 3–5 atoms, optionally 1 heteroatom, substituted with hydroxy, acyloxy, alkoxycarboxy, or aryloxycarboxy attached to a carbon atom that is three atoms from an oxygen attached to the phosphorus; or together V and W are connected to form a cyclic group containing 3 carbon atoms substituted with hydroxy, acyloxy, alkoxycarboxy, alkylthiocarboxy, hydroxymethyl, and aryloxycarboxy attached to a carbon atom that is three atoms from an oxygen attached to the phosphorus;

Z is selected from the group consisting of —CH₂OH, —CH₂OCOR³, —CH₂OC(O)SR³, —CH₂OCO₂R³, —SR³, —S(O)R³, —CH₂N₃, —CH₂NR²₂, —CH₂Ar, —CH(Ar)OH, —CH(CH=CR²R²)OH, —CH(C≡CR²)OH, and —R²;

with the provisos that:
a) V, Z, W are not all —H; and
b) when Z is —R², then at least one of V and W is not —H or —R⁹;

R² is selected from the group consisting of R³ and —H;

R³ is selected from the group consisting of alkyl, aryl, alicyclic, and aralkyl; and R⁹ is selected from the group consisting of alkyl, aralkyl, and alicyclic.

24. The compounds of claim 23 wherein V and W both form a 6-membered carbocyclic ring substituted with 0–4 groups, selected from the group consisting of hydroxy, acyloxy, alkoxycarbonyloxy, and alkoxy; and Z is —R².

25. The compounds of claim 23 wherein V and W are hydrogen; and Z is selected from the group consisting of hydroxyalkyl, acyloxyalkyl, alkyloxyalkyl, and alkoxycarboxyalkyl.

26. The compounds of claim 23 wherein V and W are independently selected from the group consisting of hydrogen, optionally substituted aryl, and optionally substituted heteroaryl, with the proviso that at least one of V and W is optionally substituted aryl or optionally substituted heteroaryl.

27. The compounds of claim 1 wherein together R¹ and R¹ are optionally substituted lactones attached at the omega position.

28. The compounds of claim 17 wherein R¹ is alicyclic where the cyclic moiety contains carbonate or thiocarbonate.

29. The compounds of claim 28 wherein together R¹ and R¹ are optionally substituted 2-oxo-1,3-dioxolenes attached through a methylene to the phosphorus oxygen.

30. The compounds of claim 1 wherein

A, L and E are independently selected from the group consisting of —NR⁸₂, —H, hydroxy, halogen, lower alkoxy, lower alkyl, and lower perhaloalkyl;

X is selected from the group consisting of aryl, alkoxyalkyl, alkyl, alkylthio, 1,1-dihaloalkyl, carbonylalkyl, alkyl(hydroxy), alkyl(sulfonate), alkylaminocarbonyl, and alkylcarbonylamino;

and each R⁴ and R⁷ is independently selected from the group consisting of —H and lower alkyl.

31. The compounds of claim 30 wherein A, L, and E are independently selected from the group consisting of —H, lower alkyl, halogen, and —NR⁸₂;

J is selected from the group consisting of —H, halogen, haloalkyl, hydroxyalkyl, —R⁸₂ N-alkyl, lower alkyl, lower aryl, heterocyclic and alicyclic, or together with Y forms a cyclic group; and X is selected from the group consisting of heteroaryl, alkylaminocarbonyl, 1,1-dihaloalkyl, and alkoxyalkyl.

32. The compounds of claim 31 wherein A is selected from the group consisting of —H, —NH₂, —F, and —CH₃;

L is selected from the group consisting of —H, —F, —OCH₃, Cl and —CH₃;

E is selected from the group consisting of —H, and —Cl;

J is selected from the group consisting of —H, halo, C1–C5 hydroxyalkyl, C1–C5 haloalkyl, C1–C5 R⁸₂ N-alkyl, C1–C5 alicyclic, and C1–C5 alkyl;

X is —CH₂OCH₂—, 2,5-furanyl; and

Y is lower alkyl.

33. The compounds of claim 32 where A is —NH₂, L is —F, E is —H, J is —H, Y is isobutyl, and X is 2,5-furanyl.

34. The compounds of claim 32 where A is —NH₂, L is —F, E is —H, J is —Cl, Y is isobutyl, and X is 2,5-furanyl.

35. The compounds of claim 32 where A is —H, L is —H, E is —Cl, J is —H, Y is isobutyl, and X is 2,5-furanyl.

36. The compounds of claim 32 where A is —NH₂, L is —F, E is —H, J is —H, Y is cyclopropylmethyl, and X is 2,5-furanyl.

37. The compounds of claim 32 where A is —NH₂, L is —F, E is —H, J is ethyl, Y is isobutyl, and X is 2,5-furanyl.

38. The compounds of claim 32 where A is —CH₃, L is —Cl, E is —H, J is —H, Y is isobutyl, and X is 2,5-furanyl.

39. The compounds of claim 32 where A is —NH₂, L is —F, E is —H, J is —Br, Y is isobutyl, and X is —CH₂OCH₂—.

40. The compounds of claim 32 where A is —NH₂, L is —F, E is —H, J is selected from the group consisting of bromopropyl, bromobutyl, chlorobutyl, cyclopropyl, hydroxypropyl, N,N-dimethylaminopropyl, and X is 2,5-furanyl.

41. The compound of claim 32 wherein A is —CH₃, L is —CH₃, E is —CH₃, J is —CH₃, Y is cyclopropylmethyl, and X is 2,5-furanyl.

42. The compounds of claims 33, 34, 35, 36, 37, 38, 39, 40, or 41 wherein R¹ is pivaloyloxymethyl or their HCl salts.

43. A method of treating an animal for diabetes mellitus, comprising administering to said animal a therapeutically effective amount of a compound of formula 1:

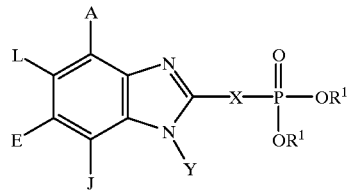

wherein:
  A, E, and L are selected from the group consisting of —$NR^8_2$, —$NO_2$, —H, —$OR^7$, —$SR^7$, —$C(O)NR^4_2$, halo, —$COR^{11}$, —$SO_2R^3$, guanidine, amidine, —$NHSO_2R^5$, —$SO_2NR^4_2$, —CN, sulfoxide, perhaloacyl, perhaloalkyl, perhaloalkoxy, C1–C5 alkyl, C2–C5 alkenyl, C2–C5 alkynyl, and lower alicyclic, or together A and L form a cyclic group, or together L and E form a cyclic group, or together E and J form a cyclic group including aryl, cyclic alkyl, and heterocyclic;
  J is selected from the group consisting of —$NR^8_2$, —$NO_2$, —H, —$OR^7$, —$SR^7$, —$C(O)NR^4_2$, halo, —$C(O)R^{11}$, —CN, sulfonyl, sulfoxide, perhaloalkyl, hydroxyalkyl, perhaloalkoxy, alkyl, haloalkyl, aminoalkyl, alkenyl, alkynyl, alicyclic, aryl, and aralkyl, or together with Y forms a cyclic group including aryl, cyclic alkyl and heterocyclic alkyl;
  X is selected from the group consisting of alkylamino, alkyl(hydroxy), alkyl(carboxyl), alkyl(phosphonate), alkyl, alkenyl, alkynyl, alkyl(sulfonate), aryl, carbonylalkyl, 1,1-dihaloalkyl, aminocarbonylamino, alkylaminoalkyl, alkoxyalkyl, alkylthioalkyl, alkylthio, alkylaminocarbonyl, alkylcarbonylamino, alicyclic, aralkyl, and alkylaryl, all optionally substituted; or together with Y form a cyclic group including aryl, cyclic alkyl, and heterocyclic;
  Y is selected from the group consisting of —H, alkyl, alkenyl, alkynyl, aryl, alicyclic, aralkyl, aryloxyalkyl, alkoxyalkyl, —$C(O)R^3$, —$S(O)_2R^3$, —$C(O)$—$R^{11}$, —$CONHR^3$, —$NR^2_2$, and —$OR^3$, all except H are optionally substituted; or together with X form a cyclic group including aryl, cyclic alkyl, and heterocyclic;
  $R^1$ is independently selected from the group consisting of —H, alkyl, aryl, alicyclic where the cyclic moiety contains a carbonate or thiocarbonate, —$C(R^2)_2$—aryl, alkylaryl, —$C(R^2)_2OC(O)NR^2_2$, —$NR^2$—$C(O)$—$R^3$, —$C(R^2)_2$—$OC(O)R^3$, $C(R^2)_2$—O—$C(O)OR^3$, —$C(R^2)_2OC(O)SR^3$, alkyl—S—$C(O)R^3$, alkyl—S—S—alkylhydroxy, and alkyl—S—S—S—alkylhydroxy, or together $R^1$ and $R^1$ are —alkyl—S—S—alkyl to form a cyclic group, or together $R^1$ and $R^1$ are

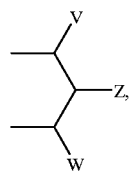

wherein
  V and W are independently selected from the group consisting of hydrogen, aryl, substituted aryl, heteroaryl, substituted heteroaryl, 1-alkenyl, 1-alkynyl, and —$R^9$; or together V and Z are connected to form a cyclic group containing 3–5 atoms, optionally 1 heteroatom, substituted with hydroxy, acyloxy, alkoxycarboxy, or aryloxycarboxy attached to a carbon atom that is three atoms from an oxygen attached to the phosphorus; or together V and W are connected to form a cyclic group containing 3 carbon atoms substituted with hydroxy, acyloxy, alkoxycarboxy, alkylthiocarboxy, hydroxymethyl, and aryloxycarboxy attached to a carbon atom that is three atoms from an oxygen attached to the phosphorus;

Z is selected from the group consisting of —$CH_2OH$, —$CH_2OCOR^3$, —$CH_2OC(O)SR^3$, —$CH_2OCO_2R^3$, —$SR^3$, —$S(O)R^3$, —$CH_2N_3$, —$CH_2NR^2_2$, —$CH_2Ar$, —$CH(Ar)OH$, —$CH(CH=CR^2R^2)OH$, —$CH(C≡CR^2)OH$, and —$R^2$;

with the provisos that:
  a) V, Z, W are not all —H; and
  b) when Z is —$R^2$, then at least one of V and W is not —H or —$R^9$;
$R^2$ is selected from the group consisting of $R^3$ and —H;
$R^3$ is selected from the group consisting of alkyl, aryl, alicyclic, and aralkyl;
$R^4$ is independently selected from the group consisting of —H, lower alkyl, lower alicyclic, lower aralkyl, and lower aryl;
$R^5$ is selected from the group consisting of lower alkyl, lower aryl, lower aralkyl, and lower alicyclic;
$R^6$ is independently selected from the group consisting of —H, and lower alkyl;
$R^7$ is independently selected from the group consisting of —H, lower alkyl, lower alicyclic, lower aralkyl, lower aryl, and —$C(O)R^{10}$;
$R^8$ is independently selected from the group consisting of —H, lower alkyl, lower aralkyl, lower aryl, lower alicyclic, —$C(O)R^{10}$, or together they form a bidendate alkyl;
$R^9$ is selected from the group consisting of alkyl, aralkyl, and alicyclic;
$R^{10}$ is selected from the group consisting of —H, lower alkyl, —$NH_2$, lower aryl, and lower perhaloalkyl;
$R^{11}$ is selected from the group consisting of alkyl, aryl, —OH, —$NH_2$ and —$OR^3$; and
pharmaceutically acceptable prodrugs and salts thereof.

44. A method of lowering blood glucose levels in an animal in need thereof, comprising administering to said animal a pharmaceutically acceptable amount of a compound of formula 1:

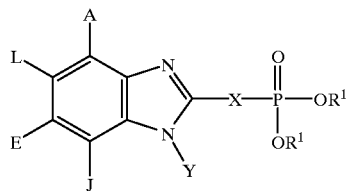

wherein:
  A, E, and L are selected from the group consisting of —$NR^8_2$, —$NO_2$, —H, —$OR^7$, —$SR^7$, —$C(O)NR^4_2$, halo, —$COR^{11}$, —$SO_2R^3$, guanidine, amidine, —$NHSO_2R^5$, —$SO_2NR^4_2$, —CN, sulfoxide, perhaloacyl, perhaloalkyl, perhaloalkoxy, C1–C5 alkyl, C2–C5 alkenyl, C2–C5 alkynyl, and lower alicyclic, or together A and L form a cyclic group, or together L and E form a cyclic group, or together E and J form a cyclic group including aryl, cyclic alkyl, and heterocyclic;

J is selected from the group consisting of —NR$^8_2$, —NO$_2$,
—H, —OR$^7$, —SR$^7$, —C(O)NR$^4_2$, halo, —C(O)R$^{11}$,
—CN, sulfonyl, sulfoxide, perhaloalkyl, hydroxyalkyl,
perhaloalkoxy, alkyl, haloalkyl, aminoalkyl, alkenyl,
alkynyl, alicyclic, aryl, and aralkyl, or together with Y
forms a cyclic group including aryl, cyclic alkyl and
heterocyclic alkyl;

X is selected from the group consisting of alkylamino,
alkyl(hydroxy), alkyl(carboxyl), alkyl(phosphonate),
alkyl, alkenyl, alkynyl, alkyl(sulfonate), aryl,
carbonylalkyl, 1,1-dihaloalkyl, aminocarbonylamino,
alkylaminoalkyl, alkoxyalkyl, alkylthioalkyl, alkylthio,
alkylaminocarbonyl, alkylcarbonylamino, alicyclic,
aralkyl, and alkylaryl, all optionally substituted; or
together with Y form a cyclic group including aryl,
cyclic alkyl, and heterocyclic;

Y is selected from the group consisting of —H, alkyl,
alkenyl, alkynyl, aryl, alicyclic, aralkyl, aryloxyalkyl,
alkoxyalkyl, —C(O)R$^3$, —S(O)$_2$R$^3$, —C(O)—R$^{11}$,
—CONHR$^3$, —NR$^2_2$, and —OR$^3$, all except H are
optionally substituted; or together with X form a cyclic
group including aryl, cyclic alkyl, and heterocyclic;

R$^1$ is independently selected from the group consisting of
—H, alkyl, aryl, alicyclic where the cyclic moiety
contains a carbonate or thiocarbonate, —C(R$^2$)$_2$—aryl,
alkylaryl, —C(R$^2$)$_2$OC(O)NR$^2_2$, —NR$^2$—C(O)—R$^3$,
—C(R$^2$)$_2$—OC(O)R$^3$, C(R$^2$)$_2$—O—C(O)OR$^3$,
—C(R$^2$)$_2$OC(O)SR$^3$, alkyl—S—C(O)R$^3$, alkyl—S—
S—alkylhydroxy, and alkyl—S—S—S—
alkylhydroxy, or together R$^1$ and R$^1$ are —alkyl—S—
S—alkyl to form a cyclic group, or together R$^1$ and R$^1$
are

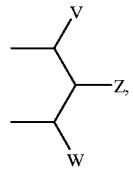

wherein
V and W are independently selected from the group
consisting of hydrogen, aryl, substituted aryl,
heteroaryl, substituted heteroaryl, 1-alkenyl, 1-alkynyl,
and —R$^9$; or together V and Z are connected to form a cyclic group
containing 3–5 atoms, optionally 1 heteroatom, substituted with hydroxy, acyloxy, alkoxycarboxy, or aryloxycarboxy attached to a carbon atom that is three
atoms from an oxygen attached to the phosphorus; or together V and W are connected to form a cyclic group
containing 3 carbon atoms substituted with hydroxy,
acyloxy, alkoxycarboxy, alkylthiocarboxy,
hydroxymethyl, and aryloxycarboxy attached to a carbon atom that is three atoms from an oxygen attached
to the phosphorus;

Z is selected from the group consisting of —CH$_2$OH,
—CH$_2$OCOR$^3$, —CH$_2$OC(O)SR$^3$, —CH$_2$OCO$_2$R$^3$,
—SR$^3$, —S(O)R$^3$, —CH$_2$N$_3$, —CH$_2$NR$^2_2$, —CH$_2$Ar,
—CH(Ar)OH, —CH(CH=CR$^2$R$^2$)OH, —CH
(C≡CR$^2$)OH, and —R$^2$;

with the provisos that:
a) V, Z, W are not all —H; and
b) when Z is —R$^2$, then at least one of V and W is not
—H or —R$^9$;

R$^2$ is selected from the group consisting of R$^3$ and —H;
R$^3$ is selected from the group consisting of alkyl, aryl,
alicyclic, and aralkyl;
R$^4$ is independently selected from the group consisting
of —H, lower alkyl, lower alicyclic, lower aralkyl,
and lower aryl;
R$^5$ is selected from the group consisting of lower alkyl,
lower aryl, lower aralkyl, and lower alicyclic;
R$^6$ is independently selected from the group consisting
of —H, and lower alkyl;
R$^7$ is independently selected from the group consisting
of —H, lower alkyl, lower alicyclic, lower aralkyl,
lower aryl, and —C(O)R$^{10}$;
R$^8$ is independently selected from the group consisting
of —H, lower alkyl, lower aralkyl, lower aryl, lower
alicyclic, —C(O)R$^{10}$, or together they form a bidentate alkyl;
R$^9$ is selected from the group consisting of alkyl,
aralkyl, and alicyclic;
R$^{10}$ is selected from the group consisting of —H, lower
alkyl, —NH$_2$, lower aryl, and lower perhaloalkyl;
R$^{11}$ is selected from the group consisting of alkyl, aryl,
—OH, —NH$_2$ and —OR$^3$; and
pharmaceutically acceptable prodrugs and salts thereof.

45. A method of inhibiting FBPase at the AMP site in
patients in need thereof, comprising administering to said
patients an FBPase inhibitory amount of a compound of
formula 1:

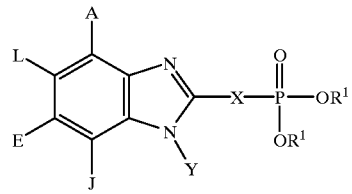

wherein:
A, E, and L are selected from the group consisting of
—NR$^8_2$, —NO$_2$, —H, —OR$^7$, —SR$^7$, —C(O)NR$^4_2$,
halo, —COR$^{11}$, —SO$_2$R$^3$, guanidine, amidine,
—NHSO$_2$R$^5$, —SO$_2$NR$^4_2$, —CN, sulfoxide,
perhaloacyl, perhaloalkyl, perhaloalkoxy, C1–C5 alkyl,
C2–C5 alkenyl, C2–C5 alkynyl, and lower alicyclic, or
together A and L form a cyclic group, or together L and
E form a cyclic group, or together E and J form a cyclic
group including aryl, cyclic alkyl, and heterocyclic;

J is selected from the group consisting of —NR$^8_2$, —NO$_2$,
—H, —OR$^7$, —SR$^7$, —C(O)NR$^4_2$, halo, —C(O)R$^{11}$,
—CN, sulfonyl, sulfoxide, perhaloalkyl, hydroxyalkyl,
perhaloalkoxy, alkyl, haloalkyl, aminoalkyl, alkenyl,
alkynyl, alicyclic, aryl, and aralkyl, or together with Y
forms a cyclic group including aryl, cyclic alkyl and
heterocyclic alkyl;

X is selected from the group consisting of alkylamino,
alkyl(hydroxy), alkyl(carboxyl), alkyl(phosphonate),
alkyl, alkenyl, alkynyl, alkyl(sulfonate), aryl,
carbonylalkyl, 1,1-dihaloalkyl, aminocarbonylamino,
alkylaminoalkyl, alkoxyalkyl, alkylthioalkyl, alkylthio,
alkylaminocarbonyl, alkylcarbonylamino, alicyclic,
aralkyl, and alkylaryl, all optionally substituted; or
together with Y form a cyclic group including aryl,
cyclic alkyl, and heterocyclic;

Y is selected from the group consisting of —H, alkyl,
alkenyl, alkynyl, aryl, alicyclic, aralkyl, aryloxyalkyl, alkoxyalkyl, —C(O)R³, —S(O)₂R³, —C(O)—R¹¹, —CONHR³, —NR²₂, and —OR³, all except H are optionally substituted; or together with X form a cyclic group including aryl, cyclic alkyl, and heterocyclic;

R¹ is independently selected from the group consisting of —H, alkyl, aryl, alicyclic where the cyclic moiety contains a carbonate or thiocarbonate, —C(R²)₂—aryl, alkylaryl, —C(R²)₂OC(O)NR²₂, —NR²—C(O)—R³, —C(R²)₂—OC(O)R³, C(R²)₂—O—C(O)OR³, —C(R²)₂OC(O)SR³, alkyl—S—C(O)R³, alkyl—S—S—alkylhydroxy, and alkyl—S—S—S—alkylhydroxy, or together R¹ and R¹ are —alkyl—S—S—alkyl to form a cyclic group, or together R¹ and R¹ are

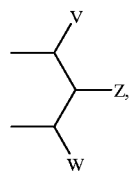

wherein

V and W are independently selected from the group consisting of hydrogen, aryl, substituted aryl, heteroaryl, substituted heteroaryl, 1-alkenyl, 1-alkynyl, and —R⁹; or together V and Z are connected to form a cyclic group containing 3–5 atoms, optionally 1 heteroatom, substituted with hydroxy, acyloxy, alkoxycarboxy, or aryloxycarboxy attached to a carbon atom that is three atoms from an oxygen attached to the phosphorus; or together V and W are connected to form a cyclic group containing 3 carbon atoms substituted with hydroxy, acyloxy, alkoxycarboxy, alkylthiocarboxy, hydroxymethyl, and aryloxycarboxy attached to a carbon atom that is three atoms from an oxygen attached to the phosphorus;

Z is selected from the group consisting of —CH₂OH, —CH₂OCOR³, —CH₂OC(O)SR³, —CH₂OCO₂R³, —SR³, —S(O)R³, —CH₂N₃, —CH₂NR²₂, —CH₂Ar, —CH(Ar)OH, —CH(CH═CR²R²)OH, —CH(C≡CR²)OH, and —R²;

with the provisos that:
a) V, Z, W are not all —H; and
b) when Z is —R², then at least one of V and W is not —H or —R⁹;

R² is selected from the group consisting of R³ and —H;

R³ is selected from the group consisting of alkyl, aryl, alicyclic, and aralkyl;

R⁴ is independently selected from the group consisting of —H, lower alkyl, lower alicyclic, lower aralkyl, and lower aryl;

R⁵ is selected from the group consisting of lower alkyl, lower aryl, lower aralkyl, and lower alicyclic;

R⁶ is independently selected from the group consisting of —H, and lower alkyl;

R⁷ is independently selected from the group consisting of —H, lower alkyl, lower alicyclic, lower aralkyl, lower aryl, and —C(O)R¹⁰;

R⁸ is independently selected from the group consisting of —H, lower alkyl, lower aralkyl, lower aryl, lower alicyclic, —C(O)R¹⁰, or together they form a bidendate alkyl;

R⁹ is selected from the group consisting of alkyl, aralkyl, and alicyclic;

R¹⁰ is selected from the group consisting of —H, lower alkyl, —NH₂, lower aryl, and lower perhaloalkyl;

R¹¹ is selected from the group consisting of alkyl, aryl, —OH, —NH₂ and —OR³; and pharmaceutically acceptable prodrugs and salts thereof.

46. A method of inhibiting gluconeogenesis in animal in need thereof, comprising administering to said animal an effective amount of a compound of formula 1:

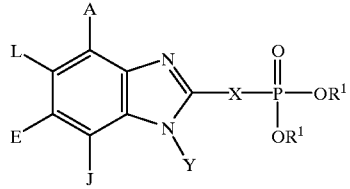

wherein:

A, E, and L are selected from the group consisting of —NR⁸₂, —N₂, —H, —OR⁷, —SR⁷, —C(O)NR⁴₂, halo, —COR¹¹, —SO₂R³, guanidine, amidine, —NHSO₂R⁵, —SO₂NR⁴₂, —CN, sulfoxide, perhaloacyl, perhaloalkyl, perhaloalkoxy, C1–C5 alkyl, C2–C5 alkenyl, C2–C5 alkynyl, and lower alicyclic, or together A and L form a cyclic group, or together L and E form a cyclic group, or together E and J form a cyclic group including aryl, cyclic alkyl, and heterocyclic;

J is selected from the group consisting of —NR⁸₂, —NO₂, —H, —OR⁷, —SR⁷, —C(O)NR⁴₂, halo, —C(O)R¹¹, —CN, sulfonyl, sulfoxide, perhaloalkyl, hydroxyalkyl, perhaloalkoxy, alkyl, haloalkyl, aminoalkyl, alkenyl, alkynyl, alicyclic, aryl, and aralkyl, or together with Y forms a cyclic group including aryl, cyclic alkyl and heterocyclic alkyl;

X is selected from the group consisting of alkylamino, alkyl(hydroxy), alkyl(carboxyl), alkyl(phosphonate), alkyl, alkenyl, alkynyl, alkyl(sulfonate), aryl, carbonylalkyl, 1,1-dihaloalkyl, aminocarbonylamino, alkylaminoalkyl, alkoxyalkyl, alkylthioalkyl, alkylthio, alkylaminocarbonyl, alkylcarbonylamino, alicyclic, aralkyl, and alkylaryl, all optionally substituted; or together with Y form a cyclic group including aryl, cyclic alkyl, and heterocyclic;

Y is selected from the group consisting of —H, alkyl, alkenyl, alkynyl, aryl, alicyclic, aralkyl, aryloxyalkyl, alkoxyalkyl, —C(O)R³, —S(O)₂R³, —C(O)—R¹¹, —CONHR³, —NR²₂, and —OR³, all except H are optionally substituted; or together with X form a cyclic group including aryl, cyclic alkyl, and heterocyclic;

R¹ is independently selected from the group consisting of —H, alkyl, aryl, alicyclic where the cyclic moiety contains a carbonate or thiocarbonate, —C(R²)₂—aryl, alkylaryl, —C(R²)₂OC(O)NR²₂, —NR²—C(O)—R³, —C(R²)₂—OC(O)R³, C(R²)₂—O—C(O)OR³, —C(R²)₂OC(O)SR³, alkyl—S—C(O)R³, alkyl—S—S—alkylhydroxy, and alkyl—S—S—S—alkylhydroxy, or together R¹ and R¹ are —alkyl—S—S—alkyl to form a cyclic group, or together R¹ and R¹ are

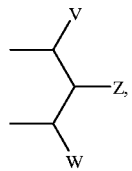

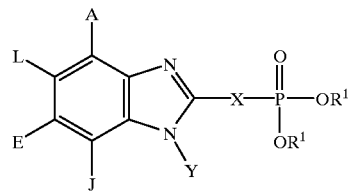

wherein

V and W are independently selected from the group consisting of hydrogen, aryl, substituted aryl, heteroaryl, substituted heteroaryl, 1-alkenyl, 1-alkynyl, and —$R^9$; or together V and Z are connected to form a cyclic group containing 3–5 atoms, optionally 1 heteroatom, substituted with hydroxy, acyloxy, alkoxycarboxy, or aryloxycarboxy attached to a carbon atom that is three atoms from an oxygen attached to the phosphorus; or together V and W are connected to form a cyclic group containing 3 carbon atoms substituted with hydroxy, acyloxy, alkoxycarboxy, alkylthiocarboxy, hydroxymethyl, and aryloxycarboxy attached to a carbon atom that is three atoms from an oxygen attached to the phosphorus;

Z is selected from the group consisting of —$CH_2OH$, —$CH_2OCOR^3$, —$CH_2OC(O)SR^3$, —$CH_2OCO_2R^3$, —$SR^3$, —$S(O)R^3$, —$CH_2N_3$, —$CH_2NR^2{}_2$, —$CH_2Ar$, —CH(Ar)OH, —CH(CH=$CR^2R^2$)OH, —CH(C≡$CR^2$)OH, and —$R^2$;

with the provisos that:
  a) V, Z, W are not all —H; and
  b) when Z is —$R^2$, then at least one of V and W is not —H or —$R^9$;

$R^2$ is selected from the group consisting of $R^3$ and —H;
$R^3$ is selected from the group consisting of alkyl, aryl, alicyclic, and aralkyl;
$R^4$ is independently selected from the group consisting of —H, lower alkyl, lower alicyclic, lower aralkyl, and lower aryl;
$R^5$ is selected from the group consisting of lower alkyl, lower aryl, lower aralkyl, and lower alicyclic;
$R^6$ is independently selected from the group consisting of —H, and lower alkyl;
$R^7$ is independently selected from the group consisting of —H, lower alkyl, lower alicyclic, lower aralkyl, lower aryl, and —$C(O)R^{10}$;
$R^8$ is independently selected from the group consisting of —H, lower alkyl, lower aralkyl, lower aryl, lower alicyclic, —$C(O)R^{10}$, or together they form a bidendate alkyl;
$R^{11}$ is selected from the group consisting of alkyl, aralkyl, and alicyclic;
$R^{10}$ is selected from the group consisting of —H, lower alkyl, —$NH_2$, lower aryl, and lower perhaloalkyl;
$R^{11}$ is selected from the group consisting of alkyl, aryl, —OH, —$NH_2$ and —$OR^3$; and
pharmaceutically acceptable prodrugs and salts thereof.

47. A method of treating an animal for a disease derived from abnormally elevated intherapeuticallcomprising administering to said animal a therapeutically effective amount of a fructose-1,6-bisphosphatase inhibitor which binds to the AMP site of FBPase.

48. The method of claim 47 wherein said inhibitor is a compound of formula 1:

wherein:
A, E, and L are selected from the group consisting of —$NR^8{}_2$, —$NO_2$, —H, —$OR^7$, —$SR^7$, —$C(O)NR^4{}_2$, halo, —$COR^{11}$, —$SO_2R^3$, guanidine, amidine, —$NHSO_2R^5$, —$SO_2NR^4{}_2$, —CN, sulfoxide, perhaloacyl, perhaloalkyl, perhaloalkoxy, C1–C5 alkyl, C2–C5 alkenyl, C2–C5 alkynyl, and lower alicyclic, or together A and L form a cyclic group, or together L and E form a cyclic group, or together E and J form a cyclic group including aryl, cyclic alkyl, and heterocyclic;

J is selected from the group consisting of —$NR^8{}_2$, —$NO_2$, —H, —$OR^7$, —$SR^7$, —$C(O)NR^4{}_2$, halo, —$C(O)R^{11}$, —CN, sulfonyl, sulfoxide, perhaloalkyl, hydroxyalkyl, perhaloalkoxy, alkyl, haloalkyl, aminoalkyl, alkenyl, alkynyl, alicyclic, aryl, and aralkyl, or together with Y forms a cyclic group including aryl, cyclic alkyl and heterocyclic alkyl;

X is selected from the group consisting of alkylamino, alkyl(hydroxy), alkyl(carboxyl), alkyl(phosphonate), alkyl, alkenyl, alkynyl, alkyl(sulfonate), aryl, carbonylalkyl, 1,1-dihaloalkyl, aminocarbonylamino, alkylaminoalkyl, alkoxyalkyl, alkylthioalkyl, alkylthio, alkylaminocarbonyl, alkylcarbonylamino, alicyclic, aralkyl, and alkylaryl, all optionally substituted; or together with Y form a cyclic group including aryl, cyclic alkyl, and heterocyclic;

Y is selected from the group consisting of —H, alkyl, alkenyl, alkynyl, aryl, alicyclic, aralkyl, aryloxyalkyl, alkoxyalkyl, —$C(O)R^3$, —$S(O)_2R^3$, —C(O)—$R^{11}$, —$CONHR^3$, —$NR^2{}_2$, and —$OR^3$, all except H are optionally substituted; or together with X form a cyclic group including aryl, cyclic alkyl, and heterocyclic;

$R^1$ is independently selected from the group consisting of —H, alkyl, aryl, alicyclic where the cyclic moiety contains a carbonate or thiocarbonate, —$C(R^2)_2$—aryl, alkylaryl, —$C(R^2)_2OC(O)NR^2{}_2$, —$NR^2$—C(O)—$R^3$, —$C(R^2)_2$—OC(O)$R^3$, $C(R^2)_2$—O—C(O)$OR^3$, —$C(R^2)_2OC(O)SR^3$, alkyl—S—$C(O)R^3$, alkyl—S—S—alkylhydroxy, and alkyl—S—S—S—alkylhydroxy, or together $R^1$ and $R^1$ are —alkyl—S—S—alkyl to form a cyclic group, or together $R^1$ and $R^1$ are

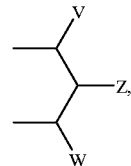

wherein
V and W are independently selected from the group consisting of hydrogen, aryl, substituted aryl, heteroaryl, substituted heteroaryl, 1-alkenyl, 1-alkynyl, and —$R^9$; or together V and Z are connected to form a cyclic group containing 3–5 atoms, optionally 1 heteroatom, substituted with hydroxy, acyloxy, alkoxycarboxy, or aryloxycarboxy attached to a carbon atom that is three atoms from an oxygen attached to the phosphorus; or together V and W are connected to form a cyclic group containing 3 carbon atoms substituted with hydroxy, acyloxy, alkoxycarboxy, alkylthiocarboxy, hydroxymethyl, and aryloxycarboxy attached to a carbon atom that is three atoms from an oxygen attached to the phosphorus;

Z is selected from the group consisting of —$CH_2OH$, —$CH_2OCOR^3$, —$CH_2OC(O)SR^3$, —$CH_2OCO_2R^3$, —$SR^3$, —$S(O)R^3$, —$CH_2N_3$, —$CH_2NR^2{}_2Ar$, —$CH(Ar)OH$, —$CH(CH=CR^2R^2)OH$, —$CH(C\equiv CR^2)OH$, and —$R^2$;

with the provisos that:
a) V, Z, W are not all —H; and
b) when Z is —$R^2$, then at least one of V and W is not —H or —$R^9$;

$R^2$ is selected from the group consisting of $R^3$ and —H;
$R^3$ is selected from the group consisting of alkyl, aryl, alicyclic, and aralkyl;
$R^4$ is independently selected from the group consisting of —H, lower alkyl, lower alicyclic, lower aralkyl, and lower aryl;
$R^5$ is selected from the group consisting of lower alkyl, lower aryl, lower aralkyl, and lower alicyclic;
$R^6$ is independently selected from the group consisting of —H, and lower alkyl;
$R^7$ is independently selected from the group consisting of —H, lower alkyl, lower alicyclic, lower aralkyl, lower aryl, and —$C(O)R^{10}$;
$R^8$ is independently selected from the group consisting of —H, lower alkyl, lower aralkyl, lower aryl, lower alicyclic, —$C(O)R^{10}$, or together they form a bidentate alkyl;
$R^9$ is selected from the group consisting of alkyl, aralkyl, and alicyclic;
$R^{10}$ is selected from the group consisting of —H, lower alkyl, —$NH_2$, lower aryl, and lower perhaloalkyl;
$R^{11}$ is selected from the group consisting of alkyl, aryl, —OH, —$NH_2$ and —$OR^3$; and
pharmaceutically acceptable prodrugs and salts thereof.

49. The method of claim 47 wherein said disease is atherosclerosis.

50. A method of treating an animal with excess glycogen storage disease, comprising administering to said animal in need thereof a therapeutically effective amount of a fructose-1,6-bisphosphatase inhibitor which binds to the AMP site of FBPase.

51. The method of claim 50 wherein said inhibitor is a compound of formula 1:

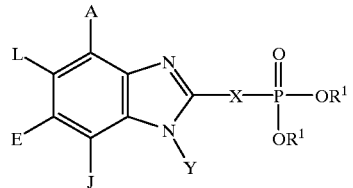

wherein:
A, E, and L are selected from the group consisting of —$NR^8{}_2$, —$NO_2$, —H, —$OR^7$, —$SR^7$, —$C(O)NR^4{}_2$, halo, —$COR^{11}$, —$SO_2R^3$, guanidine, amidine, —$NHSO_2R^5$, —$SO_2NR^4{}_2$, —CN, sulfoxide, perhaloacyl, perhaloalkyl, perhaloalkoxy, C1–C5 alkyl, C2–C5 alkenyl, C2–C5 alkynyl, and lower alicyclic, or together A and L form a cyclic group, or together L and E form a cyclic group, or together E and J form a cyclic group including aryl, cyclic alkyl, and heterocyclic;

J is selected from the group consisting of —$NR^8{}_2$, —$NO_2$, —H, —$OR^7$, —$SR^7$, —$C(O)NR^4{}_2$, halo, —$C(O)R^{11}$, —CN, sulfonyl, sulfoxide, perhaloalkyl, hydroxyalkyl, perhaloalkoxy, alkyl, haloalkyl, aminoalkyl, alkenyl, alkynyl, alicyclic, aryl, and aralkyl, or together with Y forms a cyclic group including aryl, cyclic alkyl and heterocyclic alkyl;

X is selected from the group consisting of alkylamino, alkyl(hydroxy), alkyl(carboxyl), alkyl(phosphonate), alkyl, alkenyl, alkynyl, alkyl(sulfonate), aryl, carbonylalkyl, 1,1-dihaloalkyl, aminocarbonylamino, alkylaminoalkyl, alkoxyalkyl, alkylthioalkyl, alkylthio, alkylaminocarbonyl, alkylcarbonylamino, alicyclic, aralkyl, and alkylaryl, all optionally substituted; or together with Y form a cyclic group including aryl, cyclic alkyl, and heterocyclic;

Y is selected from the group consisting of —H, alkyl, alkenyl, alkynyl, aryl, alicyclic, aralkyl, aryloxyalkyl, alkoxyalkyl, —$C(O)R^3$, —$S(O)_2R^3$, —$C(O)$—$R^{11}$, —$CONHR^3$, —$NR^2{}_2$, and —$OR^3$, all except H are optionally substituted; or together with X form a cyclic group including aryl, cyclic alkyl, and heterocyclic;

$R^1$ is independently selected from the group consisting of —H, alkyl, aryl, alicyclic where the cyclic moiety contains a carbonate or thiocarbonate, —$C(R^2)_2$—aryl, alkylaryl, —$C(R^2)_2OC(O)NR^2{}_2$, —$NR^2$—$C(O)$—$R^3$, —$C(R^2)_2$—$OC(O)R^3$, $C(R^2)_2$—O—$C(O)OR^3$, —$C(R^2)_2OC(O)SR^3$, alkyl—S—$C(O)R^3$, alkyl—S—S—alkylhydroxy, and alkyl—S—S—alkylhydroxy, or together $R^1$ and $R^1$ are —alkyl—S—S—alkyl to form a cyclic group, or together $R^1$ and $R^1$ are

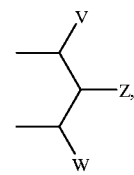

wherein
V and W are independently selected from the group consisting of hydrogen, aryl, substituted aryl, heteroaryl, substituted heteroaryl, 1-alkenyl, 1-alkynyl, and —$R^9$; or together V and Z are connected to form a cyclic group containing 3–5 atoms, optionally 1 heteroatom, substituted with hydroxy, acyloxy, alkoxycarboxy, or aryloxycarboxy attached to a carbon atom that is three atoms from an oxygen attached to the phosphorus; or together V and W are connected to form a cyclic group containing 3 carbon atoms substituted with hydroxy, acyloxy, alkoxycarboxy, alkylthiocarboxy, hydroxymethyl, and aryloxycarboxy attached to a carbon atom that is three atoms from an oxygen attached to the phosphorus;

Z is selected from the group consisting of —$CH_2OH$, —$CH_2OCOR^3$, —$CH_2OC(O)SR^3$, —$CH_2OCO_2R^3$, —$SR^3$, —$S(O)R^3$, —$OH_2N_3$, —$CH_2NR^2{}_2$, —$CH_2Ar$, —$CH(Ar)OH$, —$CH(CH=CR^2R^2)OH$, —$CH(C\equiv CR^2)OH$, and —$R^2$;

with the provisos that:
a) V, Z, W are not all —H; and
b) when Z is —$R^2$, then at least one of V and W is not —H or —$R^9$;

$R^2$ is selected from the group consisting of $R^3$ and —H;

$R^3$ is selected from the group consisting of alkyl, aryl, alicyclic, and aralkyl;

$R^4$ is independently selected from the group consisting of —H, lower alkyl, lower alicyclic, lower aralkyl, and lower aryl;

$R^5$ is selected from the group consisting of lower alkyl, lower aryl, lower aralkyl, and lower alicyclic;

$R^6$ is independently selected from the group consisting of —H, and lower alkyl;

$R^7$ is independently selected from the group consisting of —H, lower alkyl, lower alicyclic, lower aralkyl, lower aryl, and —$C(O)R^{10}$;

$R^8$ is independently selected from the group consisting of —H, lower alkyl, lower aralkyl, lower aryl, lower alicyclic, —$C(O)R^{10}$, or together they form a bidendate alkyl;

$R^9$ is selected from the group consisting of alkyl, aralkyl, and alicyclic;

$R^{10}$ is selected from the group consisting of —H, lower alkyl, —$NH_2$, lower aryl, and lower perhaloalkyl;

$R^{11}$ is selected from the group consisting of alkyl, aryl, —OH, —$NH_2$ and —$OR^3$; and pharmaceutically acceptable prodrugs and salts thereof.

52. The methods of claims 43, 44, 45, 46, 47, 48, 49, 50, or 51 wherein said compounds are administered orally.

* * * * *

UNITED STATES PATENT AND TRADEMARK OFFICE
CERTIFICATE OF CORRECTION

PATENT NO. : 6,110,903
DATED : August 29, 2000
INVENTOR(S) : Kasibhatla, Srinivas Rao et al.

It is certified that error appears in the above-identified patent and that said Letters Patent is hereby corrected as shown below:

<u>Title page,</u>
Item [73], Assignee, change name from "Sankyo Company Ltd." to -- Metabasis Therapeutics, Inc. --.

Signed and Sealed this

First Day of June, 2004

JON W. DUDAS
*Acting Director of the United States Patent and Trademark Office*